United States Patent [19]
Bernady et al.

[11] 4,060,540
[45] Nov. 29, 1977

[54] NOVEL 3-TRIPHENYLMETHOXY-1-ALKYNES, 3-TRIPHENYL-METHOXY-1-TRANS-ALKENYL-DIALKYL-ALANES, AND LITHIUM 3-TRIPHENYLMETHOXY-1-TRANS-ALKENYL-DIALKYL ALANATES

[75] Inventors: Karel Francis Bernady; Middleton Brawner Floyd, Jr., both of Suffern; John Frank Poletto, Nanuet, all of N.Y.; Robert Eugene Schaub, Upper Saddle River; Martin Joseph Weiss, Oradell, both of N.J.

[73] Assignee: American Cyanamid Company, Stamford, Conn.

[21] Appl. No.: 739,174

[22] Filed: Nov. 5, 1976

Related U.S. Application Data

[62] Division of Ser. No. 613,776, Sept. 18, 1975, Pat. No. 4,007,210, which is a division of Ser. No. 355,350, April 27, 1973, Pat. No. 3,932,479.

[51] Int. Cl.² ............................................. C07F 7/18
[52] U.S. Cl. ........................... 260/448.8 R; 542/413; 260/514 D; 260/345.1; 260/611 A; 260/395; 260/614 A; 260/346.22; 260/413; 260/448 A; 560/121
[58] Field of Search ................................. 260/448.8 R

[56] References Cited
U.S. PATENT DOCUMENTS

| | | | |
|---|---|---|---|
| 3,651,116 | 3/1972 | Lincoln et al. | 260/448.8 R |
| 3,873,607 | 3/1975 | Bernady et al. | 260/448.8 R X |
| 3,887,587 | 6/1975 | Schaap et al. | 260/448.8 R X |
| 3,932,467 | 1/1976 | Miyano | 260/448.8 R X |

*Primary Examiner*—Paul F. Shaver
*Attorney, Agent, or Firm*—Denis A. Polyn

[57] ABSTRACT

This disclosure describes 3-triphenylmethoxy-1-alkynes, 3-triphenylmethoxy-1-trans-alkenyl-dialkyl-alanes, and lithium 3-triphenylmethoxy-1-trans-alkenyl-dialkyl alanates useful as intermediates for the preparation of certain 11-hydroxy- and 11-deoxy-9-keto(or hydroxy)-prostanoic acid derivatives which possess bronchodilator, hypotensive, and anti-ulcer activity.

2 Claims, No Drawings

NOVEL 3-TRIPHENYLMETHOXY-1-ALKYNES, 3-TRIPHENYL-METHOXY-1-TRANS-ALKENYL-DIALKYL-ALANES, AND LITHIUM 3-TRIPHENYLMETHOXY-1-TRANS-ALKENYL-DIALKYL ALANATES

This is a division, of application Ser. No. 613,766, filed September 18, 1975, now U.S. Pat. No. 4,007,210 which in turn is a division of Ser. No. 355,350 filed Apr. 4, 1973, now U.S. Pat. No. 3,932,479.

BRIEF SUMMARY OF THE INVENTION

This invention relates to novel hydroxy substituted prostanoic acids and derivatives as well as to intermediates and methods for their preparation. These methods embrace novel and useful procedures for the preparation of prostaglandin $E_1$, 11-deoxyprostaglandin $E_1$, 13-dihydroxyprostaglandin $E_1$, and other known biologically important prostaglandin congeners. The novel compounds of this invention may be represented by the following general formula:

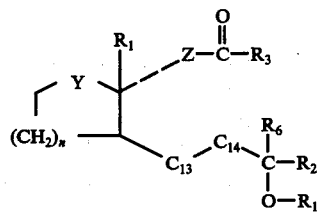

wherein $n$ is an integer having the value 1 or 2; $R_1$ is hydrogen, lower alkoxy, triphenylmethyl, or triphenylmethyl in which one or two of the phenyl rings is substituted with an alkyl or an alkoxy group having up to 3 carbon atoms; $R_2$ is a straight chain alkyl group having from 2 to 10 carbon atoms, a straight chain alkyl group having from 2 to 10 carbon atoms and substituted with one or two alkyl groups each having from one to three carbon atoms, a straight chain alkenyl group having from 3 to 10 carbon atoms, a straight chain alkenyl group having from 3 to 10 carbon atoms and substituted with one or two alkyl groups having between them from 2 to 5 carbon atoms, or a straight chain alkynyl group having from 3 to 10 carbon atoms; $R_3$ is hydroxy or an alkoxy group having from 1 to 12 carbon atoms; Y is a divalent radical selected from the group consisting of those of the formulae:

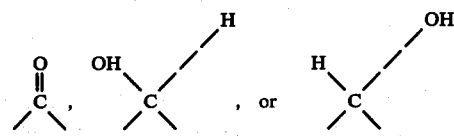

Z is a divalent radical selected from the group consisting of those of the formulae:

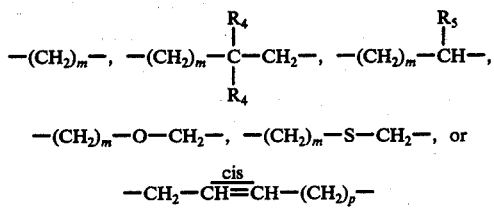

wherein $m$ is an integer from 3 to 8, inclusive, $p$ is an integer from 2 to 6 inclusive, $R_4$ is an alkyl group having up to 3 carbon atoms, and $R_5$ is an alkyl group having up to 3 carbon atoms, a fluorine atom, or a phenyl group; $R_6$ is hydrogen or an alkyl group having up to three carbon atoms; $R_7$ is hydrogen or an alkyl group having up to 3 carbon atoms; and the moiety $-C_{13}-C_{14}-$ is ethylene, trans-vinylene, or cis-vinylene; with the first proviso that when $n$ is 1, $R_1$ is hydrogen, $R_7$ is hydrogen, Z is $-(CH_2)_m-$ and $-C_{13}-C_{14}-$ is ethylene or trans-vinylene then $R_2$ does not include a straight chain alkyl group having from 2 to 10 carbon atoms; and with the second proviso that when Z is

$R_1$ is hydrogen, $R_2$ is a straight chain alkyl group having from 2 to 10 carbon atoms and $R_7$ is hydrogen then $-C_{13}-C_{14}-$ is ethylene or cis-vinylene; and with the third proviso that when $R_6$ is alkyl then $R_1$ is hydrogen; and with the fourth proviso that only one unsaturated bond can be directly adjacent to $C_{15}$; and with the fifth proviso that when $R_7$ is an alkyl group then the groups attached to the $C_8$ position may have the 8α-alkyl(8-iso) configuration of the formula:

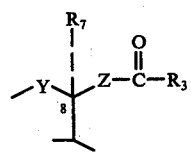

Embraced within the scope of the present invention are all the possible optical isomers of the above general formula. Also embraced within the scope of the present invention are the non-toxic, pharmaceutically acceptable salts of the novel compounds of the present invention when $R_3$ is hydroxy. The cations comprised in these salts include, for example, the non-toxic metal cations such as the sodium ion, potassium ion, calcium ion, and magnesium ion as well as the organic amine cations such as the tri(lower alkyl)amine cations (e.g., triethylamine, triethanolamine) procaine, and the like.

The novel compounds of the present invention are usually obtainable as oils having characteristic absorption spectra. They are relatively insoluble in water but are relatively soluble in common organic solvents such as ethanol, ethyl acetate, dimethylformamide, and the like. The cationic salts of the compounds when $R_3$ is hydroxy are, in general, white to yellow crystalline solids having characteristic melting points and absorption spectra. They are relatively soluble in water, methanol, and ethanol but are relatively insoluble in benzene, diethyl ether, and petroleum ether.

DETAILED DESCRIPTION OF THE INVENTION

The prostaglandins are a family of closely related compounds which have been obtained from various animal tissues, and which stimulate smooth muscle, lower arterial blood pressure, antagonize epinephrine-induced mobilization of free fatty acids, and have other pharmacological and autopharmacological effects in mammals. See Bergstrom et al., J. Biol. Chem. 238, 3555 (1963) and Horton, Experientia 21, 113 (1965) and references cited therein. All of the so called natural prostaglandins are derivatives of prostanoic acid:

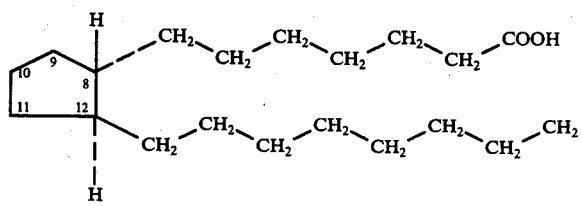

The hydrogen atoms attached to C-8 and C-12 are in trans-configuration. When the two side-chains (or the C-8 and C-12 hydrogens) are cis to each other, the compounds are referred to as 8-iso prostaglandins. The natural prostaglandins represent only one of the possible optical isomers. The compounds of this invention include all possible optical isomers.

The novel compounds of the present invention may be readily prepared from certain cycloalkenone intermediates which may be represented by the following general formula:

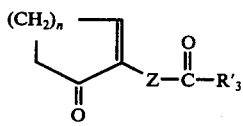

wherein $R'_3$ is an alkoxy having from 1 to 12 carbon atoms; and $n$ and $Z$ are as hereinabove defined.

The cycloalkenone intermediates may be readily prepared from 2-carbethoxycyclopentanone or 2-carbethoxycyclohexanone in accordance with the reaction schemes set forth in Flowsheets A, B, C, I and J.

FLOWSHEET A

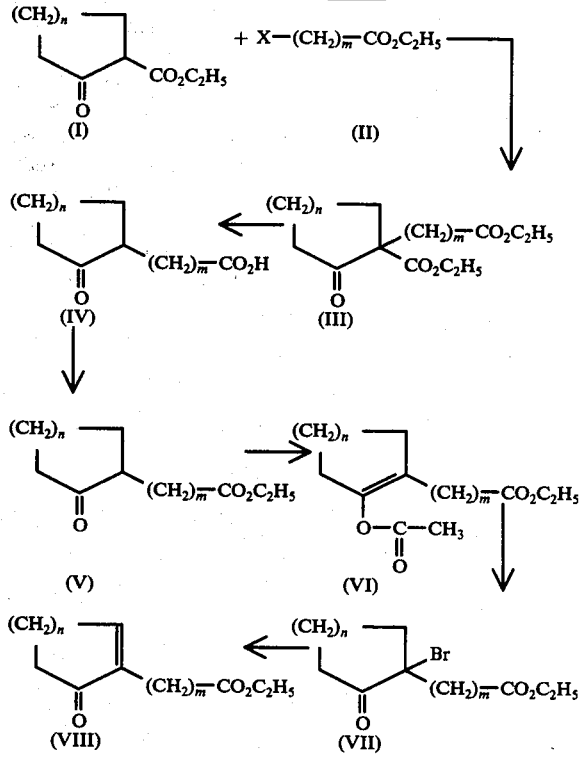

wherein $m$ and $n$ are as hereinabove defined and X is iodo or bromo. In accordance with this reaction scheme, the cycloalk-2-en-1-ones (VIII) are developed by first converting 2-carbethoxycyclopentanone or 2-carbethoxycyclohexanone (I) to the sodium enolates thereof by means of sodium hydride in dimethoxyethane and then treating the sodium enolate with an ethyl ω-haloalkanoate (II). There is thus obtained the corresponding 2-carbethoxy-2-(ω-carbethoxyalkyl)cycloalkanone (III) which is then hydrolyzed and decarboxylated to afford the 2-(ω-carboxyalkyl)cycloalkanone (IV). This acid is then esterified with ethanol whereby the 2-(ω-carbethoxyalkyl)cycloalkanone (V) is obtained. The reaction conditions for carrying out the above sequence of reactions are well known in the art. The conversion of the cycloalkanone (V) to the enol acetate (VI) is effected by heating with acetic anhydride in the presence of p-toluenesulfonic acid. Preparation of the enol acetate (VI) usually requires heating for a period of from about eight to thirty-six hours. During this period, it is preferable to allow by-product acetic acid to distill out in order to force the reaction to completion. The bromination of the enol acetates (VI) to the 2-bromocycloalkanones (VII) is preferably carried out in a two phase system as follows. A solution of bromine in chloroform is added to a rapidly stirred mixture of a solution of the enol acetate (VI) in chloroform and an aqueous solution of an acid acceptor such as calcium carbonate or soda ash. This addition is carried out at 0°–5° C. over a period of about half an hour, stirring is continued for an additional period of about half an hour to a few hours, and the product (VII) is then isolated by standard procedures. The dehydrobromination of the 2-bromocycloalkanones (VII) is preferably carried out in dimethylformamide with a mixture of lithium bromide and lithium carbonate at the reflux temperature for a period of about 30 minutes to an hour or so. The so formed cycloalk-2-en-1-ones (VIII) are also isolated by standard procedures well known in the art. Substitution of $X-(CH_2)_m-C(R_4)_2-CH_2-CO_2C_2H_5$ for (II) in Flowsheet A and carrying through the sequence of transformations illustrated therein is productive of the following cycloalk-2-en-1-one (VIIIa):

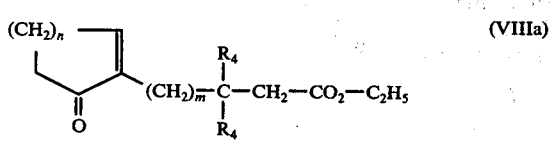

wherein $X$, $n$, $m$ and $R_4$ are as hereinabove defined.

The required cycloalk-2-en-1-one intermediates of general structure (XVI), wherein the side-chain has a lower alkyl group, fluorine atom or phenyl group alpha to the carbethoxy function, may be prepared in accordance with the following reaction scheme:

FLOWSHEET B

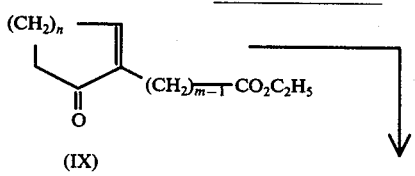

-continued
FLOWSHEET B

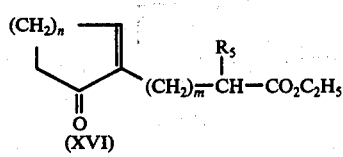

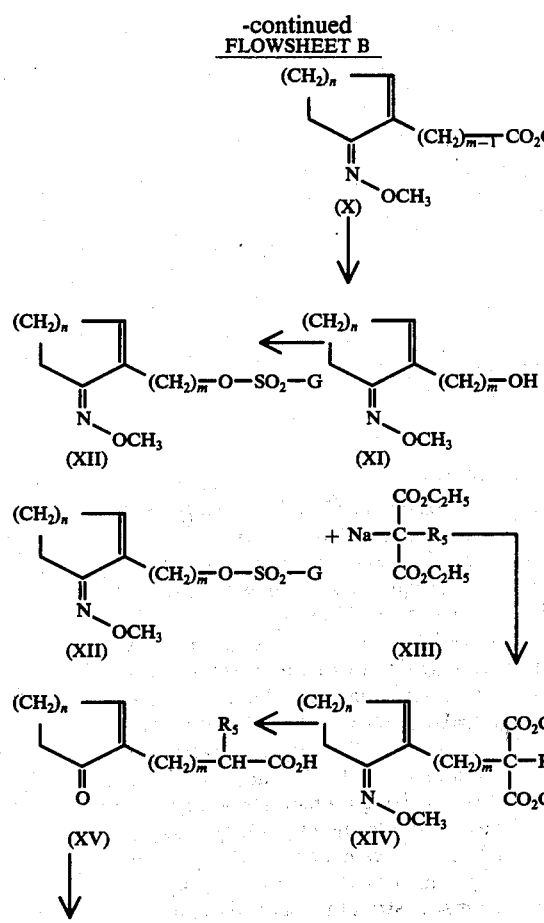

wherein $n$, $m$ and $R_5$ are as hereinabove defined and G is a lower alkyl or aryl group. In accordance with this reaction scheme, the 2-(ω-carbethoxyalkyl)cycloalk-2-en-1-ones (IX) are converted to the corresponding 1-methoximino-2-(ω-carbethoxyalkyl)-2-cycloalkenes (X) by treatment with methoxyamine. With the ring carbonyl function thus blocked it is possible to effect a preferential reduction of the ester group by treatment with diisobutylaluminum hydride. The resulting alcohol (XI) is converted to a tosylate derivative (XII), which undergoes displacement on treatment with the sodium salt of a diethyl $R_5$-substituted malonate (XIII) to provide the disubstituted malonate derivatives (XIV). Hydrolysis and decarboxylation as well as concomitant cleavage of the methoximino blocking group provides the desired 2-(ω-carboxy-ω-$R_5$-substituted-alkyl)cycloalk-2-en-1-ones (XV), which are readily converted to the corresponding ester (XVI) by the usual procedure via the acid chloride and subsequent treatment with the appropriate alcohol in the presence of a tertiary amine.

The requisite 2-(ω-carbethoxy-ω-1-oxa-alkyl)cycloalk-2-en-1-ones (XXII) and 2-(ω-carbethoxy-ω-1-thia-alkyl)-cycloalk-2-en-1-ones (XXVI) may be prepared in accordance with the reaction schemes of Flowsheet C, wherein $n$ and $m$ are as hereinbefore defined.

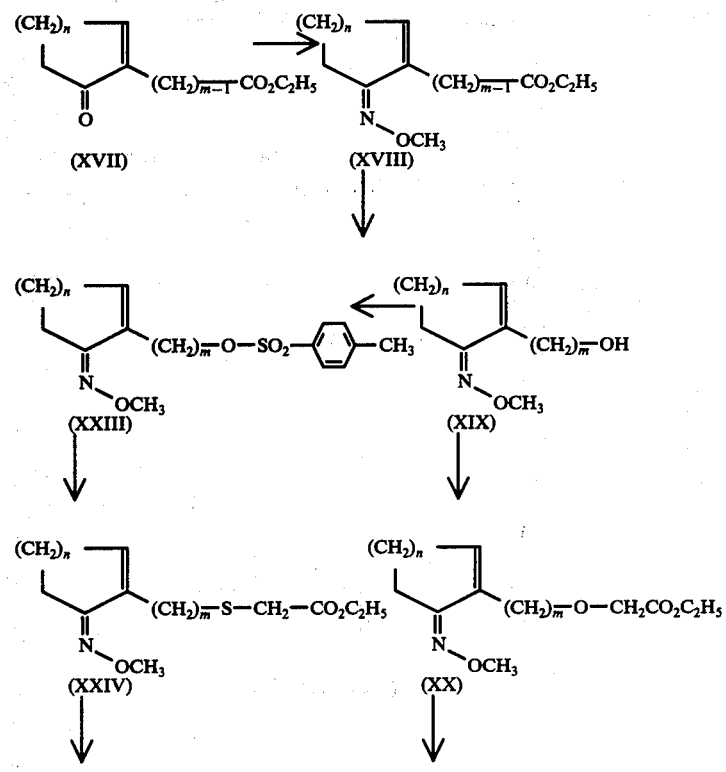

FLOWSHEET C

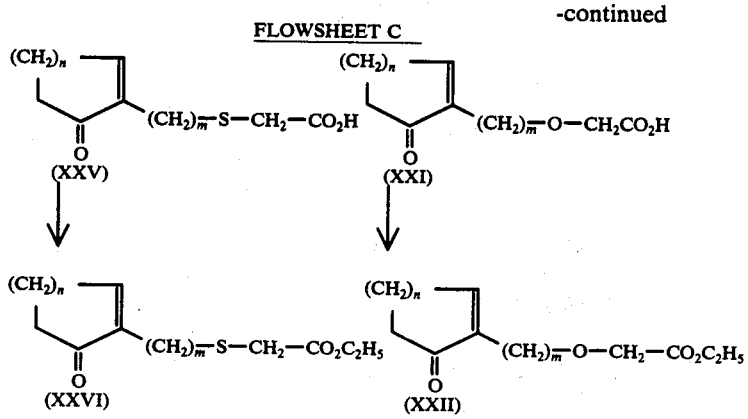

In accordance with the reaction scheme shown in Flowsheet C, for the preparation of the oxa derivative (XXII), an appropriate 2-(ω-carbethoxyalkyl)cycloalk-2-en-1-one (XVII) is converted to the corresponding methoxime (XVIII), the ester function of which is then preferentially reduced with diisobutylaluminum hydride to afford the methoxime alcohol (XIX). The alcohol (XIX) is converted on treatment with n-butyl lithium to the lithio alcoholate, which then is O-alkylated by reaction with ethyl bromoacetate to provide (XX). Hydrolysis with acetone-aqueous hydrochloric acid furnishes the deblocked keto-acid (XXI), which is then reesterified with ethanol in the presence of p-toluenesulfonic acid to give the required 2-(ω-carbethoxy-ω-1-oxa-alkyl)cycloalk-2-en-1-one (XXII). O-Alkylation can also be accomplished by treatment of the lithio alcoholate of (XIX) with sodium or other metal salt of bromoacetic acid, in which case the free carboxylic acid corresponding to ester (XX) is obtained. Hydrolysis as for (XX) provides the keto acid (XXI).

The preparation of the thia derivative (XXVI), proceeds from the intermediate alcohol (XIX), which after conversion to the tosylate intermediate (XXII) and reaction with the sodium salt of ethyl mercaptoacetate furnishes intermediate (XXIV). Deblocking of XXIV with acetone-aqueous hydrochloric acid provides the keto-acid (XXV), which on re-esterification with ethanol gives the required 2-(ωcarbethoxy-ω-1-thio-alkyl)-cycloalk-2-en-1-ones (XXVI).

Certain of the 11-deoxy-9-keto(or hydroxy)-prostanoic acid derivatives of this invention, as defined in the general formula on page 1 above, may be prepared from cycloalkenone (XXXI) and the triphenylmethoxy substituted 1-alkyne (XXVII) as depicted in Flowsheet D. In Flowsheet D, $n$, $R_3$, $R'_3$ and Z are as hereinabove defined; $R'_2$ is a straight chain alkyl group having from 2 to 10 carbon atoms, a straight chain alkyl group having from 2 to 10 carbon atoms and substituted with one or two alkyl groups each having from one to three carbon atoms, a straight chain alkenyl methyl group having from two to nine carbon atoms, or a straight chain alkenyl methyl group having from two to nine carbon atoms and substituted with one or two alkyl groups having between them 2 to 5 carbon atoms; and R is a lower alkyl group.

FLOWSHEET D

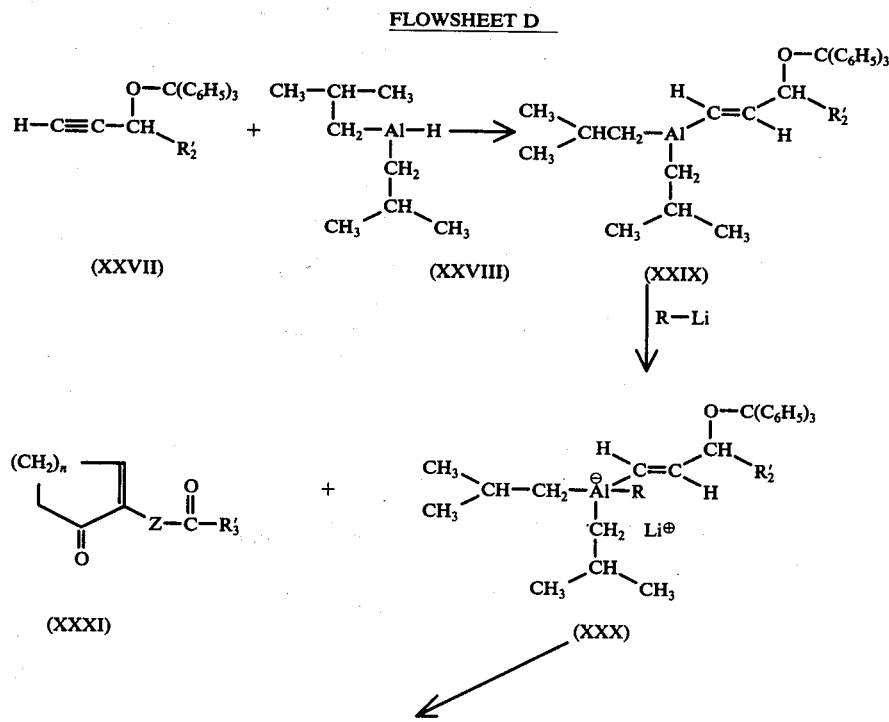

FLOWSHEET D -continued

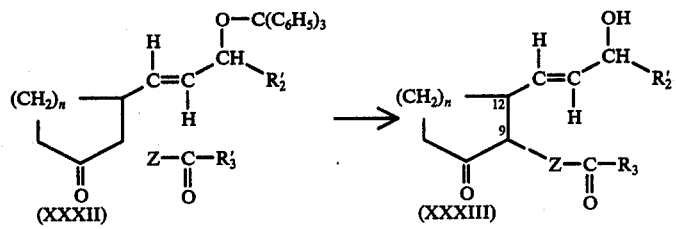

In accordance with the reaction scheme of Flowsheet D, the triphenylmethoxy substituted 1-alkyne (XXVII) is treated with diisobutylaluminum hydride (XXVIII). This reaction of the 1-alkyne (XXVII) with diisobutylaluminum hydride (XXVIII) provides the alane (XXIX) containing the trans-double bond and is carried out in an inert solvent such as benzene, toluene, and the like at temperatures in the range of 40°–60° C. for several hours. It can also be carried out in a solvent such as tetrahydrofuran, usually in an approximate 2:1 mixture with benzene or hexane; in which case the reaction requires somewhat more vigorous conditions, usually treating at about 70°–75° C. for about eighteen hours. The subsequent reaction with methyl or n-butyl lithium (R-Li) is preferably carried out in a mixture of the above solvents with an ether-type solvent such as diethyl ether, dibutyl ether, tetrahydrofuran and the like. This reaction is rapid and is preferably carried out at 0°–10° C. with cooling. The conjugate 1,4-addition of the resulting alanate salt (XXX) to the cycloalk-2-en-1-one (XXXI) is preferably carried out at ambient temperatures for a period of 12 to 24 hours. This reaction is also best carried out in an ether-type solvent such as diethyl ether, dibutyl ether, tetrahydrofuran, and the like. The intermediate alanate-enolate adduct is then carefully hydrolyzed in situ with dilute hydrochloric acid with cooling, and the products (XXXII) are isolated in the usual manner well known in the art. Removal of the triphenylmethyl blocking group can then be accomplished by treating with weak acid. A preferred procedure involves heating at 45° C. for 3.5 hours in a solvent system consisting of acetic acid:tetrahydrofuran:water in the proportion of 4:2:1. Saponification in the usual manner of the resulting alkyl ester (XXXIII, $R_3$=alkoxy) provides the corresponding carboxylic acid (XXXIII, $R_3$=OH).

All available evidence leads us to the conclusion that in the product (XXXIII) the two side-chains attached to $C_8$ and $C_{12}$ are trans to each other. However, we are not certain of the configurational relationship in product (XXXII) as it is obtained directly from the alanate process. These products may have the side-chains in a trans or cisrelationship or they may be a mixture containing both the trans- and cis-isomers. This is indicated in the nomenclature of the compounds involved by the designation of 8ξ. In order to ensure a trans-relationship in both (XXXII) and (XXXIII) these products can be submitted to conditions known in the literature to equilibrate the cis-8-iso-PGE$_1$ to a mixture containing about 90% of the transproduct. These conditions involve treatment with potassium acetate the aqueous methanol for 96 hours at room temperature.

The triphenylmethyl blocking group for the hydroxy function in (XXVII) etc. is an important feature of this process and other oxygen blocking groups, e.g., tetrahydropyranyl and alkyl, are not compatible with a clean cis-addition of diisobutyl aluminum hydride (XXVIII) to the alkyne (XXVII) to provide the desired trans-vinyl function. Alternative procedures for the preparation of novel lithio alanate reagents useful for the introduction of the $\Delta^{13}$-trans 15-oxy β-chain by conjugate 1,4-addition are illustrated in Flowsheet K further below.

The intermediates for the introduction of the $\Delta^{13}$-15-hydroxy side-chain are an integral part of this invention and they may be represented by the following general formulae (A), (B), (C), (D) and (E) wherein $R'_2$ is as hereinabove defined, R is a lower alkyl group, not necessarily the same for each use, and R' is an alkyl group having from one to ten carbon atoms not necessarily the same for each use, $W_1$ is lower alkoxy, triphenylmethyl, or a triphenylmethyl group in which one or two of the phenyl rings is substituted with a lower alkoxy group; $W_2$ is lower alkoxy, triphenylmethyl, a triphenylmethyl group in which one or two of the phenyl rings is substituted with a lower alkoxy group, tetrahydropyranyl, α-(lower alkoxy) substituted lower alkyl, t-butyl, or a tri(lower alkyl)silyl group; $X_1$ is iodo or bromo; s is an integer having the value of one to three inclusive, and t is an integer having the value of one to three inclusive, with the proviso that the sum of s and t must be equal to four.

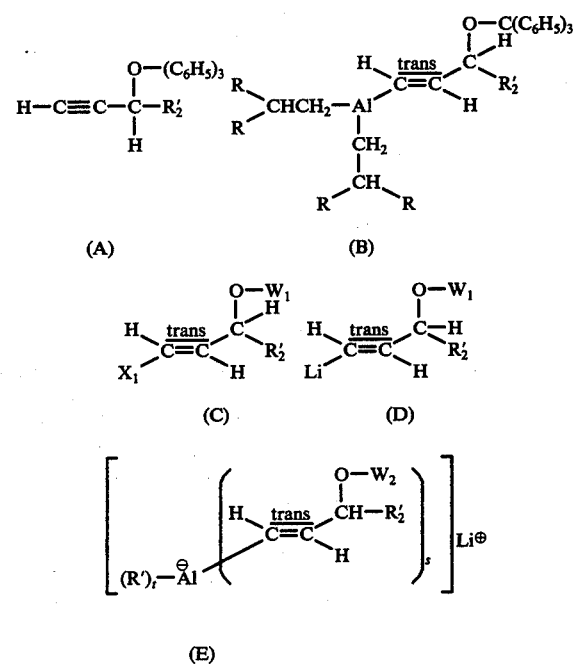

The alanate conjugate addition procedure is also useful for the synthesis of prostaglandin E$_1$ (XL) as illustrated in Flowsheet E. This reaction sequence is carried out in the same manner as described for the sequence in Flowsheet D. It is to be noted that the introduction of the Δ¹³-15-oxy chain proceeds trans to the 11-oxy function. For this synthesis, it is best to use the tetrahydropyranyl or trialkylsilyl esters, since these esters can be hydrolyzed under conditions compatible with the stability of the β-ketol feature of prostaglandin E₁. Alkyl esters would be hydrolyzed by fermentation with Baker's Yeast. The tetrahydropyranyl or trialkylsilyl, and triphenylmethoxy blocking groups are removed by mild acid treatment, for example with acetic acid-tetrahydrofuran:water (4:2:1) as described hereinabove. Application of the lithio alanate conjugate addition process to the synthesis of prostaglandins E₂ and E₃ is described below in connection with Flowsheet N.

FLOWSHEET E

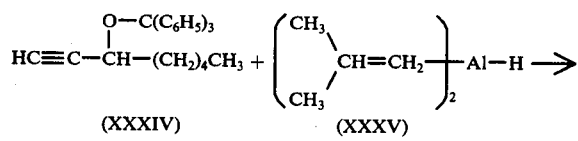

(XXXIV)    (XXXV)

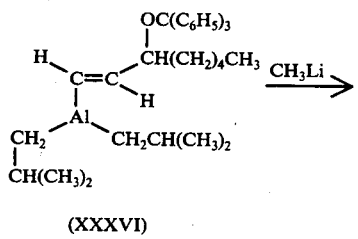

(XXXVI)

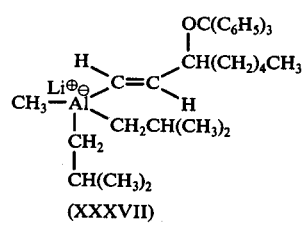

(XXXVII)

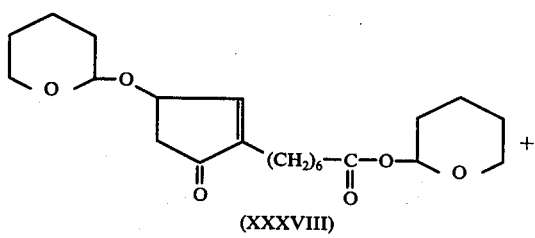

(XXXVIII)

(XXXVII) →

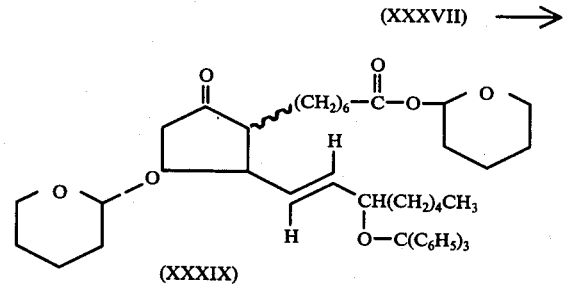

(XXXIX)

-continued
FLOWSHEET E

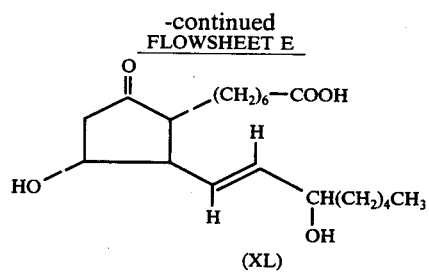

(XL)

The 13-dihydro derivatives ($C_{13}$–$C_{14}$ is ethylene) of this invention can be prepared by reduction of the $\Delta^{13}$ function in the corresponding 13-prostenoic acids or esters. This reduction can be accomplished by hydrogenation. However this procedure is not cleanly applicable in the presence of other double bonds in the molecule. In the latter instance the 13-dihydro derivatives are preparable via conjugate addition of a Grignard derivative (XLII) to cycloalkenone (XLI) in the presence of a catalyst such as the tributylphosphine cuprous iodide complex as set forth in Flowsheet F, wherein $n$, $Z$, $R_2$ and $R'_3$ are as hereinabove defined; Q is a blocking group; and X is chlorine, bromine or iodine, preferably bromine or iodine. The blocking group (Q) for the hydroxyl function in (XLII) can be any group stable to the Grignard reagent and which can later be removed by chemical treatment (e.g., mild hydrolysis or catalytic hydrogenolysis in the absence of carbon to carbon double bonds elsewhere in the molecule) to which the remainder of the molecule is stable. Suitable blocking groups, therefore, may be, for example, benzyl, diphenylmethyl, triphenylmethyl, tetrahydropyranyl, or a moiety of the formula:

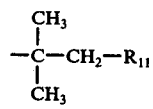

wherein $R_{11}$ is hydrogen, methyl or ethyl. Among the above-described blocking groups, we have found tert-butyl to be particularly convenient and useful.

Flowsheet F

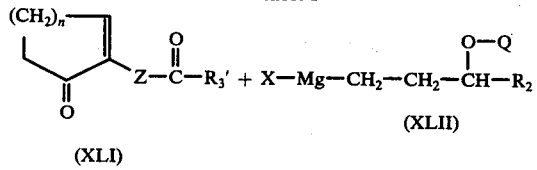

(XLI)        (XLII)

↓

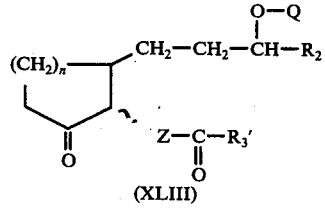

(XLIII)

↓

-continued
Flowsheet F

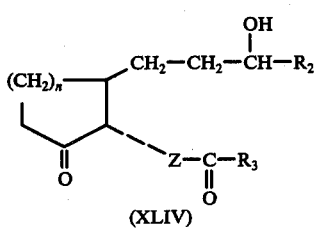

(XLIV)

In accordance with the above reaction scheme, the conjugate 1,4-addition of a 3-(substituted hydroxy)alkyl or alkenyl magnesium halide (XLII) to a cycloalk-2-en-1-one (XLI) is carried out in the presence of a catalyst. In general, Grignard reactions with conjugated ketones provide 1,2-addition products; conjugate 1,4-addition is usually accomplished when the reaction is carried out in the presence of a cuprous chloride or cuprous acetate catalyst. It is therefore most unexpected that the reaction of the cycloalkenone (XLI) with a Grignard reagent (XLII) in the presence of either of the aforementioned catalysts does not give appreciable amounts of the desired 1,4-conjugate addition products. The novel feature of our process is provided by the use, as a catalyst, of a cuprous halide complex with a trisubstituted phosphine, a trialkyl phosphonate, a tertiary amine or a heterocycle containing a basic nitrogen (e.g., pyridine). We have found it preferable to use tributylphosphine-cuprous iodide complex; $(C_4H_9)_3P.CuI$. The reaction is best carried out in the usual way in an ether-type solvent such as diethyl ether, dibutyl ether, tetrahydrofuran, and the like, at room temperature for a period of time of from two to eighteen hours. The intermediate magnesium halide-enolate adduct is then hydrolyzed in situ, preferably with ammonium chloride, at room temperature and the product (XLIII) is isolated in the usual manner well known in the art.

When the blocking group is a tertiary alkyl moiety such as tert-butyl, deblocking of (XLIII) to afford (XLIV) is conveniently effected by treatment with glacial trifluoroacetic acid at from $-5°$ C. to $10°$ C. for a period of one to three hours. Since this procedure may lead to partial trifluoroacetylation of the free hydroxy function, it is preferably followed by treatment with aqueous ammonia (about 1.0N concentration) for about 15 minutes at ambient temperatures. When the blocking group is tetrahydropyranyl, its removal is readily effected with dilute acid. When the blocking group is a moiety such as benzyl, diphenylmethyl or triphenylmethyl, deblocking of (XLIII) is convenientyl effected by catalytic hydrogenolysis, procedures for which are well known in the art. In the instance of triphenylmethyl, deblocking is preferably effected by treating with acetic acid:tetrahydrofuran: water (4:2:1) at about $45°$ C. for about 3.5 hours.

Mild acid treatment results in hydrolysis of the tetrahydropyranyl esters; alkyl esters can be hydrolyzed by the usual saponification techniques.

When the cycloalkanone esters (XLIII) are formed by quenching of the reaction mixture with aqueous ammonium chloride solution, the relative stereochemical relationship of the two side-chains is not known with certainty. Therefore, the bond linking the Grignard-derived side-chain to the cycloalkyl ring is indicated by a ∿ bond in (XLIII). However, in any case, the subsequent deblocking and ester hydrolysis procedures ensure the development, at least in predominant proportion, of the thermodynamically favored trans-relationship between the two side-chains, as is depicted in structure (XLIV) of the reaction scheme.

An alternative method for the introduction of the $\Delta^{13}$--15-hydroxy side-chain involves 1,4-conjugate addition to cycloalkenone (LV) of a vinyl Grignard reagent [(LIII) + (LVI)] in the presence of a catalyst such as the tributylphosphine cuprous iodide complex followed by deblocking. From this process, in addition to the product (LVIII) containing the $C_{13}$-$C_{14}$ moiety as a trans-vinylene function there also is obtained the corresponding product (LIX) in which the $C_{13}$-$C_{14}$ moiety is a cis-vinylene function. These novel cis-$\Delta^{13}$ derivatives are also embraced within the scope of this invention. The reaction sequence for the "vinyl" Grignard process is illustrated in flowsheet G, which follows, and in which $W_2$, $n$, $Z$, $R_3$ and $R'_3$ are as hereinabove defined, and $R''_2$ is a straight chain alkyl group having from 2 to 10 carbon atoms, or a straight chain alkyl group having from 2 to 10 carbon atoms and substituted with one or two alkyl groups having from one to three carbon atoms.

FLOWSHEET G

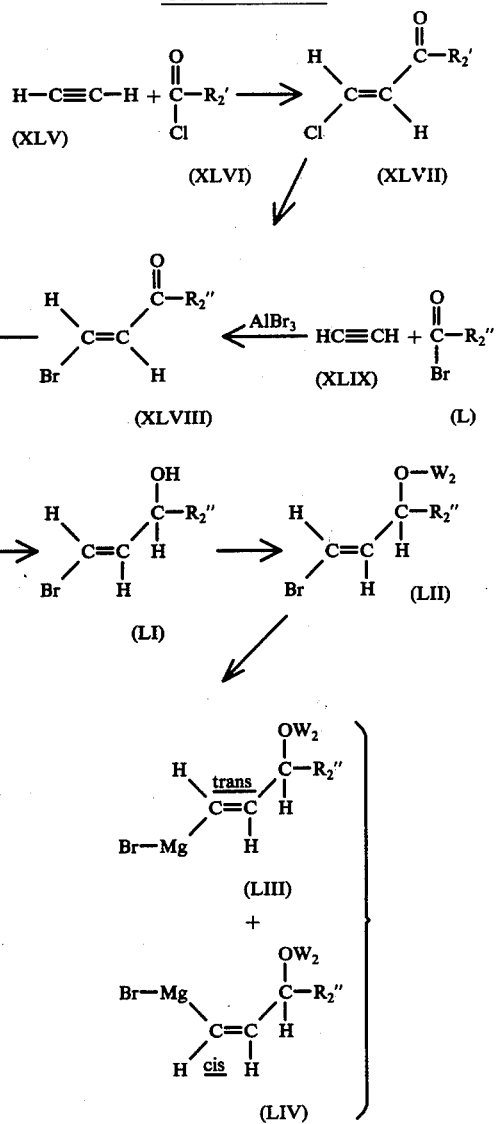

-continued
FLOWSHEET G

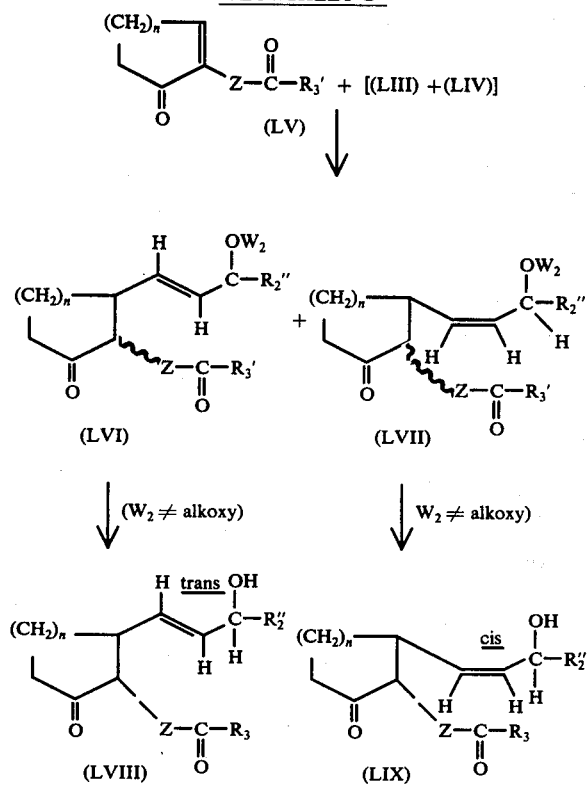

In accord with the reaction sequence of Flowsheet G the vinyl Grignard reagent (LIII + LIV), is prepared under an inert atmosphere in a relatively limited amount of anhydrous tetrahydrofuran. More vigorous conditions (e.g., heating in an oil bath at 70°-80° C., one hour), for the formation of the Grignard reagent (LIII + LIV) favors the proportion of $\Delta^{13}$-cis isomer (LIX) in the product of conjugate addition. Milder conditions (for example 35°-47° C., one hour) favors the proportion of $\Delta^{13}$-trans isomer (LVIII) in the final product.

Conjugate addition of the vinyl Grignard reagent mixture [(LIII) + (LIV)] to cycloalkenone (LV) is then preferably carried out by addition of the Grignard to the cycloalkenone dissolved in an ether type solvent, e.g., diethylether, containing a catalyst such as the tributylphosphine-cuprous iodide complex at a temperature of about 0° C. After a period of about thirty minutes to three hours the reaction mixture is poured onto aqueous concentrated ammonium chloride solution to give (LVI) + (LVII). As explained hereinabove, at this stage the relationship of the two side-chains to each other is not determined. In any event, deblocking the 15-hydroxy function with weak acid (which procedure also hydrolyzes trialkylsilyl or tetrahydropyranyl esters) provides the product (LVIII) and (LIX) in which the chains are trans to each other. In the instance of alkyl esters, saponification provides the corresponding carboxylic acids. The $\Delta^{13}$-cis and $\Delta^{13}$-trans-isomers can be separated from each other by the usual techniques of chromatography; particularly useful is liquid-liquid partition chromatography.

The precursor 3-hydroxy-1-trans-alkenyl bromides (LI) can be prepared, as illustrated in Flowsheet G, by condensation of acetylene (XLV) with an acid chloride (XLVI) in the presence of aluminum trichloride. The resulting 3-oxo-1-chloro-trans-1-alkylene (XLVII) is then converted to the corresponding 1-bromo derivative (XLVIII), by reaction with excess lithium bromide. This reaction is preferably carried out in ketone solvents, such as 2-pentanone or acetone. Reduction of the 3-keto function in (XLVIII), with for example, sodium borohydride provides the alcohol (LI). The alcohol function is then blocked to give (LII). Alternatively, the 3-oxo vinyl bromide (XLVIII) can be prepared directly from the acyl bromide (L) and acetylene (XLIX) in the presence of aluminum tribromide, preferably in ethylene dibromide.

The "vinyl Grignard" procedure outlined in Flowsheet G represents a novel, useful and convenient procedure for the synthesis of 13-prostenoic acids and the novel Grignard reagents represented by formulae (LIII) and (LIV) are to be considered as embraced within the scope of this invention.

The "vinyl Grignard" technique can also be applied to a useful synthesis of prostaglandin $E_1$ and the novel $\Delta^{13}$-cis-prostaglandin-$E_1$ as illustrated in Flowsheet H, below. Thus, treatment of cyclopentenone (LX) with Grignard [(LXI) + (LXII)] in accordance with the considerations discussed hereinabove, provides the conjugate addition products (LXIII) plus (LXIV), mild acid hydrolysis of which furnishes prostaglandin $E_1$ (LXV) and $\Delta^{13}$-cis prostaglandin $E_1$(LXVI), separable by chromatography.

FLOWSHEET H

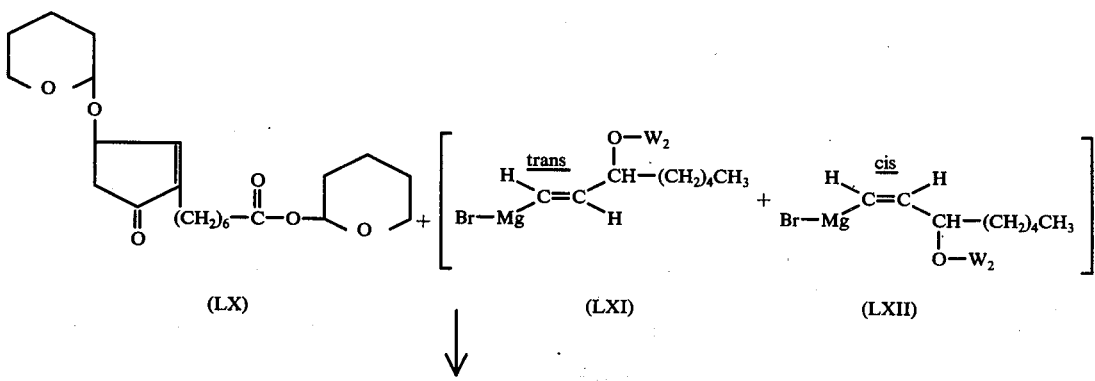

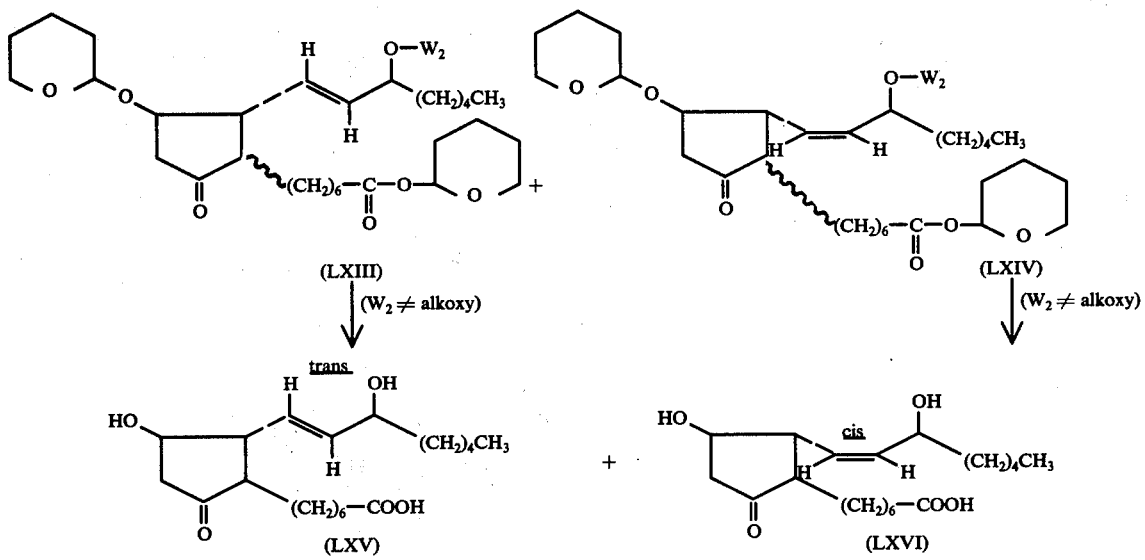

(LXIII)  (LXIV)

($W_2 \neq$ alkoxy)   ($W_2 \neq$ alkoxy)

(LXV)  (LXVI)

The preparation of the cycloalkenone intermediates (LXXVI, LXXVII) bearing a cis double bond in the carboxylic acid side chain can be accomplished by the sequence illustrated in Flowsheet I, which follows and in which $n$ and $p$ are as hereinabove defined.

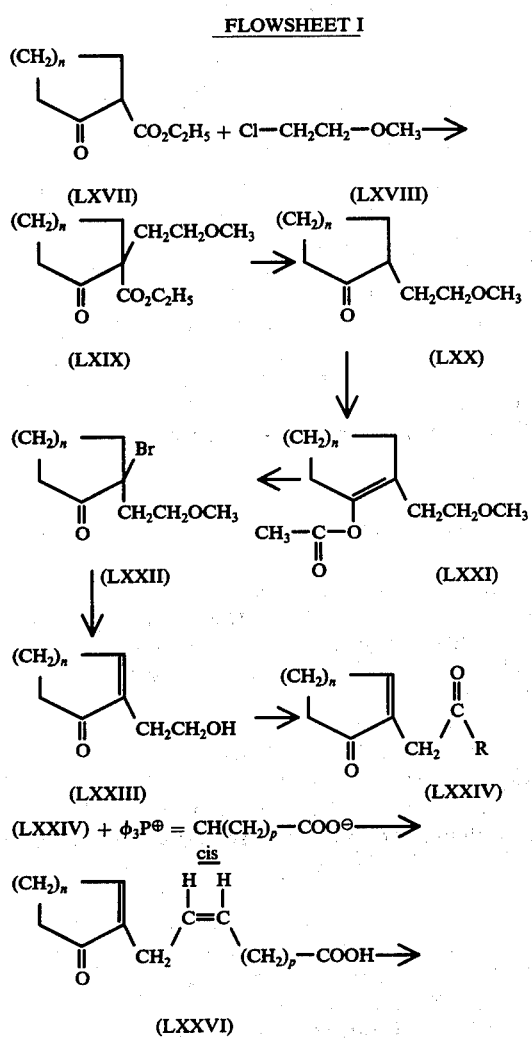

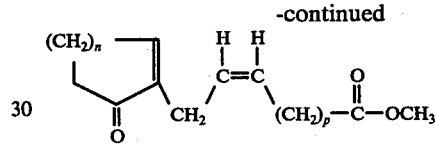

(LXXVII)

In the above Flowsheet I, the sequence wherein a 2-carbalkoxycycloalkanone (LXVII) is transformed to a 2-($\beta$-hydroxyethyl)cycloalk-2-en-1-one (LXXIII) is carried out in the manner described in Flowsheet A. Methyl ether cleavage of the corresponding 2-($\beta$-methoxymethyl)cycloalkenone is achieved by treating with boron tribromide. Oxidation of the alcohol (LXXIII) with Collins reagent [chromium trioxide-pyridine complex in methylene chloride under anhydrous conditions; J. C. Collins, W. W. Hess, and F. J. Frank, Tetrahedron Letters, 3363 (1968)] provides the aldehyde (LXXIV), which is then treated in anhydrous dimethylsulfoxide with the ylid (LXXV) prepared from an ($\omega$-carboxyalkyl)-triphenyl phosphonium bromide and sodium hydride. The use of dimethylsulfoxide as a solvent for this reaction leads to the predominant formation of the desired cis double bond derivative (LXXVI). The acid function in (LXXVI) can be esterified in the usual fashion; with diazomethane, the methyl ester (LXXVII) is obtained.

Cyclopentenones such as (LXXVI wherein $n=1$) may also be prepared by the sequence illustrated in Flowsheet J, which follows and in which $p$ is as hereinabove defined.

FLOWSHEET J

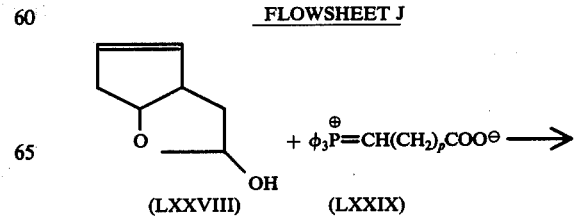

(LXXVIII)   (LXXIX)

-continued

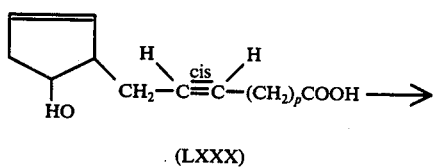
(LXXX)

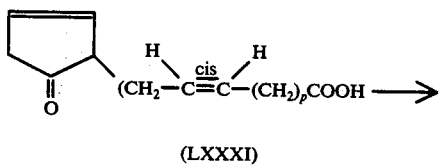
(LXXXI)

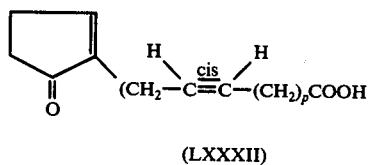
(LXXXII)

In Flowsheet J above the bicyclic hemiacetal (LXXVIII) [P. A. Grieco, Journ. Org. Chem., 37, 2363 (1972)] is treated with ylid (LXXIX) to give the 1-hydroxy-3-cyclopentene (LXXX). Oxidation with Jones reagent gives the corresponding ketone (LXXXI), which on base treatment furnishes the required cyclopentenone (LXXXII), which can then be esterified in the usual manner.

Certain of the intermediates illustrated in Flowsheets I and J, in particular the compounds of formulae (LXXI), (LXXII), (LXXIII), (LXXIV), (LXXVI) (LXXVII) (and related esters), (LXXX) and (LXXXI) are novel and useful compounds and are embraced within the scope of this invention.

Alternative procedures for the preparation of the alanate intermediates to that discussed in connection with Flowsheet D above are illustrated below in Flowsheet K, wherein R', R'$_2$, R''$_2$ and W$_2$ are as hereinabove defined.

FLOWSHEET K

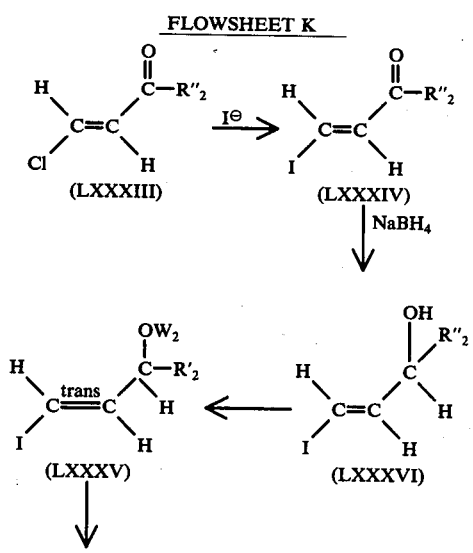

-continued

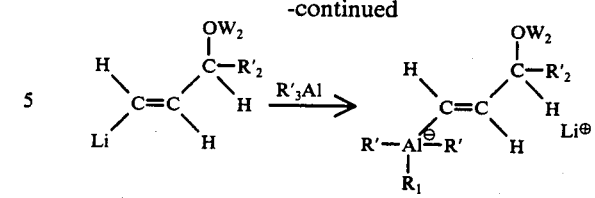
(LXXXVII)   (LXXXVIII)

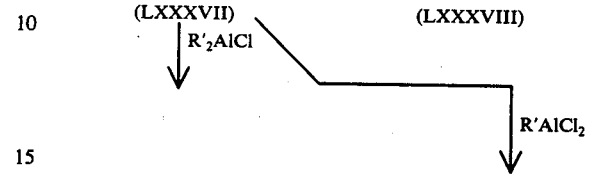

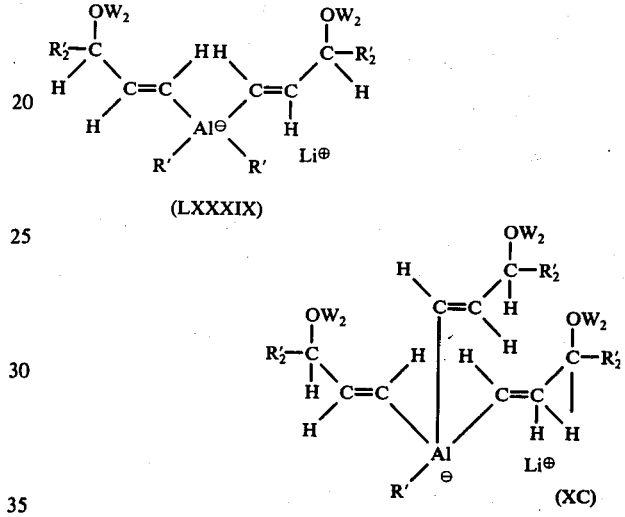
(XC)

In accordance with the sequence of Flowsheet K above the 1-iodo-trans-1-alkenyl-3-oxo derivative (LXXXIV) is prepared by iodide interchange, preferably in acetone or similar ketone, from the corresponding chloride (LXXXIII), the preparation of which is described in connection with Flowsheet G above. Reduction of (LXXXIV) to the alcohol (LXXXVI) can be accomplished in the usual manner with sodium borohydride. The hydroxy function is then blocked to give (LXXXV, R'$_2$-R''$_2$). Treatment of the acetylene,

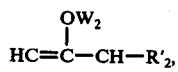

with one equivalent of disiamylborane (prepared in situ from diborane and 2-methyl-2-butene) and then with excess anhydrous trimethylamine oxide followed by treatment with an aqueous solution of excess sodium hydroxide and a tetrahydrofuran solution of excess iodine is also productive of (LXXXV). Treatment of the trans-1-alkenyl iodide (LXXXV) at low temperatures, preferably at about −30° C. to −78° C., in an inert solvent, e.g., hexane or toluene, with an alkyl lithium, e.g., butyl lithium, provides the trans-1-alkenyl lithium reagent (LXXXVII). Treatment of this lithio derivative with a tri-alkyl aluminum furnishes the trans-1-alkenyl tri-alkyl alanate (LXXXVIII). Treatment of a dialkyl aluminum chloride with two molar equivalents of lithio reagent (LXXXVII) gives the bis(trans-1-alkenyl)dialkyl alanate (LXXXIX) and treatment of an alkylaluminum dichloride with three molar equivalents of lithio reagent (LXXXVII) affords the tris(trans-1-alkenyl)alkyl alanate (XC).

Each of the three types of alanates, (LXXXVIII), (LXXXIX) and (XC), can be utilized for 1,4-conjugate addition reactions as described hereinabove in connection with Flowsheets D and E aboe. Thus, substitution of (LXXXVIII), (LXXXIX) or (XC) for alanate (XXX) in Flowsheet D will provide the indicated products of the Flowsheet. Similarly, substitution of (LXXXVIII), (LXXXIX) or (XC) in which $R'_2$ is n-pentyl for alanate (XXXVII) in Flowsheet E provides prostaglandins $E_1$. In general the mono alkenyl alanate (LXXXVIII) is preferred because it is more economical in the use of vinyl halide.

With regard to the cycloakenones of Flowsheets D, E, F, G and H it should be noted that the blocking groups for the 4-hydroxy function as well as for the carboxylic acid may also be a tri-alkylsilyl group, e.g., trimethylsilyl, dimethyl-t-butylsilyl or dimethylisopropylsilyl. Cyclopentenones blocked in this manner are illustrated below in formula (XCI) and (XCII) wherein $m$, $n$, $Z$ and $R'$ (not necessarily the same for each use) are as hereinabove defined.

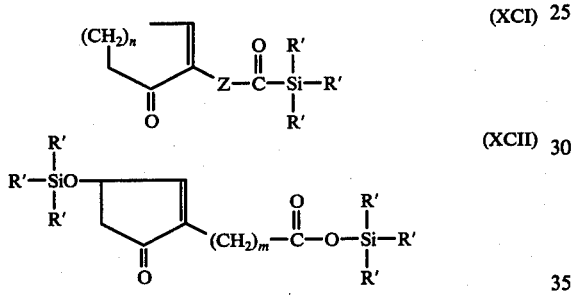

All the novel products of this invention exclusive of certain intermediates bear a hydroxy or oxy function substituted at or at what ultimately becomes the $C_{15}$ atom of the product prostanoic acids and esters. Thus in at least most instances a 15-"normal" and a 15-"epi" racemate is obtained in at least near equal proportions. Each of the racemates contains equal amounts of the enantiomer wherein $C_{15}$ is in the S configuration and the enantiomer wherein it is in the R configuration. The racemates are separable from each other by the usual techniques of chromatography. Also, resolution in the usual way of the β-chain precursor [for example, the resolution of 3-hydroxy-1-octyne is described in the literature [see R. Pappo, P. Collins and C. Jung. Ann. N.Y. Acad. of Science, 180 (Prostaglandins), 64(1971); J. Fried et al., ibid, p. 381.] Resolution prior to the conjugate addition operation will provide the diastereomers wherein the $C_{15}$ atom is either in the 15(S) or 15(R) configuration, as desired. Separation of the diastereomers so obtained, for example, by chromatrography, will give the fully resolved ($d$ and $l$) products provided there are no asymmetric carbon atoms other than at $C_8$ and $C_{12}$. The presence of other asymmetric sites requires additional resolution steps in order to obtain a single atipode. The compounds of this invention embrace all possible optical isomers.

The 11-deoxy-9-keto derivatives (XCIV) of this invention can be converted to the corresponding 9-hydroxy derivatives. If this conversion is effected with sodium borohydride, the product is a mixture of 9α- and 9β-hydroxy derivatives (XCIII) and (XCV) as set forth in the following reaction scheme:

FLOWSHEET L

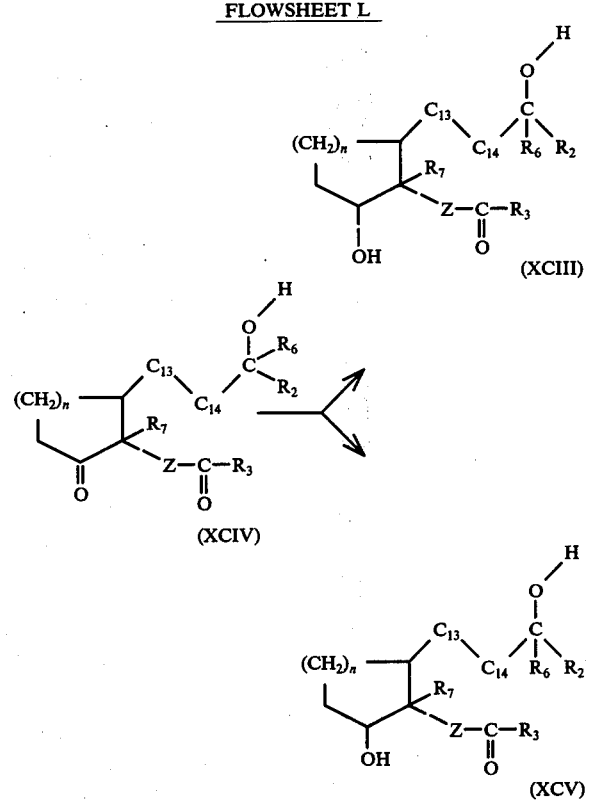

wherein $R_2$, $R_3$, $R_6$, $R_7$, $Z$, $n$ and $-C_{13}-C_{14}-$ are as hereinabove defined. In general, when the reaction is carried out with lithium perhydro-9b-boraphenalyl hydride [H. C. Brown and W. C. Dickason, Journ. Amer. Chem. Soc., 92, 709 (1970)] the product is at least predominantly the 9β-hydroxy derivative (XCIII), wherein the 9-hydroxy group is cis to the side-chain attached to $C_8$.

In accordance with accepted convention, an α-substituent at the 8-, 9-, or 12-positions is behind the plane of the paper whereas a β-substituent at these positions is in front of the plane of the paper. This is usually represented by a bond for α-substitutent, a bond for a β-substituent, and a ~ bond where both are indicated. Thus, the 9-hydroxy derivatives may be variously represented as follows:

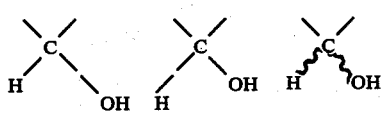

A useful procedure for the introduction of the 15-lower alkyl group ($R_6$) is illustrated by the sequences of Flowsheet M, which follows.

FLOWSHEET M

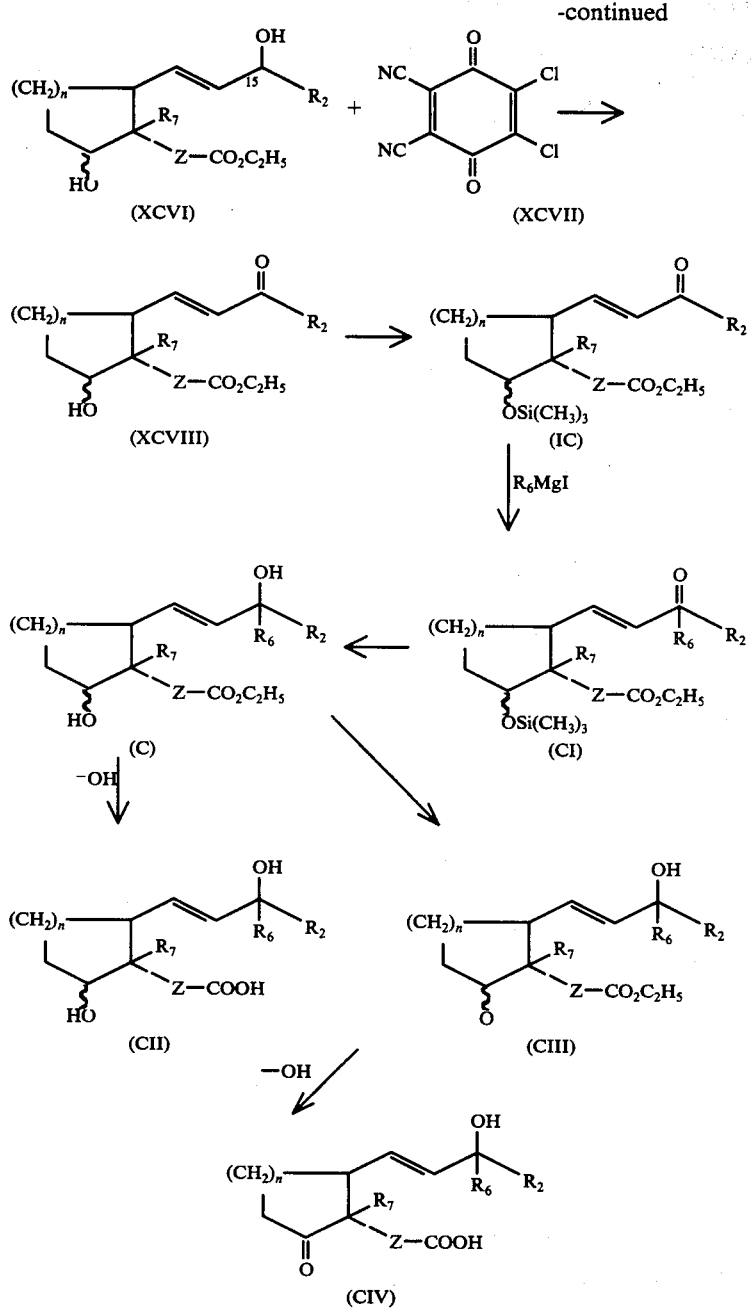

In Flowsheet M above $n$, $Z$, $R_2$, $R_7$ and $R_6$ are as hereinabove defined. In the sequence depicted in Flowsheet M the 9,15-diol (XCVI) is treated with 2,3-dichloro-5,6dicyanobenzoquinone (DDQ) (XCVII), which preferentially oxidizes the allylic alcohol function at $C_{15}$ to give the 15-ketone (XCVIII). Blocking of the remaining hydroxy function as a trimethylsilyl ether gives (IC) which is reacted with the alkyl Grignard, $R_6MgI$, to give the 15-alkyl-15-hydroxy derivative (CI). Hydrolysis of the silyl ether blocking group then gives the diol ester (C),saponification of which gives (CII). Oxidation of the secondary 9-hydroxy function in (C) provides the 15-alkyl-9-oxo ester (CIII), saponification of which furnishes (CIV). (A similar sequence can be effected with the $\Delta^{13}$-cis-series.)

The processes of this invention are also useful for the preparation of prostaglandin $E_2$ and prostaglandin $E_3$ and thus also $PGF_{2\alpha}$ and $PGF_{3\alpha}$ by reduction, for example within lithium perhydro-9b-boraphenalyl hydride. The 4-hydroxycyclopentenone intermediate (CXI) required for these syntheses is prepared in accordance with the procedure illustrated in Flowsheet N which follows and in which is also shown the transformation of this compound to prostaglandins $E_2$ and $E_3$. In Flowsheet N, J is an appropriate blocking group for the hydroxy and ester function in (CXI) which is compatible with the conjugate addition reaction and also is ultimately removable by acid-catalyzed hydrolysis or other techniques which will not disrupt the sensitive 11-oxy-9-keto system in the products (CXIII), (CXV), (CXVIII) and (CXVII). Particularly useful for this purpose are the tetrahydropyranyl group and various trialkylsilyl groups (e.g., dimethylisopropylsilyl, trimethylsilyl, dimethyl-t-butyl-silyl and the like.

FLOWSHEET N
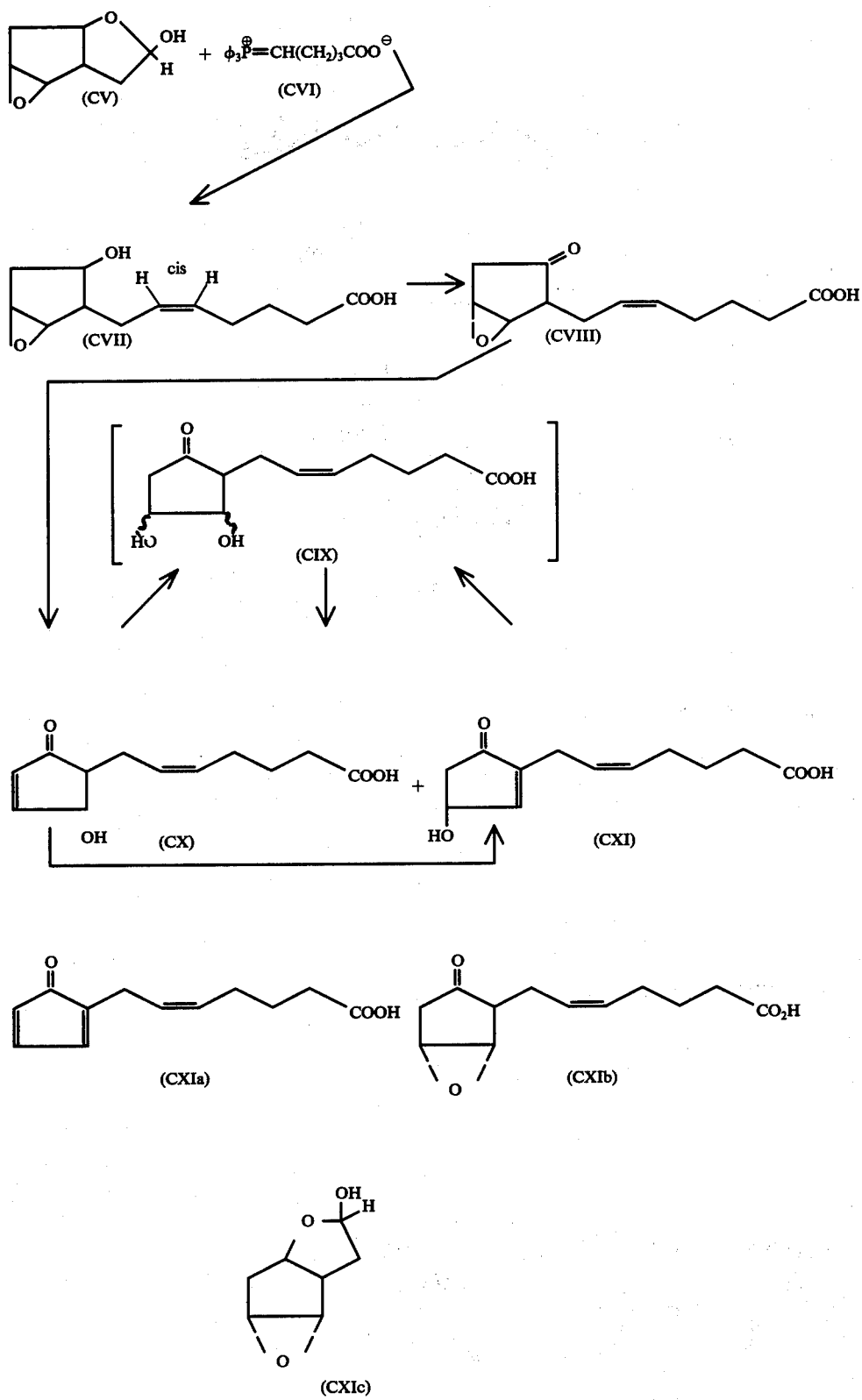

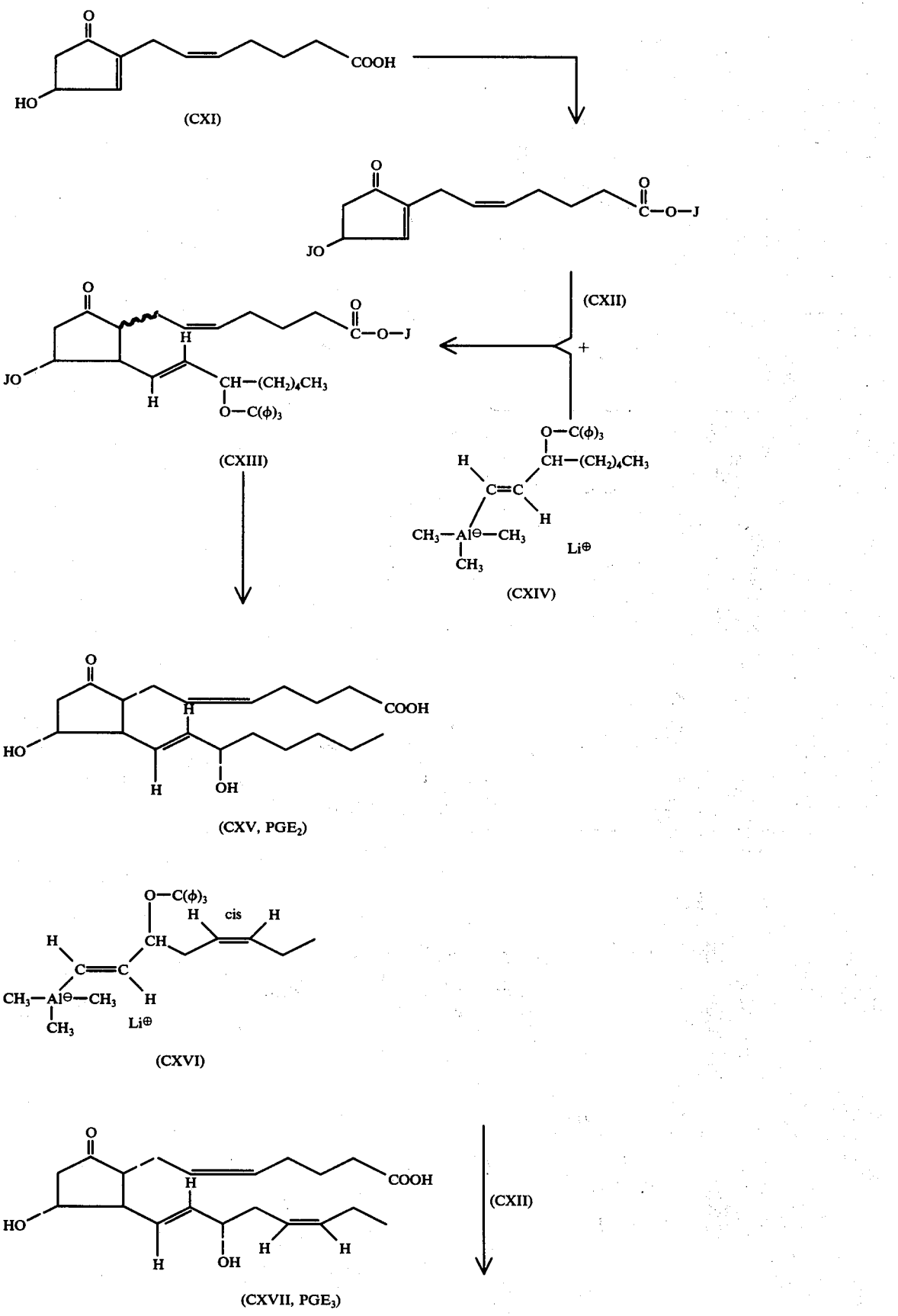

-continued

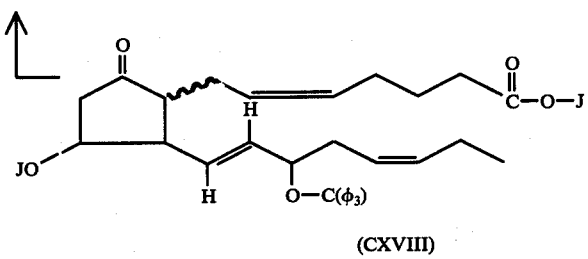

(CXVIII)

In accordance with the above reaction scheme the 3,4-epoxylactol (CV) [E. J. Corey and R. Noyori, Tetrahedron Letters, 311 (1970)] is treated with the ylide (CVI) to give the 3,4-epoxycyclopentanol (CVII) bearing the α-chain of the prostaglandin 2 series. Oxidation (for example with $H_2CrO_4$. —$H_2SO_4$-ether or Jones reagent) of (CVII) provides the epoxy ketone (CVIII), mild base treatment of which results in the initial formation of the 4-hydroxycyclopent-2-en-1-one (CXI) and the isomeric 3-hydroxycyclopent-4-en-1-one (CX) as a mixture. Further treatment of this mixture with dilute base under mild conditions (preferably pH 10.3–10.6 for 24 hours) results in the isomerization of the 3-hydroxy isomer (CX) to the desired (CXI). We believe that the transformation of the epoxy ketone (CVIII) to the hydroxycyclopentenones (CX) and (CXI) and the isomerization of (CX) to (CXI) may take place through the intermediacy of the 3,4-diol (CIX). It is also conceivable that isomerization of (CX) to (CXI) procedes via the epoxy derivative (CVIII) or the corresponding α-epoxide (CVIb); it is further conceivable that (CVIII) procedes to (CX) and (CXI) directly without the intermediacy of (CXI). Another possible intermediate for the isomerization of (CX) to (CXI) is the corresponding diene (CXIa). The preparation of (CXI) is also possible via the α-epoxide series from (CXIc) via the α-epoxide corresponding to (CVII) and (CVIII) such as (CXIb) or via a mixture of the α and β epoxides. In practice, it is most convenient to utilize a mixture of α- and β-epoxides (CXIc and CV). The hydroxy and acid function in the 4-hydroxycyclopentenones(CXI) are then appropriately blocked to give (CXII). Appropriate blocking groups are tetrahydropyranyl, trimethylsilyl, dimethylisopropylsilyl, dimethyl-t-butylsilyl and the like. Treatment of (CXII) with the lithio alanate (CXIV) or its equivalent (see the discussion hereinabove for Flowsheets K and E) gives the conjugate addition product (CXIII) in which the configuration at $C_8$ is undetermined. Mild acid treatment, for example with acetic acid:tetrahydrofuran:water, (4:2:1), of (CXIII) results in the removal of blocking groups, and if necessary equilibration to the all-trans configuration, to give prostaglandin $E_2$ (CXV). Similarly treatment of (CXII) with the lithio alanate (CXVI) gives prostaglandin $E_3$ (CXVII).

Substitution in Flowsheet N, of ylide (CXIX), wherein p is as hereinabove defined, for the ylide (CVI) provides, by transformations analogous to those described in Flowsheet N [(CV) to (CXI) and (CXII)], the 4-hydroxycyclopent-2-en-1-ones (CXX) and their blocked ether-esters (CXXI). These novel and useful intermediates are a part of the present invention.

(CXIX)

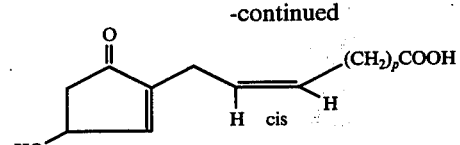

(CXX)

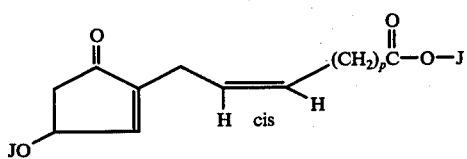

(CXXI)

The 8β-lower alkyl group ($R_7'$) is introduced as illustrated in Flowsheet O below via the bromomagnesium enolate (CXXV). This novel and useful intermediate is obtained by conjugate addition of the 1-alkenyl Grignard reagent [(CXXIII) + (CXXIV)], preferably prepared at about 35° C., to the cycloalkenone (CXXII) in the presence of a catalyst such as the tri-n-butylphosphine cuprous iodide complex as described hereinabove in connection with Flowsheets G and H. It is also possible to utilize for these purposes in an analogous manner the magnesio enolate (CXXVIII) obtained by conjugate addition of Grignard (XLII) to cycloalkenone (XLI) as described hereinabove in connection with Flowsheet F, in which case the 13,14-dihydro derivative of this invention are obtained. In Flowsheet O below, n, Z, $R_3$, $R'_3$, $R'_2$, $W_2$, $R_2$, Q and X are as hereinabove defined and $R'_7$ is an alkyl group having up to 3 carbon atoms. When the magnesio enolate (CXXV) is treated with a lower alkyl halide, e.g., methyl iodide, it undergoes alkylation at the 8β-site providing, after deblocking of the 15-oxy group in intermediate (CXXVI), the 8β-alkyl derivative (CXXVII). In the instance of alkyl esters, saponification gives the corresponding carboxylic acids (CXXVII, $R_3$=OH). The compounds corresponding to (CXXVII) wherein $C_{13}$–$C_{14}$ is a cis-vinylene double bond are preferably prepared by utilizing the vinyl Grignard reagent prepared at temperatures in the range of 70°–75° C., as discussed hereinabove (Flowsheets G and H).

Also obtained from the alkylation of (CXXV) is the 8α-alkyl-8-iso derivative corresponding to (CXXVI), which after deblocking provides the 8α-alkyl-8-iso-products (CXXIX). Usually the 8α-product is formed to a significantly lesser extent than the 8β-product (CXXVI). The 8α and 8β products are seperable from each other by the usual techniques of chromatography.

FLOWSHEET O

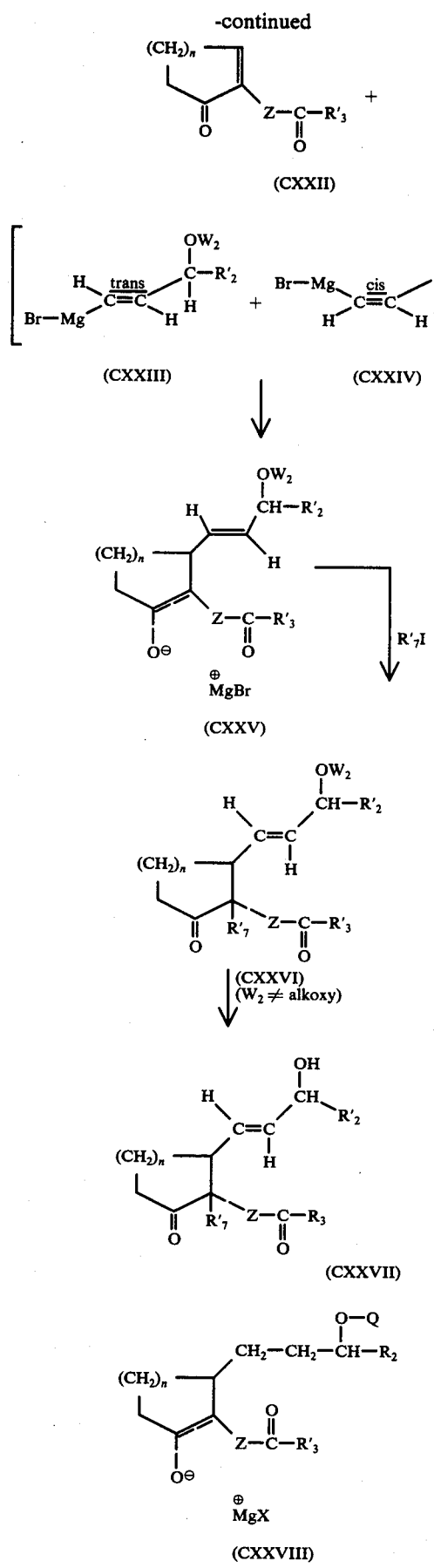

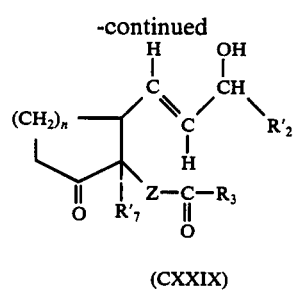

(CXXIX)

Application of the 8-alkylation process to the 11-oxy series provides the novel compounds of formula (CXXX), wherein $R_1$, $R_2$, $R_6$, Y and $C_{13}$-$C_{14}$ are as hereinabove defined and wherein $R'_7$ is an alkyl group having up to 3 carbon atoms, $R_8$ is selected from the group consisting of hydrogen, lower alkanoyl, tetrahydropyranyl and tri-lower alkylsilyl groups, $R_9$ is selected from the group consisting of hydroxy, alkoxy having from 1 to 12 carbon atoms, tetrahydropyranyloxy and tri-lower alkyl silyloxy groups, $Z_2$ is a divalent radical selected from the group consisting of those of the formulae:

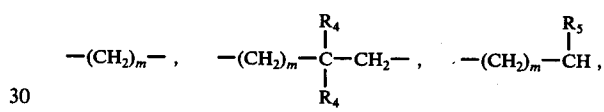

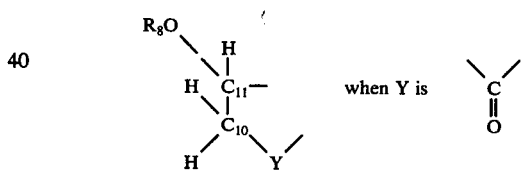

wherein $m$, $p$, $R_4$ and $R_5$ are as hereinabove defined; and the moiety

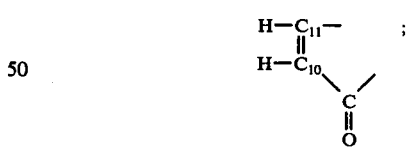

can also be the divalent radical

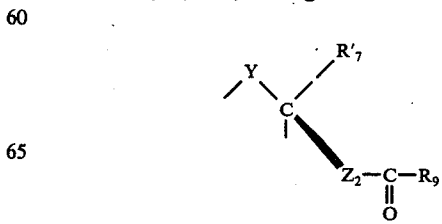

with the proviso that only one unsaturated bond can be directly adjacent to $C_{15}$; and with the second proviso that when $R_6$ is alkyl then $R_1$ is hydrogen; and with the third proviso that the groups attached to $C_8$ may be in the 8β-alkyl (8-iso) configuration:

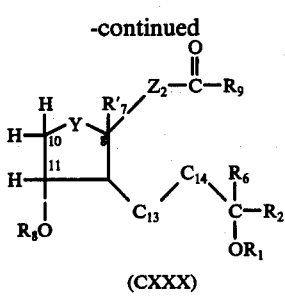

(CXXX)

The novel compounds of formula (CXXX) are also embraced by this invention. The preparation of these compounds may be illustrated by the reaction sequence of Flowsheet P below, wherein $R_9$, $Z_2$, $W_2$, $R''_2$, $R'_7$ and $R_3$ are as hereinabove defined and $R'_8$ has all the possibilities defined above for $R_8$ except that it is not hydrogen.

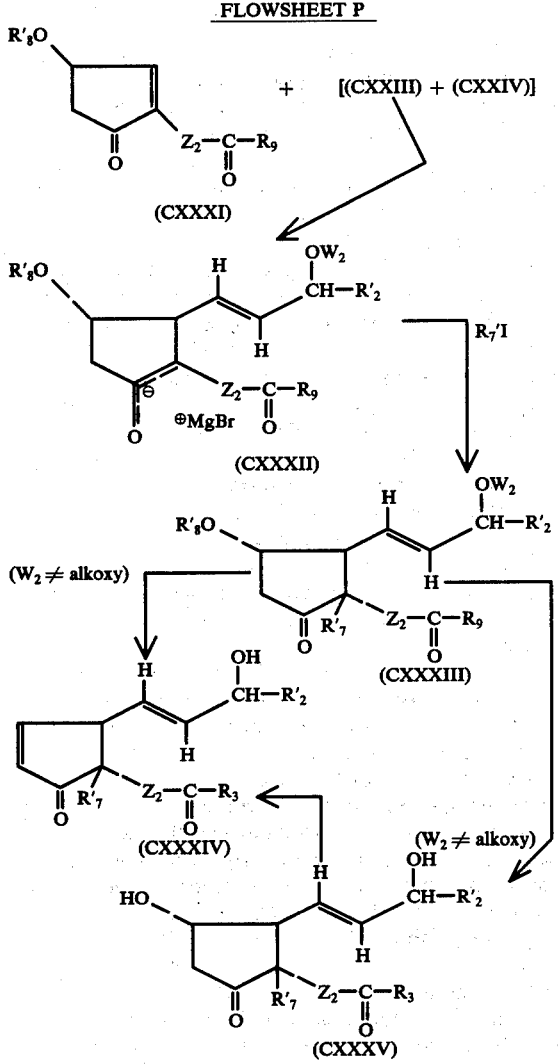

In accordance with the sequence of Flowsheet P above, treatment of the ether-ester 4-oxycyclopentenone (CXXXI) with the 1-alkylene Grignard reagents [(CXXIII) + (CXXIV)] (see Flowsheet O) gives the bromomagnesio enolate (CXXXII). This operation also results in the introduction of the trans $C_{13}$–$C_{14}$ double bond (as shown in CXXXII), as well as the corresponding compound with the cis-double bond. The trans bond is favored when the Grignard is prepared at lower temperatures, about 35° C.; the cis-bond at higher temperatures, about 70°–75° C. This point is more fully discussed above in connection with Flowsheets G and H.

The magnesio enolate (CXXXII) is a key intermediate and when it is treated with a lower alkyl halide, e.g. methyliodide, it undergoes alkylation to give the 8β-lower alkyl derivative (CXXXIII). Deblocking of the 15-hydroxy blocking group (e.g., triphenylmethyl), and of the 11-hydroxy tetrahydropyranyl or trialkylsilyl ether blocking groups as well as of the tetrahydropyranyl or trialkyl silyl esters is accomplished under mild acid conditions, e.g. heating at 45° C. for 3.5 hours in a solvent system consisting of acetic acid:tetrahydrofuran:water (4:2:1). This procedure provides (CXXXV). The compounds of structure (CXXXV) or (CXXXIII) can be converted to 8β-alkyl prostaglandins of the A class (CXXXIV) by treatment with acid or base, a preferred procedure involves treatment in tetrahydrofuran:water (2:1) solvent 0.5N in hydrochloric acid for about seventy hours at ambient temperatures.

The novel compounds of this invention represented by formula (CXXXIV) and related compounds are particularly interesting sunce they represent "stabilized" prostaglandin A types, which cannot rearrange to the biologically relatively inactive prostaglandins of the B series.

Utilization of Grignard (XLII) (see Flowsheet F, hereinabove) in the sequence of Flowsheet P provides the compounds of (CXXX) wherein $C_{13}$–$C_{14}$ is ethylene. Provided there are no other double bonds in the molecule these substances can also be obtained by catalytic hydrogenation of the compounds represented by formula (CXXXV).

The alkylation process described above for Flowsheets O and P also gives the corresponding 8α-alkyl derivatives which are separable from the 8β-alkyl isomer by chromatography. Thus, for example, in Flowsheet O treatment of enolate (CXXV) with $R'_7I$ gives not only the 8β-alkyl product (CXXVI) as shown, but there also is obtained the 8α-alkyl derivative (CXXXVI) shown below. In Flowsheet P, alkylation of enolate (CXXXII) also provides, in addition to (CXXXIII) shown, the 8α-alkyl-8-iso product (CXXXVII), shown below. These 8α-alkyl-8-iso derivatives can be deblocked and carried through the same series of transformation shown for the 8β-derivatives (CXXVI) and (CXXXIII) in Flowsheets O and P, respectively. These novel 8α-alkyl-8-iso derivatives and their transformation products are also a part of this invention, as are the key intermediate enolates represented by structures (CXXV) and (CXXXII).

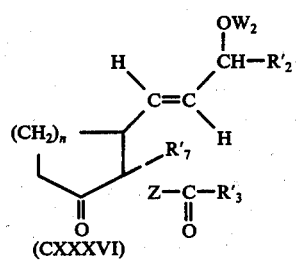

(CXXXVI)

-continued

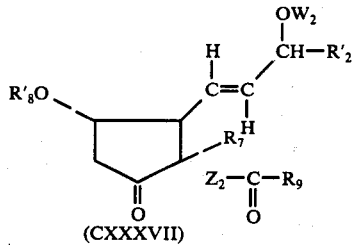

(CXXXVII)

The novel compounds of the present invention have potential utility as hypotensive agents, anti-ulcer agents, agents for the treatment of gastric hypersecretion and gastric erosion, bronchodilators, antimicrobial agents, anticonvulsants, abortifacients, agents for the induction of labor, agents for the induction of menses, fertility-controlling agents, central nervous system regulatory agents, analgesic agents, salt and water-rentention regulatory agents, diuretics, fat metabolic regulatory agents, serum-cholesterol lowering agents, anti-inflammatory agents and as agents for the inhibition of platelet aggregation, and for the treatment of periodontal disease, glaucoma, uveitis, sickle cell anemia and psoriasis. Certain of the novel compounds of this invention possess utility as intermediates for the preparation of other of the novel compounds of this invention.

The compounds of this invention provide protection against the ulcerogenic properties of indomethacin. This assay was carried out in the following manner.

Rats were starved for 48 hours (water was given ad libitum). Indomethacin (20 mg./kg. of body weight) was administered by the subutaneous route and one-half the dose of the test compound was administered by gavage at the same time. After three hours, the second half of the test compound was administered also by Gavage. Five hours after the administration of indomethacin the animals were decapitated and the stomachs removed. The stomachs were washed with distilled water, blotted on gauze, cut along the larger curvature, and the contents rinsed with distilled water. The stomachs were spread out, pinned on a cork and visualized under magnifying glass for ulcers. The criteria for scoring of ulcers was as previously reported. [Abdel-Galil et al. Brit. J. Pharmac. Chemotherapy 33:1-14 (1968)].

| Score | |
|---|---|
| 0 | Normal stomach |
| 1 | Petechial hemmorrhage or pin point ulcer |
| 2 | 1 or 2 small ulcers |
| 3 | Many ulcers, a few large |
| 4 | Many ulcers, mainly large |

Control animals treated with indomethacin but not test compound consistently give scores of about 3.0-3.5. Control animals treated with neither indomethacin nor test compound give scores of about 0.5-0.8. The results obtained in this assay with typical compounds of the present invention are set forth in Table 1 below. Compounds producing a score of 2.5 or lower are considered to be active.

TABLE I

| Compound | Total Oral dose; mg./kg. of body weight | Score Treated | Control |
|---|---|---|---|
| 9-oxo-15-hydroxy-16-ethyl-13-trans-prostenoic acid | 25 | 1.7 | 3.2 |
| 9-oxo-15-hydroxy-13-cis-prostenoic acid | 100 | 1.3 | 3.0 |
| 9-oxo-15-hydroxy-2-ethyl-13-trans-prostenoic acid | 50 | 2.2 | 3.0 |
| 9-oxo-8β-methyl-15-hydroxy-13-trans-prostenoic acid | 12.5 | 2.0 | 3.0 |
| 9-oxo-3-thia-15-hydroxy-13-trans-prostenoic acid | 25 | 1.8 | 3.2 |
| 9-oxo-3-thia-15-epi-hydroxy-13-trans-prostenoic acid | 25 | 2.3 | 3.2 |

The novel compounds of the present invention are also effective inhibitors of gastric acid secretion and of ulcer development in experimental animals, and thus are potentially valuable as agents for the control of gastric acid secretion and of gastric erosion and as anti-ulcer agents. Gastric acid secretion inhibitory action is usually measured by the "Shay rat" procedure [1,2] with some modifications as follows.

The rats (male, CFE strain) were starved for 48 hours (water was given ad libitum) to permit evacuation of stomach contents. On the morning of the experiment, under ether anesthesia, the abdominal region was shaved and a midline incision (1-1½ inches) was made with a scapel. With the help of a closed curved hemostate the duodenum was picked up. Upon getting the duodenum into view, fingers were used to pull the stomach through the opening, the stomach was then gently manipulated with fingers to rid the stomach of air and residual matter which were pushed through the pylorus. Two-5 inch sutures were drawn under the pyloric-duodenal puncture. A ligature, at the juncture was formed with one of the threads. The second ligature was also formed but not tightened.

The test compound or the vehicle, usually 1 ml./mg. body weight, were injected into the duodenum as close as possible to the first ligature. After injection the second ligature was tightened below the injection site to minimize leakage. The stomach was placed back through the opening into the abdominal cavity, the area of incision was washed with saline and the incision was closed with autoclips. (Occasionally, instead of an intraduodenal injection, animals were dosed by the oral or subcutaneous route. In the latter case, dosing was done thirty to sixty minutes before the operation.)

Three hours later, the rats were decapitated and exanguinated, taking care that blood did not drain into the estophagus. The abdominal cavity was exposed by cutting with scissors and the esophagus close to the stomach was clamped off with a hemostat, the stomach was removed by cutting above the hemostat (the esophagus was cut) and between the two sutures. Extraneous tissue was removed, the stomach washed with saline and blotted on gauze. A slit was carefully made in the stomach which was held over a funnel and the contents were collected in a centrifuge tube. The stomach was further cut along the outside edge and turned inside out. Two ml. H₂O were used to wash the stomach contents into the respective centrifuged tube. The combined stomach contents and wash were then centrifuged out for 10 minutes in the International Size 2 Centrifuge (setting at 30). The supernatant was collected, volume measured and recorded, 2 drops of a phenolphthalein indicator (1% in 95% ethanol) were added and the solution was titrated with 0.02N NaOH (or with 0.04N NaOH when large volumes of stomach contents were encountered) to pH 8.4 (because of usual coloring of the stomach contents, phenolphthalein was only used to permit visual indication that the end point was near) and the amount of acid present was calculated.

Compounds inducing inhibition of gastric acid secretion of 20% or more were considered active. In a representative operation, and merely by way of illustration, the results obtained with this assay with a typical compound of the present invention are given in Table 2, below.

TABLE 2

| Compound | Intraduodenal dose, mg./kg. of body weight | Percent Inhibition |
|---|---|---|
| 9-oxo-15-hydroxy-3,3-dimethyl-13-trans-prostenoic acid | 100 | 51 |

Bronchodilator activity was determined in guinea pigs against bronchospasms elicited by intravenous injections of 5-hydroxytryptamine, histamine or acetylcholine by the Konzett procedure. [See J. Lulling, P. Lievens, F. El Sayed and J. Prignot, Arzeimittel-Forschung, 18 995 (1968).]

In the Table which follows bronchodilator activity for representative compounds of this invention against one or more of the three spasmogenic agents is expressed as an $ED_{50}$ determined from the results obtained with three logarithemic cumulative intravenous doses.

TABLE 2A

| | Bronchodilator Activity (Konzett Assays) $ED_{50}$, mg./kg. | | |
|---|---|---|---|
| | Spasmogenic Agent | | |
| Compound | 5-hydroxy-tryptamine | histamine | choline |
| 9-oxo-15-hydroxy-16-ethyl-13-trans-prostenoic acid | — | $81.3 \times 10^{-6}$ | — |
| 9-oxo-15-hydroxy-13-cis-prostenoic acid | $106 \times 10^{-6}$ | $81.3 \times 10^{-6}$ | $320 \times 10^{-6}$ |
| 9-oxo-15-hydroxy-2-ethyl-13-trans-prostenoic acid | $329 \times 10^{-6}$ | $145 \times 10^{-6}$ | $533 \times 10^{-6}$ |
| 9-oxo-15-hydroxy-16-prostynoic acid | $50.8 \times 10^{-6}$ | $92.6 \times 10^{-6}$ | $320 \times 10^{-6}$ |

The novel compounds of the present invention are useful as hypotensive agents and their prostaglandin-like hypotensive activity was demonstrated in the following test procedure. This procedure is a modification of the technique described by Pike et al., Prostaglandins, Nobel Symposium 2, Stockholm, June, 1966; p. 165.

Male Wistar strain rats (Royal Hart Farms) averaging approximately 250 grams in weight were fastened to rat boards in a supine position by means of canvas vests and limb ties. The femoral area was infiltrated subcutaneously with lidocaine and the iliac artery and vein were exposed and cannulated. Arterial blood pressure (systolic/diastolic) was recorded using a Statham $P_{23}$ Db pressure, the animals were anethetized before use with pentobarbital, 30 mg./kg. of body weight intravenously, and also were given hexamethoxium bitartrate, 2 mg./kg. of body weight intravenously. The test compounds were prepared by ultrasonic dispersion in a saline-Tween 80 ® vehicle. A constant intravenous dose volume of 0.5 ml. was administered and test doses ranged from 0.1 to 10.0 mg./kg. of body weight. Increasing or decreasing doses were selected depending on the dose response obtained. In Table 2B below are set forth the minimal doses required to produce a decrease of about 10 mm. in diastolic blood pressure for typical compounds of the present invention.

TABLE 2B

HYPOTENSIVE ACTIVITY

| Compound | Minimal effective hypotensive dose (mg./kg. of body wt.) |
|---|---|
| 2-ethyl-9-oxo-15-hydroxy-13-trans-prostenoic acid | <2 |
| 2-ethyl-9-oxo-15-epi-hydroxy-13-trans-prostenoic acid | 2–4 |
| 2-ethyl-9-oxo-15-hydroxy-prostanoic acid | 0.2 |
| 2-methyl-9-oxo-15-epi-hydroxy-13-trans-prostenoic acid | 2 |
| 2-methyl-9-oxo-15-hydroxy-13-trans-prostenoic acid | 2 |
| 8β-methyl-9-oxo-15-hydroxy-13-trans-prostenoic acid | 2 |
| 9-oxo-15-hydroxy-16-ethyl-13-trans-prostenoic acid | <8 |
| 3,3-dimethyl-9-oxo-15-hydroxy-13-trans-prostenoic acid | 8 |
| 9-oxo-15-hydroxy-13-cis-prostenoic acid | 2–4 |
| 9-oxo-15-hydroxy-13-trans,17-cis-prostadienoic acid | <2 |
| 9-oxo-15-hydroxy-16-prostynoic acid | 2 |
| 9-oxo-15-hydroxy-5-cis,13-trans,17-cis-prostatrienoic acid | <2 |
| 3-oxa-9-oxo-15-hydroxy-13-trans-prostenoic acid | <2 |
| 3-oxa-9-oxo-15-epi-hydroxy-13-trans-prostenoic acid | 1–2 |
| 3-thia-9-oxo-15-hydroxy-13-trans-prostenoic acid | 2 |
| 3-thia-9-oxo-15-epi-hydroxy-13-trans-prostenoic acid | 2 |
| 9-oxo-15-hydroxy-16-trans-prostenoic acid | <2 |
| 2-phenyl-9-oxo-15-hydroxy-13-trans-prostenoic acid | 8 |
| 2-phenyl-9-oxo-15-epi-hydroxy-13-trans-prostenoic acid | 2–8 |
| 2-fluoro-9-oxo-15-hydroxy-13-trans-prostenoic acid | 8 |
| 7a,7b-bishomo-9-oxo-15-hydroxy-13-trans-prostenoic acid | <8 |
| 9-oxo-10a-homo-15-hydroxy-13-trans-prostenoic acid | 2 |
| 9-oxo-10a-homo-15-epi-hydroxy-13-trans-prostenoic acid | 2 |
| 9-oxo-15-hydroxy-15-methyl-5-cis,13-trans, | |

TABLE 2B-continued
HYPOTENSIVE ACTIVITY

| Compound | Minimal effective hypotensive dose (mg./kg. of body wt.) |
| --- | --- |
| 17-cis-prostatrienoic acid | <2 |
| Ethyl 3-oxa-9-oxo-15-hydroxy-13-trans-prostenoate | 0.2 |
| Ethyl 3-oxa-9-oxo-15-epi-hydroxy-13-trans-prostenoate | 0.2 |
| Ethyl 9-oxo-10a-homo-15-hydroxy-13-trans-prostenoate | 2 |
| 9-oxo-15-hydroxy-16,16-dimethyl-13-trans-prostenoic acid | <2 |
| 9-oxo-15-hydroxy-17,17-dimethyl-13-trans-prostenoic acid | 2 |
| 3-thia-9-oxo-15-hydroxy-16,16-dimethyl-13-trans-prostenoic acid | <2 |
| 3-oxa-9-oxo-15-hydroxy-16,16-dimethyl-13-trans-prostenoic acid | <2 |

This invention will be described in greater detail in conjunction with the following specific examples. In these examples it is to be noted that Example 724 follows directly after Example 699.

In the examples which follow reference to 15-hydroxy or 15-oxy derivatives, unless otherwise indicated is inclusive of both the 15-epi and 15-normal racemates. In addition, all possible antipodes resulting from asymmetry at $C_8$, $C_{12}$ and elsewhere in the prostenoic acid molecule are included.

EXAMPLE 1

Preparation of 2-carbalkoxy(methyl/ethyl)-2-(4-carbethoxybutyl)-cyclopentan-1-one To a stirred solution of the sodium cyclopentanone carboxylate enolate in dimethoxyethane, prepared from 187 g. (1.248 moles) of 2-cyclopentanone carboxylate (mixed methyl and ethyl esters), 52.4 g. (1.248 moles) sodium hydride (57.2% in mineral oil) and 1.6 l. of dimethoxyethane, is added dropwise 309 g. (1.212 moles) of ethyl 5-iodovalerate. The reaction mixture is stirred and heated at reflux for 18 hours. The mixture is cooled and filtered. The solvent is removed from the filtrate by evaporation and the residue is poured into dilute hydrochloric acid and extracted with ether. The combined extracts are washed with water and saline, dried over magnesium sulfate and evaporated to give an oil. The oil is distilled under reduced pressure to give 274 g. of a light yellow oil, b.p. 140°–143° C. (0.17 mm).

EXAMPLE 2

Preparation of 2-(4-carboxybutyl)cyclopentan-1-one

A stirred mixture of 274 g. of 2-carbalkoxy(mixed methyl and ethyl esters)-2-(4-carbethoxybutyl)cyclopentan-1-one (Example 1), 600 ml. of 20% hydrochloric acid and 325 ml. of acetic acid is heated at reflux for 20 hours. Solution occurs in approximately one-half hour. The solution is cooled and diluted with water and extracted with ether. The combined extracts are washed with saline and dried over magnesium sulfate and evaporated. The residue is evaporated twice with toluene to give 144 g. of an oil.

EXAMPLE 3

Preparation of 2-(4-carbethoxybutyl)cyclopentan-1-one

A stirred solution of 124 g. (0.673 mole) of 2-(4-carboxybutyl)cyclopentan-1-one (Example 2), 800 ml. of ethanol and 1 g. of p-toluenesulfonic acid monohydrate is heated at reflux for 18 hours. The solvent is evaporated and the residue is dissolved in ether. The ether solution is washed with saline, dilute sodium bicarbonate solution and again with saline, dried over magnesium sulfate and evaporated. The oil is distilled under reduced pressure to give 149 g. of a colorless oil, b.p. 106°–109° C. (0.23 mm).

EXAMPLE 4

Preparation of 2-carbalkoxy(methyl/ethyl)-2-(3-carbethoxypropyl)cyclopentan-1-one In the manner described in Example 1, treatment of 2-cyclopentanone carboxylate (mixed methyl and ethyl esters) with sodium hydride in dimethoxyethane followed by ethyl 4-iodobutyrate gives a yellow oil, b.p. 136°–137° C. (0.16 mm).

EXAMPLE 5

Preparation of 2-(3-carboxypropyl)cyclopentan-1-one

In the manner described in Example 2, treatment of 2-carbalkoxy(mixed methyl and ethyl esters)-2-(3-carbethoxypropyl)cyclopentan-1-one (Example 4) with a 20% hydrochloric acid and acetic acid mixture gives a yellow oil.

EXAMPLE 6

Preparation of 2-(3-carbethoxypropyl)cyclopentan-1-one

In the manner described in Example 3, treatment of 2-(3-carboxypropyl)cyclopentan-1-one (Example 5) with p-toluenesulfonic acid monohydrate in ethanol gives a colorless oil, b.p. 93° C. (0.10 mm).

EXAMPLE 7

Preparation of ethyl and methyl 2-(6-carbethoxyhexyl)-1-cyclopentanon-2-carboxylate In the manner described in Example 1, ethyl and methyl 2-cyclopentanone carboxylate is reacted with ethyl 7-bromoheptanoate to furnish the subject product, b.p. 147° C. (0.09 mm).

EXAMPLE 8

Preparation of 2-(6-carboxyhexyl)cyclopentan-1-one

In the manner described in Example 2, ethyl and methyl 2-(6-carbethoxyhexyl)-1-cyclopentanone-2-carboxylate (Example 7) is hydrolyzed to furnish the subject product, b.p. 143° C. (0.05 mm).

EXAMPLE 9

Preparation of 2-(6-carbethoxyhexyl)cyclopentan-1-one

In the manner described in Example 3, 2-(6-carboxyhexyl)cyclopentan-1-one (Example 8) is esterified to furnish the subject product, b.p. 110° C. (0.03 mm).

EXAMPLE 10

Preparation of 1-acetoxy-2-(6-carbethoxyhexyl)cyclopent-1-ene

A stirred solution of 100 g. of 2-(6-carbethoxyhexyl)-cyclopentan-1-one (Example 9) in 250 ml. of acetic anhydride containing 0.940 g. of p-toluenesulfonic acid monohydrate is heated to boiling under partial reflux allowing distillate at 118° C. or less (i.e., acetic acid) to escape through a Vigreaux column equipped with a condenser to collect the distillate. After 16 hours, during which period acetic anhydride is added in portions in order to keep the solvent level at at least 100 ml., the solution is cooled and poured cautiously into a stirred cold mixture of saturated sodium bicarbonate solution (400 ml.) and hexane (250 ml.). The resulting mixture is stirred for an additional 30 minutes during which period solid sodium bicarbonate is added periodically to insure a basic solution. The hexane layer is separated and washed with saturated sodium chloride solution, dried with anhydrous magnesium sulfate and taken to dryness. Distillation of the residual oil gives 102 g. (87%) of pale yellow oil, b.p. 118° C. (0.07 mm).

EXAMPLE 11

Preparation of 1-acetoxy-2-(3-carbethoxypropyl)cyclopent-1-ene

In the manner described in Example 10, treatment of 2-(3-carbethoxypropyl)cyclopentan-1-one (Example 6) with acetic anhydride and p-toluenesulfonic acid monohydrate gives a yellow oil, b.p. 98°–103° C. (0.35 mm).

EXAMPLE 12

Preparation of 1-acetoxy-2-(4-carbethoxybutyl)cyclopent-1-ene

In the manner described in Example 10, treatment of 2-(4-carbethoxybutyl)cyclopentan-1-one (Example 3) with acetic anhydride and p-toluenesulfonic acid monohydrate gives a yellow oil, b.p. 109°–110° C. (0.37 mm).

EXAMPLE 13

Preparation of 2-(6-carbethoxyhexyl)cyclopent-2-en-1-one

To a rapidly stirred mixture of 50 g. of 1-acetoxy-2-(6-carbethoxyhexyl)cyclopent-1-ene (Example 10) in 150 ml. of chloroform, 200 ml. of water and 18.8 g. of calcium carbonate, cooled in an ice bath, is added dropwise over a period of about 30 minutes, a solution of 30 g. of bromine in 50 ml. of carbon tetrachloride. After stirring for an additional 45 minutes the chloroform layer is separated and washed successively with dilute sodium thiosulfate solution, saturated sodium chloride solution, dried with anhydrous magnesium sulfate and taken to dryness under reduced pressure.

The residual oil is dissolved in 50 ml. of N,N-dimethylformamide and added to a mixture of 33 g. of lithium bromide and 32 g. of lithium carbonate in 375 ml. of N,N-dimethylformamide, previously dried by refluxing with 375 ml. of benzene under a Dean-Stark apparatus followed by distillation of the benzene. The mixture is stirred at the reflux temperature for 30 minutes, then cooled and poured into 850 ml. of ice-cold water. The resulting mixture is acidified (cautiously) with 4N hydrochloric acid and extracted with ether three times. The combined ether extracts are washed with saturated sodium chloride solution, dried with anhydrous magnesium sulfate and taken to dryness under reduced pressure to afford 41.5 g. of an amber oil. In order to convert any isomeric material to the desired product, 41.5 g. of the above material is treated with 0.500 g. of p-toluenesulfonic acid monohydrate in 450 ml. of absolute alcohol at the reflux temperature for 18 hours. The solution is taken to dryness under reduced pressure. The resulting gum is dissolved in ether and washed with saturated sodium bicarbonate solution, saturated sodium chloride solution, dried with anhydrous magnesium sulfate and taken to dryness under reduced pressure. The residual oil is distilled to give 30.2 g. of product; b.p. 118° C. (0.05 mm); $\lambda_{max}^{MeOH}$ 229 m$\mu$ ($\epsilon$9950); $\lambda_{max}$ 5.75, 5.85, 6.15, 8.45 $\mu$; vapor phase chromatography shows 99% product, containing 1% 2-(6-carbethoxyhexyl)cyclopentan-1-one.

This product can be purified by the following procedure. A mixture of 120 g. of 2-(6-carbethoxyhexyl)-2-cyclopentenone, containing approximately 5% of the saturated analogue, and 7.67 g. (10 mole percent) of p-carboxyphenylhydrazine in 400 ml. of absolute ethanol is stirred at ambient temperatures for 18 hours and is then refluxed for 1 hour. The mixture is cooled, the solvent is evaporated, and the residue is taken up into 150 ml. of chloroform and passed through a column of 450 g. of aluminum oxide (Merck). The filtrate is evaporated to yield a colorless oil containing <0.5% of the saturated impurity.

EXAMPLE 14

Preparation of 2-(3-carbethoxypropyl)cyclopent-2-en-1-one

In the manner described in Example 13, bromination of 1-acetoxy-2-(3-carbethoxypropyl)cyclopent-1-ene (Example 11) followed by dehydrobromination with lithium bromide and lithium carbonate is productive of the subject compound.

EXAMPLE 15

Preparation of 2-(4-carbethoxybutyl)cyclopent-2-en-1-one

In the manner described in Example 13, treatment of 1-acetoxy-2-(4-carbethoxybutyl)cyclopent-1-ene (Example 12) with bromine and subsequent treatment of the brominated product with a mixture of lithium bromide and lithium carbonate in N,N-dimethylformamide is productive of the subject compound. Treatment of this product with p-carboxyphenylhydrazine by the procedure of Example 13 furnishes a product which contains less than 0.5% of the corresponding saturated ketone.

EXAMPLE 16

Preparation of 1-methoximino-2-(6-carbethoxyhexyl)-2-cyclopentene

To a mixture of 35.97 g. (0.151 mole) of 2-(6-carbethoxyhexyl)-2-cyclopentenone (Example 13) and 15.0 g. (0.180 mole) of methoxyamine hydrochloride in 300 ml. of absolute ethanol is added 25 ml. of pyridine and the resulting solution is stirred for 20 hours at ambient temperatures. The solvent is evaporated and the residue is partitioned between water and diethyl ether. The organic phase is washed with water and saturated brine, dried ($Na_2SO_4$), and the solvent is evaporated to yield an oil. Distillation yields 38.7 g. of a colorless oil, b.p. 115°–118° C. (0.075 mm). IR (film): 1740, 1627, 1053, 890 cm$^{-1}$. $\lambda_{max}$ (MeOH) 243 (13,000). NMR $\delta$(CDCl$_3$): 3.89.

EXAMPLE 17

Preparation of
1-methoximino-2-(7-hydroxyheptyl)-2-cyclopentene

To an ice cooled solution of 34.10 g. (0.128 mole) of 1-methoximino-2-(6-carbethoxyhexyl)-2-cyclopentene (Example 16) in 200 ml. of benzene under nitrogen is added dropwise 225 ml. of a 25% solution of diisobutyl aluminum hydride in hexane. The resulting solution is stirred for 2 hours at 0°–5° C., poured onto ice and dilute hydrochloric acid, and the aqueous phase is saturated with sodium chloride. The organic phase is separated, washed with saturated brine, dried ($Na_2SO_4$), and evaporated to yield an oil. The latter is dissolved in 100 ml. of hot hexane and cooled to yield 24.3 g. of crystals, m.p. 62°–64° C. IR (KBr) 3260, 1630, 1059, 893 cm$^{-1}$; $\lambda_{max}$ 243 (14,200). NMR (CDCl$_3$)$\delta$: 2.37.

EXAMPLE 18

Preparation of
1-methoximino-2-(7-p-toluenesulfonyloxyheptyl)-2-cyclopentene

To a solution of 5.00 g. (0.0222 mole) of 1-methoximino-2-(7-hydroxyheptyl)-2-cyclopentene (Example 17) in 50 ml. of dry pyridine at 0° C. is added 8.45 g. (0.0444 mole) of p-toluenesulfonyl chloride and the resulting solution is chilled at 5° C. overnight. The mixture is partitioned between 300 ml. of ice water and diethyl ether. The organic phase is washed with 1:1 ice cold hydrochloric acid, cold water, and cold saturated brine, dried ($NaSO_4/K_2CO_3$), and evaporated under reduced pressure at room temperature to yield an oil. The latter is dissolved in 600 ml. of hexane, treated with 0.5 g. of Darco, filtered and evaporated to yield 7.7 g. of a colorless oil. IR (film) 1600, 1192, 1182, 1053, 890 cm$^{-1}$. $\lambda_{max}$ (MeOH) 228 and 243.

EXAMPLE 19

Preparation of
1-methoximino-2-(8,8-dicarbethoxyoctyl)-2-cyclopentene

To an alcoholic solution of sodiodiethyl malonate, prepared from 0.847 g. (0.0368 g. atoms) of sodium, 100 ml. of absolute ethanol, and 7.05 g. (0.0440 mole) of diethyl malonate is added 7.7 g. of the tosylate of Example 18 and the mixture is refluxed for 2 hours under a nitrogen atmosphere. The mixture is partitioned between cold dilute hydrochloric acid and diethyl ether, and the organic phase is washed with water and saturated brine, dried ($Na_2SO_4$), and evaporated to yield an oil. The excess diethyl malonate is distilled off under reduced pressure to yield 6.45 g. of a yellowish oil. IR (film) 1755, 1728, 1625, 1054, 890 cm$^{-1}$.

EXAMPLE 20

Preparation of
1-methoximino-2-(8,8-dicarboxyoctyl)-2-cyclopentene

A mixture of 6.45 g. of the diester of Example 19 and 6.72 g. of potassium hydroxide in 150 ml. of 1:1 aqueous methanol is refluxed for 1 hour, cooled, and is partitioned between water and diethyl ether. The aqueous phase is acidified with hydrochloric acid, extracted with ether, and the organic phase is washed with water and saturated brine, dried ($Na_2SO_4$) and evaporated to yield a solid. The solid is crystallized from benzene to yield 4.15 g. of tan crystals, m.p. 135°–137° C. (-$CO_2$).

EXAMPLE 21

Preparation of
1-methoximino-2-(8-carboxyoctyl)-2-cyclopentene

A solution of 3.926 g. (0.0126 mole) of the diacid of Example 20 in 20 ml. of xylene is refluxed for 1.5 hours, cooled, and evaporated to yield a tan solid. IR (KBr) 1720, 1618, 1179, 1050, 986 cm$^{-1}$.

EXAMPLE 22

Preparation of 2-(8-carboxyoctyl)cyclopent-2-en-1-one

The acid methoxime from Example 21 is refluxed for 5 hours with 55 ml. of acetone and 20 ml. of 2N hydrochloric acid. The mixture is cooled, the solvent is evaporated, and the residue is partitioned between water and diethyl ether. The organic phase is washed with water and saturated brine, dried ($Na_2SO_4$), and evaporated to yield a tan solid. IR (KBr) 1745, 1665 cm$^{-1}$. $\lambda_{max}$ (MeOH) 228 (12,600).

EXAMPLE 23

Preparation of
2-(8-carbethoxyoctyl)cyclopent-2-en-1-one

The acid ketone from Example 22 is Fisher esterified with 100 ml. of absolute ethanol, 100 ml. of benzene, and 20 mg. of p-toluenesulfonic acid for 6 hours, cooled, and the solvent is evaporated. The resulting oil is dissolved in 3:1 benzene-ether and the solution is passed through a column of 100 g. of Florisil ®. The filtrate is evaporated and the residue is distilled to yield 2.97 g. of a colorless oil, b.p. 137°–139° C. (0.05 Torr).

EXAMPLE 24

Preparation of 2-(4-carbethoxybutyl)-2-cyclopentenone methoxime

Treatment of 2-(4-carbethoxybutyl)-2-cyclopentenone (Example 15) with methoxyamine hydrochloride in the manner described in Example 16 gives an oil, b.p. 107°–109° C. (0.05 mm). IR (film): 1740, 1628, 1050, 885 cm$^{-1}$. $\lambda_{max}$ (MeOH) 243 (13,600).

EXAMPLE 25

Preparation of 2-(5-hydroxypentyl)-2-cyclopentenone methoxime

Treatment of 2-(4-carbethoxybutyl)-2-cyclopentenomethoxime (Example 24) with diisobutyl aluminum hydride in the manner described in Example 17 gives crystals, m.p. 33°–35° C. IR (KBr) 3420, 1630, 1050, 886 cm$^{-1}$. $\lambda_{max}^{MeOH}$ 243 (12,020).

EXAMPLE 26

Preparation of
2-(5-p-toluenesulfonyloxpentyl)-2-cyclopentenone methoxime

Treatment of 2-(5-hydroxypentyl)-2-cyclopentenone methoxime (Example 25) with p-toluenesulfonyl chloride in pyridine in the manner described in Example 18 gives a colorless oil. IR (film) 1600, 1190, 1180, 1050, 885 cm$^{-1}$.

EXAMPLE 27

Preparation of
2-(6,6-dicarbethoxyoctyl)-2-cyclopentenone
methoxime

To a solution of sodio diethyl ethylmalonate, prepared from 1.63 g. (0.0387 mole) of sodium hydride in mineral oil (57.2%), 100 ml. of ethylene glycol dimethyl ether and 8.5 g. (0.0452 mole) of ethyl diethyl malonate, is added 7.5 g. of tosylate from Example 26 in 20 ml. of ethylene glycol dimethyl ether and the mixture is refluxed for 3 hours and then allowed to stand at room temperature for 18 hours under nitrogen atmosphere. The reaction mixture is filtered and most of the solvent is removed. The mixture is partitioned between cold dilute hydrochloric acid and diethyl ether, and the organic phase is washed with water and saturated brine, dried (MgSO$_4$), and evaporated to yield an oil. The excess ethyl diethyl malonate is distilled off under reduced pressue to yield 6.7 g. of a yellow oil. IR (film) 1755, 1728, 1627, 1050, 885 cm$^{-1}$.

EXAMPLE 28

Preparation of
2-(6,6-dicarboxyoctyl)-2-cyclopentenone methoxime

Treatment of 2-(6,6-dicarbethoxyoctyl)-2-cyclopenteno methoxime (Example 26 ) with potassium hydroxide, and 1:1 aqueous methanol in the manner described in Example 20 1 gives a light yellow oil.

EXAMPLE 29

Preparation of 2-(6-carboxyoctyl)-2-cyclopentenone methoxime

In the manner described in Example 21, treatment of 2-(6,6-dicarboxyoctyl)-2-cyclopentenone methoxime (Example 28) with xylene at reflux for 18 hours gives a yellow oil.

EXAMPLE 30

Preparation of 2-(6-carboxyoctyl)-2-cyclopentenone

Treatment of 2-(6-carboxyoctyl)-2-cyclopentenone methoxime (Example 29 ) with acetone and 2N hydrochloric acid in the manner described in Example 22 gives a light yellow oil.

EXAMPLE 31

Preparation of 2-(6-carbethoxyoctyl)-2-cyclopentenone

Treatment of 2-(6-carboxyoctyl)-2-cyclopentenone (Example 30) with thionyl chloride and then treatment of the acid chloride with ethanol in the usual manner gives an amber oil. The oil is placed on a magnesia-silica gel column and eluted with 3:1 benzene:ether. The solvent is removed and the residue is distilled, b.p. 122° C. (0.06 mm).

EXAMPLE 32

Preparation of diethyl
1,1-dimethyl-5-tetrahydropyranylpentylmalonate

To 486 mg. (0.02 g.-atoms) of magnesium in 5 ml. of toluene containing one molar equivalent of tetrahydrofuran per equivalent of magnesium and one percent iodine (calculated in weight of magnesium) is added dropwise 3.86 g. (0.02 mole) of 4-chloro-1-tetrahydropyranyloxybutane over a period of one hour with stirring, under nitrogen at 70° C. The reaction mixture is stirred at 70° C. for four hours. This reagent is then added dropwise to 3 g. (0.015 mole) of ethyl isopropylidenemalonate in 40 ml. of tetrahydrofuran containing 392 mg. of tetrakis [iodo(tri-n-butylphosphine)-copper (I)]0 and stirred at room temperature for 2 hours. The reaction mixture is poured into cold dilute hydrochloric acid and extracted with ether. The ether extract is dried over magnesium sulfate and concentrated to give 5.92 g. of subject product as an oil.

EXAMPLE 33

Preparation of diethyl
1,1-dimethyl-5-hydroxypentylmalonate

A solution of 3.5 g. (0.01 mole) of diethyl 1,1-dimethyl-5-tetrahydrofuranyloxypentylmalonate in 70 ml. of ethanol containing 3 ml. of hydrochloric acid is allowed to stir at room temperature for 18 hours. The solution is concentrated, diluted with water and extracted with ether. The ether extract is washed with water, dried over magnesium sulfate and concentrated to give 3.262 g. of a light yellow oil. The oil is purified by distillation, b.p. 116°-117° C. (0.05 mm).

EXAMPLE 34

Preparation of 3,3-dimethyl-7-hydroxyheptanoic acid

A mixture of 32 g. (0.117 mole) of diethyl 1,1-dimethyl-5-hydroxypentylmalonate, 25 g. of potassium hydroxide and 600 ml. of methanol-water (1:1) is heated at reflux for 8 hours and then allowed to stand at room temperature for 18 hours. The methanol is removed, diluted with water and the reaction mixture is acidified with concentrated hydrochloric acid. The mixture is extracted with ether. The extract is washed with water and saline, dried over anhydrous magnesium sulfate and concentrated to give 27 g. of 1,1-dimethyl-5-hydroxypentylmalonic acid. This crude oil is dissolved in 200 ml. of bis-(2-methoxyethyl)ether and is heated at reflux for 4 hours and then allowed to stand at room temperature overnight. The solvent is removed and the reaction mixture is diluted with water and extracted with ether. The organic solution is washed with saline, dried over magnesium sulfate and concentrated to give 18 g. of product as an oil.

EXAMPLE 35

Preparation of ethyl 3,3-dimethyl-7-chloroheptanoate

To a solution of 3.484 g. (0.02 mole) of 3,3-dimethyl-7-hydroxyheptanoic acid in 25 ml. of chloroform containing 3 drops of dimethylformamide is added 5.8 ml (0.08 mole) of thionyl chloride and the solution is then heated at reflux for 3–4 hours. The solution is concentrated to give the intermediate 3,3-dimethyl-7-chloro-1-heptanoyl chloride. The acid chloride is dissolved in a minimum amount of benzene and added slowly to 20 ml. benzene, 10 ml. of ethanol and 2.65 ml. of collidine. The solution is heated at reflux for one hour and then concentrated. The residue is dissolved in ether, washed with water, dilute sodium bicarbonate solution and saline. The organic solution is dried over magnesium sulfate and concentrated to give 3.57 g. of product as a yellow oil.

EXAMPLE 36

Preparation of ethyl 3,3-dimethyl-7-iodoheptanoate

To a solution of 3.57 g. (0.0162 mole) of ethyl 3,3-dimethyl-7-chloroheptanoate in 100 ml. of methyl ethyl ketone is added 4 g. of sodium iodide and the mixture heated at reflux for 18 hours. The reaction mixture is cooled, filtered and concentrated. The residue is partitioned between ether and water. The aqueous phase is extracted several times with ether. The extract is washed with sodium bisulfite solution, water and saline. The organic solution is dried over magnesium sulfate and concentrated to give 4.182 g. of a yellow oil. The material is purified by distillation, b.p. 86°–87° C. (0.18 Torr).

EXAMPLE 37

Preparation of 2-carbalkoxy(methyl/ethyl)-2-(6-carbethoxy-5,5-dimethylhexyl)cyclopentan-1-one This compound is prepared by treatment of sodio cyclopentanone carboxylate enolate with ethyl 3,3-dimethyl-7-iodoheptanoate by the procedure described in Example 1.

EXAMPLE 38

Preparation of 2-(6-carboxy-5,5-dimethylhexyl)cyclopentan-1-one

This compound is prepared by decarbalkoxylation of 2-carbalkoxy (mixed methyl and ethyl ester)-2-(6-carbethoxy-5,5-dimethylhexl)cyclopentan-1-one by the procedure described in Example 2.

EXAMPLE 39

Preparation of 2-(6-carbethoxy-5,5-dimethylhexyl)cyclopentan-1-one

Esterification of 2-(6-carboxy-5,5-dimethylhexyl)cyclopentan-1-one with ethanol by the procedure described in Example 3 is productive of the subject compound.

EXAMPLE 40

Preparation of 1-acetoxy-2-(6-carbethoxy-5,5-dimethylhexyl)cyclopent-1-ene

This compound is prepared from 2-(6-carbethoxy-5,5-dimethylhexyl)cyclopentan-1-one and acetic anhydride by the process described in Example 10.

EXAMPLE 41

Preparation of 2-(6-carbethoxy-5,5-dimethylhexyl)cyclopent-2-en-1-one

This compound is prepared from 1-acetoxy-2-(6-carbethoxy-5,5-dimethylhexyl)cyclopent-1-ene via bromination and dehydrobromination according to the procedure described in Example 13.

EXAMPLE 42

Preparation of 2-(3-carbethoxypropyl)-1-methoximino-2-cyclopentene

In the manner described for the preparation of the compound of Example 16, 2-(3-carbethoxypropyl)-1-methoximino-2-cyclopentene is prepared from 2-(3-carbethoxypropyl)-2-cyclopentenone (Example 14) and methoxyamine hydrochloride.

EXAMPLE 43

Preparation of 2-(4-hydroxybutyl)-1-methoximino-2-cyclopentene

In the manner described for the preparation of the compound of Example 17, 2-(4-hydroxybutyl)-1-methoximino-2-cyclopentene is prepared from 2-(3-carbethoxypropyl)-1-methoximino-2-cyclopentene and diisobutylaluminum hydride.

EXAMPLE 44

Preparation of 2-(6-carbethoxy-5-oxahexyl)-1-methoximino-2-cyclopentene

To an ice cold solution of 4.833 g. (0.0266 mole) of 2-(4-hydroxypentane)-1-methoximino-2-cylopentene is 50 ml. of dry tetrahydrofuran under nitrogen is added 16.7 ml. of 1.6 molar n-butyl lithium is hexane, dropwise. The reaction mixture is stirred for 0.5 hour and then 4.85 g. (0.029 mole) of ethyl bromoacetate is added dropwise. The reaction mixture is stirred overnight at room temperature and then refluxed for 1.5 hours. The reaction is cooled and poured into water and extracted several times with ether. The ether extracts are washed with saline, dried over magnesium sulfate, and concentrated. The residue is placed on an alumina column, chloroform being used as a wash solvent. The combined washings are concentrated to dryness to give 4.903 g. of product an a yellow oil.

EXAMPLE 45

Preparation of 2-(6-carboxy-5-oxahexyl)-2-cyclopentenone

In the manner described in Example 22, treatment of 2-(6-carbethoxy-5-oxahexyl)-1-methoximino-2-cyclopentene with acetone and 2N hydrochloric acid at reflux gives the subject compound as a yellow oil.

EXAMPLE 46

Preparation of 2-(6-carbethoxy-5-oxahexyl)-2-cyclopentenone

In the manner described in Example 23, treatment of 2-(6-carboxy-5-oxahexyl)-2-cyclopentenone with p-toluenesulfonic acid in ethanol produces the subject product as a light yellow oil.

EXAMPLE 47

Preparation of 2-(6-carboxy-5-oxahexyl)-1-methoximino-2-cyclopentene

To an ice cold solution of 3.66 g. (0.02 mole) of 2-(4-hydroxybutyl)-1-methoximino-2-cyclopentene (Example 43) in 50 ml. of 1,2-dimethoxyethane under nitrogen is added dropwise 17 ml. of 1.6 M n-butyl lithium in hexane. The reaction mixture is stirred for half an hour and then the lithium salt of chloroacetic acid, prepared from 1.89 g. (0.02 mole) of chloroacetic acid and 16 ml. of 1.6M n-butyl lithium in 20 ml. of dimethoxyethane, is added and the reaction mixture is heated at reflux for 48 hours. The solvent is evaporated and the residue is partitioned between ether and water. The aqueous phase is acidified with hydrochloric acid and extracted with ether. The organic phase is washed with water and saturated saline solution, dried (MgSO$_4$), and evaporated to give 3.35 g. of a yellow oil.

EXAMPLE 48

Preparation of 2-(6-carboxy-5-oxahexyl)-2-cyclopenten-1-one

In the manner described in Example 22, treatment of 2-(6-carboxy-5-oxahexyl)-1-methoximino-2-cyclopentene (Example 47) with acetone and 2N hydrochloric acid at reflux gives the subject compound as a yellow oil.

EXAMPLE 49

Preparation of 1-methoximino-2-(4-methanesulfonyloxybutyl)-2-cyclopentene

To a solution of 1.83 g. (0.01 mole) of 1-methoximino-2-(4-hydroxybutyl)-2-cyclopentene (Example 43) in 10 ml. of methylene chloride containing 1.52 g. (0.015 mole) of triethylamine is added 1.265 g. (0.011 mole) of methanesulfonyl chloride over a period of 5–10 minutes at −10°–0° C. Stirring is continued for 15 minutes and the solution is then washed with cold water, cold 10% hydrochloric acid, cold sodium bicarbonate solution, and cold saline solution. The organic phase is dried (MgSO$_4$) and concentrated to give an oil which solidifies upon cooling. Crystallization from ether-petroleum ether (30°–60° C.) gives 1.797 g. of white crystals, m.p. 67°–68° C.

EXAMPLE 50

Preparation of 1-methoximino-2-(5-cyanopentyl)-2-cyclopentene

A mixture of 2.75 g. (0.01 mole) of 1-methoximino-2-(5-methanesulfonyloxypentyl)-2-cyclopentene (Example 60) and 1.47 g. (0.03 mole) of sodium cyanide in 20 ml. of dry N,N-dimethylformamide is heated at 65°–70° C. for 3 hours. The cooled reaction mixture is poured into water and extracted with diethyl ether. The organic phase is washed with water and saturated saline solution, dried (MgSO$_4$), and evaporated to give 1.89 g. of a light yellow oil.

EXAMPLE 51

Preparation of 1-methoximino-2-(5-carboxypentyl)-2-cyclopentene

A mixture of 1.89 g. (0.0092mole) of 1-methoximino-2-(5-cyanopentyl)-2-cyclopentene (Example 50) and 1 g. (0.025 mole) of sodium hydroxide in 50 ml. of 1:1 aqueous-ethanol is refluxed for 48 hours, cooled, and partitioned between water and diethyl ether. The aqueous phase is acidified with hydrochloric acid, extracted with diethyl ether, and the organic phase is washed with water and saturated saline solution, dried (MgSO$_4$), and evaporated to give 1.86 g. of a yellow oil.

EXAMPLE 52

Preparation of 2-(5-carboxypentyl)-2-cyclopentenone

A solution of 1.86 g. (0.00825 mole) 1-methoximino-2-(5-carboxypentyl)-2-cyclopentene (Example 51 ) in 44 ml. of acetone and 13.1 ml. of 2N hydrochloric acid is refluxed for 5 hours. The solvent is partially evaporated and a solid precipitates and is collected. The residue is extracted with diethyl ether and the organic phase is washed with saturated saline solution, dried (MgSO$_4$), and evaporated to yield additional solid. The combined solid material is crystallized from ether/pet ether (30°–60° C ) to yield crystalline material, m.p. 70°–72° C.

EXAMPLE 53

Preparation of 2-(5-carbethoxypentyl)-2-cyclopentenone

A solution of 1.309 g. (0.00668 mole) of 2-(5-carboxypentyl)-2-cyclopentenone (Example 52) and 90 mg. of p-toluenesulfonic acid in 150 ml. of ethanol is refluxed for 18 hours. The solvent is evaporated and the residue is dissolved in ether. The organic phase is washed with water, sodium bicarbonate solution, and saturated saline solution, dried (MgSO$_4$), and evaporated to give 1.371 g. of a light yellow oil.

EXAMPLE 54

Preparation of 2-(5-acetoxypentyl)-2-carbomethoxy/carbethoxycyclopentanone

A mixture of sodiocyclopentanone carboxylate, prepared from 1200 g. (8.0 moles) of cyclopentanone carboxylate (methyl and ethyl esters) and 200 g. (8.3 moles) of mineral oil free sodium hydride in 10 l. of 1,2-dimethoxyethane, 1320 g. (8.0 moles) of 5-chloro-1-amyl acetate [M. E. Synerholm, Journ. Amer. Chem. Soc., 69, 2681 (1947)], and 1200 g. (8.0 moles) of sodium iodide is refluxed under nitrogen for 18 hours. The mixture is cooled, concentrated to 4.1 and partitioned between dilute hydrochloric acid and diethyl ether. The organic phase is washed with water and saturated brine, dried (MgSO$_4$), and evaporated to yield 1920 g. of an oil.

EXAMPLE 55

Preparation of 2-(5-hydroxypentyl)cyclopentanone/2-(5-acetoxypentyl)-cyclopentanone A mixture of 4,500 g. (16.2 moles) of 2-(5-acetoxypentyl)-2-carbomethoxy/carboethoxy-cyclopentanone (Example 54), 2.2 l. of glacial acetic acid, 1 l. of concentrated hydrochloric acid, and 1 l. of water is refluxed for 18 hours, cooled, and partitioned between saturated brine and benzene. The organic phase is washed with saturated brine, dried (MgSO$_4$), and evaporated in vacuo to yield 3155 g. of an oil.

EXAMPLE 56

Preparation of 1-acetoxy-2-(5-acetoxypentyl)-1-cyclopentene

A solution of 400 g. (2.04 moles) of a mixture of 2-(5-hydroxypentyl)cyclopentanone and 2-(5-acetoxypentyl)cyclopentanone (Example 55 ) and 4.0 g. of p-toluenesulfonic acid monohydrate in 1 l. of acetic anhydride is refluxed at a rate to maintain a steady distillation of acetic acid from the reaction through a helix-packed fractionation column. The reaction is continued with the addition of acetic anhydride to maintain a constant volume until complete conversion of starting materials to product is evident. The mixture is cooled and partitioned between 2 l. of hexane and 3 l. of cold water containing solid sodium bicarbonate to maintain a neutral pH. The organic phase is washed with saturated brine, dried (MgSO$_4$), and evaporated to yield 452 g. of an oil.

EXAMPLE 57

Preparation of 2-(5-acetoxypentyl)-2-cyclopentenone

To a well stirred mixture of 405 g. (4.05 moles) of calcium carbonate, 3 l. of water, and 2.5 l. of chloroform cooled to 5° C. is added simultaneously 1016 g. (4.0 moles) of 1-acetoxy-2-(5-acetoxy-pentyl)-1-cyclopentene (Example 56) and a solution of 648 g. (4.05 moles) of bromine in 500 ml. of carbon tetrachloride at a rate to maintain a temperature below 10° C. The mixture is stirred for half an hour after addition of the reagents and the phases are then separated. The organic phase is washed with 2% sodium thiosulfate solution, water, and saturated brine, dried (MgSO$_4$) and evaporated in vacuo to an oil. The oil is immediately added to a refluxing slurry of 500 g. (5.0 moles) of calcium carbonate in 2.5 l. of N,N-dimethylacetamide under nitrogen and the mixture is then refluxed for thirty minutes. The mixture is cooled, filtered, and partitioned between water and diethyl ether. The organic phase is washed with water and saturated brine, dried (MgSO$_4$), and evaporated to yield 757 g. of an oil, b.p. 116°–118° C. (0.25 mm.).

EXAMPLE 58

Preparation of 1-methoximino-2-(5-acetoxypentyl)-2-cyclopentene

In the manner described for Example 16, 2-(5-acetoxypentyl)-2-cyclopentenone (Example 57) is treated with methoxyamine hydrochloride in pyridine and ethanol to yield the subject compound, b.p. 101°–103° C. (0.20 mm.).

EXAMPLE 59

Preparation of 1-methoximino-2-(5-hydroxypentyl)-2-cyclopentene

A mixture of 74 g. (0.22 mole) of 1-methoximino-2-(5-acetoxypentyl)-2-cyclopentene (Example58) and 56 g. (1.0 mole) of potassium hydroxide in 300 ml. of 1:1 aqueous methanol is refluxed for 2 hours and then cooled. The solvent is partially removed in vacuo and the residue is partitioned between saturated brine and diethyl ether. The organic phase is washed with saturated brine, dried (MgSO$_4$), and evaporated to yield an oil which crystallized, m.p. 35°–36° C.

EXAMPLE 60

Preparation of 1-methoximino-2-(5-methanesulfonyloxypentyl)-2-cyclopentene

To a cold solution of 9.85 g. (0.05 mole) of 1-methoximino-2-(5-hydroxypentyl)-2-cyclopentene (Example 59) and 7.6 g. (0.075 mole) of triethylamine in 100 ml. of methylene chloride at −10° C. is added 6.3 g. (0.55 mole) of methanesulfonyl chloride at a rate to maintain a temperature of −10° to 0° C. The mixture is then stirred for 15 minutes and then poured into ice water. The organic phase is washed with cold 10% hydrochloric acid, cold saturated sodium bicarbonate solution, and cold saturated brine, dried (MgSO$_4$), and evaporated to yield a solid, m.p. 78°–80° C.

EXAMPLE 61

Preparation of 1-methoximino-2-(6,6-dicarbethoxyhexyl)-2-cyclopentene

To a suspension of sodiodiethylmalonate in 1,2-dimethoxyethane, prepared from 248 g. (1.55 moles) of diethyl malonate and 17.2 g. (0.95 mole) of mineral oil free sodium hydride in 1 l. of 1,2-dimethoxyethane under nitrogen, is added 170 g. (0.62 mole) of 1-methoximino-2-(5-methanesulfonyloxypentyl)-2-cyclopentene (Example 60) in 1.5 l. of 1,2-dimethoxyethane and the mixture is refluxed for 5 hours. The mixture is cooled, filtered, and the solvent is evaporated. The residue is partitioned between cold dilute hydrochloric acid and water, and the organic phase is washed with saturated brine, dried (MgSO$_4$), and evaporated to remove solvent and excess diethyl malonate to yield 209 g. of an oil.

EXAMPLE 62

Preparation of 1-methoximino-2-(6,6-dicarboxyhexyl)-2-cyclopentene

In the manner described in Example 20, 1-methoximino-2-(6,6-dicarbethoxyhexyl)-2-cyclopentene is treated with potassium hydroxide in 1:1 aqueous methanol and then hydrochloric acid to yield the desired compound as crystals from diethyl ether, m.p. 110°–115° C.

EXAMPLE 63

Preparation of 1-methoximino-2-(6-carboxyhexyl)-2-cyclopentene

A solution of 141 g. (0.50 mole) of 1-methoximino-2-(6,6-dicarboxyhexyl)-2-cyclopentene in 500 ml. of bis-(2- -methoxyethyl) ether is refluxed for 2 hours, cooled, and evaporated to yield an oil. The latter is crystallized from hexane to yield 92 g. of solid, m.p. 70°–72° C.

EXAMPLE 64

Preparation of 2-(6-carboxyhexyl)-2-cyclopentenone

In the manner described in Example 22, treatment of 1-methoximino-2-(6-carboxyhexyl)-2-cyclopentene (Example 63) with acetone and 2N hydrochloric acid at reflux provides the subject compound.

EXAMPLE 65

Preparation of 2-(6-carbethoxyhexyl)-2-cyclopentenone

Fischer estification of 2-(6-carboxyhexyl)-2-cyclopentenone (Example 64) in the manner of Example 23 provides the subject compound.

EXAMPLE 66

Preparation of 1-methoximino-2-(6-fluoro-6,6-dicarbethoxyhexyl)-2-cyclopentene

To a solution of sodiodiethyl fluoromalonate, prepared from 2.062 g. (0.0491 mole) of sodium hydride in mineral oil (57.26), 40 ml. of dry N,N-dimethylformanide and 8.174 g. (0.0458 mole) of diethyl fluoromalonate is added dropwise 11.32 g. (0.0413 mole) of 1-methoximino-2-(5-methylsulfonyloxypentyl)-2-cyclopentene (Example 60) in 60 ml. of N,N-dimethylformamide. The mixture is reluxed for 2 hours under a nitrogen atmosphere. The mixture is concentrated and partitioned between cold dilute hydrochloric acid and diethyl ether, and the organic phase is washed with saturated brine, dried (MgSO$_4$), and evaporated to yield 13.631 g. (92%) of a yellow oil.

EXAMPLE 67

Preparation of 1-methoximino-2-(6-fluoro,6,6-dicarboxyhexyl)-2-cyclopentene

A mixture of 13.631 g. of the diester of Example 66 and 16 g. of potassium hydroxide in 364 ml. of 1:1 aqueous methanol is refluxed for 5 hours, cooled, concentrated, and is partitioned between water and diethyl ether. The aqueous phase is acidified with hydrochloric acid, extracted with ether, and the organic phase is washed with saturated brine, dried (MgSO$_4$) and evaporated to yield a solid. The solid is crystallized from diethyl ether petroleum ether (30°–60° C.) to give 10 g. (90%) of white crystals, m.p. 143°–145° C. (-CO$_2$).

EXAMPLE 68

Preparation of 1-methoximino-2-(6-fluoro-6-carboxyhexyl)-2-cyclopentene

A solution of 10 g. of the diacid of Example 67 in 60 ml. of 2-methoxyethyl ether is refluxed for 7 hours, cooled, and evaporated to yield 8.5 g. (95%) of a tan solid. A sample is crystallized from diethyl ether-petroleum ether (30°–60° C.) to give white crystals, m.p. 98°–100° C.

EXAMPLE 69

Preparation of 2-(6-fluoro-6-carboxyhexyl)cyclopent-2-en-1-one

The acid methoxime (8.5 g.) from Example 68 is refluxed for 5 hours with 180 ml. of acetone and 64 ml. of 2N hydrochloric acid. The mixture is cooled, the solvent is evaporated, and the residue is partitioned between water and diethyl ether. The organic phase is washed with saturated brine, dried (MgSO$_4$) and evaporated to yield 7.4 g. (98%) of a light yellow oil.

EXAMPLE 70

Preparation of 2-(6-fluoro-6-carbethoxyhexyl)cyclopent-2-en-1-one

The acid ketone (7.4 g.) from Example 69 is Fisher esterified with 300 ml. of absolute ethanol and 400 mg. of p-toluenesulfonic acid for 18 hours, cooled, and the solvent is evaporated. The resulting oil is dissolved in ether, washed with dilute sodium bicarbonate solution, and saline, dried (MgSO$_4$), and evaporated to give 7.306 g. (86%) of a light yellow oil.

EXAMPLE 71

Preparation of 2-(7-cyanoheptyl)-1-methoximino-2-cyclopentene

Treatment of 1-methoximino-2-(7-p-toluenesulfonyloxy)-2-cyclopentene (Example 18) with sodium cyanide in the manner of Example 50 is productive of the subject compound.

EXAMPLE 72

Preparation of 2-(7-carboxyheptyl)-1-methoximino-2-cyclopentene

Alkaline hydrolysis of 2-(7-cyanoheptyl)-1-methoximino-2-cyclopentene (Example 71) by the procedure of Example 51 is productive of the subject compound.

EXAMPLE 73

Preparation of 2-(7-carboxyheptyl)-2-cyclopenten-1-one

Hydrolysis of the methoxime of Example 72 with acetone-hydrochloric acid by the procedure of Example 52 is productive of the subject compound.

EXAMPLE 74

Preparation of 2-(7-carbethoxyheptyl)-2-cyclopenten-1-one

Fisher estification of the carboxylic acid of Example 73 by the procedure of Example 53 is productive of the subject compound.

EXAMPLE 75

Preparation of 2-(6,6-dicarbethoxy-6-phenylhexyl)-1-methoximino-2-cyclopentene

Treatment of 1-methoximino-2-(5-methanesulfonyloxypentyl)-2-cyclopentene (Example 60) with sodio diethyl phenylmalonate by the procedure of Example 61 is productive of the subject compound.

EXAMPLE 76

Preparation of 2-(6,6-dicarboxy-6-phenylhexyl)-1-methoximino-2-cyclopentene

Alkaline hydrolysis of 2-(6,6-dicarbethoxy-6-phenylhexyl)-1-methoximino-2-cyclopentene (Example 75) by the procedure of Example 20 is productive of the subject diacid.

EXAMPLE 77

Preparation of 2-(6-carboxy-6-phenylhexyl)-1-methoximino-2-cyclopentene

Decarboxylation of 2-(6,6-dicarboxy-6-phenylhexyl)-1-methoximino-2-cyclopentene (Example 76) by the procedure of Example 63 is productive of the subject compound.

EXAMPLE 78

Preparation of 2-(6-carboxy-6-phenylhexyl)-2-cyclopentene-1-one

Methoxime cleavage of 2-(6-carboxy-6-phenylhexyl)-1-methoximino-2-cyclopentene (Example 77) in the manner of Example 69 is productive of the subject ketone.

EXAMPLE 79

Preparation of 2-(6-carbethoxy-6-phenylhexyl)-2-cyclopenten-1-one

Fisher esterification of the carboxylic acid of Example 78 in the manner of Example 70 is productive of the subject keto-ester.

EXAMPLE 80

Preparation of 2-(6-fluoro-6,6-dicarbethocyhexyl)-1-methoximino-2-cyclopentene

An ethanolic solution of sodium ethoxide, prepared from 0.389 g. of sodium and 40 ml. of absolute ethanol, is treated at ambient temperatures with 5.05 g. of 2-(6,6-dicarbethoxyhexyl)-1-methoximino-2-cyclopentene (Example 61). The resulting solution is cooled to −20° C. and then treated with a stream of perchloryl fluoride until the mixture becomes neutral. The excess perchloryl fluoride is removed with a stream of nitrogen and the mixture is retreated with 10 ml. of an ethanolic solution of sodium ethoxide (from 0.350 g. of sodium) and then with perchloryl fluoride until the mixture becomes neutral. The excess perchloryl fluoride is removed with a stream of nitrogen and the mixture is filtered and evaporated to an oil. The latter is partitioned between ether and water and the organic phase is washed with saturated saline, dried ($Na_2SO_4$) and evaporated to afford the subject compound.

EXAMPLE 81

Preparation of 2-(6-carbo-n-butoxyhexyl)cyclopent-2-en-1-one

A solution of 50 g. of 2-(6-carboxyhexyl)cyclopent-2-en-1-one [Bagli et al., Tetrahedron Letters, No. 5, 465 (1966)] in 1400 ml. of n-butanol containing 2.7 g. of p-toluenesulfonic acid monohydrate is allowed to stand at room temperature in a stoppered flask for about 24 hours. The solution is taken to dryness. The residue is taken up in ether and the ethereal solution is washed several times with saline solution, dried with anhydrous magnesium sulfate, and taken to dryness to afford the subject butyl ester.

EXAMPLES 82-84

Treatment of 2-(6-carboxyhexyl)cyclopent-2-en-1-one by the procedure of Example 81 with the appropriate alcohol affords the esters of the following table.

TABLE IV

| Ex. | Alcohol | Product Ester |
|---|---|---|
| 82 | isopropanol | 2-(6-carboisopropoxyhexyl)cyclopent-2-en-1-one |
| 83 | methanol | 2-(6-carbomethoxyhexyl)cyclopent-2-en-1-one |
| 84 | 1-hydroxy-n-decane | 2-(6-carbo-n-decyloxyhexyl)cyclopent-2-en-1-one |

EXAMPLE 85

Preparation of diethyl (5-chloro-1,1-dimethylpentyl)malonate

To magnesium (71 g. 2.92 moles) under 1 l. of ether containing a few crystals of iodine is added dropwise 1-chloro-4-bromobutane (500 g., 2.92 moles) over a period of 30 minutes with stirring under nitrogen. The reaction is maintained at a temperature of 0° C. to 5° C. by immersing in an acetone-Dry Ice bath periodically. After stirring for 30 minutes at room temperature, the solution is chilled to below 0° C. and is then transferred to a dropping funnel from which it is added dropwise to diethyl isopropylidene malonate (440 g., 2.19 moles) [A. C. Cope and E. M. Hancock, J.A.C.S. 60, 2644 (1938)] dissolved in 1000 ml. of ether containing the tri(n-butyl)phosphine complex of copper (I) iodide (57g.) [G. B. Kaufman and L. A. Teter, Inorganic Synthesis, 7, 9(1963)] at −10° C. with stirring under nitrogen over a period of two hours. After stirring at room temperature for four hours, the reaction mixture is poured into cold dilute hydrochloric acid and is extracted with ether. The combined ether extracts are washed with saline solution, dried over magnesium sulfate, and concentrated in vacuo to give 700 g. of crude amber oil, which is distilled under vacuum to yield two fractions: 212.4 g. with b.p. at 110°-135° C. at 0.3 mm. and 100.0 g. with b.p. at 135°-145° C. at 0.3 mm. The total yield is 312.4 g. (49%).

EXAMPLE 86

Preparation of 3,3-diemethyl-7-chloroheptanoic acid

A mixture containing diethyl 5-(5-chloro-1,1-dimethylpentyl)malonate (648 g., 2.22 moles) potassium hydroxide (460 g.) and eight liters of 1:1 isopropanol: water is stirred at room temperature overnight. Most of the isopropanol is distilled and the residue is diluted with water, and then carefully acidified with conc. hydrochloric acid. The mixture is extracted with ether and the extracts are washed with water and saline, dried over magnesium sulfate and concentrated in vacuo to give 548 g. of crude oil. The oil is dissolved in three liters of diglyne which is heated under reflux for sixteen hours. About 2.7 l. of solvent is distilled, and the remainder is diluted with water and extracted with ether. The extracts are washed with saline, dried over magnesium sulfate and concentrated in vacuo to give 428 g. of crude oil (99%).

EXAMPLE 87

Preparation of ethyl 3,3-dimethyl-7-chloroheptanoate

To a solution of 3,3-dimethyl-7-chloroheptanoic acid (428 g., 2.21 moles) in 3 l. of chloroform containing 3 ml. of N,N-dimethylformamide is added 500 ml. of thionyl chloride and the resulting solution is tested under reflux for three hours. The reaction solution then is concentrated in vacuo and the residual acid chloride is dissolved in a minimum amount of benzene and added slowly to a solution containing 1260 ml. of 95% ethanol and 2520 ml. of benzene and 390 ml. of collidine. After heating under reflux for one hour, the solution is concentrated and the residue is dissolved in ether washed with water, dilute sodium bicarbonate solution and saline solution, dried over magnesium sulfate and concentrated to give 415 g. of crude oil, which is distilled under vacuum to yield two fractions: 46.6 g. boiling at 75° C. (0.3 mm.) and 236.7 g. boiling at 75°-80° C. (0.3 mm). The total yield is 283.3 g. (60%) and the product is indicated to be 95% pure by g.l.c.

EXAMPLE 88

Preparation of methyl/ethyl 2-(6-carbethoxy-5,5-dimethylhexyl) cyclopentanone-2-carboxylate Sodium hydride (67 g., 1.55 moles) is placed in a three l. round-bottom flask and to this is added 1.1 liters of glyme from a dropping funnel under nitrogen flow and with stirring. To the resulting grayish mixture is added the 2-carbalkoxycyclopentanone (mixed methyl and ethyl esters) dropwise over a period of 45 minutes with nitrogen flow whilst the temperature is maintained in the range of 40°-55°. Ethyl 3,3-dimethyl-7-chloroheptanoate (283 g., 1.28 moles) and potassium iodide (195 g., 1.32 moles) are added and the mixture is heated at reflux overnight. After most of the solvent is distilled, the residue is made acidic with dilute hydrochloric acid and is then extracted with ether. The ether extracts are washed with water and saline solution, dried over magnesium sulfate, and concentrated in vacuo to 500 g. of crude yellow oil, which is distilled to give 405 g. (94% yield) of oil with b.p. 140°–180° (0.8 mm).

EXAMPLE 89

Preparation of 7-(2-Cyclopentanone)-3,3 dimethylheptanoic acid

Methyl/Ethyl 2-(6-carbethoxy-5,5-dimethylhexyl) cyclopentanone-2-carboxylate (200 g., 0.6 moles), glacial acetic acid (180 ml) and 240 ml. of diluted hydrochloric acid, prepared from 100 ml. of conc. hydrochloric acid and 300 ml. of water, are placed in a 2 l. flask, containing a reflux condenser and a magnetic stirrer. The mixture then is stirred at reflux for 24 hours. The reaction mixture is cooled, 1 l. of water is added and the mixture is extracted several times with benzene. The organic extracts are combined, washed with saturated sodium chloride solution, dried over magnesium sulfate, filtered and concentrated to an oil (173.5 g.). The oil is rendered basic with sodium hydroxide solution, extracted with benzene and made acidic with hydrochloric acid and reextracted with benzene several times. The benzene layers are combined and washed with water, saturated sodium chloride solution, dried over magnesium sulfate, filtered and concentrated to yield 109.8 g. (78%) of crude oil, which was used without further purification in the next step.

EXAMPLE 90

Preparation of Ethyl 7-(2-Cyclopentanone)-3,3-dimethylheptanoate

To a solution of 7-(2-cyclopentanone)-3,3-dimethylheptanoic acid (45 g., 0.22 mol.) in 285 ml. of chloroform containing three drops of N,N-dimethylformamide is added dropwise 25 ml. of thionyl chloride. The solution is stirred at room temperature for twenty minutes, the solvent is removed at reduced pressure and the residual acid chloride is dissolved in a minimum amount of benzene and added slowly to a solution containing 115 ml. of ethanol, 230 ml. benzene and 30 ml. of collodine. This solution is heated under reflux for 15 minutes and then concentrated. The residue is dissolved in ether, washed with water, diluted sodium bicarbonate solution and saline solution, dried over magnesium sulfate and concentrated to give 51 g. of crude oil. Distillation gives 40 g. (67%) b.p. 135°–145° (0.1 mm.) of oil.

EXAMPLE 91

Preparation of 1-Acetoxy-2-(6-carbethoxy-5,5-dimethylhexyl)cyclopent-1-ene

A solution of ethyl 7-(2-cyclopentanone)-3,3-dimethylheptanoate (90 g., 0.336 mol.) and p-toluenesulfonic acid (0.94 g.) in 250 ml. of acetic anhydride is heated to boiling under partial reflux, allowing distillate at 118° or less (i.e. acetic acid) to escape thru a Vigreux column equipped with a condenser to collect the distillate. After ten hours 130 ml. of distillate is collected. Another 50 ml. of acetic anhydride is added and the reaction is heated for five more hours; an additional 125 ml. of acetic anhydride is added, the reaction is heated for seven more hours; finally another 50 ml. of acetic anhydride is added and heating is continued for 4 more hours. The solution is cooled and poured (cautiously) into a cold (0°–5°) mixture of saturated aqueous sodium bicarbonate (400 ml.) and hexane (250 ml.). The resulting cold mixture is stirred for thirty minutes during which time portions of solid sodium bicarbonate are added periodically until carbon dioxide evalution ceases. The hexane layer is separated and washed with saturated sodium chloride solution until the washings are neutral, dried over magnesium sulfate and treated with Darco decolorizing charcoal for clarification and then evaporated to dryness leaving an amber colored oil (87.5 g., 84%).

EXAMPLE 92

Preparation of 2-(6-Carboxy-5,5-dimethylhexyl)cyclopent-2-en-1-one

To a rapidly stirred mixture of 1-acetoxy-2-(6-carbethoxy-5,5-dimethylhexyl)cyclopent-1-ene (35 g., 0.113 mole) chloroform (95 ml.), water (125 ml.) and calcium carbonate (11.8 g.) cooled in an ice-bath is added dropwise over a period of thirty minutes a solution of bromine (18.8 g.) in carbon tetrachloride (31 ml.) After stirring in the cold for an additional 45 minutes the orange colored chloroform layer is separated and washed with dilute sodium bisulfite and saturated saline solution, dried over magnesium sulfate and taken to dryness in vacuo (bath temperature: 35°–40°) leaving an amber colored oil. A slurry of 100 ml. of N,N-dimethylacetamide and 16.5 g. of $CaCO_3$ is stirred and heated to reflux under nitrogen flow. The above dried oil is added from a dropping funnel rapidly, maintaining reflux and nitrogen flow for thirty minutes. The cooled reaction mixture is filtered, and the precipitate is washed with other. The filtrate is poured into two liters ice-cold water and is extracted with ether. The combined extracts and washing is washed with water, saturated saline, treated with decolorizing charcoal, filtered. The solvent evaporated in vacuo to give 24 g. (77%) of subject product.

EXAMPLE 93

Preparation of 4-bromo-2(6-carboxyhexyl)cyclopent-2-en-1-one

A stirred mixture of 35.9 g. (0.171 moles) of 2-(6-carboxyhexyl)cyclopent-2-en-1-one [Bagli et al., Tetrahedron Letters, No. 5, 465 (1966)], 35.0 g. (0.197 moles) of N-bromosuccinimide, and 600 ml. of carbon tetrachloride is refluxed for 35 minutes. The mixture is cooled to 5° C. and filtered. The filtrate is washed with cold water, dried over magnesium sulfate, and taken to dryness to give an oil, $\lambda_{max}^{MeOH} = 225$ mµ (8850); νmax. = 1705 (carbonyl groups) and 1625. $cm^{-1}$ (olefin group).

EXAMPLE 94

Preparation of 2-(6-carboxyhexyl)-4-hydroxy-cyclopent-2-en-1-one

To a stirred solution of 10.6 g. (ca. 34 mmoles) of crude 4-bromo-2-(6-carboxyhexyl)cyclopent-2-en-1-one (Example 93) in 100 ml. of acetone and 65 ml. of water is added 8.80 g. (45.2 mmoles) of silver fluoborate during 2 minutes. The temperature is maintained at 25°–30° C. by external cooling. The mixture is stirred for 90 minutes, filtered, saturated with sodium chloride, and extracted with ether. The extract is extracted with half saturated sodium bicarbonate solutions. The basic solutions is reacidified with dilute hydrochloric acid, saturated with sodium chloride, and extracted with ether. The extract is washed with water and saturated sodium chloride solution, dried over magnesium sulfate, and concentrated. The crude product is purified by partition chromatography on Celite to give an oil; $\lambda_{max.}^{MeOH}$ = 233 mµ (7360); ν max. = 3380 (hydroxyl groups), 1710 (carbonyl groups), and 1632 cm$^{-1}$ (olefin group).

EXAMPLE 95

Preparation of 4-tetrahydropyranyloxy-2-(6-tetrahydropyranylcarboxyhexyl)cylopent-2-en-1-one To a stirred solution of 5.59 g. (24.6 mmoles) of 4-hydroxy-2-(6-carboxyhexyl)cylopent-2-en-1-one (Example 94) and 20.7 g. (246 mmoles) of dihydropyran in 100 ml. of methylene chloride at 20° C. is added 47 mg. (0.246 mmoles) of p-toluenesulfonic acid monohydrate in one portion. The temperature is maintained at 20°-25° C. by cooling and is stirred for one hour at that temperature. The solution is diluted with 200 ml. of ether and poured into a mixture of 40 ml. of saturated sodium bicarbonate solution, 40 ml. of saturated sodium chloride solution, and 80 ml. of water. The phases are separated, and the aqueous phase is extracted with additional ether. The total extract is washed successively with water and saturated sodium chloride solution, dried over potassium carbonate, and freed of volatile matter by concentration at reduced pressure to give an oil, $\lambda_{max.}^{MeOH}$ = 223 mµ (9500); ν max. 1730 (ester carbonyl group), 1705 (ketone carbonyl group), and 1030 cm$^{-1}$ (tetrahydropyranyloxy groups).

EXAMPLE 96

Preparation of 2-(6,6-dicarbethoxyheptyl)-2-cyclopentenone methoxime

The subject compound is prepared from sodio diethyl methylmalonate and 2-(5-methanesulfonyloxypentyl)-2-cyclopentenone methoxime (Example 60) by the procedure described in Example 61.

EXAMPLE 97

Preparation of 2-(6-carboxyheptyl)-2-cyclopentenone methoxime

Saponification of 2-(6,6-dicarbethoxyheptyl)-2-cyclopentenone methoxime (Example 96) with potassium hydroxide by the method of Example 20 is productive of 2-(6,6-dicarboxyheptyl)-2-cyclopentenone methoxime, decarboxylation of which in the manner of Example 63 provides the subject compound.

EXAMPLE 98

Preparation of 2-(6-carboxyheptyl)-2-cyclopentenone

Methoxime cleavage of 2-(6-carboxyheptyl)-2-cyclopentenone methoxime (Example 97) in the manner of Example 22 provides the subject ketone.

EXAMPLE 99

Preparation of 2-(6-carbethoxyheptyl)-2-cyclopentenone

Esterification with ethanol of the acid chloride derived from 2-(6-carboxyheptyl)-2-cyclopentenone in the manner of Example 31 is productive of the subject compound.

EXAMPLE 100

Preparation of ethyl (methyl)7-(2-carbethoxycyclohexan-1-on-2-yl)heptanoate

To a stirred suspension of 51 g. of sodium hydride (57% in mineral oil) in 675 ml. of dimethylformamide is added 200 g. of 2-cyclohexanone carboxylate (60% ethyl - 40% methyl esters) over a 1-5 hr. period with external cooling to maintain the temperature at 20°-25° C. The reaction mixture is stirred at ambient temperature for 15 minutes and heated to 50° C. over 15 minutes. To the stirred mixture is added 300 g. of ethyl 7-bromoheptanoate during a 10 minute period. The reaction mixture is stirred at 50°-60° C. for 4 hours, cooled, and poured into water. The product is obtained by ether extraction. The extract is washed successively with water and saturated sodium chloride, dried and evaporated to give a liquid which is purified by distillation, IR 1735 cm$^{-1}$ (ester carbonyls) and 1710 cm$^{-1}$ (ketone carbonyl).

EXAMPLE 101

Preparation of 7-(cyclohexan-1-on-2-yl)heptanoic acid

A stirred mixture of 380 g. of mixed methyl and ethyl esters of 7-(2-carbethoxycyclohexan-1-on -2-yl)heptanoate (Example 10), 202 ml. of concentrated sulfuric acid, 970 ml. of glacial acetic acid, and 970 ml. of water is refluxed for 22.5 hours. The cooled reaction mixture is treated with 380 g. of sodium carbonate and 2 liters of water and is extracted with ether. Acidic material is partitioned from the ether extract with 1.0M sodium carbonate. The aqueous phase is acidified with concentrated hydrochloric acid and extracted with ether. The extract is washed successively with water and saturated sodium chloride, dried, and evaporated to give an oil.

EXAMPLE 102

Preparation of ethyl 7-(cyclohexan-1-on-2-yl)heptanoate

A solution of 232 g. of 7-(cyclohexan-1-on-2yl)heptanoic acid in 2500 ml. of ethanol is refluxed for 4.5 hours with 3.8 g. of p-toluenesulfonic acid monohydrate. The solution is diluted with 200 ml. of benzene, and boiling is continued for 2 hours as 200 ml. of distillate is removed. The volume of the solution is concentrated to 500 ml. After dilution with 500 ml. of ether the solution is extracted with a solution prepared from 50 ml. of saturated sodium bicarbonate, 50 ml. of saturated sodium chloride, and 100 ml. of water. The extract is washed with saturated sodium chloride, dried, and evaporated. The product is purified by distillation to give a liquid, IR 1740 cm$^{-1}$ (ester carbonyl) and 1715 cm$^{-1}$ (ketone carbonyl).

EXAMPLE 103

Preparation of 2-carbalkoxy (methyl/ethyl)-2-(3-carbethoxypropyl)-cyclohexane-1-one The subject compound is prepared in the manor described in Example 10 by treatment of 2-cyclohexanone carboxylate (mixed methyl and ethyl esters) with sodium hydride and ethyl4-iodobutyrate.

EXAMPLE 104

Preparation of 2-(3-carbethoxypropyl)cyclohexan-1-one

This compound is prepared from 2-carbalkoxy(methyl/ethyl)-2-(carbethoxypropyl)cyclohexan-1-one (Example 13) by decarbalkoxylation according to the procedure described in Example 11 followed by esterification by the procedure of Example 12.

EXAMPLE 105

Preparation of 2-(5-carbethoxypentyl)cyclohexan-1-one

This compound is prepared by alkylation of 2-cyclohexanone carboxylate (mixed methyl and ethyl esters) with ethyl 6-bromohexanoate according to the procedure of Example 10, followed by decarbalkoxylation according to the procedure of Example 11 and finally esterification by the procedure of Example 12.

EXAMPLE 106

Preparation of 2-(7-carbethoxyheptyl)cyclohexan-1-one

Alkylation of 2-cyclohexanone carboxylate (mixed methyl and ethyl esters) with ethyl 8-bromoctanote in accordance with the procedure of Example 10, followed by decarbalkoxylation by the procedure of Example 11 and then esterification by the procedure of Example 12 is productive of the subject compound.

EXAMPLE 107

Preparation of ethyl 7-(1-acetoxycyclohex-1-en-2-yl)heptanoate

A stirred solution of 28.0 g. of ethyl 7-(cyclohexan-1-on-2-yl)heptanoate (Example 12), 170 mg. of p-toluenesulfonic acid monohydrate, and 25.6 g. of acetic anhydride is heated for 5 hours while allowing 8.0 g. of distillate to distill. The cooled solution is poured into a stirred, ice-cold mixture of 500 ml. of saturated sodium bicarbonate and 250 ml. of hexane. After one hour the hexane phase is separated, dried, and evaporated. The crude product is distilled to give a liquid, IR 1760 cm$^{-1}$ (vinyl ester carbonyl) and 1740 cm$^{-1}$ (ethyl ester carbonyl).

EXAMPLE 108

Preparation of 1-acetoxy-2-(3-carbethoxypropyl)cyclohex-1-ene

Treatment of 2-(3-carbethoxypropyl)cyclohexane-1-one (Example 14) with acetic anhydride by the procedure of Example 24 is productive of the subject compound.

EXAMPLE 109

Preparation of 1-acetoxy-2-(5-carbethoxypentyl-cyclohex-1-ene

Treatment of 2-(5-carbethoxypentyl)cyclohexan-1-one (Example 15) with acetic anhydride by the procedure of Example 24 is productive of the subject compound.

EXAMPLE 110

Preparation of 1-acetoxy-2-(7-carbethoxyheptyl)cyclohex-1-ene

Treatment of 2-(7-carbethoxyheptyl)cyclohexan-1-one (Example 16) with acetic anhydride by the procedure of Example 24 is productive of the subject compound

EXAMPLE 111

Preparation of ethyl 7-(cyclohex-2-en-1-one-2-yl)heptanoate

To a stirred solution of ethyl 7-(1-acetoxycyclohex-1-en-2-yl)heptanoate (Example 24) in 750 ml. of acetic acid and 125 ml. of pyridine at 10° C. is added a solution of 13.8 g. of bromine in 200 ml. of acetic acid over 20 minutes. The resulting solution is allowed to stand at ambient temperature for 45 minutes and is then decolorized with sodium sulfite. The solution is poured into 800 ml. of half-saturated sodium chloride and extracted with 1:1 hexane-ether. The extract is washed successively with water and saturated sodium chloride, dried over sodium carbonate, and evaporated to give 32 g. of the crude bromoketone. To a stirred suspension of 14.2 g. of lithium bromide and 16.6 g. of lithium carbonate in 250 ml. of anhydrous dimethylformamide at 80° C. is added the above bromoketone. The stirred mixture is heated to boiling over 20 minutes and refluxed for 15 minutes. The cooled mixture is poured into 1000 ml. of water, acidified with dilute hydrochloric acid, and extracted with ether. The extract is washed successively with water and saturated sodium chloride, dried, and evaporated. The product is purified by distillation to give a liquid, IR 1740 cm$^{-1}$ (ester carbonyl), 1685 cm$^{-1}$ (ketone carbonyl), and 1650 cm$^{-1}$ (olefin); NMR (CCl$_4$) 6.63 (multiplet, vinyl proton).

EXAMPLE 112

Preparation of 2-(3-carbethoxypropyl)cyclohex-2-en-1-one

In accordance with the procedure of Example 40, bromination of 1-acetoxy-2-(3-carbethoxypropyl)cyclohex-1-ene (Example 25) followed by treatment with lithium bromide and lithium carbonate is productive of the subject compound.

EXAMPLE 113

Preparation of 2-(5-carbethoxypentyl)cyclohex-2-en-1-one

By the procedure of Example 40, bromination of 1-acetoxy-2-(5-carbethoxypentyl)cyclohex-1-ene (Example 26) followed by treatment with lithium bromide and lithium carbonate is productive of the subject compound.

EXAMPLE 114

Preparation of 2-7-carbethoxyheptyl)cyclohex-1-en-2-one

By the procedure of Example 40, bromination of 1-acetoxy-2-(7-carbethoxyheptyl)cyclohex-1-ene (Example 27)followed by treatment with lithium bromide and lithium carbonate is productive of the subject compound.

EXAMPLE 115

Preparation of 2-(4-p-toluenesulfonyloxybutyl)-1-methoximino-2-cyclopentene

In the manner described in Example 34, treatment of 2-(4-hydroxybutyl)-1-methoximino-2-cyclopentene with p-toluene sulfonyl chloride in pyridine gives the subject product as a light yellow oil; IR (film): 1600, 1190, 1050, 885 cm$^{-1}$.

EXAMPLE 116

Preparation of 2-(6-carbethoxy-5-thiahexyl)-1-methoximino-2-cyclopentene

To a stirred mixture of 1.465 g. (0.0348 mole) of sodium hydride (57.2% in mineral oil) in 50 ml. of dimethoxyethane, under nitrogen, is added slowly 4.8 g. (0.0347 mole) of ethyl-2-mercaptoacetate. The reaction mixture is stirred at room temperature for one hour and then a solution of 7.8 g. (0.0231 mole) of 2-(4-p-toluenesulfonyloxybutyl)-1-methoximino-2-cyclopentene in 30 ml. of dimethoxyethane is added dropwise and stirred at room temperature for 18 hours. The solution is heated at reflux for one hour, cooled and poured into cold dilute hydrochloric acid and then extracted with ether. The combined ether extracts are washed with saline, dried over magnesium sulfate and evaporated to give 7.6 g. of subject product as a yellow oil.

EXAMPLE 117

Preparation of 2-(6-carboxy-5-thiahexyl)-2-cyclopentenone

In the manner described in Example 38, treatment of 2-(6-carbethoxy-5-thiahexyl)-1-methoximino-2-cyclopentene with acetone and 2N hydrochloric acid at reflux gives the subject product as a yellow oil.

EXAMPLE 118

Preparation of 2-(6-carbethoxy-5-thiahexyl)-2-cyclopentenone

In the manner described in Example 39, treatment of 2-(6-carboxy-5-thiahexyl)-2-cyclopentenone with p-toluenesulfonic acid in ethanol gives the subject ester as a yellow oil.

EXAMPLE 119

Preparation of 3-triphenylmethoxy-1-octyne

A mixture of 1.26 g. (10.0 mmoles) of 1-octyn-3-ol, 4.85 g. (15.0 mmoles) of triphenylmethyl bromide, and 50 ml. of dry pyridine is heated at 95° C. for 60 minutes with occasional swirling. The solution is cooled, treated with water, and extracted with ether. The extract is washed successively with water and saturated sodium chloride solution, dried over magnesium sulfate, and concentrated. The crude product is purified by chromatography on Florisil and recrystallization from petroleum ether to give white crystals, m.p. 65–66.5°, $\nu$ max. (KBr) 3280 (acetylenic hydrogen), 1605, 1030, and 702 cm$^{-1}$ (triphenylmethoxy group).

EXAMPLE 120

Preparation of ethyl 9-oxo-15-triphenylmethoxy-13-trans-8ξ-prostenoate

A stirred solution of 7.37 g. (20.0 mmoles of 3-triphenylmethoxy-1-octyne (Example 119) in 10 ml. of benzene is treated with 16.7 mg. of 1.2 M diisobutylaluminum hydride in hexane, and the resulting solution is heated at 50° C. for 2 hours. The solution is cooled to 0° C. and treated with 10.5 ml. of 1.7 M methyl lithium in ether. After stirring for a 20 minute period at ambient temperature, the alanate solution is cooled to 0° C. and treated with a solution of 3.98 g. (16.7 mmoles) of 2(6-carbethoxyhexyl)cyclopent-2-en-1-one (Example 13) in 5 ml. of ether. The resulting solution is stirred at ambient temperature for 22.5 hours, diluted with ether, and poured into a stirred mixture 2N acetic acid and ice. After stirring until methane evolution ceases, the organic phase is separated and washed successively with water and saturated sodium chloride solution. The extract is dried over magnesium sulfate and concentrated. The crude product in the residue is purified by chromatography on silica gel to give an oil, $\nu$ max. 1735 (carbonyl groups), 967 (trans vinyl group), and 705 cm$^{-1}$ (triphenylmethoxy group).

EXAMPLE 121

Preparation of ethyl 15-hydroxy-9-oxo-13-trans-prostenoate

A 0.05M solution of ethyl 9-oxo-15-triphenylmethoxy-13-trans-8$\nu$-prostenoate (Example 120) in glacial acetic acid-tetrahydrofuran-water (4:2:1) is heated at 45° C. for 3.5 hours. The solvents are evaporated at reduced pressure, and the residue is dissolved in ether. The solution is washed successively with water, 0.5N sodium bicarbonate solution, and saturated sodium chloride solution; dried over magnesium sulfate; and concentrated. Column chromatography of the crude product on silica gel gives two epimeric substances which are purified separately by thin layer chromatography to give oils differing only in chromatographic behavior, 84 max. 3470 (hydroxyl group), 1735 (carbonyl groups), and 967 cm$^{-1}$ (trans vinyl group).

EXAMPLE 122

Preparation of 15-hydroxy-9-oxo-13trans-prostenoic acid

A solution of 2 g. of ethyl 15-hydroxy-9-oxo-13,14-trans-prostenoate (Example 121) (mixture of racemates) in 32 ml. of methanoal-water (1:1), containing 850 mg. of potassium hydroxide is stirred at ambient temperature for 18 hours. After acidification with 10% hydrochloric acid, the solution is extracted with ether several times. The combined ether extracts are washed with saturated sodium chloride solution, dried with anhydrous magnesium sulfate and taken to dryness to give 1.69 g. (92%) of an oil which partially crystallizes. Recrystallized from etherhexane gives white crystals, m.p. 79°–81° C,; nmrδ6.36 (s, hydroxyl and carboxyl groups), 5.61 (t, olefinic protons), 4.12 (s, c$_{15}$-H) and 0.90 (s, terminal methyl).

EXAMPLE 123

Preparation of tetrahydropyran-2-yl 9-oxo-11-tetrahydropyranyloxy-15-triphenylmethoxy-13-trans-8ξ-prostenoate In the manner described in Example 120, 13.6 g. (37 mmoles) of 3-triphenylmethoxy-1-octyne (Example 119)contained in 18.5 ml. of benzene is converted to an alanate reagent by treatment with 31 ml. of 1-2m diisobutylaluminum hydride in hexane and 21 ml. of 1.7m methyl lithium in ether. To the stirred, ice-cold reagent is added a solution of 10.97 g. (24.6 mmoles) of 2-(6-tetrahydropyranylcarboxyhexyl)-4-tetrahydropyranyloxycyclopent-2-en-1-one (Example 95) in 10 ml. of ether during 10 minutes. The resulting solution is stirred at ambient temperature for 20 hours, diluted with ether, and poured into a stirred mixture of 2N hydrochloric acid and ice. The organic phase is separated and washed successively with water and saturated sodium chloride solution. The extract is dried over magnesium sulfate, and the solvents are evaporated at reduced pressure to give the crude product as an oil, $\nu$ max. 1735 (carbonyl groups), 1030 (tetrahydropyranyloxy groups), 970 (trans vinyl group), and 705 cm$^{-1}$ (triphenylmethoxy group).

EXAMPLE 124

Preparation of 11,15-dihydroxy-9-oxo-13-trans-prostenoic acids

A 0.05M solution of crude tetrahydropyran-2-yl 9-oxo-11-tetrahydropyranyloxy-15-triphenylmethoxy-13-trans-prostenoate (Example 123) in glacial acetic acid-tetrahydrofuran-water (4:2:1) is heated at 45° C. for 3.5 hours. The solution is diluted with water and extracted with ether. The extract is washed successively with water and saturated sodium chloride solution and dried over magnesium sulfate. The solvents are removed at reduced pressure. Column chromatography of the residue on acid-washed silica gel gives the title compounds as a pair of epimeric substances which are purified separately by partition chromatography.

The fast-running epimer (15-epi-d,1-prostaglandin E$_1$) is obtained as an oil, $\nu$ max, 1735 (ketone carbonyl group), 1710 acid carbonyl group), and 967 cm$^{-1}$ (trans vinyl group); NMR (acetone-d$_e$) 5.68 (multiplet vinyl hydrogen) and 4.11$\delta$ (multiplet, carbinolic hydrogens.)

The slow-running epimer (d,1-prostaglandin E$_1$) is recrystallized from ethyl acetate-petroleum ether to give white crystals, m.p. 100°–105° C., $\nu$ max. (KBr) 1725 (ketone carbonyl group), 1700 (acid carbonyl group), and 970 cm$^{-1}$ (trans vinyl group); NMR (acetone-d$_e$) 5.67 (multiplet, vinyl hydrogens) and 4.12 (multiplet, carbinolic hydrogens).

EXAMPLES 125 to 139

In accordance with the method described in Example 119, the various 3-hydroxy-1-alkynes listed in the table below are converted to the corresponding 3-triphenylmethoxy-1-alkynes by treatment with triphenylmenthyl bromide.

TABLE

| | | |
|---|---|---|
| 125 | 1-heptyn-3-ol | 3-triphenylmethoxyheptyne-1 |
| 126 | 1-hexyn-3-ol | 3-triphenylmethoxy-hexyne-1 |
| 127 | 1-pentyn-3-ol | 3-triphenylmethoxy-pentyne-1 |
| 128 | 1-nonyne-3-ol[a] | 3-triphenylmethoxy-nonyne-1 |
| 129 | 1-decyne-3-ol[b] | 3-triphenylmethoxy-decyne-1 |
| 130 | 4-ethyl-1-octyne-3-ol | 3-triphenylmethoxy-4-ethyl-octyne-1 |
| 131 | 4-ethyl-1-hexyne-3-ol | 3-triphenylmethoxy-4-ethyl-hexyne-1 |
| 132 | 4-methyl-1-heptyne-3-ol | 3-triphenylmethoxy-4-methyl-heptyne-1 |
| 133 | 4-methyl-1-pentyne-3-ol | 3-triphenylmethoxy-4-methyl-pentyne-1 |
| 134 | 7-methyl-6-en-1-octyne-3-ol[c] | 3-triphenylmethoxy-7-methyl-6-en-octyne-1 |
| 135 | 6,7-dimethyl-6-en-1-octyne-3-ol[c] | 3-triphenylmethoxy-6,7-dimethyl-6-en-octyne-1 |
| 136 | 7-isobutyl-6-en-1-octyne-3-ol[c] | 3-triphenylmethoxy-7-isobutyl-6-en-1-octyne-1 |
| 137 | 5-en-1-hexyne-3-ol[d] | 3-triphenylmethoxy-5-en-hexyne-1 |
| 138 | 5,9-dimethyl-9-en-1-decyne-3-ol[e] | 3-triphenylmethoxy-5,9-dimethyl-9-en-decyne-1 |
| 139 | cis-5-en-1-octyne-3-ol[f] | 3-triphenylmethoxy-cis-5-en-octyne-1 |

References:
[a] M. Bertrand, Bull. Soc. Chim. France, 461 (1956).
[b] F. Bohlmann and D. Ratz, Chem. Ber., 90, 2265 (1957).
[c] U.S. Pat. No. 3,452,105 (June 24, 1969); Chem. Abs., 71, 60678 (1969).
[d] A. Viola and J. H. MacMillan, Jour. Amer. Chem. Soc., 92, 2404 (1970).
[e] Sequin, Bull. Soc. Chim. France, 12, 948 (1945).
[f] J. Fried et al., Jour. Amer. Chem. Soc., 94, 4342 (1972).

EXAMPLES 140–256

Treatment of the cycloalkenone designated in the table below with the alanate prepared by treatment of the listed 3-triphenylmethoxy-1-alkyne with diisobutyl aluminum hydride followed with methyl lithium, all by the procedure described in Example 120, is productive 9-oxo-15-triphenylmethoxy-13-trans-8-$\xi$-prostenoates of the table.

Table 3

| Example | Starting Cycloalkenone of Example | Starting 3-triphenyl-methoxy-1-alkyne of Example | Product Alkyl 9-oxo-15-triphenylmethoxy-13-trans-8$\xi$-prostenoate |
|---|---|---|---|
| 140 | 14 | 119 | ethyl 9-oxo-15-triphenylmethoxy-5,6,7-trinor-13-trans-8$\xi$-prostenoate |
| 141 | 23 | 119 | ethyl 9-oxo-15-triphenylmethoxy-7a,7b-bis-homo-13-trans-8$\xi$-prostenoate |
| 142 | 31 | 119 | ethyl 9-oxo-15-triphenylmethoxy-2-ethyl-13-trans-8$\xi$-prostenoate |
| 143 | 41 | 119 | ethyl 9-oxo-15-triphenylmethoxy-3,3-dimethyl-13-trans-8$\xi$-prostenoate |
| 144 | 46 | 119 | ethyl 9-oxo-15-triphenylmethoxy-3-oxa-13-trans-8$\xi$-prostenoate |
| 145 | 53 | 119 | ethyl 9-oxo-15-triphenylmethoxy-7-nor-13-trans-8$\xi$-prostenoate |
| 146 | 70 | 119 | ethyl 9-oxo-15-triphenylmethoxy-2-fluoro-13-trans-8$\xi$-prostenoate |
| 147 | 74 | 119 | ethyl 9-oxo-15-triphenylmethoxy-7a-homo-13-13-trans-8$\xi$-prostenoate |
| 148 | 79 | 119 | ethyl 9-oxo-15-triphenylmethoxy-2-phenyl-13-trans-8$\xi$-prostenoate |
| 149 | 99 | 119 | ethyl 9-oxo-15-triphenylmethoxy-2-methyl-13-trans-8$\xi$-prostenoate |
| 150 | 111 | 119 | ethyl 9-oxo-15-triphenylmethoxy-10a-homo-13-trans-8$\xi$-prostenoate |
| 151 | 112 | 119 | ethyl 9-oxo-15-triphenylmethoxy-10a-homo-5,-6,7-trinor-13-trans-8$\xi$-prostenoate |
| 152 | 113 | 119 | ethyl 9-oxo-15-triphenylmethoxy-10a-homo-7-nor-13-trans-8$\xi$-prostenoate |
| 153 | 114 | 119 | ethyl 9-oxo-15-triphenylmethoxy-7a,10a-bis-homo-13-trans-8$\xi$-prostenoate |
| 154 | 118 | 119 | ethyl 9-oxo-15-triphenylmethoxy-3-thia-13-13-trans-8$\xi$-prostenoate |
| 155 | 81 | 119 | butyl 9-oxo-15-triphenylmethoxy-13-trans-8$\xi$-prostenoate |
| 156 | 82 | 119 | isopropyl 9-oxo-15-triphenylmethoxy-13-trans-8$\xi$-prostenoate |
| 157 | 83 | 119 | methyl 9-oxo-15-triphenylmethoxy-13-trans-8$\xi$-prostenoate |

| Example | Starting Cycloalkenone of Example | Starting 3-triphenyl-methoxy-1-alkyne of Example | Product Alkyl 9-oxo-15-triphenylmethoxy-13-trans-8ξ-prostenoate |
|---|---|---|---|
| 158 | 84 | 119 | n-decyl 9-oxo-15-triphenylmethoxy-13-trans-8ξ-prostenoate |
| 159 | 900 | 119 | methyl 9-oxo-15-triphenylmethoxy-5-cis,13-trans-8ξ-prostadienoate |
| 160 | 13 | 125 | ethyl 9-oxo-15-triphenylmethoxy-20-nor-13-trans-8ξ-prostenoate |
| 161 | 13 | 128 | ethyl 9-oxo-15-triphenylmethoxy-20-methyl-13-trans-8ξ-prostenoate |
| 162 | 13 | 130 | ethyl 9-oxo-15-triphenylmethoxy-16-ethyl-13-trans-8ξ-prostenoate |
| 163 | 13 | 132 | ethyl 9-oxo-15-triphenylmethoxy-16-methyl-20-nor-13-trans-8ξ-prostenoate |
| 164 | 13 | 134 | ethyl 9-oxo-15-triphenylmethoxy-19-methyl-13-trans,18-8ξ-prostadienoate |
| 165 | 13 | 135 | ethyl 9-oxo-15-triphenylmethoxy-18,19-dimethyl-13-trans-18-8ξ-prostadienoate |
| 166 | 13 | 139 | ethyl 9-oxo-15-triphenylmethoxy-8ξ-13-trans,17-cis-prostadienoate |
| 167 | 14 | 139 | ethyl 9-oxo-15-triphenylmethoxy-5,6,7-trinor-8ξ-13-trans,17-cis-prostadienoate |
| 168 | 15 | 139 | ethyl 9-oxo-15-triphenylmethoxy-6,7-dinor-8ξ-13-trans,17-cis-prostadienoate |
| 169 | 23 | 139 | ethyl 9-oxo-15-triphenylmethoxy-7a,7b-bishomo-8ξ-13-trans,17-cis-prostadienoate |
| 170 | 31 | 139 | ethyl -9-oxo-15-triphenylmethoxy-2-ethyl-8ξ-13-trans,17-cis-prostadienoate |
| 171 | 41 | 139 | ethyl 9-oxo-15-triphenylmethoxy-3,3-dimethyl-8ξ-13-trans,17-cis-prostadienoate |
| 172 | 46 | 139 | ethyl 9-oxo-15-triphenylmethoxy-3-oxa-8ξ-13-trans,17-cis-prostadienoate |
| 173 | 53 | 139 | ethyl 9-oxo-15-triphenylmethoxy-7-nor-8ξ-13-trans,17-cis-prostadienoate |
| 174 | 70 | 139 | ethyl 9-oxo-15-triphenylmethoxy-2-fluoro-8ξ-13-trans,17-cis-prostadienoate |
| 175 | 74 | 139 | ethyl 9-oxo-15-triphenylmethoxy-7a-homo-8ξ-13-trans,17-cis-prostadienoate |
| 176 | 79 | 139 | ethyl 9-oxo-15-triphenylmethoxy-2-phenyl-8ξ-13-trans,17-cis-prostadienoate |
| 177 | 99 | 139 | ethyl 9-oxo-15-triphenylmethoxy-2-methyl-8ξ-13-trans,-17-cis-prostadienoate |
| 178 | 111 | 139 | ethyl 9-oxo-15-triphenylmethoxy-10a-homo-8ξ-13-trans,17-cis-prostadienoate |
| 179 | 112 | 139 | ethyl 9-oxo-15-triphenylmethoxy-10a-homo-5,6,7-trinor-13-trans,17-cis-prostadienoate |
| 180 | 113 | 139 | ethyl 9-oxo-15-triphenylmethoxy-10a-homo-7-nor-8ξ-13-trans,17-cis-prostadienoate |
| 181 | 114 | 139 | ethyl 9-oxo-15-triphenylmethoxy-7a-10a-bishomo-8ξ-13-trans,17-cis-prostadienoate |
| 182 | 118 | 139 | ethyl 9-oxo-15-triphenylmethoxy-3-thia-8ξ-13-trans,17-cis-prostadienoate |
| 183 | 81 | 139 | butyl 9-oxo-15-triphenylmethoxy-8ξ-13-trans,17-cis-prostadienoate |
| 184 | 82 | 139 | isopropyl 9-oxo-15-triphenylmethoxy-8ξ-13-trans,cis-prostadienoate |
| 185 | 83 | 139 | methyl 9-oxo-15-triphenylmethoxy-8ξ-13-trans,17-cis-prostadienoate |
| 186 | 84 | 139 | n-decyl 9-oxo-15-triphenylmethoxy-8ξ-13-trans,17-cis-prostadienoate |
| 187 | 14 | 136 | ethyl 9-oxo-15-triphenylmethoxy-5,6,7-trinor-19-isobutyl-8ξ-13-trans,18-prostadienoate |
| 188 | 14 | 137 | ethyl 9-oxo-15-triphenylmethoxy-5,6,7,19,20-pentanor-8ξ-13-trans,17,prostadienoate |
| 189 | 13 | 137 | ethyl 9-oxo-15-triphenylmethoxy-19,20-dinor-8ξ-13-trans,18-prostadienoate |
| 190 | 13 | 138 | ethyl 9-oxo-15-triphenylmethoxy-17-methyl-20-isopropenyl-8ξ-trans-prostenoate |
| 191 | 15 | 131 | ethyl 9-oxo-15-triphenylmethoxy-16-ethyl-6,7,19,20-tetranor-8ξ-13-trans-prostenoate |
| 192 | 15 | 135 | ethyl 9-oxo-15-triphenylmethoxy-18,19-dimethyl-6,7-dinor-8ξ-13-trans,18-prostadienoate |
| 193 | 23 | 130 | ethyl 9-oxo-15-triphenylmethoxy-16-ethyl-7a,7b-bishomo-8ξ-13-trans-prostenoate |
| 194 | 23 | 134 | ethyl 9-oxo-15-triphenylmethoxy-19-methyl-7a,7b-bishomo-8ξ-13-trans,18-prostadienoate |
| 195 | 31 | 126 | ethyl 9-oxo-15-triphenylmethoxy-2-ethyl-19,20-dinor-8ξ-13-trans-prostenoate |
| 196 | 31 | 129 | ethyl 9-oxo-15-triphenylmethoxy-2,20-diethyl-8ξ-13-trans-prostenoate |
| 197 | 31 | 132 | ethyl 9-oxo-15-triphenylmethoxy-2-ethyl-16-methyl-8ξ-20-nor-13-trans-prostenoate |
| 198 | 31 | 135 | ethyl 9-oxo-15-triphenylmethoxy-2-ethyl-18,19-dimethyl-8ξ-13-trans,18-prostadienoate |
| 199 | 41 | 127 | ethyl 9-oxo-15-triphenylmethoxy-3,3-dimethyl-18,19,20-trinor-8ξ-13-trans-prostenoate |
| 200 | 41 | 128 | ethyl 9-oxo-15-triphenylmethoxy-3,3,20-trimethyl-8ξ-13-trans-prostenoate |
| 201 | 41 | 132 | ethyl 9-oxo-15-triphenylmethoxy-3,3,16-trimethyl-20-nor-8ξ-13-trans-prostenoate |
| 202 | 41 | 136 | ethyl 9-oxo-15-triphenylmethoxy-3,3-dimethyl-19-isobutyl-8ξ-13-trans,18-prostadienoate |
| 203 | 41 | 137 | ethyl 9-oxo-15-triphenylmethoxy-3,3-dimethyl- |

Table 3-continued

| Example | Starting Cycloalkenone of Example | Starting 3-triphenyl-methoxy-1-alkyne of Example | Product Alkyl 9-oxo-15-triphenylmethoxy-13-trans-8ξ-prostenoate |
|---|---|---|---|
| 204 | 46 | 125 | 19,20-dinor-8ξ-13-trans,17-prostadienoate ethyl 9-oxo-15-triphenylmethoxy-3-oxa-20-nor-8ξ-13-trans-prostenoate |
| 205 | 46 | 128 | ethyl 9-oxo-15-triphenylmethoxy-3-oxa-20-methyl-8ξ-13-trans-prostenoate |
| 206 | 46 | 130 | ethyl 9-oxo-15-triphenylmethoxy-3-oxa-16-ethyl-8ξ-13-trans-prostenoate |
| 207 | 46 | 132 | ethyl 9-oxo-15-triphenylmethoxy-3-oxa-16-methyl-20-nor-8ξ-13-trans-prostenoate |
| 208 | 46 | 137 | ethyl 9-oxo-15-triphenylmethoxy-3-oxa-19,20-dinor-8ξ-13-trans,17-prostadienoate |
| 209 | 53 | 137 | ethyl 9-oxo-15-triphenylmethoxy-7,19,20-tri nor-8ξ-13-trans,17-prostadienoate |
| 210 | 53 | 135 | ethyl 9-oxo-15-triphenylmethoxy-7-nor-18,19-dimethyl-8ξ-13-trans,18-prostadienoate |
| 211 | 53 | 133 | ethyl 9-oxo-15-triphenylmethoxy-7,18,19,20-tetranor-16-methyl-8ξ-13-trans-prostenoate |
| 212 | 70 | 125 | ethyl 9-oxo-15-triphenylmethoxy-2-fluoro-20-nor-8ξ-13-trans-prostenoate |
| 213 | 70 | 129 | ethyl 9-oxo-15-triphenylmethoxy-2-fluoro-20-ethyl-8ξ-13-trans-prostenoate |
| 214 | 70 | 131 | ethyl 9-oxo-15-triphenylmethoxy-2-fluoro-16-ethyl-19,20-dinor-ξ -13-trans-prostenoate |
| 215 | 70 | 132 | ethyl 9-oxo-15-triphenylmethoxy-2-fluoro-16-methyl-20-nor-8ξ-13-trans-prostenoate |
| 216 | 70 | 134 | ethyl 9-oxo-15-triphenylmethoxy-2-fluoro-19-methyl-8ξ-13-trans,18-prostadienoate |
| 217 | 74 | 135 | ethyl 9-oxo-15-triphenylmethoxy-7a-homo-18,19-dimethyl-8ξ-13-trans,18-prostadienoate |
| 218 | 74 | 137 | ethyl 9-oxo-15-triphenylmethoxy-7a-homo-19,20-dinor-8ξ-13-trans,17-prostadienoate |
| 219 | 79 | 125 | ethyl 9-oxo-15-triphenylmethoxy-2-phenyl-20-nor-8ξ-13-trans-prostenoate |
| 220 | 79 | 129 | ethyl 9-oxo-15-triphenylmethoxy-2-phenyl-20-ethyl-8ξ-13-trans-prostenoate |
| 221 | 79 | 130 | ethyl 9-oxo-15-triphenylmethoxy-2-phenyl-16-ethyl-8ξ-13-trans-prostenoate |
| 222 | 79 | 133 | ethyl 9-oxo-15-triphenylmethoxy-2-phenyl-16-methyl-18,19,20-trinor-8ξ-trans-prostenoate |
| 223 | 79 | 135 | ethyl 9-oxo-15-triphenylmethoxy-2-phenyl-18,19,-dimethyl-8ξ-13-trans,18-prostadienoate |
| 224 | 99 | 125 | ethyl 9-oxo-15-triphenylmethoxy-2-methyl-20-nor-8ξ-13-trans-prostenoate |
| 225 | 99 | 128 | ethyl 9-oxo-15-triphenylmethoxy-2,20-dimethyl-8ξ-13-trans-prostenoate |
| 226 | 99 | 131 | ethyl 9-oxo-15-triphenylmethoxy-2-methyl-16-ethyl-19,20-dinor-8ξ-13-trans-prostenoate |
| 227 | 99 | 134 | ethyl 9-oxo-15-triphenylmethoxy-2,19-dimethyl-8ξ-13-trans,18-prostadienoate |
| 228 | 99 | 137 | ethyl 9-oxo-15-triphenylmethoxy-2-methyl-19,20-dinor-8ξ-13-trans,17-prostadienoate |
| 229 | 111 | 125 | ethyl 9-oxo-15-triphenylmethoxy-10a-homo-20-nor-8ξ-13-trans-prostenoate |
| 230 | 111 | 128 | ethyl 9-oxo-15-triphenylmethoxy-10a-homo-20-methyl-8ξ-13-trans-prostenoate |
| 231 | 111 | 130 | ethyl 9-oxo-15-triphenylmethoxy-10a-homo-16-ethyl-8ξ-13-trans-prostenoate |
| 232 | 111 | 135 | ethyl 9-oxo-15-triphenylmethoxy-10a-homo-18,19-dimethyl-8ξ-13-trans,18-prostadienoate |
| 233 | 111 | 137 | ethyl 9-oxo-15-triphenylmethoxy-10a-homo-19,20-dinor-8ξ-13-trans,17-prostadienoate |
| 234 | 112 | 129 | ethyl 9-oxo-15-triphenylmethoxy-10a-homo-5,6,7-trinor-20-ethyl-8ξ-13-trans-prostenoate |
| 235 | 112 | 132 | ethyl 9-oxo-15-triphenylmethoxy-10a-homo-5,6,7,20-tetranor-16-methyl-8ξ-13-trans-prostenoate |
| 236 | 112 | 136 | ethyl 9-oxo-15-triphenylmethoxy-10a-homo-5,6,7-trinor-19-isobutyl-8ξ-13-trans,18-prostadienoate |
| 237 | 113 | 128 | ethyl 9-oxo-15-triphenylmethoxy-10a-homo-20-methyl-8ξ-13-trans-prostenoate |
| 238 | 113 | 134 | ethyl 9-oxo-15-triphenylmethoxy-10a-homo-19-methyl-8ξ-13-trans,18-prostadienoate |
| 239 | 114 | 125 | ethyl 9-oxo-15-triphenylmethoxy-7a,10a-bis-homo-20-nor-8ξ-13-trans-prostenoate |
| 240 | 114 | 129 | ethyl 9-oxo-15-triphenylmethoxy-7a-10a-bis-homo-20-ethyl-8ξ-13-trans-prostenoate |
| 241 | 114 | 132 | ethyl 9-oxo-15-triphenylmethoxy-7a,10a-bis-homo-16-methyl-20-nor-8ξ-13-trans-prostenoate |
| 242 | 114 | 134 | ethyl 9-oxo-15-triphenylmethoxy-7a,10a-bis-homo-19-methyl-8ξ-13-trans,18-prostadienoate |
| 243 | 118 | 125 | ethyl 9-oxo-15-triphenylmethoxy-3-thia-20-nor-8ξ-13-trans-prostenoate |
| 244 | 118 | 128 | ethyl 9-oxo-15-triphenylmethoxy-3-thia-20-methyl-8ξ-13-trans-prostenoate |
| 245 | 118 | 130 | ethyl 9-oxo-15-triphenylmethoxy-3-thia-16-ethyl-8ξ-13-trans-prostenoate |
| 246 | 118 | 133 | ethyl 9-oxo-15-triphenylmethoxy-3-thia-16-methyl-18,19,20-trinor-8ξ-13-trans-prostenoate |
| 247 | 118 | 134 | ethyl 9-oxo-15-triphenylmethoxy-3-thia-19-methyl-8ξ-13-trans,prostadienoate |
| 248 | 118 | 137 | ethyl 9-oxo-15-triphenylmethoxy-3-thia-19,20- |

Table 3-continued

| Example | Starting Cycloalkenone of Example | Starting 3-triphenyl-methoxy-1-alkyne of Example | Product Alkyl 9-oxo-15-triphenylmethoxy-13-trans-8ξ-prostenoate |
|---|---|---|---|
| 249 | 900 | 125 | dinor-8ξ-13-trans,17-prostadienoate |
| 250 | 900 | 128 | methyl 9-oxo-15-triphenylmethoxy-20-nor-8ξ-5-cis,13-trans-prostadienoate |
| 251 | 900 | 130 | methyl 9-oxo-15-triphenylmethoxy-20-methyl-8ξ-5-cis,13-trans-prostadienate |
| 252 | 900 | 132 | methyl 9-oxo-15-triphenylmethoxy-16-ethyl-8ξ-5-cis,13-trans-prostadienoate |
| 253 | 900 | 134 | methyl 9-oxo-15-triphenylmethoxy-16-methyl-20-nor-8ξ-5-cis,13-trans-prostadienoate |
| 254 | 900 | 135 | methyl 9-oxo-15-triphenylmethoxy-19-methyl-8ξ-5-cis,13-trans,18-prostadienoate |
| 255 | 900 | 137 | methyl 9-oxo-15-triphenylmethoxy-18,19-dimethyl-8ξ-5-cis,13-trans,18-prostatrienoate |
| 256 | 900 | 139 | methyl 9-oxo-15-triphenylmethoxy-19,20-dinor-8ξ-5-cis,13-trans,17-prostatrienoate |
|  |  |  | methyl 9-oxo-15-triphenylmethoxy-8ξ-5-cis,13-trans,17-cis-prostatrienoate |

EXAMPLE 257

Preparation of ethyl 9α/β,15-dihydroxy-13-trans-prostenoate

A solution containing 3 g. of ethyl 9-oxo-15-hydroxy-13-trans-prostenoate (Example 121) in 120 ml. of absolute alcohol containing 115 mg. of sodium borohydride is stirred at ambient temperature for 18 hours. The solution is poured into 300 ml. of saturated sodium chloride solution and the oil precipitate is extracted with ether. The ether is washed with saturated sodium chloride solution. dried with anhydrous magnesium sulfate and taken to dryness to give subject product as an oil; λ max. 2195, 5178, 8.45 μ; the product is a mixture of 9α-and 9β-hydroxy derivatives.

EXAMPLES 258–374

Treatment of the designated 9-oxo-15-triphenylmethoxy derivatives listed in the table below, with glacial acetic acid-tetrahydropyran-water (4:2:1) in the manner described in Example 121 is productive of the corresponding 15-hydroxy derivative of the table. This acid treatment also ensures a trans-relationship between the two side-chains attached to $C_8$ and $C_{12}$.

TABLE 4

| Example | Starting 15-triphenylmethoxy derivative of Example | Product Alkyl 9-oxo-15-hydroxy-13-trans-prostenoates |
|---|---|---|
| 258 | 140 | Ethyl 9-oxo-15-hydroxy-5,6,7-trinor-13-trans-prostenoate |
| 259 | 141 | Ethyl 9-oxo-15-hydroxy-7a,7b-bishomo-13-trans-prostenoate |
| 260 | 142 | Ethyl 9-oxo-15-hydroxy-2-ethyl-13-trans-prostenoate |
| 261 | 143 | Ethyl 9-oxo-15-hydroxy-3,3-dimethyl-13-trans-prostenoate |
| 262 | 144 | Ethyl 9-oxo-15-hydroxy-3-oxa-13-trans-prostenoate |
| 263 | 145 | Ethyl 9-oxo-15-hydroxy-7-nor-13-trans-prostenoate |
| 264 | 146 | Ethyl 9-oxo-15-hydroxy-2-fluoro-13-trans-prostenoate |
| 265 | 147 | Ethyl 9-oxo-15-hydroxy-7a-homo-13-trans-prostenoate |
| 266 | 148 | Ethyl 9-oxo-15-hydroxy-2-phenyl-13-trans-prostenoate |
| 267 | 149 | Ethyl 9-oxo-15-hydroxy-2-methyl-13-trans-prostenoate |
| 268 | 150 | Ethyl 9-oxo-15-hydroxy-10a-homo-13-trans-prostenoate |
| 269 | 151 | Ethyl 9-oxo-15-hydroxy-10a-homo-5,6,7-trinor-13-trans-prostenoate |
| 270 | 152 | Ethyl 9-oxo-15-hydroxy-10a-homo-7-nor-13-trans-prostenoate |
| 271 | 153 | Ethyl 9-oxo-15-hydroxy-7a,10a-bishomo-13-trans-prostenoate |
| 272 | 154 | Ethyl 9-oxo-15-hydroxy-3-thia-13-trans-prostenoate |
| 273 | 155 | Butyl 9-oxo-15-hydroxy-13-trans-prostenoate |
| 274 | 156 | Isopropyl 9-oxo-15-hydroxy-13-trans-prostenoate |
| 275 | 157 | Methyl 9-oxo-15-hydroxy-13-trans-prostenoate |
| 276 | 158 | n-decyl 9-oxo-15-hydroxy-13-trans-prostenoate |
| 277 | 159 | Methyl 9-oxo-15-hydroxy-5-cis,-13-trans-prostadienoate |
| 278 | 160 | Ethyl 9-oxo-15-hydroxy-20-nor-13-trans-prostenoate |
| 279 | 161 | Ethyl 9-oxo-15-hydroxy-20-methyl-13-trans-prostenoate |
| 280 | 162 | Ethyl 9-oxo-15-hydroxy-16-ethyl-13-trans-prostenoate |
| 281 | 163 | Ethyl 9-oxo-15-hydroxy-16-methyl-20-nor-13-trans-prostenoate |
| 282 | 164 | Ethyl 9-oxo-15-hydroxy-19-methyl-13-trans,18-prostadienoate |
| 283 | 165 | Ethyl 9-oxo-15-hydroxy-18,19-dimethyl-13-trans,18-prostadienoate |
| 284 | 166 | Ethyl 9-oxo-15-hydroxy-13-trans,17-cis-prostadienoate |
| 285 | 167 | Ethyl 9-oxo-15-hydroxy-5,6,7-trinor-13-trans,17-cis-prostadienoate |
| 286 | 168 | Ethyl 9-oxo-15-hydroxy-6,7-dinor-13-trans-17-cis-prostadienoate |
| 287 | 169 | Ethyl 9-oxo-15-hydroxy-7a,7b-bishomo-13-trans,17-cis-prostadienoate |
| 288 | 170 | Ethyl 9-oxo-15-hydroxy-2-ethyl-13-trans,17-cis-prostadienoate |
| 289 | 171 | Ethyl 9-oxo-15-hydroxy- |

TABLE 4-continued

| Example | Starting 15-triphenylmethoxy derivative of Example | Product Alkyl 9-oxo-15-hydroxy-13-trans-prostenoates |
|---|---|---|
| 290 | 172 | 3,3-dimethyl-13-trans,17-cis-prostadienoate<br>Ethyl 9-oxo-15-hydroxy-3-oxa-13-trans,17-cis-prostadienoate |
| 291 | 173 | Ethyl 9-oxo-15-hydroxy-7-nor-13-trans,17-cis-prostadienoate |
| 292 | 174 | Ethyl 9-oxo-15-hydroxy-2-fluoro-13-trans,17-cis-prostadienoate |
| 293 | 175 | Ethyl 9-oxo-15-hydroxy-7a-homo-13-trans,17-cis-prostadienoate |
| 294 | 176 | Ethyl 9-oxo-15-hydroxy-2-phenyl-13-trans,17-cis-prostadienoate |
| 295 | 177 | Ethyl 9-oxo-15-hydroxy-2-methyl-13-trans,17-cis-prostadienoate |
| 296 | 178 | Ethyl 9-oxo-15-hydroxy-10a-homo-13-trans,17-cis-prostadienoate |
| 297 | 179 | Ethyl 9-oxo-15-hydroxy-10a-homo-5,6,7-trinor-13-trans,17-cis-prostadienoate |
| 298 | 180 | Ethyl 9-oxo-15-hydroxy-10a-homo-7-nor-13-trans,17-cis-prostadienoate |
| 299 | 181 | Ethyl 9-oxo-15-hydroxy-7a,10a-bishomo-13-trans,17-cis-prostadienoate |
| 300 | 182 | Ethyl 9-oxo-15-hydroxy-3-thia-13-trans,17-cis-prostadienoate |
| 301 | 183 | Butyl 9-oxo-15-hydroxy-13-trans,17-cis-prostadienoate |
| 302 | 184 | Isopropyl 9-oxo-15-hydroxy-13-trans,17-cis-prostadienoate |
| 303 | 185 | Methyl 9-oxo-15-hydroxy-13-trans,17-cis-prostadienoate |
| 304 | 186 | n-decyl-9-oxo-15-hydroxy-13-trans,17-cis-prostadienoate |
| 305 | 187 | Ethyl 9-oxo-15-hydroxy-5,6,7-trinor-19-iso-butyl-13-trans,18-prostadienoate |
| 306 | 188 | Ethyl 9-oxo-15-hydroxy-5,6,7,19,20-pentanor-13-trans,17-prostadienoate |
| 307 | 189 | Ethyl 9-oxo-15-hydroxy-19,20-dinor-13-trans,18-prostadienoate |
| 308 | 190 | Ethyl 9-oxo-15-hydroxy-17-methyl-20-isopropenyl-13-trans-prostadienoate |
| 309 | 191 | Ethyl 9-oxo-15-hydroxy-16-ethyl-6,7,19,20-tetranor-13-trans-prostenoate |
| 310 | 192 | Ethyl 9-oxo-15-hydroxy-18,19-dimethyl-6,7-dinor-13-trans,18-prostadienoate |
| 311 | 193 | Ethyl 9-oxo-15-hydroxy-16-ethyl-7a,7b-bishomo-13-trans-prostenoate |
| 312 | 194 | Ethyl 9-oxo-15-hydroxy-19-methyl-7a,7b-bishomo-13-trans,18-prostadienoate |
| 313 | 195 | Ethyl 9-oxo-15-hydroxy-2-ethyl-19,20-dinor-13-trans-prostenoate |
| 314 | 196 | Ethyl 9-oxo-15-hydroxy-2,20-diethyl-13-trans-prostenoate |
| 315 | 197 | Ethyl 9-oxo-15-hydroxy-2-ethyl-16-methyl-20-nor-trans-prostenoate |
| 316 | 198 | Ethyl 9-oxo-15-hydroxy-2-ethyl-18,19-dimethyl-13-trans,18-prostadienoate |
| 317 | 199 | Ethyl 9-oxo-15-hydroxy-3,3-dimethyl-18,19,20-trinor-13-trans-prostenoate |
| 318 | 200 | Ethyl 9-oxo-15-hydroxy-3,3,20-trimethyl-13-trans-prostenoate |
| 319 | 201 | Ethyl 9-oxo-15-hydroxy-3,3,16-trimethyl-20-nor-13-trans-prostanoate |
| 320 | 202 | Ethyl 9-oxo-15-hydroxy-3,3-dimethyl-19-isobutyl-13-trans,18-prostadienoate |
| 321 | 203 | Ethyl 9-oxo-15-hydroxy-3,3-dimethyl-19,20-dinor-13-trans,17-prostadienoate |
| 322 | 204 | Ethyl 9-oxo-15-hydroxy-3-oxa-20-nor-13-trans-prostenoate |
| 323 | 205 | Ethyl 9-oxo-15-hydroxy-3-oxa-20-methyl-13-trans-prostenoate |
| 324 | 206 | Ethyl 9-oxo-15-hydroxy-3-oxa-16-ethyl-13-trans-prostenoate |
| 325 | 207 | Ethyl 9-oxo-15-hydroxy-3-oxa-16-methyl-20-nor-13-trans-prostenoate |
| 326 | 208 | Ethyl 9-oxo-15-hydroxy-3-oxa-19,20-dinor-13-trans,17-prostadienoate |
| 327 | 209 | Ethyl 9-oxo-15-hydroxy-7,19,20-trinor-13-trans,17-prostadienoate |
| 328 | 210 | Ethyl 9-oxo-15-hydroxy-7-nor-18,19-dimethyl-13-trans,18-prostadienoate |
| 329 | 211 | Ethyl 9-oxo-15-hydroxy-7,18,19,20-tetranor-16-methyl-13-trans-prostenoate |
| 330 | 212 | Ethyl 9-oxo-15-hydroxy-2-fluoro-20-nor-13-trans-prostenoate |
| 331 | 213 | Ethyl 9-oxo-15-hydroxy-2-fluoro-20-ethyl-13-trans-prostenoate |
| 332 | 214 | Ethyl 9-oxo-15-hydroxy-2-fluoro-16-ethyl-19,20-dinor-13-trans-prostenoate |
| 333 | 215 | Ethyl 9-oxo-15-hydroxy-2-fluoro-16-methyl-20-nor-13-trans-prostenoate |
| 334 | 216 | Ethyl 9-oxo-15-hydroxy-2-fluoro-19-methyl-13-trans,18-prostadienoate |
| 335 | 217 | Ethyl 9-oxo-15-hydroxy-7a-homo-18,19-dimethyl-13-trans,18-prostadienoate |
| 336 | 218 | Ethyl 9-oxo-15-hydroxy-7a-homo-19,20-dinor-13-trans,17-prostadienoate |
| 337 | 219 | Ethyl 9-oxo-15-hydroxy-2-phenyl-20-nor-13-trans-prostenoate |
| 338 | 220 | Ethyl 9-oxo-15-hydroxy-2-phenyl-20-ethyl-13-trans-prostenoate |
| 339 | 221 | Ethyl 9-oxo-15-hydroxy-2-phenyl-16-ethyl-13-trans-prostenoate |
| 340 | 222 | Ethyl 9-oxo-15-hydroxy-2-phenyl-16-methyl-18,19,20-trinor-13-trans-prostenoate |
| 341 | 223 | Ethyl 9-oxo-15-hydroxy- |

TABLE 4-continued

| Example | Starting 15-triphenylmethoxy derivative of Example | Product Alkyl 9-oxo-15-hydroxy-13-trans-prostenoates |
|---|---|---|
| | | 2-phenyl-18,19-dimethyl-13-trans,18-prostadienoate |
| 342 | 224 | Ethyl 9-oxo-15-hydroxy-2-methyl-20-nor-13-trans-prostenoate |
| 343 | 225 | Ethyl 9-oxo-15-hydroxy-2,20-dimethyl-13-trans-prostenoate |
| 344 | 226 | Ethyl 9-oxo-15-hydroxy-2-methyl-16-ethyl-19,20-dinor-13-trans-prostenoate |
| 345 | 227 | Ethyl 9-oxo-15-hydroxy-2,19-dimethyl-13-trans,18-prostadienoate |
| 346 | 228 | Ethyl 9-oxo-15-hydroxy-2-methyl-19,20-dinor-13-trans,17-prostadienoate |
| 347 | 229 | Ethyl 9-oxo-15-hydroxy-10a-homo-20-nor-13-trans-prostenoate |
| 348 | 230 | Ethyl 9-oxo-15-hydroxy-10a-homo-20-methyl-13-trans-prostenoate |
| 349 | 231 | Ethyl 9-oxo-15-hydroxy-10a-homo-16-ethyl-13-trans-prostenoate |
| 350 | 232 | Ethyl 9-oxo-15-hydroxy-10a-homo-18,19-dimethyl-13-trans,18-prostadienoate |
| 351 | 233 | Ethyl 9-oxo-15-hydroxy-10a-homo-19,20-dinor-13-trans,17-prostadienoate |
| 352 | 234 | Ethyl 9-oxo-15-hydroxy-10a-homo-5,6,7-trinor-20-ethyl-13-trans-prostenoate |
| 353 | 235 | Ethyl 9-oxo-15-hydroxy-10a-homo-5,6,7,20-tetranor-16-methyl-13-trans-prostenoate |
| 354 | 236 | Ethyl 9-oxo-15-hydroxy-10a-homo-5,6,7-trinor-19-isobutyl-13-trans,18-prostadienoate |
| 355 | 237 | Ethyl 9-oxo-15-hydroxy-10a-homo-20-methyl-13-trans-prostenoate |
| 356 | 238 | Ethyl 9-oxo-15-hydroxy-10a-homo-19-methyl-13-trans,18-prostadienoate |
| 357 | 239 | Ethyl 9-oxo-15-hydroxy-7a,10a-bishomo-20-nor-13-trans-prostenoate |
| 358 | 240 | Ethyl 9-oxo-15-hydroxy-7a,10a-bishomo-20-ethyl-13-trans-prostenoate |
| 359 | 241 | Ethyl 9-oxo-15-hydroxy-7a,10a-bishomo-16-methyl-20-nor-13-trans-prostenoate |
| 360 | 242 | Ethyl 9-oxo-15-hydroxy-7a,10a-bishomo-19-methyl-13-trans,18-prostadienoate |
| 361 | 243 | Ethyl 9-oxo-15-hydroxy-3-thia-20-nor-13-trans-prostenoate |
| 362 | 244 | Ethyl 9-oxo-15-hydroxy-3-thia-20-methyl-13-trans-prostenoate |
| 363 | 245 | Ethyl 9-oxo-15-hydroxy-3-thia-16-ethyl-13-trans-prostenoate |
| 364 | 246 | Ethyl 9-oxo-15-hydroxy-3-thia-16-methyl-18,19,20-trinor-13-trans-prostenoate |
| 365 | 247 | Ethyl 9-oxo-15-hydroxy-3-thia-19-methyl-13-trans,18-prostadienoate |
| 366 | 248 | Ethyl 9-oxo-15-hydroxy-3-thia-19,20-dinor-13-trans,17-prostadienoate |
| 367 | 249 | Methyl 9-oxo-15-hydroxy-20-nor-5-cis,13-trans-prostadienoate |
| 368 | 250 | Methyl 9-oxo-15-hydroxy-20-methyl-5-cis,13-trans-prostadienoate |
| 369 | 251 | Methyl 9-oxo-15-hydroxy-16-ethyl-5-cis,13-trans-prostadienoate |
| 370 | 252 | Methyl 9-oxo-15-hydroxy-16-methyl-20-nor-5-cis,13-trans-prostadienoate |
| 371 | 253 | Methyl 9-oxo-15-hydroxy-19-methyl-5-cis,13-trans,18-prostatrienoate |
| 372 | 254 | Methyl 9-oxo-15-hydroxy-18,19-dimethyl-5-cis,13-trans,18-prostatrienoate |
| 373 | 255 | Methyl 9-oxo-15-hydroxy-19,20-dinor-5-cis,13-trans,17-prostatrienoate |
| 374 | 256 | Methyl 9-oxo-15-hydroxy-5-cis,13-trans,17-cis-prostatrienoate |

EXAMPLES 375–491

Saponification of the alkyl esters designated in the following table by the method described in Example 122 is productive of the prostenoic acids of the table.

Table 5

| Example | Starting alkyl 9-oxo-prostenoate of example | Product 9-Oxo-15-hydroxy-13-trans-prostenoic acid |
|---|---|---|
| 375 | 258 | 9-oxo-15-hydroxy-5,6,7-trinor-13-trans-prostenoic acid |
| 376 | 259 | 9-oxo-15-hydroxy-7a,7b-bishomo-13-trans-prostenoic acid |
| 377 | 260 | 9-oxo-15-hydroxy-2-ethyl-13-trans-prostenoic acid |
| 378 | 261 | 9-oxo-15-hydroxy-3,3-dimethyl-13-trans-prostenoic acid |
| 379 | 262 | 9-oxo-15-hydroxy-3-oxa-13-trans-prostenoic acid |
| 380 | 263 | 9-oxo-15-hydroxy-7-nor-13-trans-prostenoic acid |
| 381 | 264 | 9-oxo-15-hydroxy-2-fluoro-13-trans-prostenoic acid |
| 382 | 265 | 9-oxo-15-hydroxy-7a-homo-13-trans-prostenoic acid |
| 383 | 266 | 9-oxo-15-hydroxy-2-phenyl-13-trans-prostenoic acid |
| 384 | 267 | 9-oxo-15-hydroxy-2-methyl-13-trans-prostenoic acid |
| 385 | 268 | 9-oxo-15-hydroxy-10a-homo-13-trans-prostenoic acid |
| 386 | 269 | 9-oxo-15-hydroxy-10a-homo-5,6,7-trinor-13-trans-prostenoic acid |
| 387 | 270 | 9-oxo-15-hydroxy-10a-homo-7-nor-13-trans-prostenoic acid |
| 388 | 271 | 9-oxo-15-hydroxy-7a,10a-bishomo-13-trans-prostenoic acid |
| 389 | 272 | 9-oxo-15-hydroxy-3-thia-13-trans-prostenoic acid |
| 390 | 273 | 9-oxo-15-hydroxy-13-trans-prostenoic acid |

Table 5-continued

| Example | Starting alkyl 9-oxo-prostenoate of example | Product 9-Oxo-15-hydroxy-13-trans-prostenoic acid |
|---|---|---|
| 391 | 274 | 9-oxo-15-hydroxy-13-trans-prostenoic acid |
| 392 | 275 | 9-oxo-15-hydroxy-13-trans-prostenoic acid |
| 393 | 276 | 9-oxo-15-hydroxy-13-trans-prostenoic acid |
| 394 | 277 | 9-oxo-15-hydroxy-5-cis,13-trans-prostadienoic acid |
| 395 | 278 | 9-oxo-15-hydroxy-20-nor-13-trans-prostenoic acid |
| 396 | 279 | 9-oxo-15-hydroxy-20-methyl-13-trans-prostenoic acid |
| 397 | 280 | 9-oxo-15-hydroxy-16-ethyl-13-trans-prostenoic acid |
| 398 | 281 | 9-oxo-15-hydroxy-16-methyl-20-nor-13-trans-prostenoic acid |
| 399 | 282 | 9-oxo-15-hydroxy-19-methyl-13-trans,18-prostadienoic acid |
| 400 | 283 | 9-oxo-15-hydroxy-18,19-dimethyl-13-trans,18-prostadienoic acid |
| 401 | 284 | 9-oxo-15-hydroxy-13-trans,17-cis-prostadienoic acid |
| 402 | 285 | 9-oxo-15-hydroxy-5,6,7-trinor-13-trans,17-cis-prostadienoic acid |
| 403 | 286 | 9-oxo-15-hydroxy-6,7-dinor-13-trans,17-cis-prostadienoic acid |
| 404 | 287 | 9-oxo-15-hydroxy-7a,7b-bishomo-13-trans,17-cis-prostadienoic acid |
| 405 | 288 | 9-oxo-15-hydroxy-2-ethyl-13-trans,17-cis-prostadienoic acid |
| 406 | 289 | 9-oxo-15-hydroxy-3,3-dimethyl-13-trans,17-cis-prostadienoic acid |
| 407 | 290 | 9-oxo-15-hydroxy-3-oxa-13-trans,17-cis-prostadienoic acid |
| 408 | 291 | 9-oxo-15-hydroxy-7-nor-13-trans,17-cis-prostadienoic acid |
| 409 | 292 | 9-oxo-15-hydroxy-2-fluoro-13-trans,17-cis-prostadienoic acid |
| 410 | 293 | 9-oxo-15-hydroxy-7a-homo-13-trans,17-cis-prostadienoic acid |
| 411 | 294 | 9-oxo-15-hydroxy-2-phenyl-13-trans,17-cis-prostadienoic acid |
| 412 | 295 | 9-oxo-15-hydroxy-2-methyl-13-trans,17-cis-prostadienoic acid |
| 413 | 296 | 9-oxo-15-hydroxy-10a-homo-13-trans,17-cis-prostadienoic acid |
| 414 | 297 | 9-oxo-15-hydroxy-10a-homo-5,6,7-trinor-13-trans,17-cis-prostadienoic acid |
| 415 | 298 | 9-oxo-15-hydroxy-10a-homo-7-nor-13-trans,17-cis-prostadienoic acid |
| 416 | 299 | 9-oxo-15-hydroxy-7a,10a-bishomo-13-trans,17-cis-prostadienoic acid |
| 417 | 300 | 9-oxo-15-hydroxy-3-thia-13-trans,17-cis-prostadienoic acid |
| 418 | 301 | 9-oxo-15-hydroxy-13-trans,17-cis-prostadienoic acid |
| 419 | 302 | 9-oxo-15-hydroxy-13-trans,17-cis-prostadienoic acid |
| 420 | 303 | 9-oxo-15-hydroxy-13-trans,17-cis-prostadienoic acid |
| 421 | 304 | 9-oxo-15-hydroxy-13-trans,17-cis-prostadienoic acid |
| 422 | 305 | 9-oxo-15-hydroxy-5,6,7-trinor-19-isobutyl-13-trans,18-prostadienoic acid |
| 423 | 306 | 9-oxo-15-hydroxy-5,6,7,19,20-pentanor-13-trans,17-prostadienoic acid |
| 424 | 307 | 9-oxo-15-hydroxy-19,20-dinor-13-trans,18-prostadienoic acid |
| 425 | 308 | 9-oxo-15-hydroxy-17-methyl-20-isopropenyl-13-trans-prostenoic acid |
| 426 | 309 | 9-oxo-15-hydroxy-16-ethyl-6,7,19,20-tetranor-13-trans-prostenoic acid |
| 427 | 310 | 9-oxo-15-hydroxy-18,19-dimethyl-6,7-dinor-13-trans,18-prostadienoic acid |
| 428 | 311 | 9-oxo-15-hydroxy-16-ethyl-7a,7b-bishomo-13-trans-prostenoic acid |
| 429 | 312 | 9-oxo-15-hydroxy-19-methyl-7a,7b-bishomo-13-trans,18-prostadienoic acid |
| 430 | 313 | 9-oxo-15-hydroxy-2-ethyl-19,20-dinor-13-trans-prostenoic acid |
| 431 | 314 | 9-oxo-15-hydroxy-2,20-diethyl-13-trans-prostenoic acid |
| 432 | 315 | 9-oxo-15-hydroxy-2-ethyl-16-methyl-20-nor-13-trans-prostenoic acid |
| 433 | 316 | 9-oxo-15-hydroxy-2-ethyl-18,19-dimethyl-13-trans,18-prostadienoic acid |
| 434 | 317 | 9-oxo-15-hydroxy-3,3-dimethyl-18,19,20-trinor-13-trans-prostenoic acid |
| 435 | 318 | 9-oxo-15-hydroxy-3,3,20-trimethyl-13-trans-prostenoic acid |
| 436 | 319 | 9-oxo-15-hydroxy-3,3,16-trimethyl-20-nor-13-trans-prostenoic acid |
| 437 | 320 | 9-oxo-15-hydroxy-3,3-dimethyl-19-isobutyl-13-trans,18-prostadienoic acid |
| 438 | 321 | 9-oxo-15-hydroxy-3,3-dimethyl-19,20-dinor-13-trans,17-prostadienoic acid |
| 439 | 322 | 9-oxo-15-hydroxy-3-oxa-20-nor-13-trans-prostenoic acid |
| 440 | 323 | 9-oxo-15-hydroxy-3-oxa-20-methyl-13-trans-prostenoic acid |
| 441 | 324 | 9-oxo-15-hydroxy-3-oxa-16-ethyl-13-trans-prostenoic acid |
| 442 | 325 | 9-oxo-15-hydroxy-3-oxa-16-methyl-20-nor-13-trans-prostenoic acid |
| 443 | 326 | 9-oxo-15-hydroxy-3-oxa-19,20-dinor-13-trans,17-prostadienoic acid |
| 444 | 327 | 9-oxo-15-hydroxy-7,19,20-trinor-13-trans,17-prostadienoic acid |
| 445 | 328 | 9-oxo-15-hydroxy-7-nor-18,19-dimethyl-13-trans,18-prostadienoic acid |
| 446 | 329 | 9-oxo-15-hydroxy-7,18,19,20-tetranor-16-methyl-13-trans-prostenoic acid |

Table 5-continued

| Example | Starting alkyl 9-oxo-prostenoate of example | Product 9-Oxo-15-hydroxy-13-trans-prostenoic acid |
|---|---|---|
| 447 | 330 | 9-oxo-15-hydroxy-2-fluoro-20-nor-13-trans-prostenoic acid |
| 448 | 331 | 9-oxo-15-hydroxy-2-fluoro-20-ethyl-13-trans-prostenoic acid |
| 449 | 332 | 9-oxo-15-hydroxy-2-fluoro-16-ethyl-19,20-dinor-13-trans-prostenoic acid |
| 450 | 333 | 9-oxo-15-hydroxy-2-fluoro-16-methyl-20-nor-13-trans-prostenoic acid |
| 451 | 334 | 9-oxo-15-hydroxy-2-fluoro-19-methyl-13-trans,18-prostadienoic acid |
| 452 | 335 | 9-oxo-15-hydroxy-7a-homo-18,19-dimethyl-13-trans,18-prostadienoic acid |
| 453 | 336 | 9-oxo-15-hydroxy-7a-homo-19,20-dinor-13-trans,17-prostadienoic acid |
| 454 | 337 | 9-oxo-15-hydroxy-2-phenyl-20-nor-13-trans-prostenoic acid |
| 455 | 338 | 9-oxo-15-hydroxy-2-phenyl-20-ethyl-13-trans-prostenoic acid |
| 456 | 339 | 9-oxo-15-hydroxy-2-phenyl-16-ethyl-13-trans-prostenoic acid |
| 457 | 340 | 9-oxo-15-hydroxy-2-phenyl-16-methyl-18,19,20-trinor-13-trans-prostenoic acid |
| 458 | 341 | 9-oxo-15-hydroxy-2-phenyl-18,19-dimethyl-13-trans,18-prostadienoic acid |
| 459 | 342 | 9-oxo-15-hydroxy-2-methyl-20-nor-13-trans-prostenoic acid |
| 460 | 343 | 9-oxo-15-hydroxy-2,20-dimethyl-13-trans-prostenoic acid |
| 461 | 344 | 9-oxo-15-hydroxy-2-methyl-16-ethyl-19,20-dinor-13-trans-prostenoic acid |
| 462 | 345 | 9-oxo-15-hydroxy-2,19-dimethyl-13-trans,18-prostadienoic acid |
| 463 | 346 | 9-oxo-15-hydroxy-2-methyl-19,20-dinor-13-trans,17-prostadienoic acid |
| 464 | 347 | 9-oxo-15-hydroxy-10a-homo-20-nor-13-trans-prostenoic acid |
| 465 | 348 | 9-oxo-15-hydroxy-10a-homo-20-methyl-13-trans-prostenoic acid |
| 466 | 349 | 9-oxo-15-hydroxy-10a-homo-16-ethyl-13-trans-prostenoic acid |
| 467 | 350 | 9-oxo-15-hydroxy-10a-homo-18,19-dimethyl-13-trans,18-prostadienoic acid |
| 468 | 351 | 9-oxo-15-hydroxy-10a-homo-19,20-dinor-13-trans,17-prostadienoic acid |
| 469 | 352 | 9-oxo-15-hydroxy-10a-homo-5,6,7-trinor-20-ethyl-13-trans-prostenoic acid |
| 470 | 353 | 9-oxo-15-hydroxy-10a-homo-5,6,7,20-tetranor-16-methyl-13-trans-prostenoic acid |
| 471 | 354 | 9-oxo-15-hydroxy-10a-homo-5,6,7-trinor-19-isobutyl-13-trans,18-prostadienoic acid |
| 472 | 355 | 9-oxo-15-hydroxy-10a-homo-20-methyl-13-trans-prostenoic acid |
| 473 | 356 | 9-oxo-15-hydroxy-10a-homo-19-methyl-13-trans,18-prostadienoic acid |
| 474 | 357 | 9-oxo-15-hydroxy-7a,10a-bishomo-20-nor-13-trans-prostenoic acid |
| 475 | 358 | 9-oxo-15-hydroxy-7a,10a-bishomo-20-ethyl-13-trans-prostenoic acid |
| 476 | 359 | 9-oxo-15-hydroxy-7a,10a-bishomo-16-methyl-20-nor-13-trans-prostenoic acid |
| 477 | 360 | 9-oxo-15-hydroxy-7a,10a-bishomo-19-methyl-13-trans,18-prostadienoic acid |
| 478 | 361 | 9-oxo-15-hydroxy-3-thia-20-nor-13-trans-prostenoic acid |
| 479 | 362 | 9-oxo-15-hydroxy-3-thia-20-methyl-13-trans-prostenoic acid |
| 480 | 363 | 9-oxo-15-hydroxy-3-thia-16-ethyl-13-trans-prostenoic acid |
| 481 | 364 | 9-oxo-15-hydroxy-3-thia-16-methyl-18,19,20-trinor-13-trans-prostenoic acid |
| 482 | 365 | 9-oxo-15-hydroxy-3-thia-19-methyl-13-trans,18-prostadienoic acid |
| 483 | 366 | 9-oxo-15-hydroxy-3-thia-19,20-dinor-13-trans,17-prostadienoic acid |
| 484 | 367 | 9-oxo-15-hydroxy-20-nor-5-cis,13-trans-prostadienoic acid |
| 485 | 368 | 9-oxo-15-hydroxy-20-methyl-5-cis,13-trans-prostadienoic acid |
| 486 | 369 | 9-oxo-15-hydroxy-16-ethyl-5-cis,13-trans-prostadienoic acid |
| 487 | 370 | 9-oxo-15-hydroxy-16-methyl-20-nor-5-cis,13-trans-prostadienoic acid |
| 488 | 371 | 9-oxo-15-hydroxy-19-methyl-5-cis,13-trans,18-prostatrienoic acid |
| 489 | 372 | 9-oxo-15-hydroxy-18,19-dimethyl-5-cis,13-trans-18-prostatrienoic acid |
| 490 | 373 | 9-oxo-15-hydroxy-19,20-dinor-5-cis,13-trans,17-prostatrienoic acid |
| 491 | 374 | 9-oxo-15-hydroxy-5-cis,13-trans,17-cis-prostatrienoic acid |

EXAMPLE 492

Preparation of 3-(tert-butoxy)-1-iodooctane

Into a solution of 16.7 g. of 1-iodo-3-octanol [Shriner et al., J. Org. Chem. 4, 103 (1939)] in 250 ml. of methylene chloride is bubbled isobutylene at a fast rate until the solution is saturated. The solution is cooled and 2 ml. of concentrated sulfuric acid is added. The solution is stoppered and allowed to stand at room temperature for 3 days. After the solution is poured into 300 ml. of 5% sodium carbonate, the organic phase is separated, washed with brine, dried with anhydrous magnesium sulfate and evaporated to dryness. Distillation gave 13.9 g. (68%) of product, b.p. 59° C. (0.008 mm).

EXAMPLE 493

Preparation of 15-(tert-butoxy)-9-oxoprostanoic acid, ethyl ester

To a Grignard solution, prepared from 5.05 g. of magnesium and 65.8 g. of 3-(tert-butoxy)-1-iodooctane in 150 ml. of diethyl ether under nitrogen atmosphere, is added 4.0 g. of copper iodide-tri-n-butylphosphine complex followed by dropwise addition of 49 g. of 2-(6-carbethoxyhexyl)cyclopent-2-en-1-one [Hardegger et al., Helv. Chim. Acta 50, 2501 (1967)] and the resulting mixture is stirred for 18 hours. Saturated ammonium chloride (110 ml.) is added followed by 100 ml. of water and 100 ml. of diethyl ether. Unreacted magnesium is removed by filtration. The ethereal layer is washed successively with aqueous sodium thiosulfate solution, ammonium chloride solution, and water, dried over magnesium sulfate and taken to dryness to give an oil. Distillation at 0.05 mm. (bath 100°–185° C.) gives 45.4 g. of material containing unreacted starting material and 30 g. (85% yield based on a non-recovered starting material; see below) of residue which contains the desired product. This material is chromatographed on silica gel. The product is eluted with diethyl ether to give 25.2 g. (71% based on recovered starting material) of a syrup; this material has no significant ultraviolet absorption; $\lambda_{max}^{KBr}$ 5.74, 7.20, 7.35, 8.35 $\mu$; nmr 2H quartet $\delta$4.09 (OCH$_2$ of ester), 1H broad singlet 3.57 (carbinolic proton), 5H overlapping multiplets 2.0–2.4 (protons next to C=O), 3H triplet 1.22 (CH$_3$ of ethyl), 9H singlet 1.17 (CH$_3$'s to t-butyl) and 3H triplet 0.9 (terminal methyl); mass spectrum: m/e 424.

EXAMPLE 494

Preparation of 15-hydroxy-9-oxoprostanoic acid, ethyl ester

A solution of 25 g. of 15-(tert-butoxy)-9-oxoprostanoic acid, ethyl ester in 100 ml. of trifluoroacetic acid is stirred in an ice bath for 1 hour and is then poured into 500 ml. of ice water and extracted several times with chloroform. The combined chloroform extracts are washed with saturated sodium bicarbonate solution, saturated sodium chloride solution, dried with anhydrous magnesium sulfate, and taken to dryness. The resulting oil is dissolved in 200 ml. of 1N ammonium hydroxide in ethanol, kept at ambient temperature for 15 minutes, then taken to dryness. The residual oil is dissolved in chloroform and washed with 1N hydrochloric acid, saturated sodium chloride solution, dried and taken to dryness to give 21.7 g. (100%) of product as a yellow syrup. There is essentially no uv absorption; $\lambda_{max}^{KBr}$ 2.90, 5.75, 8.45 $\mu$; nmr 2H quartet $\delta$4.13 (OCH$_2$ of ester), 1H broad singlet 3.63 (carbinolic proton), 3H triplet (CH$_3$ of ester), and 3H distorted triplet 0.92 (terminal methyl); mass spectrum: m/e 368.

EXAMPLE 495

Preparation of 15-hydroxy-9-oxoprostanoic acid

A suspension of 15 g. of 15-hydroxy-9-oxoprostanoic acid, ethyl ester in 230 ml. of aqueous methanol (1:1) containing 6.45 g. of potassium hydroxide is stirred at 50° C. for 1 hour and then at room temperature for 18 hours. The resulting solution is acidified with 1N hydrochloric acid, saturated with sodium chloride, and extracted several times with diethyl ether. The combined ether extracts are washed twice with saturated sodium chloride solution, dried with anhydrous magnesium sulfate, and taken to dryness to give 13.1 g. (94%) of product as an oil. There is essentially to uv absorption; $[\alpha]_D^{25}$ 0° (1.0% in CHCl$_3$); $\lambda_{max}^{KBr}$ 2.80–3.70 (broad), 5.75, 5.87 $\lambda$; nmr 2H singlet $\delta$6.65 (hydroxyl and carboxyl protons), 1H broad singlet 3.63 (carbinolic proton), and 3H distorted triplet 0.93 (terminal methyl); mass spectrum: m/e 340.

EXAMPLE 496

Preparation of 1-chloro-3-hydroxy-4-octyne

To 68 ml. of 1.6M butyllithium in hexane at $-50°$ C. is added dropwise, with stirring, 7.4 g. of 1-pentyne. The resulting white sludge is diluted with 20 ml. of hexane, brought to 10° C. and treated with 11 g. of freshly prepared $\beta$-chloropropionaldehyde (Org. Syn., Coll. Vol. I, p. 166) at such a rate that the temperature is maintained at 10°–15° C. The solution is allowed to stir at ambient temperature for 18 hours then treated with saturated ammonium chloride solution. The organic phase is separated, washed with dilute hydrochloric solution, dried with anhydrous magnesium sulfate and taken to dryness. Distillation gives 5.1 g. of product b.p. 65°–66° C. at 0.3 nm.; $\lambda$max. 2.95 (—OH) and 4.55 $\mu$ (—C≡C—); vapor phase chromatography shows one peak.

EXAMPLE 497

Preparation of 1-chloro-3-hydroxy-4-cis-octene

A solution of 2 g. of 1-chloro-3-hydroxy-4-octyne (Example 496) is hydrogenated in 50 ml. absolute alcohol using 200 mg. of Lindlar catalyst (5% Pd on CaCO$_3$). The catalyst is removed by filtration and the mother liquor is taken to dryness to give 2 g. of an oil; $\lambda$max. 2.95 (—OH) and 7.25 $\mu$

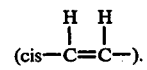

EXAMPLE 498

Preparation of 3-hydroxy-1-iodo-4-octyne

A mixture of 15 g. of sodium iodide in 100 ml. of 2-butanone is stirred at the reflux temperature for 30 minutes. To the cooled mixture is added 12 g. of 1-chloro-3-hydroxy-4-octyne in 150 ml. of 2-butanone. The resulting mixture is stirred at the reflux temperature for 18 hours then cooled and filtered. The mother liquor is taken to dryness and the residue is triturated with benzene and filtered. The benzene is taken to dryness to give the subject product as an oil. The material is shown to be homogeneous by vapor phase chromatography and thin layer chromatography.

EXAMPLE 499

Preparation of 3-hydroxy-1-iodo-4-cis-octene

The subject compound is prepared from 3-hydroxy-1-chloro-4-cis-octene and sodium iodide by the method of Example 498.

EXAMPLE 500

Preparation of 3-t-butoxy-1-iodo-4-octyne

The subject compound is prepared from 3-hydroxy-1-iodo-4-octyne (Example 498) and isobutylene by the method of Example 492.

EXAMPLE 501

Preparation of 3-t-butoxy-1-iodo-4-cis-octene

The subject compound is prepared from 3-hydroxy-1-iodo-4-cis-octene (Example 499) and isobutylene by the method of Example 492.

EXAMPLE 502

Preparation of 3-(tert-butoxy)-1-iodohexane

A mixture of 23.4 g. of 1-chloro-3-hexanol [Fourneau, et. al., Bull. Soc. Chem. France, 25, 367 (1919)] in 300 ml. of 2-butanone containing 30 g. of sodium iodide is stirred at the reflux temperature for 18 hours. The cooled solution is filtered and the mother liquor is taken to dryness. Distillation of the residue affords 32.9 g. (84%) of 1-iodo-3-hexanol, b.p. 105° C. (10 mm). Treatment of this material in 500 ml. of methylene chloride, containing 4 ml. of concentrated sulfuric acid, with isobutylene according to the procedure described in Example 492 gives 27 g. of crude material. Chromatography on florisil affords 16 g. of product; λmax. 7.22 and 7.37 μ (tert-butyl group).

EXAMPLES 503–558

Treatment of the cyclopentenones designated in the table below with the designated Grignard reagents by the procedure of Example 493 is productive of the alkyl 9-oxo-15-t-butoxy-8 ξ-prostanoates and prostenoates of the table. 3-t-Butoxyoctylmagnesium iodide was prepared from 3-t-butoxy-1-iodooctane (Example 492); 3-t-butoxyhexyl magnesium iodide was prepared from 3-t-butoxy-1-iodohexane (Example 502), 3-t-butoxy-4-octynyl magnesium iodide was prepared from 3-t-butoxy-1-iodo-4-octyne (Example 500); and 3-t-butoxy-4-cis-octenyl magnesium iodide was prepared from 3-t-butoxy-1-iodo-4-cis-octene (Example 501).

Table 6

| Example | Starting cyclopentenone of Example | Grignard Reagent | Product Alkyl 9-Oxo-t-butoxy-8ξ-prostanoates, prostynoates and prostenoates |
|---|---|---|---|
| 503 | 31 | 3-t-butoxyoctyl magnesium iodide | ethyl 9-oxo-15-t-butoxy-2-ethyl-8ξ-prostanoate |
| 504 | 41 | 3-t-butoxyoctyl magnesium iodide | ethyl 9-oxo-15-t-butoxy-3,3-dimethyl-8ξ-prostanoate |
| 505 | 46 | 3-t-butoxyoctyl magnesium iodide | ethyl 9-oxo-15-t-butoxy-3-oxa-8ξ-prostanoate |
| 506 | 70 | 3-t-butoxyoctyl magnesium iodide | ethyl 9-oxo-15-t-butoxy-2-fluoro-8ξ-prostanoate |
| 507 | 79 | 3-t-butoxyoctyl magnesium iodide | ethyl 9-oxo-15-t-butyoxy-2-phenyl-8ξ-prostanoate |
| 508 | 99 | 3-t-butoxyoctyl magneisum iodide | ethyl 9-oxo-15-t-butoxy-2-methyl-8ξ-prostanoate |
| 509 | 118 | 3-t-butoxyoctyl magnesium iodide | ethyl 9-oxo-15-t-butoxy-3-thia-8ξ-prostanoate |
| 510 | 900 | 3-t-butoxyoctyl magensium iodide | methyl 9-oxo-15-t-butoxy-8ξ-5-cis-prostenoate |
| 511 | 31 | 3-t-butoxyhexyl magnesium iodide | ethyl 9-oxo-15-t-butoxy-2-ethyl-19,20-dinor-8ξ-prostanoate |
| 512 | 41 | 3-t-butoxyhexyl magnesium iodide | ethyl 9-oxo-15-t-butoxy-3,3-dimethyl-19,20-dinor-8ξ-prostanoate |
| 513 | 46 | 3-t-butoxyhexyl magneisum iodide | ethyl 9-oxo-15-t-butoxy-3-oxa-19,20-dinor-8ξ-prostanoate |
| 514 | 70 | 3-t-butoxyhexyl magnesium iodide | ethyl 9-oxo-15-t-butoxy-2-fluoro-19,20-dinor-8ξ-prostanoate |
| 515 | 79 | 3-t-butoxyhexyl magnesium iodide | ethyl 9-oxo-15-t-butoxy-2-phenyl-19,20-dinor-8ξ-prostanoate |
| 516 | 99 | 3-t-butoxyhexyl magnesium iodide | ethyl 9-oxo-15-t-butoxy-2-methyl-19,20-dinor-8ξ-prostanoate |
| 517 | 118 | 3-t-butoxyhexyl magnesium iodide | ethyl 9-oxo-15-t-butoxy-3-thia-19,20-dinor--8ξ-prostanoate |
| 518 | 900 | 3-t-butoxyhexyl magnesium iodide | methyl 9-oxo-15-t-butoxy-19,20-dinor-8ξ-5-cis-prostenoate |
| 519 | 13 | 3-t-butoxy-4-octynyl magensium iodide | ethyl 9-oxo-15-t-butoxy-8ξ-16-prostynoate |
| 520 | 15 | 3-t-butoxy-4-octynyl magnesium iodide | ethyl 9-oxo-15-t-butoxy-6,7-dinor-8ξ-16-prostynoate |
| 521 | 23 | 3-t-butoxy-4-octynyl magnesium iodide | ethyl 9-oxo-15-t-butoxy-7a,7b-bishomo-8ξ-16-prostynoate |
| 522 | 31 | 3-t-butoxy-4-octynyl magnesium iodide | ethyl 9-oxo-15-t-butoxy-2-ethyl-8ξ-16-prostynoate |
| 523 | 41 | 3-t-butoxy-4-octynyl magnesium iodide | ethyl 9-oxo-15-t-butoxy-3,3-dimethyl-8ξ-16-prostynoate |
| 524 | 46 | 3-t-butoxy-4-octynyl magnesium iodide | ethyl 9-oxo-15-t-butoxy-3-oxa-8ξ-16-prostynoate |
| 525 | 53 | 3-t-butoxy-4-octynyl magnesium iodide | ethyl 9-oxo-15-t-butoxy-7-nor-8ξ-16-prostynoate |
| 526 | 70 | 3-t-butoxy-4-octynyl magnesium iodide | ethyl 9-oxo-15-t-butoxy-2-fluoro-8ξ-16-prostynoate |
| 527 | 74 | 3-t-butoxy-4-octynyl magnesium iodide | ethyl 9-oxo-15-t-butoxy-7a-homo-8ξ-16-prostynoate |
| 528 | 79 | 3-t-butoxy-4-octynyl magnesium iodide | ethyl 9-oxo-15-t-butoxy-2-phenyl-8ξ-16-prostynoate |
| 529 | 81 | 3-t-butoxy-4-octynyl magnesium iodide | butyl 9-oxo-15-t-butoxy-8ξ-16-prostynoate |

Table 6-continued

| Example | Starting cyclopentenone of Example | Grignard Reagent | Product Alkyl 9-Oxo-t-butoxy-8ξ-prostanoates, prostynoates and prostenoates |
|---|---|---|---|
| 530 | 82 | 3-t-butoxy-4-oct-ynyl magnesium iodide | isopropyl 9-oxo-15-t-butoxy-8ξ-16-prostynoate |
| 531 | 83 | 3-t-butoxy-4-oct-ynyl magnesium iodide | methyl 9-oxo-15-t-butoxy-8ξ-16-prostynoate |
| 532 | 84 | 3-t-butoxy-4-oct-ynyl magnesium iodide | decyl 9-oxo-15-t-butoxy-8ξ-16-prostynoate |
| 533 | 99 | 3-t-butoxy-4-oct-ynyl magnesium iodide | ethyl 9-oxo-15-t-butoxy-2-methyl-8ξ-16-prostynoate |
| 534 | 118 | 3-t-butoxy-4-oct-ynyl magnesium iodide | ethyl 9-oxo-15-t-butoxy-3-thia-8ξ-16-prostynoate |
| 535 | 111 | 3-t-butoxy-4-oct-ynyl magnesium iodide | ethyl 9-oxo-15-t-butoxy-10a-homo-8ξ-16-prostynoate |
| 536 | 113 | 3-t-butoxy-4-oct-ynyl magnesium iodide | ethyl 9-oxo-15-t-butoxy-10a-homo-7-nor-8ξ-16-prostynoate |
| 537 | 114 | 3-t-butoxy-4-oct-ynyl magnesium iodide | ethyl 9-oxo-15-t-butoxy-7a,10a-bishomo-8ξ-16-prostynoate |
| 538 | 900 | 3-t-butoxy-4-oct-ynyl magnesium iodide | methyl 9-oxo-15-t-butoxy-8ξ-16-yne-5-cis-prostenoate |
| 539 | 13 | 3-t-butoxy-4-cis-octenyl magnesium iodide | ethyl 9-oxo-15-t-butoxy-8ξ-16-cis-prostenoate |
| 540 | 15 | 3-t-butoxy-4-cis-octenyl magnesium iodide | ethyl 9-oxo-15-t-butoxy-6,7-dinor-8ξ-16-cis-prostenoate |
| 541 | 23 | 3-t-butoxy-4-cis-octenyl magnesium iodide | ethyl 9-oxo-15-t-butoxy-7a,7b-bishomo-8ξ-16-cis-prostenoate |
| 542 | 31 | 3-t-butoxy-4-cis-octenyl magnesium iodide | ethyl 9-oxo-15-t-butoxy-2-ethyl-ξ-16-cis-prostenoate |
| 543 | 41 | 3-t-butoxy-4-cis-octenyl magnesium iodide | ethyl 9-oxo-15-t-butoxy-3,3-dimethyl-8ξ-16-cis-prostenoate |
| 544 | 46 | 3-t-butoxy-4-cis-octenyl magnesium iodide | ethyl 9-oxo-15-t-butoxy-3-oxa-8ξ-16-cis-prostenoate |
| 545 | 53 | 3-t-butoxy-4-cis-octenyl magnesium iodide | ethyl 9-oxo-15-t-butoxy-7-nor-8ξ-16-cis-prostenoate |
| 546 | 70 | 3-t-butoxy-4-cis-octenyl magnesium iodide | ethyl 9-oxo-15-t-butoxy-2-fluoro-8ξ-16-cis-prostenoate |
| 547 | 74 | 3-t-butoxy-4-cis-octenyl magnesium iodide | ethyl 9-oxo-15-t-butoxy-7a-homo-8ξ-16-cis-prostenoate |
| 548 | 79 | 3-t-butoxy-4-cis-octenyl magnesium iodide | ethyl 9-oxo-15-t-butoxy-2-phenyl-8ξ-16-cis-prostenoate |
| 549 | 81 | 3-t-butoxy-4-cis-octenyl magnesium iodide | butyl 9-oxo-15-t-butoxy-8ξ-16-cis-prostenoate |
| 550 | 82 | 3-t-butoxy-4-cis-octenyl magnesium iodide | isopropyl 9-oxo-15-t-butoxy-8ξ-16-cis-prostenoate |
| 551 | 83 | 3-t-butoxy-4-cis-octenyl magnesium iodide | methyl 9-oxo-15-t-butoxy-8ξ-16-cis-prostenoate |
| 552 | 84 | 3-t-butoxy-4-cis-octenyl magnesium iodide | decyl 9-oxo-15-t-butoxy-8ξ-16-cis-prostenoate |
| 553 | 99 | 3-t-butoxy-4-cis-octenyl magnesium iodide | ethyl 9-oxo-15-t-butoxy-2-methyl-8ξ-16-cis-prostenoate |
| 554 | 118 | 3-t-butoxy-4-cis-octenyl magnesium iodide | ethyl 9-oxo-15-t-butoxy-3-thia-8ξ-16-cis-prostenoate |
| 555 | 111 | 3-t-butoxy-4-cis-octenyl magnesium iodide | ethyl 9-oxo-15-t-butoxy-10a-homo-8ξ-16-cis-prostenoate |
| 556 | 113 | 3-t-butoxy-4-cis-octenyl magnesium iodide | ethyl 9-oxo-15-t-butoxy-10a-homo-7-nor-8ξ-16-cis-prostenoate |
| 557 | 114 | 3-t-butoxy-4-cis-octenyl magnesium iodide | ethyl 9-oxo-15-t-butoxy-7a,10a-bishomo-8ξ-16-cis-prostenoate |
| 558 | 900 | 3-t-butoxy-4-cis-octenyl magnesium iodide | methyl 9-oxo-15-t-butoxy-8ξ-5-cis-16-cis-prostadienoate |

EXAMPLES 559-614

Treatment of the 9-oxo-15-t-butoxy derivatives designated in the table below with trifluoroacetic acid and then with aqueous ammonia by the method described in Example 494 is productive of the 9-oxo-15-hydroxy esters of the table.

TABLE 7

| Example | Starting 15-t-butoxy derivative of Example | Product Alkyl 9-oxo-15-hydroxy derivative |
|---|---|---|
| 559 | 503 | Ethyl 9-oxo-15-hydroxy-2-ethyl-prostanoate |
| 560 | 504 | Ethyl 9-oxo-15-hydroxy-3,3-dimethyl-prostanoate |
| 561 | 505 | Ethyl 9-oxo-15-hydroxy-3-oxa-prostanoate |
| 562 | 506 | Ethyl 9-oxo-15-hydroxy-2-fluoro-prostanoate |
| 563 | 507 | Ethyl 9-oxo-15-hydroxy-2-phenyl-prostanoate |
| 564 | 508 | Ethyl 9-oxo-15-hydroxy-2-methyl-prostanoate |
| 565 | 509 | Ethyl 9-oxo-15-hydroxy-3-thia-prostanoate |
| 566 | 510 | Methyl 9-oxo-15-hydroxy-5-cis-prostenoate |
| 567 | 511 | Ethyl 9-oxo-15-hydroxy-2-ethyl-19,20-dinor-prostanoate |
| 568 | 512 | Ethyl 9-oxo-15-hydroxy-3,3-dimethyl-19,20-dinor-prostanoate |
| 569 | 513 | Ethyl 9-oxo-15-hydroxy-3-oxa-19,20-dinor-prostanoate |
| 570 | 514 | Ethyl 9-oxo-15-hydroxy-2-fluoro-19,20-dinor-prostanoate |
| 571 | 515 | Ethyl 9-oxo-15-hydroxy-2-phenyl-19,20-dinor-prostanoate |
| 572 | 516 | Ethyl 9-oxo-15-hydroxy-2-methyl-19,20-dinor-prostanoate |
| 573 | 517 | Ethyl 9-oxo-15-hydroxy-3-thia-19,20-dinor-prostanoate |
| 574 | 518 | Methyl 9-oxo-15-hydroxy-19,20-dinor-5-cis-prostenoate |
| 575 | 519 | Ethyl 9-oxo-15-hydroxy-16-prostynoate |
| 576 | 520 | Ethyl 9-oxo-15-hydroxy-6,7-dinor-16-prostynoate |
| 577 | 521 | Ethyl 9-oxo-15-hydroxy-7a,7b-bishomo-16-prostynoate |
| 578 | 522 | Ethyl 9-oxo-15-hydroxy-2-ethyl-16-prostynoate |
| 579 | 523 | Ethyl 9-oxo-15-hydroxy-3,3-dimethyl-16-prostynoate |
| 580 | 524 | Ethyl 9-oxo-15-hydroxy-3-oxa-16-prostynoate |
| 581 | 525 | Ethyl 9-oxo-15-hydroxy-7-nor-16-prostynoate |
| 582 | 526 | Ethyl 9-oxo-15-hydroxy-2-fluoro-16-prostynoate |
| 583 | 527 | Ethyl 9-oxo-15-hydroxy-7a-homo-16-prostynoate |
| 584 | 528 | Ethyl 9-oxo-15-hydroxy-2-phenyl-16-prostynoate |
| 585 | 529 | Butyl 9-oxo-15-hydroxy-16-prostynoate |
| 586 | 530 | Isopropyl 9-oxo-15-hydroxy-16-prostynoate |
| 587 | 531 | Methyl 9-oxo-15-hydroxy-16-prostynoate |
| 588 | 532 | Decyl 9-oxo-15-hydroxy-16-prostynoate |
| 589 | 533 | Ethyl 9-oxo-15-hydroxy-2-methyl-16-prostynoate |
| 590 | 534 | Ethyl 9-oxo-15-hydroxy-3-thia-16-prostynoate |
| 591 | 535 | Ethyl 9-oxo-15-hydroxy-10a-homo-16-prostynoate |
| 592 | 536 | Ethyl 9-oxo-15-hydroxy-10a-homo-7-nor-16-prostynoate |
| 593 | 537 | Ethyl 9-oxo-15-hydroxy-7a,10a-bishomo-16-prostynoate |
| 594 | 538 | Methyl 9-oxo-15-hydroxy-16-yne-5-cis-prostenoate |
| 595 | 539 | Ethyl 9-oxo-15-hydroxy-16-cis-prostenoate |
| 596 | 540 | Ethyl 9-oxo-15-hydroxy-6,7-dinor-16-cis-prostenoate |
| 597 | 541 | Ethyl 9-oxo-15-hydroxy-7a,7b-bishomo-16-cis-prostenoate |
| 598 | 542 | Ethyl 9-oxo-15-hydroxy-2-ethyl-16-cis-prostenoate |
| 599 | 543 | Ethyl 9-oxo-15-hydroxy-3,3-dimethyl-16-cis-prostenoate |
| 600 | 544 | Ethyl 9-oxo-15-hydroxy-3-oxa-16-cis-prostenoate |
| 601 | 545 | Ethyl 9-oxo-15-hydroxy-7-nor-16-cis-prostenoate |
| 602 | 546 | Ethyl 9-oxo-15-hydroxy-2-fluoro-16-cis-prostenoate |
| 603 | 547 | Ethyl 9-oxo-15-hydroxy-7a-homo-16-cis-prostenoate |
| 604 | 548 | Ethyl 9-oxo-15-hydroxy-2-phenyl-16-cis-prostenoate |
| 605 | 549 | Butyl 9-oxo-15-hydroxy-16-cis-prostenoate |
| 606 | 550 | Isopropyl 9-oxo-15-hydroxy-16-cis-prostenoate |
| 607 | 551 | Methyl 9-oxo-15-hydroxy-16-cis-prostenoate |
| 608 | 552 | Decyl 9-oxo-15-hydroxy-16-cis-prostenoate |
| 609 | 553 | Ethyl 9-oxo-15-hydroxy-2-methyl-16-cis-prostenoate |
| 610 | 544 | Ethyl 9-oxo-15-hydroxy-3-thia-16-cis-prostenoate |
| 611 | 555 | Ethyl 9-oxo-15-hydroxy-10a-homo-16-cis-prostenoate |
| 612 | 556 | Ethyl 9-oxo-15-hydroxy-10a-homo-7-nor-16-cis-prostenoate |
| 613 | 557 | Ethyl 9-oxo-15-hydroxy-7a,10a-bishomo-16-cis-prostenoate |
| 614 | 558 | Methyl 9-oxo-15-hydroxy-5-cis-16-cis-prostadienoate |

EXAMPLES 615-662

Saponification of the 9-oxo-15-hydroxy alkyl esters designated in the table below by the procedure described in Example 495 is productive of the carboxylic acids of the table.

TABLE 8

| Example | Starting alkyl ester of Example | Product 9-oxo-15-hydroxy-prostanoic acid |
|---|---|---|
| 615 | 559 | 9-oxo-15-hydroxy-2-ethyl-prostanoic acid |
| 616 | 560 | 9-oxo-15-hydroxy-3,3-dimethyl-prostanoic acid |
| 617 | 561 | 9-oxo-15-hydroxy-3-oxa-prostanoic acid |
| 618 | 562 | 9-oxo-15-hydroxy-2-fluoro-prostanoic acid |
| 619 | 563 | 9-oxo-15-hydroxy-2-phenyl-prostanoic acid |
| 620 | 564 | 9-oxo-15-hydroxy-2-methyl-prostanoic acid |
| 621 | 565 | 9-oxo-15-hydroxy-3-thia-prostanoic acid |
| 622 | 566 | 9-oxo-15-hydroxy-5-cis-prostenoic acid |

TABLE 8-continued

| Example | Starting alkyl ester of Example | Product 9-oxo-15-hydroxy-prostanoic acid |
|---|---|---|
| 623 | 567 | 9-oxo-15-hydroxy-2-ethyl-19,20-dinor-prostanoic acid |
| 624 | 568 | 9-oxo-15-3,3-dimethyl-19,20-dinor-prostanoic acid |
| 625 | 569 | 9-oxo-15-hydroxy-3-oxa-19,20-dinor-prostanoic acid |
| 626 | 570 | 9-oxo-15-hydroxy-2-fluoro-19,20-dinor-prostanoic acid |
| 627 | 571 | 9-oxo-15-hydroxy-2-phenyl-19,20-dinor-prostanoic acid |
| 628 | 572 | 9-oxo-15-hydroxy-2-methyl-19,20-dinor-prostanoic acid |
| 629 | 573 | 9-oxo-15-hydroxy-3-thia-19,20-dinor-prostanoic acid |
| 630 | 574 | 9-oxo-15-hydroxy-19,20-dinor-5-cis-prostanoic acid |
| 631 | 575 | 9-oxo-15-hydroxy-16-prostanoic acid |
| 632 | 576 | 9-oxo-15-hydroxy-6,7-dinor-16-prostynoic acid |
| 633 | 577 | 9-oxo-15-hydroxy-7a,7b-bishomo-16-prostynoic acid |
| 634 | 578 | 9-oxo-15-hydroxy-2-ethyl-16-prostynoic acid |
| 635 | 579 | 9-oxo-15-hydroxy-3,3-dimethyl-16-prostynoic acid |
| 636 | 580 | 9-oxo-15-hydroxy-3-oxa-16-prostynoic acid |
| 637 | 581 | 9-oxo-15-hydroxy-7-nor-16-prostynoic acid |
| 638 | 582 | 9-oxo-15-hydroxy-2-fluoro-16-prostynoic acid |
| 639 | 583 | 9-oxo-15-hydroxy-7a-homo-16-prostynoic acid |
| 640 | 584 | 9-oxo-15-hydroxy-2-phenyl-16-prostynoic acid |
| 641 | 589 | 9-oxo-15-hydroxy-2-methyl-16-prostynoic acid |
| 642 | 590 | 9-oxo-15-hydroxy-3-thia-16-prostynoic acid |
| 643 | 591 | 9-oxo-15-hydroxy-10a-homo-16-prostynoic acid |
| 644 | 592 | 9-oxo-15-hydroxy-10a-homo-7-nor-16-prostynoic acid |
| 645 | 593 | 9-oxo-15-hydroxy-7a,10a-bishomo-16-prostynoic acid |
| 646 | 594 | 9-oxo-15-hydroxy-16-yne-5-cis-prostenoic acid |
| 647 | 595 | 9-oxo-15-hydroxy-16-cis-prostenoic acid |
| 648 | 596 | 9-oxo-15-hydroxy-6,7-dinor-16-cis-prostenoic acid |
| 649 | 597 | 9-oxo-15-hydroxy-7a,7b-bishomo-16-cis-prostenoic acid |
| 650 | 598 | 9-oxo-15-hydroxy-2-ethyl-16-cis-prostenoic acid |
| 651 | 599 | 9-oxo-15-hydroxy-3,3-dimethyl-16-cis-prostenoic acid |
| 652 | 600 | 9-oxo-15-hydroxy-3-oxa-16-cis-prostenoic acid |
| 653 | 601 | 9-oxo-15-hydroxy-7-nor-16-cis-prostenoic acid |
| 654 | 602 | 9-oxo-15-hydroxy-2-fluoro-16-cis-prostenoic acid |
| 655 | 603 | 9-oxo-15-hydroxy-7a-homo-16-cis-prostenoic acid |
| 656 | 604 | 9-oxo-15-hydroxy-2-phenyl-16-cis-prostenoic acid |
| 657 | 609 | 9-oxo-15-hydroxy-2-methyl-16-cis-prostenoic acid |
| 658 | 610 | 9-oxo-15-hydroxy-3-thia-16-cis-prostenoic acid |
| 659 | 611 | 9-oxo-15-hydroxy-10a-homo-16-cis-prostenoic acid |
| 660 | 612 | 9-oxo-15-hydroxy-10a-homo-7-nor-16-cis-prostenoic acid |
| 661 | 613 | 9-oxo-15-hydroxy-7a,10a-bishomo-16-cis-prostenoic acid |
| 662 | 614 | 9-oxo-15-hydroxy-5-cis-16-cis-prostadienoic acid |

EXAMPLE 663

Ethyl 9-oxo-15-hydroxy-16-trans-prostenoate

To a mixture of 1 g. of ethyl 9-oxo-15-hydroxy-16-prostynoate (Example 575), 11 ml. of water and 27 ml. of dimethylformamide is added 27 ml. of 0.45 N chromous sulfate solution. The mixture is stirred for 48 hours under nitrogen atmosphere. The mixture then is extracted with ether several times and the combined extracts are taken to dryness. Silica gel chromatography gives the subject product as an oil.

EXAMPLES 664 - 682

Treatment of the 9-oxo-15-hydroxy-16-prostynoates listed in Table 8A below with chromous sulfate in the manner of Example 663 is productive of the product 9-oxo-15-hydroxy-16-trans-prostenoates of the table.

TABLE 8A

| Example | Starting 16-prostenoate of Example | Product 9-oxo-15-hydroxy-16-trans-prostenoate |
|---|---|---|
| 664 | 576 | Ethyl 9-oxo-15-hydroxy-6,7-dinor-16-trans-prostenoate |
| 665 | 577 | Ethyl 9-oxo-15-hydroxy-7a,7b-bishomo-16-trans-prostenoate |
| 666 | 578 | Ethyl 9-oxo-15-hydroxy-2-ethyl-16-trans-prostenoate |
| 667 | 579 | Ethyl 9-oxo-15-hydroxy-3,3-dimthyl-16-trans-prostenoate |
| 668 | 580 | Ethyl 9-oxo-15-hydroxy-3-oxa-16-trans-prostenoate |
| 669 | 581 | Ethyl 9-oxo-15-hydroxy-7-nor-16-trans-prostenoate |
| 670 | 582 | Ethyl 9-oxo-15-hydroxy-2-fluoro-16-trans-prostenoate |
| 671 | 583 | Ethyl 9-oxo-15-hydroxy-7a-homo-16-trans-prostenoate |
| 672 | 584 | Ethyl 9-oxo-15-hydroxy-2-phenyl-16-trans-prostenoate |
| 673 | 585 | Butyl 9-oxo-15-hydroxy-16-trans-prostenoate |
| 674 | 586 | Isopropyl 9-oxo-15-hydroxy-16-trans-prostenoate |
| 675 | 587 | Methyl 9-oxo-15-hydroxy-16-trans-prostenoate |
| 676 | 588 | Decyl 9-oxo-15-hydroxy-16-trans-prostenoate |
| 677 | 589 | Ethyl 9-oxo-15-hydroxy-2-methyl-16-trans-prostenoate |
| 678 | 590 | Ethyl 9-oxo-15-hydroxy-3-thia-16-trans-prostenoate |
| 679 | 591 | Ethyl 9-oxo-15-hydroxy-10a-homo-16-trans-prostenoate |
| 680 | 592 | Ethyl 9-oxo-15-hydroxy-10a-homo-7-nor-16-trans-prostenoate |
| 681 | 593 | Ethyl 9-oxo-15-hydroxy-7a,10a-bishomo-16-trans-prostenoate |
| 682 | 594 | Methyl 9-oxo-15-hydroxy-5-cis,16-trans-prostadienoate |

EXAMPLES 683-698

Saponification of the alkyl 9-oxo-15-hydroxy-16-trans-prostenoates listed in Table 8B below by the procedure described in Example 495 is productive of the corresponding prostenoic acids of the table.

TABLE 8B

| Example | Starting alkyl ester of Example | Product 9-oxo-15-hydroxy-16-trans prostenoic acids |
|---|---|---|
| 683 | 663 | 9-oxo-15-hydroxy-16-trans-prostenoic acid |
| 684 | 664 | 9-oxo-15-hydroxy-6,7-dinor-16-trans-prostenoic acid |
| 685 | 665 | 9-oxo-15-hydroxy-7a,7b-bishomo-16-trans-prostenoic acid |
| 686 | 666 | 9-oxo-15-hydroxy-2-ethyl-16-trans-prostenoic acid |
| 687 | 667 | 9-oxo-15-hydroxy-3,3-dimethyl-16-trans-prostenoic acid |
| 688 | 668 | 9-oxo-15-hydroxy-3-oxa-16-trans-prostenoic acid |
| 689 | 669 | 9-oxo-15-hydroxy-7-nor-16-trans-prostenoic acid |
| 690 | 670 | 9-oxo-15-hydroxy-2-fluoro-16-trans-prostenoic acid |
| 691 | 671 | 9-oxo-15-hydroxy-7a-homo-16-trans-prostenoic acid |
| 692 | 672 | 9-oxo-15-hydroxy-2-phenyl-16-trans-prostenoic acid |
| 693 | 677 | 9-oxo-15-hydroxy-2-methyl-16-trans-prostenoic acid |
| 694 | 678 | 9-oxo-15-hydroxy-3-thia-16-trans-prostenoic acid |
| 695 | 679 | 9-oxo-15-hydroxy-10a-homo-16-trans-prostenoic acid |
| 696 | 680 | 9-oxo-15-hydroxy-10a-homo-7-nor-16-trans-prostenoic acid |
| 697 | 681 | 9-oxo-15-hydroxy-7a,10a-bishomo-16-trans-prostenoic acid |
| 698 | 682 | 9-oxo-15-hydroxy-5-cis,16-trans-prostadienoic acid |

EXAMPLE 699

Preparation of 9-oxo-15-hydroxy-3,3-dimethylprostanoic acid

A 2 g. sample of 9-oxo-15-hydroxy-3,3-dimethyl-13-trans-prostenoic acid is hydrogenated using 700 mg. of 10% palladium on carbon in 50 ml. of absolute alcohol. The catalyst is removed by filtration and the mother liquid is taken to dryness to give 2 g. of subject compound as an oil.

EXAMPLE 723

Preparation of 1-chloro-trans-1-octen-3-one

To a slurry of 233.5 g. (1.75 moles) of aluminum chloride in 390 ml. of carbon tetrachloride, saturated with acetylene and cooled in an ice bath, is added over 20 minutes 201.9 g. (1.50 moles) of hexanol chloride. After the addition is complete, acetylene is bubbled into the mixture as rapidly as it is absorbed and for 1 hour after absorption becomes slow. The mixture is poured onto 1700 g. of ice and 720 ml. of saturated brine. The organic phase is separated and the aqueous phase is washed with ether. The combined organic phase and washings are washed with saturated brine, dried ($Na_2SO_4$) and evaporated. The residual oil is combined with 10 g. of hydroquinone and distilled to yield a colorless oil, b.p. 51°–52° C. (0.10 torr).

EXAMPLE 724

Preparation of 1-iodo-trans-1-octen-3-one

A mixture of 54.5 g. (0.364 mole) of sodium iodide and 40 g. (0.249 mole) of 1-chloro-trans-1-octen 3-one (Example 723) in 360 ml. of acetone is stirred and refluxed for 24 hours. The reaction mixture is cooled, filtered and concentrated. The residue is partitioned between water and ether. The organic phase is washed with dilute sodium bicarbonate solution, brine, dried ($MgSO_4$) and evaporated to an oil. This material is used directly without purification.

EXAMPLE 725

A mixture of 68.0 g. (0.424 mole) of 1-chloro-trans-1-octen3 one (Example 723) and 444 g. (4.24 moles) of anhydrous lithium bromide in 900 ml. of 2pentanone is refluxed for 30 minutes, cooled, and partitioned between ice water and ether. The organic phase is washed with water and saturated brine, dried ($NaSO_4$), and evaporated to an oil. This material is used directly without purification.

EXAMPLE 726

Preparation of 1-bromo-trans-1-octen-3-ol

To an ice cooled mixture of 14.29 g. (0.378 mole) of sodium borohydride in 400 ml. of anhydrous ethanol is added the crude 1-bromo-trans-1-octen-3-one (Example 725), from 0.424 mole of 1-chloro-trans-1-octen-3-one) over 30 minutes. The mixture is stirred for 2 hours with ice cooling and is then partitioned between ice water and benzene. The organic phase is washed with water and saturated brine, dried ($Na_2SO_4$), and evaporated to an oil. Fractional distillation yields the title compound as a colorless oil, b.p. 66°–68° C. (0.025 torr).

Example 727

Preparation of 1-chloro-trans-1-octen-3-ol

Treatment of 1-chloro-trans-1-octen-3-one (Example 723) with sodium borohydride in the manner of Example 726 is productive of the subject compound.

EXAMPLE 728

Preparation of 1-bromo-3-triphenylmethoxy-trans-1-octene

A mixture of 6.212 g (0.030 mole) of 1-bromo-trans-1-octen-3ol (Example 726) and 10.67 g. (0.033 mole) of triphenylmethyl bromide in 40 ml. of pyridine is heated to 100° C. for 1.5 hours under an inert atmosphere. The mixture is cooled and filtered. The filtrate is partitioned between ice water and ether. The organic phase is washed with water dilute hydrochloric acid, saturated sodium bicarbonate solution, and saturated brine, dried ($NaSO_4$), and evaporated to an oil. The latter is dissolved in hexane and passed through 250 g. of Florisil ® to yield after evaporation a colorless oil. Found for $C_{27}H_{29}OBr$ : C, 72.13; H, 6.61; Br, 17.57.

EXAMPLE 729

Preparation of 1-iodo-trans-1-octen-3-ol

Treatment of 63 g. (0.25 mole) of 1-iodo-trans-1-octen3-one (Example 724) with sodium borohydride in the manner described in Example 726 gave 58 g. of yellow oil. The oil is purified by adsorption chromatography on a magnesia silica gel column using benzene as eluent to give a light yellow oil.

EXAMPLE 730

Preparation of 1-iodo-3-triphenylmethoxy-trans-1-octene

Treatment of 7.62 g. (0.03 mole) of 1-iodo-trans-1-octen-3-ol with 10.67 g. (0.033 mole) of triphenylmethyl bromide in pyridine in the manner described in Example 728 gave 13.448 g. (90%) of a colorless oil.

EXAMPLE 731

Preparation of 1-chloro-3-triphenylmethoxy-trans-1-octene

Treatment of 1-chloro-trans-1-octen-3-ol (Example 727) with triphenylmethyl chloride by the method described in Example 728 except that the heating period is extended to six hours provides the subject compound.

EXAMPLE 732

Preparation of 11-deoxy-prostaglandin-$E_1$ methyl ester and methyl 15-hydroxy-9-oxo-13-cis-prostenoate To a slurry of 0.535 g. (0.022 g. atom) of magnesium in 6 ml. of tetrahydrofuran is added under an inert atmosphere 2 ml. of a solution of 6.548 g. (0.01455 mole) of 1-bromo-3-trityloxy-trans-1-octene (Example 728) in 8 ml. of tetrahydrofuran. Reaction is initiated by warming the mixture to 45° C. and adding 1 drop of methyl iodide. The remainder of the halide is added at a rate to maintain a temperature of 43°-46° C. and the mixture is heated at 45° C. for 1 hour after complete addition of the halide. The Grignard reagent is cooled and added to an ice cooled solution of 2.615 g. (0.0117 mole) of 2-(6-carbomethoxyhexyl) 2-cyclopentenone (Example 83) and 0.229 g. of Copper (I) iodide-tri-in-butylphosphine in 6 ml. of ether over 6 minutes. The mixture is stirred with ice cooling for 30 minutes and poured into 200 ml. of saturated ammonium chloride. The mixture is extracted into ether and the organic phase is washed with water and saturated brine, dried ($NaSO_4$) and evaporated. The residual oil is heated to 80° C. for 30 minutes with 80% aqueous acetic acid under an inert atmosphere. This mixture is cooled, evaporated to dryness, and the residue is separated by dry column chromatography on silica gel using benzene-ethyl acetate 4:1 as eluent. The title compounds are isolated as oils with $\Delta 13$ trans / $\Delta 13$ cis in ratio of 10:1. Complete resolution is effected with partition chromatography [for a description see M.J, Weiss et al., Tetrahedron, 20, 357 (1964)] on acid-washed Celite -545 using heptane: acetonitrile (Hold Back Volume-1000 ml.); 11-deoxy-prostaglandin-$E_1$ methyl ester is obtained in Hold Back Volume 3-5 and methyl 15-hydroxy-9-oxo-13-cis-prostenoate is obtained in Hold Back Volume 6-8.

EXAMPLE 733

Preparation of 11-deoxy-prostaglandin-$E_1$ methyl ester and methyl 15-hydroxy-9-oxo-13-cis-prostenoate To a slurry of 0.243 g. (0.010 g. atom) of magnesium in 4 ml. of tetrahydrofuran is added under an inert atmosphere 2 ml. of a solution of 4.494 g. (0.010 mole) of 1-bromo-3-trityloxy-trans-1octene in 4 ml. of tetrahydrofuran. Reaction is initiated by warming the mixture to 65° C. and adding 1 drop of methyl iodide. The remainder of the halide is added at a rate to maintain a temperature of 65°-70° C. and the mixture is heated at 75°-80° C. for 30 minutes after complete addition of the halide. The Grignard reagent is cooled and added to 2.243 g. (0.010 mole) of 2-(6-carbomethoxyhexyl)-2-cyclopentenone and 0.200 g. of copper (I) iodide-tri-n-butylphosphine in 6 ml. of ether and worked up with saturated ammonium chloride solution and aqueous acetic acid in the manner of Example 121. The products are isolated as described in Example 723 to yield 11-deoxy-prostaglandin $E_1$ methyl ester and methyl 15-hydroxy-9-oxo-13-cis-prostenoate in a ratio of 2:1.

EXAMPLE 734

Preparation of 15-hydroxy-9-oxo-13-cis-prostenoic acid

Methyl 15-hydroxy-9-oxo-13-cis-prostenoic acid is treated with potassium hydroxide in aqueous methanol and worked up as described in Example 495 to yield the title compound, m.p. 71°-75° C.

EXAMPLE 735

Preparation of Prostaglandin-$E_1$ and 9-oxo-11$\alpha$, 15-dihydroxy-13-cis-prostenoic acid A Grignard reagent is prepared as described in Example 732 from 0.535 g. (0.022 g. atom) of magnesium, 6.742 g. (0.015 mole) of 1-bromo-3-triphenylmethoxy-trans-1-octene (Example 728), and 11 ml. of tetrahydrofuran at a temperature of 40°-42° C. The Grignard reagent is added to 3.95 g. of 2-(6-carbotetrahydropyranyloxyhexyl)-4-tetrahydropyranyloxy-2-cyclopentenone (Example 95) and 0.589 g. of copper (I) iodide tri-n-butylphosphine in 10 ml. of tetrahydrofuran and is worked up with ammonium chloride as described in Example 732. The protecting groups are removed by treating the worked up material, as described in Example 121, with 320 mol of acetic acid-water-tetrahydrofuran 2:1:1 at 45° C. and the products are isolated by chromatography on silica gel with a benzene-ethyl acetate gradient and resolved via partition chromatography on acid-washed Celite 545.

EXAMPLE 736

Preparation of Prostaglandin-$E_1$, and 9-oxo-11$\alpha$,15-dihydroxy-13-cis-prostenoic acid Treatment of 2-(6-carbotetrahydropyranylhexyl)-4-tetrahydropyranyloxy-2-cyclopentenone (Example 95) with the Grignard reagent prepared from 1-bromo-3-triphenylmethoxy-trans-1-octen (Example 728) in the presence of Copper (I) iodide tri-n-butylphosphine complex by the procedure described in Example 733 is productive of the subject compounds.

EXAMPLE 737

Preparation of 9$\alpha$,15-dihydroxy-13-trans-prostenoic acid

To a solution of 433 mg. of 9-oxo-15-hydroxy-13-trans-prostenoic acid in 4.5 ml. of tetrahydrofuran, stirred in an ice bath under nitrogen atmosphere, is added dropwise 3.7 ml. of 0.76M lithium perhydro-9b-boraphenalylhydride. After 40 minutes at 0° C. there is added 1.62 ml. of 3N sodium hydroxide followed by 1.62 ml. of 30% hydrogen peroxide. Ether is added and the resulting solution is acidified with 2N hydrochloric acid. The ether layer is washed several times with saturated sodium chloride solution, dried with anhydrous magnesium sulfate and taken to dryness to give the subject product as an oil.

EXAMPLES 738–893

Treatment of the 9-oxo derivatives designated in the table below with lithium perhydro-9b-boraphenalyl hydride by the procedure described in Example 737 provides the 9α,15-dihydroxy derivatives of the table.

TABLE 9

| Example | Starting 9-oxo-derivative of Example | Product 9α,15-Dihydroxy Derivative |
|---|---|---|
| 738 | 375 | 9α,15-dihydroxy-5,6,7-trinor-13-trans-prostenoic acid |
| 739 | 376 | 9α,15-dihydroxy-7a,7b-bishomo-13-trans-prostenoic acid |
| 740 | 377 | 9α,15-dihydroxy-2-ethyl-13-trans-prostenoic acid |
| 741 | 378 | 9α,15-dihydroxy-3,3-dimethyl-13-trans-prostenoic acid |
| 742 | 379 | 9α,15-dihydroxy-3-oxa-13-trans-prostenoic acid |
| 743 | 380 | 9α,15-dihydroxy-7-nor-13-trans-prostenoic acid |
| 744 | 381 | 9α,15-dihydroxy-2-fluoro-13-trans-prostenoic acid |
| 745 | 382 | 9α,15-dihydroxy-7a-homo-13-trans-prostenoic acid |
| 746 | 383 | 9α,15-dihydroxy-2-phenyl-13-trans-prostenoic acid |
| 747 | 384 | 9α,15-dihydroxy-2-methyl-13-trans-prostenoic acid |
| 748 | 385 | 9α,15-dihydroxy-10a-homo-13-trans-prostenoic acid |
| 749 | 386 | 9α,15-dihydroxy-10a-homo-5,6,7-trinor-13-trans prostenoic acid |
| 750 | 387 | 9α,15-dihydroxy-10a-homo-7-nor-13-trans-prostenoic acid |
| 751 | 388 | 9α,15-dihydroxy-7a,10a-bishomo-13-trans-prostenoic acid |
| 752 | 389 | 9α,15,-dihydroxy-3-thia 13-trans-prostenoic acid |
| 753 | 390 | 9α,15-dihydroxy-13-trans-prostenoic acid |
| 754 | 391 | 9α,15-dihydroxy-13-trans-prostenoic acid |
| 755 | 392 | 9α,15-dihydroxy-13-trans-prostenoic acid |
| 756 | 393 | 9α,15-dihydroxy-13-trans-prostenoic acid |
| 757 | 394 | 9α,15-dihydroxy-5-cis,13-trans-prostadienoic acid |
| 758 | 395 | 9α,15-dihydroxy-2-nor-13-trans-prostenoic acid |
| 759 | 396 | 9α,15-dihydroxy-20-methyl-13-trans-prostenoic acid |
| 760 | 397 | 9α,15-dihydroxy-16-ethyl-13-trans-prostenoic acid |
| 761 | 398 | 9α,15-dihydroxy-16-methyl-20-nor-13-trans-prostenoic acid |
| 762 | 399 | 9α,15-dihydroxy-19-methyl-13-trans, 18-prostadienoic acid |
| 763 | 400 | 9α,15-dihydroxy-18,19-dimethyl-13-trans, 18-prostadienoic acid |
| 764 | 401 | 9α,15-dihydroxy-13-trans, 17-cis-prostadienoic acid |
| 765 | 402 | 9α,15-dihydroxy-5,6,7-trinor-13-trans, 17-cis-prostadienoic acid |
| 766 | 403 | 9α,15-dihydroxy-6,7-dinor-13-trans, 17-cis-prostadienoic acid |
| 767 | 404 | 9α,15-dihydroxy-7a,7b-bishomo-13-trans, 17-cis-prostadienoic acid |
| 768 | 405 | 9α,15-dihydroxy-2-ethyl-13-trans, 17-cis-prostadienoic acid |
| 769 | 406 | 9α,15-dihydroxy-3,3-dimethyl-13-trans, 17-cis-prostadienoic acid |
| 770 | 407 | 9α,15-dihydroxy-3-oxa-13-trans, 17-cis-prostadienoic acid |
| 771 | 408 | 9α,15-dihydroxy-7-nor-13-trans, 17-cis-prostadienoic acid |
| 772 | 409 | 9α,15-dihydroxy-2-fluoro-13-trans, 17-cis-prostadienoic acid |
| 773 | 410 | 9α,15-dihydroxy-7a-homo-13-trans, 17-cis-prostadienoic acid |
| 774 | 411 | 9α,15-dihydroxy-2-phenyl-13-trans, 17-cis-prostadienoic acid |
| 775 | 412 | 9α,15-dihydroxy-2-methyl-13-trans, 17-cis-prostadienoic acid |
| 776 | 413 | 9α,15-dihydroxy-10a-homo-13-trans, 17-cis-prostadienoic acid |
| 777 | 414 | 9α,15-dihydroxy-10a-homo-5,6,7-trinor-13-trans, 17-cis-prostadienoic acid |
| 778 | 415 | 9α,15-dihydroxy-10a-homo-7-nor-13-trans, 17-cis-prostadienoic acid |
| 779 | 416 | 9α,15-dihydroxy-7a,10a-bishomo-13-trans, 17-cis-prostadienoic acid |
| 780 | 417 | 9α,15-dihydroxy-3-thia-13-trans, 17-cis-prostadienoic acid |
| 781 | 418 | 9α,15-dihydroxy-13-trans, 17-cis-prostadienoic acid |
| 782 | 419 | 9α,15-dihydroxy-13-trans, 17-cis-prostadienoic acid |
| 783 | 420 | 9α,15-dihydroxy-13-trans, 17-cis-prostadienoic acid |
| 784 | 421 | 9α,15-dihydroxy-13-trans, 17-cis-prostadienoic acid |
| 785 | 422 | 9α,15-dihydroxy-5,6,7-trinor-19-isobutyl-13-trans, 18-prostadienoic acid |
| 786 | 423 | 9α,15-dihydroxy-5,6,7,-19,20-pentanorf-13-trans, 17-prostadienoic acid |
| 787 | 424 | 9α,15-dihydroxy-19,20-dinor-13-trans, 18-prostadienoic acid |
| 788 | 425 | 9α,15-dihydroxy-17,20-dimethyl-20-isopropenyl-13-trans-prostenoic acid |
| 789 | 426 | 9α,15-dihydroxy-16-ethyl-6,7,19,20-tetranor-13-trans-prostenoic acid |
| 790 | 427 | 9α,15-dihydroxy-18,19-dimethyl-6,7-dinor-13-trans, 18-prostadienoic acid |
| 791 | 428 | 9α,15-dihydroxy-16-ethyl-7a,7b-bishomo-13-trans-prostenoic acid |
| 792 | 429 | 9α,15-dihydroxy-19-methyl-7a,7b-bishomo-13-trans, 18-prostadienoic acid |
| 793 | 430 | 9α,15-dihydroxy-2-ethyl-19,20-dinor-13-trans-prostenoic acid |
| 794 | 431 | 9α,15-dihydroxy-2,20-diethyl-13-trans-prostenoic acid |
| 795 | 432 | 9α,15-dihydroxy-2-ethyl-16-methyl-20-nor-13-trans-prostenoic acid |
| 796 | 433 | 9α,15-dihydroxy-2-ethyl-18,19-dimethyl-13-trans, 18-prostadienoic acid |
| 797 | 434 | 9α,15-dihydroxy-3,3-dimethyl-18,19,20-trinor-13-trans-prostenoic acid |

TABLE 9-continued

| Example | Starting 9-oxo-derivative of Example | Product 9α,15-Dihydroxy Derivative |
|---|---|---|
| 798 | 435 | 9α,15-dihydroxy-3,3,20-trimethyl-13-trans-prostenoic acid |
| 799 | 436 | 9α,15-dihydroxy-3,3,16-trimethyl-20-nor-13-trans-prostenoic acid |
| 800 | 437 | 9α,15-dihydroxy-3,3-dimethyl-19-isobutyl-13-trans, 18-prostadienoic acid |
| 801 | 438 | 9α,15-dihydroxy-3,3-dimethyl-19,20-dinor-13-trans, 17-prostadienoic acid |
| 802 | 439 | 9α,15-dihydroxy-3-oxa-20-nor-13-trans-prostenoic acid |
| 803 | 440 | 9α,15-dihydroxy-3-oxa-20-methyl-13-trans-prostenoic acid |
| 804 | 441 | 9α,15-dihydroxy-3-oxa-16-ethyl-13-trans-prostenoic acid |
| 805 | 442 | 9α,15-dihydroxy-3-oxa-16-methyl-20-nor-13-trans-prostenoic acid |
| 806 | 443 | 9α,15-dihydroxy-3-oxa-19,20-dinor-13-trans, 17-prostadienoic acid |
| 807 | 444 | 9α,15-dihydroxy-7,19,20-trinor-13-trans, 17-prostadienoic acid |
| 808 | 445 | 9α,15-dihydroxy-7-nor-18,29-dimethyl-13-trans 18,prostadienoic acid |
| 809 | 446 | 9α,15-dihydroxy-7,18,19-20-tetranor-16-methyl-13-trans-prostenoic acid |
| 810 | 447 | 9α,15-dihydroxy-2-fluoro-20-nor-13-trans-prostenoic acid |
| 811 | 448 | 9α,15-dihydroxy-2-fluoro-20-ethyl-13-trans-prostenoic acid |
| 812 | 449 | 9α,15-dihydroxy-2-fluoro-16-ethyl-19,20-dinor-13-trans-prostenoic acid |
| 813 | 450 | 9α,15-dihydroxy-2-fluoro-16-methyl-20-nor-13-trans-prostenoic acid |
| 814 | 451 | 9α,15-dihydroxy-2-fluoro-19-methyl-13-trans, 18-prostadienoic acid |
| 815 | 452 | 9α,15-dihydroxy-7a-homo-18,19-dimethyl-13-trans, 18-prostadienoic acid |
| 816 | 453 | 9α,15-dihydroxy-7a-homo-19,20-dinor-13-trans, 17-prostadienoic acid |
| 817 | 454 | 9α,15-dihydroxy-2-phenyl-20-nor-13-trans-prostenoic acid |
| 818 | 455 | 9α,15-dihydroxy-2-phenyl-20-methyl-13-trans-prostenoic acid |
| 819 | 456 | 9α,15-dihydroxy-2-phenyl-16-ethyl-13-trans-prostenoic acid |
| 820 | 484 | 9α,15-dihydroxy-20-nor-5-cis, 13-trans-prostadienoic acid |
| 821 | 485 | 9α,15-dihydroxy-20-methyl-5-cis,13-trans-prostadienoic acid |
| 822 | 486 | 9α,15-dihydroxy-16-ethyl-5-cis, 13-trans-prostadienoic acid |
| 823 | 487 | 9α,15-dihydroxy-16-methyl-20-nor-5-cis, 13-trans-prostadienoic acid |
| 824 | 488 | 9α,15-dihydroxy-19-methyl-5-cis, 13-trans, 18-prostatrienoic acid |
| 825 | 489 | 9α,15-dihydroxy-18,19-dimethyl-5-cis, 13-trans, 18-prostatrienoic acid |
| 826 | 490 | 9α,15-dihydroxy-19,20-dinor-5-cis, 13-trans, 17-prostatrienoic acid |
| 827 | 20-dinor-prostanoic | 9α,15-dihydroxy-5-cis-13-trans, 17-cis-prostatrienoic acid |
| 828 | 734 | 9α,15-dihydroxy-13-cis-prostenoic acid |
| 829 | 735 | 9α,11α,15-trihydroxy-13-cis-prostenoic acid |
| 830 | 615 | 9α,15-dihydroxy-2-ethyl-prostanoic acid |
| 831 | 616 | 9α,15-dihydroxy-3,3-dimethyl-prostanoic acid |
| 832 | 617 | 9α,15-dihydroxy-3-oxa-prostanoic acid |
| 833 | 618 | 9α,15-dihydroxy-2-fluoro-prostanoic acid |
| 834 | 619 | 9α,15-dihydroxy-2-phenyl-prostanoic acid |
| 835 | 620 | 9α,15-dihydroxy-2-methyl-prostanoic acid |
| 836 | 621 | 9α,15-dihydroxy-3-thia-prostanoic acid |
| 837 | 622 | 9α,15-dihydroxy-5-cis-prostenoic acid |
| 838 | 623 | 9α,15-dihydroxy-2-ethyl-19,20-dinor-prostanoic acid |
| 839 | 624 | 9α,15-dihydroxy-3,3-dimethyl-19,20-dinor-prostanoic acid |
| 840 | 625 | 9α,15-dihydroxy-3-oxa-19,20-dinor-prostanoic acid |
| 841 | 626 | 9α,15-dihydroxy-2-fluoro-19,20-dinor-prostanoic acid |
| 842 | 627 | 9α,15-dihydroxy-2-phenyl-19,20-dinor-prostanoic acid |
| 843 | 628 | 9α,15-dihydroxy-2-methyl-19,20-dinor-prostanoic acid |
| 844 | 629 | 9α,15-dihydroxy-3-thia-19,20-dinor-prostanoic acid |
| 845 | 630 | 9α,15-dihydroxy-19,20-dinor-5-cis-prostenoic acid |
| 846 | 631 | 9α,15-dihydroxy-16-prostynoic acid |
| 847 | 632 | 9α,15-dihydroxy-6,7-dinor-16-prostynoic acid |
| 848 | 633 | 9α,15-dihydroxy-7a,7b-bishomo-16-prostynoic acid |
| 849 | 634 | 9α,15-dihydroxy-2-ethyl-16-prostynoic acid |
| 850 | 635 | 9α,15-dihydroxy-3,3-dimethyl-16-prostynoic acid |
| 851 | 636 | 9α,15-dihydroxy-3-oxa-16-prostynoic acid |
| 852 | 637 | 9α,15-dihydroxy-7-nor-16-prostynoic acid |
| 853 | 638 | 9α,15-dihydroxy-2-fluoro-16-prostynoic acid |
| 854 | 639 | 9α,15-dihydroxy-7a-homo-16-prostynoic acid |
| 855 | 640 | 9α,15-dihydroxy-2-phenyl-16-prostynoic acid |
| 856 | 641 | 9α,15-dihydroxy-2-methyl-16-prostynoic acid |
| 857 | 642 | 9α,15-dihydroxy-3-thia-16-prostynoic acid |
| 858 | 643 | 9α,15-dihydroxy-10a-homo-16-prostynoic acid |
| 859 | 644 | 9α,15-dihydroxy-10a-homo-7-nor-16-prostynoic acid |
| 860 | 645 | 9α,15-dihydroxy-7a,10a-bishomo-16-prostynoic acid |
| 861 | 646 | 9α,15-dihydroxy-16-yne-5-cis-prostenoic acid |
| 862 | 683 | 9α,15-dihydroxy-16-trans-prostenoic acid |
| 863 | 684 | 9α,15-dihydroxy-6,7-dinor-16-trans-prostenoic acid |
| 864 | 684 | 9α,15-dihydroxy-7a,7b-bishomo-16-trans-pros- |

TABLE 9-continued

| Example | Starting 9-oxo-derivative of Example | Product 9α,15-Dihydroxy Derivative |
|---|---|---|
| 865 | 686 | 9α,15-dihydroxy-2-ethyl-16-trans-protenoic acid |
| 866 | 687 | 9α,15-dihydroxy-3,3-dimethyl-16-trans-prostenoic acid |
| 867 | 688 | 9α,15-dihydroxy-3-oxa-16-trans-prostenoic acid |
| 868 | 689 | 9α,15-dihydroxy-7-nor-16-trans-prostenoic acid |
| 869 | 690 | 9α,15-dihydroxy-2-fluoro-16-trans-prostenoic acid |
| 870 | 691 | 9α,15-dihydroxy-7a-homo-16-trans-prostenoic acid |
| 871 | 692 | 9α,15-dihydroxy-2-phenyl-16-trans-prostenoic acid |
| 872 | 693 | 9α,15-dihydroxy-2-methyl-16-trans-prostenoic acid |
| 873 | 694 | 9α,15-dihydroxy-3-thia-16-trans-prostenoic acid |
| 874 | 695 | 9α,15-dihydroxy-10a-homo-16-trans-prostenoic acid |
| 875 | 696 | 9α,15-dihydroxy-10a-homo-7-nor-16-trans-prostenoic acid |
| 876 | 697 | 9α,15-dihydroxy-7a,10a-bishomo-16-trans-prostenoic acid |
| 877 | 698 | 9α,15-dihydroxy-5-cis,-16-trans-prostadienoic acid |
| 878 | 647 | 9α,15-dihydroxy-16-cis-prostenoic acid |
| 879 | 648 | 9α,15-dihydroxy-6,7-dinor-16-cis-prostenoic acid |
| 880 | 649 | 9α,15-dihydroxy-7a,7b-bishomo-16-cis-prostenoic acid |
| 881 | 650 | 9α,15-dihydroxy-2-ethyl-16-cis-prostenoic acid |
| 882 | 651 | 9α,15-dihydroxy-3,3-dimethyl-16-cis-prostenoic acid |
| 883 | 652 | 9α,15-dihydroxy-3-oxa-16-cis-prostenoic acid |
| 884 | 653 | 9α,15-dihydroxy-7-nor-16-cis-prostenoic acid |
| 885 | 654 | 9α,15-dihydroxy-2-fluoro-16-cis-prostenoic acid |
| 886 | 655 | 9α,15-dihydroxy-71-homo-16-cis-prostenoic acid |
| 887 | 656 | 9α,15-dihydroxy-2-phenyl-16-cis-prostenoic acid |
| 888 | 657 | 9α,15-dihydroxy-2-methyl-16-cis-prostenoic acid |
| 889 | 658 | 9α,15-dihydroxy-3-thia-16-cis-prostenoic acid |
| 890 | 659 | 9α,15-dihydroxy-10a-homor-16-cis-prostenoic acid |
| 891 | 660 | 9α,15-dihydroxy-10a-homo-7-nor-16-cis-prostenoic acid |
| 892 | 661 | 9α,15-dihydroxy-7a,10a-bishomo-16-cis-prostenoic acid |
| 893 | 662 | 9α,15-dihydroxy-5-cis,-16-cis-prostadienoic acid |

EXAMPLE 894

Preparation of 2-carbalkoxy (methyl/ethyl)-2-(2-methoxyethyl)-cyclopentan-1-one

Treatment of 2-cyclopentanone carboxylate (mixed methyl and ethyl esters) with 2-methoxyethyl bromide by the method of Example 1 furnishes the subject compound as an oil, b.p. 90° C. (0.1 mm).

EXAMPLE 895

Preparation of 2-(2-methoxyethyl)cyclopentan-1-one

Heating 8 g. of 2-carboalkoxy (methyl/ethyl)-2-(2-methoxyethyl)-cyclopentan-1-one (Example 894) in 8 ml. of 20% aqueous hydrochloric acid at reflux for 3.5 hours and isolating the product by the method of Example 2 furnishes the subject compound as an oil, b.p. 45°–50° C. (0.02 mm).

EXAMPLE 896

Preparation of 1-acetoxy-2-(2-methoxyethyl)cyclopent-1-one

The subject compound is prepared from 2-(2-methoxyethyl)cyclopentan-1-one (Example 895) and acetic anhydride by the procedure of Example 10. The product is an oil, b.p. 60° C. (0.2 mm.)

EXAMPLE 897

Preparation of 2-(2-hydroxyethyl)-cyclopent-2-en-1-one

The enol acetate of Example 894 is brominated and dehydrobrominated by the method described in Example 13. The crude product is then dissolved in methylene chloride and is added a7 −78° C. to a methylene chloride solution containing about seven molar equivalents of boron tribromide. After one hour at −78° C. the solution is allowed to warm to room temperature and is then kept at ambient temperatures for a total of 18 hours. The mixture is poured into water and extracted with ether. The organic phase is washed with saturated saline solution, then water and is dried. Evaporation of solvents leaves subject product, which is purified by distillation. The combined organic phases are washed with ice cold 5% sodium hydroxide solution, ice cold 5% hydrochloric acid, and saturated sodium chloride solution, dried with anhydrous magnesium sulfate and taken to dryness. Distillation gives a pale yellow oil; λ max 5.85 μ (carbonyl group).

EXAMPLE 898

Preparation of 2-formylmethylcyclopent-2en-1-one

Chromium trioxide (0.6 mol) is added to a stirring solution of (1.2 mol) of anhydrous pyridine in 1500 ml. of anhydrous methylene chloride cooled in an ice bath. The deep red suspension is stirred for 15 minutes at 0° C. and 45 minutes at ambient temperature. A solution of 01.5 mol of 2-(2-hydroxyethyl)-cyclopent-2-en-1-one (Example 897) in 50 ml. of methylene chloride is added, all at once, to the suspension. A black tarry deposit is formed immediately. After stirring the mixture for 25 minutes at ambient temperature, the methylene chloride is decanted from the tarry precipitate which is then triturated several times with ether.

EXAMPLE 899

Preparation of 2-(6-carboxy-2-cis-hexenyl)-cyclopent-2-en-1-one

A mixture of 0.194 g. (0.007952 mole) of sodium hydride (free of mineral oil) and 5.5 ml. of dimethylsulfoxide is heated to 70° C. until gas evolution ceases under a nitrogen atmosphere. The resulting solution is cooled below room temperature and treated with a solution of 1.400 g. (0.00316 mole) of 4-carboxybutyltriphenyl phosphonium bromide [E.J. Corey et al., J. Am. Chem. Soc., 91, 5675 (1969)] in 6 ml. of dimethylsulfoxide. To the resulting red solution is added 0.00263 mole of 2-formylmethylcyclopent-2-en-1-one (Example 898) in 2 ml. of dimethylsulfoxide and the mixture is stirred at room temperature for 2.25 hours. The mixture is poured into ice water, sodium hydroxide solution is added to pH 12, and the neutral materials are extracted with diethyl ether. The basic phase is acidified with dilute hydrochloric acid and is extracted with diethyl ether. THe organic phase is washed with water and saturated brine, dried (Na$_2$SO$_4$), and evaporated to a semicrystalline mass. The latter is triturated with hot hexane, the solids are filtered off, and the filtrate is evaporated to yield the subject product as an oil.

EXAMPLE 900

Preparation of 2-(6-carbomethoxy-2-cis-hexentyl)-cyclopent-2-en-1-one

Treatment of 2-(6-carboxy-2-cis-hexenyl)-cyclopent-2-en-1-one (Example 899) with diazomethane in the usual manner is productive of the subject ester.

EXAMPLES 901–909

Hydrogenation of 13-trans-prostenoic acids designated in the table below by the procedure of Example 699 is productive of the prostanoic acids of the table.

TABLE 10

| Example | Starting 13 trans-prostenoic acid of Example | Product Prostanoic Acid |
|---|---|---|
| 901 | 397 | 9-oxo-15-hydroxy-16-ethyl-prostanoic acid |
| 902 | 398 | 9-oxo-15-hydroxy-16-methyl-20-nor-prostanoic acid |
| 903 | 400 | 9-oxo-15-hydroxy-18,19-dimethyl-prostanoic acid |
| 904 | 426 | 9-oxo-15-hydroxy-16-ethyl-6,7,19,20-tetranor-prostanoic acid |
| 905 | 428 | 9-oxo-15-hydroxy-16-ethyl-7a,7b-bishomo-prostanoic acid |
| 906 | 429 | 9-oxo-15-hydroxy-19-methyl-7a,7b-bishomo-prostanoic acid |
| 907 | 433 | 9-oxo-15-hydroxy-2-ethyl-18,19-dimethyl-prostanoic acid |
| 908 | 436 | 9-oxo-15-hydroxy-3,3,16-trimethyl-20-nor-prostanoic acid |
| 909 | 476 | 9-oxo-15-hydroxy-7a,10a-bishomo-16-methyl-20-nor-prostanoic acid |

EXAMPLES 910–915

Treatment of the 9-oxo-alkyl esters designated in the table below with sodium borohydride by the procedure described in Example 257 is productive of the corresponding 9-hydroxy derivative of the table. These products are obtained as 9α- and 9β-hydroxy epimeric mixtures.

TABLE 11

| Example | Starting 9-oxo derivative of Example | Product 9α/9β-hydroxy derivative |
|---|---|---|
| 910 | 260 | ethyl 9α/9β,15-dihydroxy-2-ethyl-13-trans-prostenoate |
| 911 | 261 | ethyl 9α/9β,15-dihydroxy-3,3-dimethyl-13-trans-prostenoate |
| 912 | 262 | ethyl 9α/9β,15-dihydroxy-3-oxa-13-trans-prostenoate |
| 913 | 266 | ethyl 9α/9β,15-dihydroxy-2-phenyl-13-trans-prostenoate |
| 914 | 272 | ethyl 9α/9β,15-dihydroxy-3-thia-13-trans-prostenoate |
| 915 | 284 | ethyl 9α/9β,15-dihydroxy-13-trans,17-cis-prostadienoate |

EXAMPLES 916–921

Saponification of the ethyl ester designated in the table below by the procedure described in Example 122 furnishes the carboxylic acids of the table.

TABLE 12

| Example | Starting ethyl ester of Example | Product 9α/9β,15-dihydroxy-13-trans-prostenoic acid |
|---|---|---|
| 916 | 910 | 9α/9β,15-dihydroxy-2-ethyl-13-trans-prostenoic acid |
| 917 | 911 | 9α/9β,15-dihydroxy-3,3-dimethyl-13-trans-prostenoic acid |
| 918 | 912 | 9α/9β,15-dihydroxy-3-oxa-13-trans-prostenoic acid |
| 919 | 913 | 9α/9β,15-dihydroxy-2-phenyl-13-trans-prostenoic acid |
| 920 | 914 | 9α/9β,15-dihydroxy-3-thia-13-trans-prostenoic acid |
| 921 | 915 | 9α/9β,15-dihydroxy-13-trans,17-cis-prostadienoic acid |

EXAMPLES 922–932

Treatment of the cycloalkenones of Table 13, which follows, with the Grignard reagent, prepared from 1-bromo-3-triphenylmethoxy-trans-1-octene and magnesium according to the procedure of Example 733, hydrolizing the intermediate 15-0-triphenylmethyl derivatives with glacial acetic acid-tetrahydrofura-water (4:2:1) according to the procedure of Example 121, and isolating the products in the manner described in Example 732 is productive of the product 9-oxo-15-hydroxy-13-cis-prostenoates and 9-oxo-15-hydroxy-13-trans-prostenoates of the table.

TABLE 13

| Example | Starting cyclopentenone Ester of Example | Product 15-hydroxy-13-cis-prostenoate ester | Product 15-hydroxy-13-trans-prostenoate ester |
|---|---|---|---|
| 922 | 23 | ethyl 9-oxo-15-hydroxy-7a,7b-bishomo-13-cis-prostenoate | ethyl 9-oxo-15-hydroxy-7a,7b-bishomo-13-trans-prostenoate |
| 923 | 31 | ethyl 9-oxo-15-hydroxy-2-ethyl-13-cis-prostenoate | ethyl 9-oxo-15-hydroxy-2-ethyl-13-trans-prostenoate |
| 924 | 41 | ethyl 9-oxo-15-hydroxy-3,3-dimethyl-13-cis-prostenoate | ethyl 9-oxo-15-hydroxy-3,3-dimethyl 13-trans-prostenoate |
| 925 | 46 | ethyl 9-oxo-15-hydroxy-3-oxa-13-cis-prostenoate | ethyl 9-oxo-15-hydroxy-3-oxa-13-trans-prostenoate |
| 926 | 53 | ethyl 9-oxo-15-hydroxy-7-nor- | ethyl 9-oxo-15-hydroxy-7-nor- |

TABLE 13-continued

| Example | Starting cyclopentenone Ester of Example | Product 15-hydroxy-13-cis-prostenoate ester | Product 15-hydroxy-13-trans-prostenoate ester |
|---|---|---|---|
| 927 | 70 | 13-cis-prostenoate ethyl 9-oxo-15-hydroxy-2-fluoro-13-cis-prostenoate | 13-trans-prostenoate ethyl 9-oxo-15-hydroxy-2-fluoro-13-trans-prostenoate |
| 928 | 84 | n-decyl-oxo-15-hydroxy-13-cis-prostenoate 13-trans-prostenoate | n-decyl 9-oxo-15-hydroxy- |
| 929 | 99 | ethyl 9-oxo-15-hydroxy-2-methyl-13-cis-prostenoate | ethyl 9-oxo-15-hydroxy-2-methyl-13-trans-prostenoate |
| 930 | 111 | ethyl 9-oxo-15-hydroxy-10a-homo 13-cis-prostenoate | ethyl 9-oxo-15-hydroxy-10a-homo-13-trans-prostenoate |
| 931 | 118 | ethyl 9-oxo-15-hydroxy-3-thia-13-cis-prostenoate | ethyl 9-oxo-15-hydroxy-3-thia-13-trans-prostenoate |
| 932 | 900 | methyl 9-oxo-15-hydroxy-5-cis, 13-cis-prostadienoate | methyl 9-oxo-15-hydroxy-5-cis, 13-trans- |

EXAMPLES 933–942

Saponification of the 13-cis-prostenoate alkyl esters designated in Table 14 below by the method described in Example 122 is productive of the 13-cis-prostenoic acids of the Table.

TABLE 14

| Example | Starting 13-cis-prostenoate Ester of Example | Product 13-cis-prostenoic acids |
|---|---|---|
| 933 | 922 | 9-oxo-15-hydroxy-7a,7b-bishomo-13-cis-prostenoic acid |
| 934 | 923 | 9-oxo-15-hydroxy-2-ethyl-13-cis-prostenoic acid |
| 935 | 924 | 9-oxo-15-hydroxy-3,3-dimethyl-13-cis-prostenoic acid |
| 936 | 925 | 9-oxo-15-hydroxy-3-oxa-13-cis-prostenoic acid |
| 937 | 926 | 9-oxo-15-hydroxy-7-nor-13-cis-prostenoic acid |
| 938 | 927 | 9-oxo-15-hydroxy-2-fluoro-13-cis-prostenoic acid |
| 939 | 929 | 9-oxo-15-hydroxy-2-methyl-13-cis-prostenoic acid |
| 940 | 930 | 9-oxo-15-hydroxy-10a-homo-13-cis-prostenoic acid |
| 941 | 931 | 9-oxo-15-hydroxy-3-thia-13-cis-prostenoic acid |
| 942 | 932 | 9-oxo-15-hydroxy-5-cis, 13-cis-prostadienoic acid |

EXAMPLES 943–954

Treatment of the 9-oxo-13-cis-prostenoic acids and esters of Table 15 below with lithium perhydro-9b-boraphenalyl hydride by the procedure described in Example 737 furnishes the 9α,15-dihydroxy-13-cis-prostenoic acids and esters of the table.

TABLE 15

| Example | Starting 9-oxo-13-cis-prostenoic derivative of Example | Product 9α,15-hydroxy-13-cis-prostenoic acid and esters |
|---|---|---|
| 943 | 933 | 9,15-dihydroxy-7a,7b-bishomo-13-cis-prostenoic acid |
| 944 | 934 | 9,15-dihydroxy-2-ethyl-13-cis-prostenoic acid |
| 945 | 935 | 9,15-dihydroxy-3,3-dimethyl-13-cis-prostenoic acid |
| 946 | 936 | 9,15-dihydroxy-3-oxa-13-cis-prostenoic acid |
| 947 | 937 | 9,15-dihydroxy-7-nor-13-cis-prostenoic acid |
| 948 | 938 | 9,15-dihydroxy-2-fluoro-13-cis-prostenoic acid |
| 949 | 939 | 9,15-dihydroxy-2-methyl-13-cis-prostenoic acid |
| 950 | 940 | 9,15-dihydroxy-10a-homo-13-cis-prostenoic acid |
| 951 | 941 | 9,15-dihydroxy-3-thia-13-cis-prostenoic acid |
| 952 | 942 | 9,15-dihydroxy-5-cis,-13-cis-prostadienoic acid |
| 953 | 932 | methyl 9,15-dihydroxy-5-cis, 13-cis-prostadienoate |
| 954 | 928 | n-decyl 9,15-dihydroxy-13-cis-prostenoate |

EXAMPLE 955

Preparation of 1-iodo-trans-1-octen-3-ol

A solution of 78.2 g (0.310 moles) of 1-iodo-trans-1-octen-3-one (Example 724) in 150 ml. of absolute ethanol is added dropwise over 2 hours to a slurry of 6.49 g. (0.172 moles) of sodium borohydride in 50 ml. of absolute ethanol cooled in an ice bath. After the addition is complete, the mixture is stirred for 2 hours with ice cooling and is then poured into 1 l. of water. The mixture is extracted into benzene and the organic phase is washed with saturated brine, dried (Na$_2$SO$_4$) and evaporated. The resulting oil is dissolved into 400 ml. of absolute ethanol and treated with 5 mole percent of p-carboxyphenylhydrazine at 70° C. for 1.5 hours to remove residual ketone. The mixture is cooled and evaporated and the residue is dissolved into 400 ml. of ether and is filtered. The filtrate is washed with dilute sodium bicarbonate solution and saturated brine, dried (Na$_2$SO$_4$), and evaporated to an oil. This oil is chromatographyed upon 2 Kg. of Florisil ® packed in hexane and the product is obtained upon elution with benzene Distillation of the product yields a colorless oil, b.p. 74°–76° C. (0.005 tor.).

EXAMPLE 956

Preparation of 1-iodo-3-(p-anisyldiphenylmethoxy)-trans-1-octene

A mixture of 14.92 g. (0.0588 mole) of 1-iodo-trans-1-octen-3-ol (Example 955) and 18.2 g. (0.0588 mole) of p-anisyldiphenylmentyl chloride in 165 ml. of dry pyridine is heated at 60° C. for 18 hours under an inert atmosphere. The mixture is cooled and the solvent is evaporated in vacuo. The residue is partitioned between ether and water, and the organic phase is washed with water and saturated brine, dried (MgSO$_4$), and evaporated. The residue is chromatographed upon 300 g. of Florisil ® packed in hexane and the product is eluted with hexane and 4:1 hexane-benzene the yield a colorless oil.

EXAMPLE 957

Preparation of methyl esters of dl-11-deoxyprostaglandin-$E_1$ and dl-11-deoxy-15-epi-prostaglandin $E_1$ To a solution of 6.030 g. (0.01215 mole) of 1-iodo-3-triphenylmethoxy-trans-1-octene (Example 730) in 8 ml. of toluene cooled to −78° C. under an inert atmosphere is added 5.2 ml. of a 2.34 M solution of n-butyllithium in hexane. The resulting solution is allowed to warm to −40° C. and is maintained at this temperature for 1 hour. To the solution containing 3-triphenylmethoxy-trans-1-octenyllithium is then added 5.0 ml. of a 2.44 M (0.0122 mole) solution of trimethylaluminum in heptane and the mixture is allowed to warm to −10° C. The mixture containing lithium trimethyl(3-triphenylmethoxy-trans-1-octenyl)alanate is then cooled to −78° C. and to it is added a solution of 2.725 g. (0.01215 mole) of 2-(6-carbomethoxyhexyl)-2-cyclopentenone (Example 83) dissolved in 10 ml. of diethyl ether. The mixture is allowed to warm to room temperature and is stirred at ambient temperature for 18 hours. The mixture is then poured onto ice and diluted hydrochloric acid and is extracted into ether. The organic phase is washed with water and saturated brine, dried ($Na_2SO_4$), and evaporated to yield a colorless oil. This oil is heated with 100 ml. of 80% aqueous acetic acid at 80° C. for 1 hour under an inert atmosphere. The resulting mixture is cooled and evaporated in vacuo to dryness with 100 ml. of xylene to yield an oil. This oil is dry-column-chromatographed upon 400 g. of silica gel using 4:1 benzene-ethyl acetate as eluent to yield a total of 2.59 g. of dl-11-deoxyprostaglandin $E_1$ and dl-11-deoxy-15-epi-prostaglandin $E_1$ methyl esters.

EXAMPLE 958

Preparation of 4-(trimethylsiloxy)-2-(6-carbotrimethylsiloxyhexyl)cyclopent-2-en-1-one To a solution of 5 g. of 2-(6-carboxyhexyl)-4-hydroxy-cyclopent-2-en-1-one (Example 94) in 10 ml. of dry N,N-dimethylformamide is added 5.4 g. of trimethylsilyl chloride in a nitrogen atmosphere. To the resulting solution cooled in a top water bath is added 5.05 g. of triethylamine in 10 ml. of N,N-dimethylformamide dropwise. The resulting mixture is stirred at 60° C. in an oil-bath for 2 hours, then at ambient temperatures for 18 hours. Triethylamine hydrochloride is removed by filtration and the filtrate is taken to dryness. The residual oil is distilled to give 2.6 g of product, b.p. 156°-157° C. (0.07 mm.).

EXAMPLE 958A

Preparation of 4-(dimethylisopropylsiloxy)-2-(6-carbodimethylisopropylsiloxyhexyl)cyclopent-2-en-1-one Treatment of 1 g. of 2-(6-carboxyhexyl)-4-hydroxy-cyclopent-2-en-1-one in 2 ml. of dry N,N-dimethylformamide containing 1.81 g of dimethylisopropylsilyl chloride [E. J. Crey, R. K. Varma, J. Amer. Chem. Soc., 93, 7320 (1971)] 1.57 g. of triethylamine in 2 ml. of N,N-dimethylformamide in the manner described in Example 958 gives 1.45 g. of product after two evaporations with toluene.

EXAMPLE 959

Preparation of 4-(dimethyl-t-butylsiloxy)-2-(6-carbodimethyl-t-butylsiloxyhexyl)cyclopent-2-en-1-one To a 0° C. solution of 2.0 gm. (8.55 mole) 4-hydroxy-2-(6-carboxyhexyl)cyclopent-2-en-1-one (Example 94) and 3.65 gm. (54 mole) of imidazole in 5 ml. of dimethylformamide is added a slurry consisting of 4.07 gm. (27 mole) of dimethyl-t-butyl chlorosilane in 5 ml. of dimethylformamide. The slurry is rinsed in with an additional 1 ml. of dimethylformamide. The ice-bath is removed and the solution is stirred at 37° C. for four hours. The solution is then poured into 140 ml. of water and the aqueous solution is extracted twice with 70 ml. of isomeric hexanes. The organic layers are combined, dried with magnesium sulfate and concentrated in vacuo to an oil. Toluene (50 ml.) is added twice and evaporated in vacuo to remove unwanted low boiling impurities.

The residue is maintained under active vacuum overnight to give 3.38 gm. (7.45 mole) of an oil, that shows no hydroxyl or carboxyl absorption in the infrared. $\nu$ max: 1720 $cm^{-1}$ (unsaturated ketone and silyl ester), 840, 815, 795, 780 $cm^{-1}$ (silyl ether and silyl ester).

EXAMPLE 960

Preparation of dl-prostaglandin $E_1$ and dl-epi-prostaglandin $E_1$

To a solution of 4.790 g. (0.0091 mole) of 3-(p-anisyldiphenylmethoxy)-trans-1-iodo-1-octene (Example 956) in 5 ml. of toluene cooled to −78° C. under an inert atmosphere is added 3.9 ml. of 2.34 M n-butyllithium in hexane. The resulting solution is warmed to −40° C. and is maintained at this temperature for 1 hour. To the solution containing 2-(p-anisyldiphenylmethoxy)-trans-1-octenyllithium is then added 3.6 ml. of a 2.44 M solution of trimethylaluminum in heptane and the mixture is allowed to warm to 0° C. The solution containing lithium trimethyl[3-(p-anisyldiphenylmethoxy)-trans-1-octenyl]alanate is then added to a solution of 3.30 g. (0.00726 mole) of 2-(6-carbo-t-butyldimethylsiloxyhexyl)-4-(t-butyldimethylsiloxy)-2-cyclopentenone (Example 959) dissolved in 10 ml. of ether cooled to −45° C. under an inert atmosphere. The resulting solution is allowed to warm to room temperature and is stirred at ambient temperatures for 17 hours. The solution is then poured onto a mixture of 5 ml. of concentrated hydrochloric acid and 150 g. of ice. This mixture is stirred until the ice melts and is extracted into ether. The organic phase is washed with ice cold water and cold saturated brine, dried ($Na_2SO_4$), and is evaporated (<37° C.) in vacuo. The resulting oil is then heated to 38° C. for 23 hours under an inert atmosphere with 100 ml. of 3:1:1 (V:V:V) acetic acid-tetrahydrofuran-water. The mixture is then evaporated with 150 ml. of xylene in vacuo (<38° C.) to yield an oil. Chromatography of this oil upon 115 g. of Silic AR CC-4 (Mallinckrodt) using a benzene-ethyl acetate gradient as eluent yields dl-prostaglandin $E_1$, m.p. 108°-112° (from ethyl acetate) and dl-15-epi-prostaglandin $E_1$.

EXAMPLE 961

Preparation of
3-triphenylmethoxy-trans-1-octenyllithium

To a solution of 4.96 g. of 1-iodo-3-triphenylmethoxy-trans-1-octene (Example 730) in 10 ml. of toluene cooled to −78° C. is added under an inert atmosphere 1 molar equivalent of n-butyllithium dissolved in hexane. The reaction mixture is allowed to warm to −40° C. and is then maintained at that temperature for 1 hour to yield a hydrocarbon solution of 3-triphenylmethoxy-trans-1-octenyllithium.

EXAMPLE 962

Preparation of
3-(p-anisyldiphenylmethoxy)-trans-1-octenyllithium

To a solution of 5.26 g. of 1-iodo-3-(p-anisyldiphenylmethoxy)-trans-1-octene (Example 956) in 10 ml. of toluene, cooled to −78° C., is added under an inert atmosphere 1 molar equivalent of n-butyllithium dissolved in hexane. The reaction mixture is allowed to warm to −40° C. and is maintained at that temperature for 1 hour to yield a hydrocarbon solution of 3-(p-anisyldiphenylmethoxy)-trans-1-octenyllithium.

EXAMPLE 963

Preparation of lithium
[3-triphenylmethoxy-trans-1-octenyl]-trimethylalanate

To a hydrocarbon solution of 3-triphenylmethoxy-trans-1-octenyllithium (Example 961) cooled to −40° C. is added under an inert atmosphere 1 molar equivalent of trimethylaluminum dissolved in heptane to yield a hydrocarbon solution of the title compound.

EXAMPLE 964

Preparation of lithium
[3-p-anisyldiphenylmethoxy)-trans-1-octenyl]-trimethylalanate To a hydrocarbon solution of 3-(p-anisyldiphenylmethoxy)-trans-1-octenyllithium (Example 962) cooled to −40° C. is added under an inert atmosphere 1 molar equivalent of trimethylaluminum dissolved in hexane to yield a hydrocarbon solution of the title compound.

EXAMPLE 965

Preparation of lithium
[3-triphenylmethoxy-trans-1-octenyl]-tri-n-propylalanate

To a hydrocarbon solution of 3-triphenylmethoxy-trans-1-octenyllithium (Example 961) cooled to −40° C. is added under an inert atmosphere 1 molar equivalent of tri-n-propylaluminum dissolved in hexane to yield a hydrocarbon solution of the title compound.

EXAMPLE 966

Preparation of lithium
[3-(p-anisyldiphenylmethoxy)-trans-1-octenyl]-tri-n-hexylalanate To a hydrocarbon solution of 3-(p-anisyldiphenylmethoxy)-trans-1-octenyllithium (Example 962) cooled to −40° C. is added under an inert atmosphere 1 molar equivalent to tri-n-hexylaluminum dissolved in heptane to yield a hydrocarbon solution of the title compound.

EXAMPLE 967

Preparation of lithium
[3-triphenylmethoxy-trans-1-octenyl]-tri-n-decylalanate

To a hydrocarbon solution of 3-triphenylmethoxy-trans-1-octenyllithium (Example 961) cooled to −40° C. is added under an inert atmosphere 1 molar equivalent of tri-n-decylaluminum dissolved in heptane to yield a hydrocarbon solution of the title compound.

EXAMPLE 968

Preparation of lithium
di-(3-triphenylmethoxy-trans-1-octenyl)-dimethylalanate

To a hydrocarbon solution of dimethylaluminum chloride cooled to −78° C. is added under an inert atmosphere 2 molar equivalents of 3-triphenylmethoxy-trans-1-octenyllithium (Example 961) dissolved in toluene-hexane solvent. The mixture is allowed to warm to 0° C. to yield a hydrocarbon solution of the title compound.

EXAMPLE 969

Preparation of lithium
di-[3-(p-anisyldiphenylmethoxy)-trans-1-octenyl]-diethylalanate To a hexane solution of diethylaluminum chloride cooled to −78° C. is added under an inert atmosphere 2 molar equivalents of 3-(p-anisyldiphenylmethoxy)-trans-1-octenyllithium (Example 962) dissolved in toluene-hexane solvent. The mixture is allowed to warm to 0° C. to yield a hydrocarbon solution of the title compound.

EXAMPLE 970

Preparation of lithium
tri-(3-triphenylmethoxy-trans-1-octenyl)-ethylalanate

To a hydrocarbon solution of ethylaluminum dichloride cooled to −78° C. is added an inert atmosphere 3 molar equivalents of 3-triphenylmethoxy-trans-1-octenyllithium (Example 961) dissolved in toluene-hexane solvent. The mixture is allowed to warm to 0° C. to yield a hydrocarbon solution of the title compound.

EXAMPLE 971

Preparation of lithium
tetra-(3-triphenylmethoxy-trans-1-octenyl)alanate

To a well stirred mixture of anhydrous aluminum chloride and hexane cooled to −78° C. is added under an inert atmosphere 4 molar equivalents of 3-triphenylmethoxy-trans-1-octenyllithium (Example 961) dissolved in toluene-hexane The mixture is allowed to warm to 0° C. to yield the title compound.

EXAMPLE 972

Preparation of lithium
tetra-(3-p-anisyldiphenylmethoxy-trans-1-octenyl)alanate

To a well stirred mixture of anhydrous aluminum chloride and hexane cooled to −78° C. is added under an inert atmosphere 4 molar equivalents of 3-p-anisyldiphenylmethoxy-trans-1-octenyllithium (Example 962) dissolved in toluene-hexane. The mixture is allowed to warm to 0° C. to yield the title compound.

EXAMPLES 973–981

Substitution of lithium trimethyl(3-triphenylmethoxy-trans-1-octenyl)alanate in Example 957 with the lithium alanates of Examples 964, 965, 966, 967, 968, 969, 970, 971 or 972 is productive of the methyl esters of d,l-11-deoxy-prostaglandin $E_1$ and d,11-deoxy-15-epi-prostaglandin $E_1$.

EXAMPLES 982–990

Substitution of lithium trimethyl [3-(p-anisyldiphenylmethoxy)-trans-1-octenyl]alanate of Example 960 with the lithium alanates of Examples 965, 966, 967, 968, 969, 970, 971 or 972 is productive of d,l-prostaglandin-$E_1$ and d,l-15-epi-prostaglandin $E_1$.

EXAMPLE 991

Preparation of hexanoyl bromide

A mixture of 300 g. of hexanoic acid and 260 g. of phosphorus tribromide is heated at 80° C. for 1.5 hours with stirring and protection from moisture. The mixture is cooled and the upper phase is decanted into a distilling flask. Distillation of this material yields 400 g. of the colorless acid bromide, b.p. 51°–53° C. (10 torr.).

EXAMPLE 992

Preparation of 1-bromo-trans-1-octen-3-one

A mixture of 300 g. of aluminum bromide and 250 ml. of 1,2-dibromoethane, cooled in an ice bath and protected from moisture, is saturated with acetylene. To the mixture is added with ice cooling 150 g. of hexanoyl bromide (Example 991) over a period of 20 minutes and the resulting mixture is treated with acetylene until gas uptake ceases. The reaction mixture is poured onto 500 ml. of saturated brine and 500 g. of ice. The resulting mixture is extracted twice with 500 ml. of ether. The combined organic extracts are washed twice with 500 ml. of saturated brine and dried with anhydrous sodium sulfate. To the organic phase is added 5 g. of hydroquinone and the solvent is evaporated in vacuo to yield the crude 1-bromo-trans-1-octen-3-one.

EXAMPLE 993

Preparation of 1-bromo-trans-1-octen-3-ol

To an ice cooled mixture of 20 g. of sodium borohydride in 800 ml. of anhydrous ethanol is added 160 g. of crude 1-bromo-trans-1-octen-3-one (Example 992) over a period of 0.5 hour. The mixture is stirred for 2 hours with ice cooling and is then partitioned between ice water and benzene. The organic phase is washed with water and saturated brine, dried ($Na_2SO_4$), and evaporated to an oil. Distillation gives the product as an oil, b.p. 66°–68° C. (0.025 torr.).

EXAMPLE 994

Preparation of 4,4-dimethyl-1-octyn-3-ol

To a solution of 20.2 g. (0.220 mole) of lithium acetylide-ethylenediamine complex in 100 ml. of dry dimethylsulfoxide is added 25.6 g. (0.200 mole) of 2,2-dimethyl-1-hexanal, prepared according to the procedure of G. Stork and S. R. Dowd, J. Amer. Chem. Soc., 85, 2178 (1963), in 25 ml. of dimethylsulfoxide at a rate to maintain a temperature of 25° C. (cooling). The mixture is then maintained at 25° C. for 2 hours and is poured onto ice and excess hydrochloric acid. The mixture is extracted with ether and the organic phase is washed with water and saturated brine, dried ($Na_2SO_4$), and evaporated to an oil. Distillation in vacuo yields the product as a colorless oil.

EXAMPLE 995

Preparation of 4,4-dimethyl-3-tetrahydropyranyloxy-1-octyne

To a solution of 23.1 g. (0.150 mole) of 4,4-dimethyl-1-octyn-3-ol (Example 994) in 126 g. of freshly distilled dihydropyran is added 1 drop of phosphorus oxychloride and the solution is maintained at ambient temperature in a tightly stoppered flask for 20 hours. Five drops of triethylamine are then added and the mixture is evaporated in vacuo to an oil. The oil is chromatographed on 600 g. of silica gel and the product is eluted with 5% ethyl acetate in benzene yielding a colorless oil.

EXAMPLE 996

Preparation of 4,4-dimethyl-1-iodo-trans-1-octen-3-ol

To 233 ml. of a 0.43M solution of disiamylborane in diglyme cooled to 0° C. under an inert atmosphere is added 23.8 g. (0.100 mole) 4,4-dimethyl-3-tetrahydropyranyloxy-1-octyne (Example 995). The mixture is allowed to come to room temperature and is stirred at ambient temperature for 3 hours. The solution is cooled to 0° C. and 22.5 g. (0.30 mole) of triethylamine oxide is added portionwise such that the temperature is maintained at 0°–5° C. The mixture is stirred at 0° C. for 1 hour and is then poured into 150 ml. of 1 N sodium hydroxide followed immediately by a solution of 25.4 g. (0.100 mole) of iodine in 60 ml. of tetrahydrofuran. The mixture is stirred at ambient temperatures for 0.5 hour and poured into 500 ml. of water. The mixture is decolorized by addition of sodium thiosulfate solution and is extracted into ether. The organic phase is washed with water and the solvent is removed in vacuo. The residue is stirred at room temperature for 20 hours with 900 ml. 3:1:1 tetrahydrofuran-acetic acid-water. The solution is evaporated in vacuo and the residue is chromatographed on silica gel in benzene using 10–20% ethylacetate in benzene.

EXAMPLE 997

Preparation of 4,4-dimethyl-1-iodo-3-triphenylmethoxy-trans-1-octene

Treatment of 11.2 g. (0.0396 mole) of 4,4-dimethyl-1-iodo-trans-1-octen-3-ol (Example 996) with 12.8 g. of triphenylmethyl bromide in 50 ml. of pyridine and purification on Florisil ®, all as described in Example 728 gives the title compound.

EXAMPLE 998

Preparation of 5,5-dimethyl-1-octyn-3-ol

Treatment of 20.2 g. (0.220 mole) of lithium acetylide-ethylenediame complex in 100 ml. of dimethylsulfoxide with 25.6 g. (0.200 mole) of 3,3-dimethylhexanal [prepared according to the procedure of A. W. Burgstahler, J. Amer. Chem. Soc., 82, 4681 (1960)] and distillation of the product, all as described in Example 994 yields the title compound.

EXAMPLE 999

Preparation of 5,5-dimethyl-3-tetrahydropyranyloxy-1-octyne

Treatment of 23.1 g. (0.150 mole) of 5,5-dimethyl-1-octyn-3-ol (Example 998) with 126 g. of dihydropyran and 1 drop of phosphorus oxychloride as described in Example 995 gives the title compound.

EXAMPLE 1000

Preparation of 5,5-dimethyl-1-iodo-trans-1-octen-3-ol

Treatment of 23.8 g. (0.100 mole) of 5,5-dimethyl-3-tetrahydropyranyloxy-1-octyne (Example 999) successively with 233 ml. of 0.43 M disiamylborane in diglyme, 22.5 g. of trimethylamine oxide, 150 ml. of 1 N sodium hydroxide, 25.4 g. of iodine, and 900 ml. of 3:1:1 tetrahydrofuranacetic acid-water as described in Example 996 gives the title compound.

EXAMPLE 1001

Preparation of 5,5-dimethyl-1-iodo-3-triphenylmethoxy-trans-1-octene

Treatment of 6.0 g. of 5,5-dimethyl-1-iodo-trans-1-octen-3-ol (Example 1000) with 6.9 g. of triphenylmethyl bromide in 30 ml. of pyridine and purification on Florisil ®, all as described in Example 728 gives the title compound.

EXAMPLE 1002

Preparation of 4,4-dimethyl-3-triphenylmethoxy-trans-1-octenyllithium

Treatment of 4,4-dimethyl-1-iodo-3-triphenylmethoxy-trans-1-octene (Example 997) with n-butyllithium in the manner of Example 961 provides a toluene-hexane solution of the subject trans-vinyl lithium derivative.

EXAMPLE 1003

Preparation of 5,5-dimethyl-3-triphenylmethoxy-trans-1-octenyllithium

Treatment of 5,5-dimethyl-1-iodo-3-triphenylmethoxy-trans-1-octene (Example 1001) with n-butyllithium in the manner of Example 961 provides a toluene-hexane solution of the subject trans-vinyl lithium derivative.

EXAMPLE 1004

Preparation of lithium (4,4-dimethyl-3-triphenylmethoxy-trans-1-octenyl)-trimethylalanate The subject alanate in hydrocarbon solution is prepared according to the method of Example 963 from a hydrocarbon solution of 4,4-dimethyl-3-triphenylmethoxy-trans-1-octenyllithium (Example 1002) and trimethylaluminum.

EXAMPLE 1005

Preparation of lithium (5,5-dimethyl-3-triphenylmethoxy-trans-1-octenyl)-trimethylalanate A hydrocarbon solution of the subject alanate is prepared from a hydrocarbon solution of 5,5-dimethyl-3-triphenylmethoxy-trans-1-octenyl lithium (Example 1003) and trimethylaluminum according to the procedure of Example 963.

EXAMPLES 1006–1031

Treatment of the cycloalkenones of Table 16 which follows with the indicated alanates according to the procedure of Example 957 provides the product 16,16-dimethyl or 17,17-dimethyl 13-trans-prostenoates of the table. The intermediate corresponding 15-O-triphenylmethyl derivatives are obtained prior to treatment with aqueous acetic acid.

TABLE 16

| Example | Starting cycloalkenone of Example | Product from reaction with lithium (4,4-Dimethyl-3-triphenylmethoxy-trans-1-octenyl)trimethylalanate (Example 1004) |
|---|---|---|
| 1006 | 13 | ethyl 9-oxo-15-hydroxy-16,16-dimethyl-13-trans-prostenoate |
| 1007 | 23 | ethyl 9-oxo-15-hydroxy-16,16-dimethyl-7a,7b-bishomo-13-trans-prostenoate |
| 1008 | 31 | ethyl 9-oxo-15-hydroxy-16,16-dimethyl-2-ethyl-13-trans-prostenoate |
| 1009 | 41 | ethyl 9-oxo-15-hydroxy-16,16-dimethyl-3,3-dimethyl-13-trans-prostenoate |
| 1010 | 46 | ethyl 9-oxo-15-hydroxy-16,16-dimethyl-3-oxa-13-trans-prostenoate |
| 1011 | 53 | ethyl 9-oxa-15-hydroxy-16,16-dimethyl-7-nor-13-trans-prostenoate |
| 1012 | 70 | ethyl 9-oxo-15-hydroxy-16,16-dimethyl-2-fluoro-13-trans-prostenoate |
| 1013 | 84 | n-decyl 9-oxo-15-hydroxy-16,16-dimethyl-13-trans-prostenoate |
| 1014 | 99 | ethyl 9-oxo-15-hydroxy-16,16-dimethyl-2-methyl-13-trans-prostenoate |
| 1015 | 111 | ethyl 9-oxo-15-hydroxy-16,16-dimethyl-10a-homo-13-trans-prostenoate |
| 1016 | 118 | ethyl 9-oxo-15-hydroxy-16,16-dimethyl-3-thia-13-trans-prostenoate |
| 1017 | 900 | methyl 9-oxo-15-hydroxy-16,16-dimethyl-5-cis,13-trans-prostadienoate |
| 1018 | 79 | ethyl 9-oxo-15-hydroxy-16,16-dimethyl-2-phenyl-13-trans-prostenoate |
| 1019 | 13 | ethyl 9-oxo-15-hydroxy-17,17-dimethyl-13-trans-prostenoate |
| 1020 | 23 | ethyl 9-oxo-15-hydroxy-17,17-dimethyl-7a,7b-bishomo-13-trans-prostenoate |
| 1021 | 31 | ethyl 9-oxo-15-hydroxy-17,17-dimethyl-2-ethyl-13-trans-prostenoate |
| 1022 | 41 | ethyl 9-oxo-15-hydroxy-17,17-dimethyl-3,3-dimethyl-13-trans-prostenoate |
| 1023 | 46 | ethyl 9-oxo-15-hydroxy-17,17-dimethyl-3-oxa-13-trans-prostenoate |
| 1024 | 53 | ethyl 9-oxo-15-hydroxy-17,17-dimethyl-7-nor-13-trans-prostenoate |
| 1025 | 70 | ethyl 9-oxo-15-hydroxy-17,17-dimethyl-2-fluoro-13-trans-prostenoate |
| 1026 | 84 | n-decyl 9-oxo-15-hydroxy-17,17-dimethyl-13-trans-prostenoate |
| 1027 | 99 | ethyl 9-oxo-15-hydroxy-17,17-dimethyl-2-methyl-13-trans-prostenoate |
| 1028 | 111 | ethyl 9-oxo-15-hydroxy-17,17-dimethyl-10a-homo-13-trans-prostenoate |
| 1029 | 118 | ethyl 9-oxo-15-hydroxy-17,17-dimethyl-3-thia-13-trans-prostenoate |
| 1030 | 900 | methyl 9-oxo-15-hydroxy-17,17-dimethyl-5-cis,13-trans-prostadienoate |
| 1031 | 79 | ethyl 9-oxo-15-hydroxy-17-17-dimethyl-2-phenyl-13-trans-prostenoate |

EXAMPLES 1032–1055

Saponification of the 16,16-dimethyl or 17,17-dimethyl 13-trans-prostenoate alkyl esters of Table 17 below by the method of Example 122 provides the corresponding prostenoic acids of the Table.

TABLE 17

| Example | Starting alkyl ester of Example | Product 16,16-dimethyl or 17,17-dimethyl-9-oxo-15-hydroxy-13-trans-prostenoic acid |
|---|---|---|
| 1032 | 1006 | 9-oxo-15-hydroxy-16,16-dimethyl-13-trans-prostenoic acid |
| 1033 | 1007 | 9-oxo-15-hydroxy-16,16-dimethyl-7a,7b-bishomo-13-trans-prostenoic acid |
| 1034 | 1008 | 9-oxo-15-hydroxy-16,16-dimethyl-2-ethyl-13-trans-prostenoic acid |
| 1035 | 1009 | 9-oxo-15-hydroxy-16,16-dimethyl-3,3-dimethyl-13-trans-prostenoic acid |
| 1036 | 1010 | 9-oxo-15-hydroxy-16,16-dimethyl-3-oxa-13-trans-prostenoic acid |
| 1037 | 1011 | 9-oxo-15-hydroxy-16,16-dimethyl-7-nor-13-trans-prostenoic acid |
| 1038 | 1012 | 9-oxo-15-hydroxy-16,16-dimethyl-2-fluoro-13-trans-prostenoic acid |
| 1039 | 1014 | 9-oxo-15-hydroxy-16,16-dimethyl-2-methyl-13-trans-prostenoic acid |
| 1040 | 1015 | 9-oxo-15-hydroxy-16,16-dimethyl-10a-homo-13-trans-prostenoic acid |
| 1041 | 1016 | 9-oxo-15-hydroxy-16,16-dimethyl-3-thia-13-trans-prostenoic acid |
| 1042 | 1017 | 9-oxo-15-hydroxy-16,16-dimethyl-5-cis,13-trans-prostadienoic acid |
| 1043 | 1018 | 9-oxo-15-hydroxy-16,16-dimethyl-2-phenyl-13-trans-prostenoic acid |
| 1044 | 1019 | 9-oxo-15-hydroxy-17,17-dimethyl-13-trans-prostenoic acid |
| 1045 | 1020 | 9-oxo-15-hydroxy-17,17-dimethyl-7a,7b-bishomo-13-trans-prostenoic acid |
| 1046 | 1021 | 9-oxo-15-hydroxy-17,17-dimethyl-2-ethyl-13-trans-prostenoic acid |
| 1047 | 1022 | 9-oxo-15-hydroxy-17,17-dimethyl-3,3-dimethyl-13-trans-prostenoic acid |
| 1048 | 1023 | 9-oxo-15-hydroxy-17,17-dimethyl-3-oxa-13-trans-prostenoic acid |
| 1049 | 1024 | 9-oxo-15-hydroxy-17,17-dimethyl-7-nor-13-trans-prostenoic acid |
| 1050 | 1025 | 9-oxo-15-hydroxy-17,17-dimethyl-2-fluoro-13-trans-prostenoic acid |
| 1051 | 1027 | 9-oxo-15-hydroxy-17,17-dimethyl-2-methyl-13-trans-prostenoic acid |
| 1052 | 1028 | 9-oxo-15-hydroxy-17,17-dimethyl-10a-homo-13-trans-prostenoic acid |
| 1053 | 1029 | 9-oxo-15-hydroxy-17,17-dimethyl-3-thia-13-trans-prostenoic acid |
| 1054 | 1030 | 9-oxo-15-hydroxy-17,17-dimethyl-5-cis,13-trans-prostadienoic acid |
| 1055 | 1031 | 9-oxo-15-hydroxy-17,17-dimethyl-2-phenyl-13-trans-prostenoic acid |

EXAMPLES 1056–1081

Treatment of the 9-oxo- acids and esters of Table 18 below with lithium perhydro-9b-boraphenalyl hydride by the procedure of Example 737 provides the 9α,15-dihydroxy-16,16-dimethyl or 17,17-dimethyl-13-trans-prostenoic acid of the Table.

TABLE 18

| Example | Starting 9-oxo derivative of Example | Product 9α-15-Dihydroxy-16,16-dimethyl or 17,17-dimethyl-13-trans-prostenoic acids or esters |
|---|---|---|
| 1056 | 1032 | 9α,15-dihydroxy-16,16-dimethyl-13-trans-prostenoic acid |
| 1057 | 1033 | 9α,15-dihydroxy-16,16-dimethyl-7a,7b-bishomo-13-trans-prostenoic acid |
| 1058 | 1034 | 9α,15-dihydroxy-16,16-dimethyl-2-ethyl-13-trans-prostenoic acid |
| 1059 | 1035 | 9α,15-dihydroxy-16,16-dimethyl-3,3-dimethyl-13-trans-prostenoic acid |
| 1060 | 1036 | 9α,15-dihydroxy-16,16-dimethyl-3-oxa-13-trans-prostenoic acid |
| 1061 | 1037 | 9α,15-dihydroxy-16,16-dimethyl-7-nor-13-trans-prostenoic acid |
| 1062 | 1038 | 9α,15-dihydroxy-16,16-dimethyl-2-fluoro-13-trans-prostenoic acid |
| 1063 | 1013 | n-decyl 9α,15-dihydroxy-16,16-dimethyl-13-trans-prostenoate |
| 1064 | 1039 | 9α,15-dihydroxy-16,16-dimethyl-2-methyl-13-trans-prostenoic acid |
| 1065 | 1040 | 9α,15-dihydroxy-16,16-dimethyl-10a-homo-13-trans-prostenoic acid |
| 1066 | 1041 | 9α,15-dihydroxy-16,16-dimethyl-3-thia-13-trans-prostenoic acid |
| 1067 | 1042 | 9α,15-dihydroxy-16,16-dimethyl-5-cis,13-trans-prostadienoic acid |
| 1068 | 1043 | 9α,15-dihydroxy-16,16-dimethyl-2-phenyl-13-trans-prostenoic acid |
| 1069 | 1044 | 9α,15-dihydroxy-17,17-dimethyl-13-trans-prostenoic acid |
| 1070 | 1045 | 9α,15-dihydroxy-17,17-dimethyl-7a,7b-bishomo-13-trans-prostenoic acid |
| 1071 | 1046 | 9α,15-dihydroxy-17,17-dimethyl-2-ethyl-13-trans-prostenoic acid |
| 1072 | 1047 | 9α,15-dihydroxy-17,17-dimethyl-3,3-dimethyl-13-trans-prostenoic acid |
| 1073 | 1048 | 9α,15-dihydroxy-17,17-dimethyl-3-oxa-13-trans-prostenoic acid |
| 1074 | 1049 | 9α,15-dihydroxy-17,17-dimethyl-7-nor-13-trans-prostenoic acid |
| 1075 | 1050 | 9α,15-dihydroxy-17,17-dimethyl-2-fluoro-13-trans-prostenoic acid |
| 1076 | 1026 | n-decyl 9α,15-dihydroxy-17,17-dimethyl-13-trans-prostenoate |
| 1077 | 1051 | 9α,15-dihydroxy-17,17-dimethyl-2-methyl-13-trans-prostenoic acid |
| 1078 | 1052 | 9α,15-dihydroxy-17,17-dimethyl-10a-homo-13-trans-prostenoic acid |
| 1079 | 1053 | 9α,15-dihydroxy-17,17-dimethyl-3-thia-13-trans-prostenoic acid |
| 1080 | 1054 | 9α,15-dihydroxy-17,17-dimethyl 5-cis,13-trans-prostadienoic acid |
| 1081 | 1055 | 9α,15-dihydroxy-17,17-dimethyl-2-phenyl-13-trans-prostenoic acid |

EXAMPLE 1082

A solution of methyl 9-oxo-15-hydroxy-5-cis,13-trans,17-cis-prostatrienoate (Example 374) in tetrahydrofuran is added to 1.1 equivalent of lithium perhydro- 9b-boraphenyalyl hydride in tetrahydrofuran at −78° C. After 30 minutes equal volumes of 5% aqueous sodium carbonate and 30% aqueous hydrogen peroxide is added, and the solution is stirred 15 minutes. The solution is diluted with water and extracted with ether. The organic phase is dried (magnesium sulfate) and concentrated in vacuo to give methyl 9α,15α-dihydroxy-5-cis,13-trans,17-cis-prostatrienoate, contaminated with methyl 9β,15α-dihydroxy-5cis,13trans,17cis-prostatienoate. The crude mixture of esters is dissolved in methylene chloride and added to a refluxing solution of 1.2 equivalents of 2,3-dichloro-5,6-dicyanobenzoquinone (DDQ) in methylene chloride. After 5 hours, the solution is cooled and filtered. The filtrate is diluted with two volumes of ether, extracted with 5% aqueous sodium carbonate and dried with magnesium sulfate. The solution is concentrated in vacuo to give methyl 9α-hydroxy-15-oxo-5cis13-trans, 17cis-prostatrienoate and 9β-hydroxy-15-oxo-5cis, 13trans,17cis-prostatrienoate. The crude material is dissolved in benzene and 1.2 equivalents each of triethylamine and trimethylsilyl chloride is added. The triethylamine hydrochloride is removed by filtration and the solution is concentrated in vacuo to give methyl 9α-trimethylsiloxy-15-keto-5cis,13trans,17cis-prostatrienoate and the corresponding 9β-trimethylsiloxy derivative.

The siloxy derivatives are dissolved in ether at 0° C. and 1.05 equivalents of methyl magnesium bromide in ether is added. After the reaction is complete, the solution is poured into saturated aqueous ammonium chloride and extracted with ether. The ether is dried and concentrated in vacuo to give methyl 9α-trimethylsiloxy-15α-hydroxy-15β-methyl-5cis,13trans,17cis-prostatrienoate, and methyl 9α-trimethylsiloxy-15β-hydroxy-15α-methyl-5cis,13trans,17cis-prostatrienoate, methyl 9β-trimethylsiloxy-15α-hydroxy-15β-methyl-5cis,13trans,17cis-prostatrienoate, and methyl 9β-trimethylsiloxy-15β-hydroxy-15α-methyl 5cis,13trans,17cis-prostatrienoate. Hydrolysis of the siloxy functions of each in a solution of methanol, water and acetic acid (approximately 10:1:1, 3 hours ambient temperatures) and gives methyl 9α,15α-dihydroxy-15β-methyl-5cis-13trans,17cis-prostatrienoate, methyl 9α,15β-dihydroxy-15α-methyl-5cis,13trans, 17cis-prostatrienoate, methyl 9β,15α-dihydroxy-15β-methyl-5cis,13trans,17-cis-prostatrienoate and methyl 9β,15β-dihydroxy-15α-methyl-5-cis,13trans,17cis-prostatrienoate separated by dry column chromatography and further purified by partition chromatography saponification (method of Example 122) of each component in 50% aqueous methanol with potassium hydroxide gives the corresponding free acids.

Treatment of a solution of methyl 9α,15α-dihydroxy-15β-methyl-5cis,13trans,17cis-prostatrienoate in methylene chloride with Collins reagent (CrO3-pyridine in methylene chloride) gives methyl 9-oxo-15α-hydroxy-15β-methyl-5cis,13-trans,17cis-prostatrienoate, saponification of which (method of Example 122) gives 9-oxo-15α-hydroxy-15β-methyl-5cis,13trans,17cis-prostatrienoate acid.

Similar treatment of the 15β-hydroxy esters gives methyl 9-oxo-15β-hydroxy-15α-methyl-5cis,13trans,17-cis-prostatrienoate which gives 9-oxo-15β-hydroxy-15α-methyl-5cis,13trans,17cis-prostatrienoic acid after saponfication.

Examples 1083–1101

Treatment of the 9-oxo-15-hydroxy prostenoic esters of Table 18A below by the sequence of reactions described in Example 1082 is productive of the 9α,15-dihydroxy-15-methyl and the 9-oxo-15-hydroxy-15-methyl products of the table. Also prepared in the course of these reaction sequences are the ethyl (methyl for Example 1101) esters corresponding to the products of the table, the 9β-hydroxy derivatives corresponding to the listed 9α-hydroxy derivatives and their ethyl esters, the 15-keto derivatives of the 9α- and 9β-hydroxy compounds corresponding to the 9-oxo starting compounds, and the 9α- or 9β-trimethyl-silyloxy ethyl esters of the 15-keto and 15-hydroxy-15-methyl compounds. In all cases both the 15α-hydroxy-15β-methyl and the 15β-hydroxy-15α-methyl products and intermediates are obtained. These epimers are separable by chromatographic procedures.

TABLE 18A

| Example | Starting 9-oxo-15-hydroxy-ester of Example | Product 15-hydroxy-15-methyl derivative |
|---|---|---|
| 1083 | 260 | 9-oxo-15-methyl-15-hydroxy-2-ethyl-13-trans-prostenoic acid and 9α,15-dihydroxy-15-methyl-2-ethyl-13-trans-prostenoic acid |
| 1084 | 261 | 9-oxo-15-hydroxy-15-methyl-3,3-dimethyl-13-trans-prostenoic acid and 9α,15-dihydroxy-15-methyl-3,3-dimethyl-13-trans-prostenoic acid |
| 1085 | 262 | 9-oxo-15-hydroxy-15-methyl-3-oxa-13-trans-prostenoic acid and 9α,15-dihydroxy-15-methyl-3-oxa-13-trans-prostenoic acid |
| 1086 | 264 | 9-oxo-15-hydroxy-15-methyl-2-fluoro-13-trans-prostenoic acid and 9α,15-dihydroxy-15-methyl-2-fluoro-13-trans-prostenoic acid |
| 1087 | 266 | 9-oxo-15-hydroxy-15-methyl-2-phenyl-13-trans-prostenoic acid and 9α,15-dihydroxy-15-methyl-2-phenyl-13-trans-prostenoic acid |
| 1088 | 267 | 9-oxo-15-hydroxy-15-methyl-2-methyl-13-trans-prostenoic acid and 9α,15-dihydroxy-15-methyl-2-methyl-13-trans-prostenoic acid |
| 1089 | 268 | 9-oxo-15-hydroxy-15-methyl-10a-homo-13-trans-prostenoic acid and 9α,15-dihydroxy-15-methyl-10a-homo-13-trans-prostenoic acid |
| 1090 | 272 | 9-oxo-15-hydroxy-15-methyl-3-thia-13-trans-prostenoic acid and 9α,15-dihydroxy-15-methyl-3-thia-13-trans-prostenoic acid |
| 1091 | 362 | 9-oxo-15-hydroxy-15-methyl-3-thia-20-methyl-13-trans-prostenoic acid and 9α,15-dihydroxy-15-methyl-3-thia-20-methyl-13-trans-prostenoic acid |
| 1092 | 343 | 9-oxo-15-hydroxy-15-methyl-2,20-dimethyl-13-trans-prostenoic |

TABLE 18A-continued

| Example | Starting 9-oxo-15-hydroxy-ester of Example | Product 15-hydroxy-15-methyl derivative |
|---|---|---|
|  |  | acid and 9α,15-dihydroxy-15-methyl-2,20-dimethyl-13-trans, prostenoic acid |
| 1093 | 323 | 9-oxo-15-hydroxy-15-methyl-3-oxa-20-methyl-13-trans-prostenoic acid and 9α,15-dihydroxy-15-methyl-3-oxa-20-methyl-13-trans-prostenoic acid |
| 1094 | 284 | 9-oxo-15-dihydroxy-15-methyl-13-trans, 17-cis-prostadienoic acid and 9α,15-dihydroxy-15-methyl-13-trans,17-cis-prostadienoic acid |
| 1095 | 287 | 9-oxo-15-hydroxy-15-methyl-7a,7b-bishomo-13-trans, 17-cis-prostadienoic acid and 9a,15-dihydroxy-15-methyl-7a,7b-bishomo-13-trans, 17-cis-prostadienoic acid |
| 1096 | 290 | 9-oxo-15-hydroxy-15-methyl-3-oxa-13-trans, 17-cis-prostadienoic acid and 9a,15-dihydroxy-15-methyl-3-oxa-13-trans, 17-cis-prostadienoic acid |
| 1097 | 291 | 9-oxo-15-hydroxy-15-methyl-7-nor-13-trans, 17-cis-prostadienoic acid and 9α,15-dihydroxy-15-methyl-7-nor-13-trans, 17-cis-prostadienoic acid |
| 1098 | 292 | 9-oxo-15-hydroxy-15-methyl-2-fluoro-13-trans, 17-cis-prostadienoic acid and 9α,15-dihydroxy-15-methyl-2-fluoro-13-trans, 17-cis-prostadienoic acid |
| 1099 | 293 | 9-oxo-15-hydroxy-15-methyl-7a-homo-13-trans, 17-cis-prostadienoic acid and 9α,15-dihydroxy-15-methyl-7a-homo-13-trans, 17-cis-prostadienoic acid |
| 1100 | 300 | 9-oxo-15-hydroxy-15-methyl-3-thia-13-trans, 17-cis-prostadienoic acid and 9α,15-dihydroxy-15-methyl-3-thia-13-trans, 17-cis-prostadienoic acid |
| 1101 | 733 | 9-oxo-15-hydroxy-15-methyl-13-cis, 17-cis-prostadienoic acid and 9α,15-dihydroxy-15-methyl-13-cis, 17-cis prostadienoic acid |

*methyl 15-hydroxy-9-oxo-13-cis-prostenoate only

EXAMPLES 1102–1104

Hydrogenation of the 13-trans-prostenoic acids listed in Table 19 below by the procedure described in Example 699 is productive of the product prostanoic acids of the table. The product epimers are separable by chromatographic procedures.

TABLE 19

| Example | Starting 15-hydroxy-15-methyl-13-trans-prostenoic acid | Product 15-hydroxy-15-methyl-prostanoic acid |
|---|---|---|
| 1102 | 9-oxo-15-hydroxy-15-methyl-3-oxa-13-trans-pros- | 9-oxo-15-hydroxy-15-methyl-3-oxa-prostanoic acid |
| | tenoic acid (Example 1085) | |
| 1103 | 9α,15-dihydroxy-15-methyl-3-oxa-13-trans-prostenoic acidi (Example 1085) | 9α,15-dihydroxy-15-methyl-3-oxa-proatanoic acid |
| 1104 | 9-oxo-15-hydroxy-15-methyl-10a-prostenoic acidi (Example 1089) | 9-oxo-15-hydroxy-15-methyl-10a-homo-pros- |

EXAMPLE 1105

Preparation of all cis-2-(6-carboxy-2-cis-hexenyl)-3,4-oxido-cyclopentanol

A solution of 1.42 g. (10.0 moles) of all-cis-5-hydroxy-2,3-oxidocyclopentylacetaldehyde- -lactol (E. J. Corey and R. Noyori, Tetrahedron Letters, 1970, 311) in 5 ml. of DMSO is added to a stirred solution with the Whittig reagent [E. J. Corey et al, JACS, 91 5675 (1969)] also Example 1108 prepared from 13.3 g. (30 moles) of 4-carboxybutyltriphenylphosphonium bromide 2.52 g. (60 moles) of 57% sodium hydride dispersion, and 70 ml. of DMSO at 16° C. during 1 minute.

The solution is stirred at ambient temperature for 20 hours and poured into a stirred mixture of methylene chloride, ice, and hydrochloric acid. The organic phase is separated, and the aqueous phase is extracted with methylene chloride, saturated with sodium chloride, and extracted with ether. The combined organic extracts are partitioned with sodium bicarbonate. The aqueous basic extract is acidified with dilute HCl, saturated with sodium chloride, and extracted with ethyl acetate. The extract is washed with brine, dried over magnesium sulfate, and concentrated to give the crude title compound as an orange oil.

EXAMPLE 1106

Preparation of all-cis-2-(6-carboxy-2-cis-hexenyl)-3,4-oxidocyclopentanone

To a stirred solution of ca. 1.6 moles of crude all-cis-2-(6-carboxy-2-cis-hexenyl)-3,4-oxidocyclopentanol (Example 1105) in 1.6 ml. of ether is added 1.6 ml. of 4.0 N chromic acid in 4N sulfuric acid at 0° C. during 9 minutes. After stirring for 5 minutes at 0° C. the solution is diluted with brine, ether, and ethyl acetate. The organic phase is treated with isopropanol, washed with brine and dried over magnesium sulfate. Evaporation of the solvent gives the subject compound as an oil.

EXAMPLE 1107

Preparation of 2-(6-carboxy-2-cis-hexenyl)-4-hydroxycyclopent-2-en-one

A solution of 1.0 mmole of all-cis-2-(6-carboxy-2-cis-hexenyl)-3,4-oxidocyclopentanone (Example 1106) and 3.0 mmoles of sodium carbonate in 15 ml. of water is allowed to stand at room temperature for 3 hours. The solution is acidified with HCl, saturated with sodium chloride, and extracted with ether. The extract is washed with brine, dried over magnesium sulfate, and concentrated to give a mixture of the title compound and the isomeric compound, 2-(6-carboxy-2-cis-hexenyl)-3-hydroxycyclopent-4-en-1-one. Further treatment of this mixture with 10 sodium hydroxide at room temperature for 30 minutes causes the rearrangement of the latter isomer to the title compound, which is isolated from basic solution as above.

EXAMPLE 1107a

Preparation of 2-(6-carboxy-2-cis-hexenyl)-4-hydroxycyclopent-2-en-1-one

Treatment of cis-anti-cis-5-hydroxy-2,3-oxidocyclopentylacetaldehyde-γ-lactol (E. J. Corey and R. Noyori Tetrahedron Letters, 1970, 311) with 4-carboxybutyltriphenylphosphonium bromide as described in Example 1105 is productive of 2β-(6-carboxy-2-cis-hexenyl)-3α,4α-oxidocyclopentan-1β-ol which on on oxidation by the method of Example 1106 provides 2β-(6-carboxy-2-cis-hexenyl)-3α,4α-oxidocyclopentanone, which in time on treatment with aqueous base by the procedure of Example 1107 furnishes the subject compound.

EXAMPLE 1108

Preparation of 4-carboxybutyltriphenylphosphonium bromide

A mixture of 103 g. of 5-bromovalevic acid and 152 g. of triphenylphosphine in 400 ml. of acetonitrile is refluxed for 48 hours, cooled, diluted with 100 ml. of benzene and allowed to crystallize. The crystals are filtered, washed with benzene and ether, to yield colorless material, m.p. 207°–209° C.

EXAMPLES 1109–1111

Treatment of the indicated ω-bromoalkanoic acids of Table 20 below with triphenylphosphine by the method described in Example 1108 produces the phosphonium bromides of the table.

TABLE 20

| Example | Starting ω-bromo-alkanone acid | Product Phosphonium bromide |
|---|---|---|
| 1109 | 4-bromo-n-butyric acid | 3-carboxypropyltriphenylphosphonium bromide |
| 1110 | 6-bromo-n-hexanoic acid | 5-carboxypentyltri-Phenylphosphonium bromide |
| 1111 | 7-bromo-n-heptanoic acid | 6-carboxyhexyltriphenylphosphonium bromide |

EXAMPLES 1112–1114

Treatment of all cis-5-hydroxy-2,3-oxidocyclopentylacetaldehyde-γ-lactol with the Wittig reagent prepared from the indicated phosphonium bromides of Table 21 below, all by the procedure of Example 1105 is productive of the product compounds of the table.

TABLE 21

| Example | Reagent phosphonium bromide of Example | Product 3,4-oxidocyclopentanol |
|---|---|---|
| 1112 | 1109 | all cis-2-(5-carboxy-2-cis-pentenyl)-3,4-oxidocyclopentan-1-ol |
| 1113 | 1110 | all cis-2-(7-carboxy-2-cis-heptenyl)-3,4-oxidocyclopentan-1-ol |
| 1114 | 1111 | all cis-2-(8-carboxy-2-cis-octenyl)-3,4-oxidocyclopentan-1-ol |

TABLE 21-continued

| Example | Reagent phosphonium bromide of Example | Product 3,4-oxidocyclopentanol |
|---|---|---|
|  |  | cis-octenyl)-3,4-oxidocyclopentan-1-ol |

EXAMPLES 1115–1117

Oxidation of the cyclopentanols indicated in Table 22 below by the method described in Example 1106 furnishes the corresponding product 3,4-oxidocyclopentanones of the table.

TABLE 22

| Example | Starting cyclopentan-1-ol of Example | Product 3,4-oxidocyclopentan-1-one |
|---|---|---|
| 1115 | 1112 | all cis-2-(5-carboxy-2-cis-pentenyl)-3,4-oxidocyclopentan-1-one |
| 1116 | 1113 | all cis-2-(7-carboxy-2-cis-heptenyl)-3,4-oxidocyclopentan-1-one |
| 1117 | 1114 | all cis-2-(8-carboxy-2-cis-octenyl)-3,4-oxidocyclopentan-1-one |

EXAMPLES 1118–1120

Alkaline treatment of the 3,4-oxidocyclopentanones of Table 23 below by the process described in Example 1107 is productive of the 4-hydroxycyclopentenones of the table.

TABLE 23

| Example | Starting 3,4-oxidocyclopentanone of Example | Product 4-hydroxycyclopent-2-en-1-one |
|---|---|---|
| 1118 | 1115 | 2-(5-carboxy-2-cia-pentanyl)-4-hydroxycyclopent-2-en-1-one |
| 1119 | 1116 | 2-(7-carboxy-2-cis-heptenyl)-4-hydroxycyclopent-2-en-1-one |
| 1120 | 1117 | 2-(8-carboxy-2-cis-octenyl)-4-hydroxycyclopent-2-en-1-one |

EXAMPLES 1121–1124

Treatment of the 4-hydroxycyclopent-2-en-1-ones listed in Table 24 below with dihydropyran (in the manner of Example 95) is productive of the corresponding bis-tetrahydropyranyl ether-ester of the table.

TABLE 24

| Example | Starting 4-hydroxycyclopent-2-en-1-one of Example | Product bis-tetrahydropyranyl ether-ester |
|---|---|---|
| 1121 | 1107 | 4-tetrahydropyranyloxy-2-(6-carbotetrahydropyranyloxy-2-cis-hexanyl)cyclopent-2-en-1-one |
| 1122 | 1118 | 4-tetrahydropyranyloxy-2-(5-carbotetrahydropyranyloxy-2-cis-pentenyl)cyclopent-2-en-1-one |
| 1123 | 1119 | 4-tetrahydropyranyloxy-2-(7-carbotetrahydropyranyloxy-2-cis-heptenyl)- |

TABLE 24-continued

| Example | Starting 4-hydroxycyclopent-2-en-1-one of Example | Product bis-tetrahydropyranyl ether-ester |
|---|---|---|
| 1124 | 1120 | cyclopent-2-en-1-one 4-tetrahydropyranyloxy-2-(8-carbotetrahydropyranyloxy-2-cis-octenyl)-cyclopent-2-en-1-one |

EXAMPLES 1125–1130

Treatment of the 4-hydroxycyclopent-2-en-1-ones listed in Table 25 below with the indicated trialkylsilyl chloride by the method described in Example 958 is productive of the bis-trialkylsilyl ether-esters of the table.

TABLE 25

| Example | Starting 4-hydroxy-cyclopentenone of Example | Trialkylsilyl-chloride | Product bis-trialkylsilyl ether-ester |
|---|---|---|---|
| 1125 | 1107 | $(CH_3)_3SiCl$ | 4-trimethylsiloxy-2-(6-carbotrimethylsiloxy-2-cis-hexenyl)cyclopent-2-en-1-one |
| 1126 | 1118 | $(CH_3)_3SiCl$ | 4-trimethylsiloxy-2-(5-carbotrimethylsiloxy-2-cis-pentenyl)cyclopent-2-en-1-one |
| 1127 | 1119 | $(CH_3)_3SiCl$ | 4-trimethylsiloxy-2-(7-carbotrimethylsiloxy-2-cis-heptenyl)cyclopent-2-en-1-one |
| 1128 | 1120 | $(CH_3)_3SiCl$ | 4-trimethylsiloxy-2-(8-carbotrimethylsiloxy-2-cis-octenyl)cyclopent-2-en-1-one |
| 1130 | 1107 | dimethylisopropyl silyl chloride | 4-dimethylisopropylsiloxy-2-(6-carbodimethylisopropylsiloxy-2-cis-hexenyl)cyclopent-2-en-1-one |

EXAMPLE 1131

Preparation of 1-oxo-2-hydroxy-bicyclo[3.3.0]oct-4-ene

A solution of 6.2 g. (50 mole) of the lactone of cis-2-hydroxycyclopent-4-ene-1-acetic acid [P. A. Grieco, J. Org. Chem., 37, 2363 (1972)] in 350 ml. toluene (dried over molecular sieves) is cooled to −75° C. and treated dropwise under nitrogen with 84 ml. 0.89 M diisobutyl aluminum hydride (10.55 g., 74 mole) over a period of about one hour maintaining the temperature at −74° ± 2° C. The resulting clear solution is stirred at −75° C. for two hours and poured with stirring into a mixture of 15 ml. of concentrated hydrochloric acid and 300 ml. of ice water. The mixture is stirred while warming to room temperature. The layers are separated and the aqueous layer is treated with salt and extracted with three small portions of ether. The combined organic portions are dried over sodium sulfate and evaporated at reduced pressure (75° C. water bath) to yield the product (homogeneous by thin layer chromatography) as a pale yellow mobile liquid.

EXAMPLE 1132

Preparation of 1-hydroxy-2-(6-carboxy-2-cis-hexenyl)cyclopent-3-ene

A solution of the sodium salt of dimethyl sulfoxide is prepared by stirring under nitrogen a mixture of 160 ml. dry dimethyl sulfoxide (dried over molecular sieves and a few pellets of calcium hydride) with 6.0 g. (0.25 mole) of sodium hydride (prepared by washing 10.5 g. of 57% sodium hydride dispersion in mineral oil with two 30 ml. portions of hexane.) The mixture is warmed with stirring at 75° C. (oil bath) for 2.5 hours.

This solution is added over about five minutes to a solution under nitrogen of 44 grams (0.1 mole) of 4-carboxybutyltriphenylphosphonium bromide (Example 1108) in 180 ml. of dry dimethyl sulfoxide. The resulting dark reddish brown solution is stirred for ten minutes, cooled to room temperature and treated with a solution of crude 1-oxa-2-hydroxy-bicyclo[3.3.0]oct-4-ene (6.2 g. 50 mole) (Example 1131) in 20 ml. of anhydrous dimethyl sulfoxide. The resulting solution is stirred 16 hours and then treated with 250 ml. of ice water.

This brown solution is extracted with two portions of ether to remove neutral material then made strongly acidic with hydrochloric acid. The solution is extracted into four 100 ml. portions of methylene chloride. The combined methylene chloride extracts are washed with water, then extracted with four 100 ml. portions of 5% sodium bicarbonate. The combined aqueous extracts are washed with methylene chloride and made acidic to Congo Red with concentrated hydrochloric acid. The mixture isextracted with three 100 ml. portions of methylene chloride. The organic extracts are combined, dried over sodium sulfate and the solvent is evaporated at reduced pressure. The residue (an oily solid) is extracted several times with ether and the ethereal extracts are combined and evaporated at reduced pressure to yield the crude product as a dark oil. The product is purified by chromatograph on silica gel, eluting with ether. The product is a colorless liquid.

EXAMPLE 1133

Preparation of 2-(6-carboxy-2-cis-hexenyl)cyclopent-3-en-1-one

A solution of 3.2 g. (0.5 mole) of 1-hydroxy-2-(6-carboxy-2-cis-hexenyl)cyclopent-3-ene (Example 1132) in 60 ml. of reagent acetone is treated dropwise with a total of 6 ml. of 8N chromic acid in sulfuric acid at 0° C. The oxidation is rather slow. The resulting mixture is dissolved in 200 ml. of water and the solution is extracted with six 50 ml. portions of ether. The combined ethereal extracts are dried over sodium sulfate and the solvent is evaporated at reduced pressure to yield the product as a yellow oil.

EXAMPLE 1134

Preparation of 2-(6-carboxy-2-cis-hexenyl)cyclopent-2-en-1-one

A solution of 3 g. of crude 2-(6-carboxy-2-cis-hexenyl)cyclopent-3-en-1-one (Example 1133) in 100 ml. of 2% sodium hydroxide is stirred at 80° C. under nitrogen for 1.5 hours. The cooled solution is acidified to Congo Red and extracted into ether. The ethereal extracts are dried over sodium sulfate and evaporated at reduced pressure to afford the product.

EXAMPLES 1135–1137

Treatment of 1-oxa-2-hydroxy-bicyclo[3.3.0]oct-4-ene by the procedure described in Example 1132 with the ylids derived from the phosphonium bromides listed in Table 26 below furnishes the product 1-hydroxy-cyclopent-3-enes of the table.

TABLE 26

| Example | Starting phosphonium bromide of Example | Product 1-hydroxy-2-(ω-carboxy-2-cis-alkenyl(cyclopent-3-enes |
| --- | --- | --- |
| 1135 | 1109 | 1-hydroxy-2-(5-carboxy-2-cis-pentenyl)cyclopent-3-ene |
| 1136 | 1110 | 1-hydroxy-2-(7-carboxy-2-cis-heptenyl)cyclopent-3-ene |
| 1137 | 1111 | 1-hydroxy-2-(8-carboxy-2-cis-octenyl)cyclopent-3-ene |

EXAMPLES 1138-1140

Oxidation of the 1-hydroxycyclopent-3-enes listed in Table 27 below by the procedure described in Example 1133 is productive of the product cyclopent-3-en-1-ones of the table.

TABLE 27

| Example | Starting 1-hydroxycyclopent-3-ene of Example | Product 2-(ω-carboxy-2-cis-alkenyl)cyclopent-3-en-1-one |
| --- | --- | --- |
| 1138 | 1135 | 2-(5-carboxy-2-cis-pentenyl)cyclopent-3-en-1-one |
| 1139 | 1136 | 2-(7-carboxy-2-cis-heptenyl)cyclopent-3-en-1-one |
| 1140 | 1137 | 2-(8-carboxy-2-cis-octenyl)cyclopent-3-en-1-one |

EXAMPLES 1141-1143

Base treatment according to the procedure described in Example 1134 of the cyclopent-3-ene-1-ones listed in Table 28 below is productive of the product cyclopent-2-en-1-ones of the table.

TABLE 28

| Example | Starting 2-(ω-carboxy-2-cis-alkenyl)cyclopent-3-ene-1 one of Example | 2-(carboxy-2-cis-alkenyl)cyclopent-2-en-1-one |
| --- | --- | --- |
| 1141 | 1138 | 2-(5-carboxy-2-cis-pentenyl)cyclopent-2-en-1-one |
| 1142 | 1139 | 2-(7-carboxy-2-cis-heptenyl)cyclopent-2-en-1-one |
| 1143 | 1140 | 2-(8-carboxy-2-cis-octenyl)cyclopent-en-en-1-one |

EXAMPLE 1144-1146

Treatment of the listed 2-(ω-carboxy-2-cis-alkenyl)-cyclopent-2-en-1-one of Table 29 below with diazomethane in the usual manner is productive of the product methyl esters of the table.

TABLE 29

| Example | Starting carboxylic acid of Example | Product 2-(ω-carbomethoxy-2-cis-alkenyl)cyclopent-2-en-1-one |
| --- | --- | --- |
| 1144 | 1141 | 2-(5-carbomethoxy-2-cis-pentenyl)cyclopent-2-en-1-one |
| 1145 | 1142 | 2-(7-carbomethoxy-2-cis-heptenyl)cyclopent-2-en-1-one |
| 1146 | 1143 | 2-(8-carbomethoxy-2-cis-octenyl)cyclopent-2-en-1-one |

TABLE 29-continued

| Example | Starting carboxylic acid of Example | Product 2-(ω-carbomethoxy-2-cis-alkenyl)cyclopent-2-en-1-one |
| --- | --- | --- |

EXAMPLES 1147-1149

Treatment by the procedures of Examples 120 of the cyclopentenones listed in Table 30 below with lithium diisobutylmethyl-(3-triphenylmethoxy-1-trans-5-cis-octadienyl) alanate, also prepared by the procedure of Example 120 from 3-triphenylmethoxy-cis-5-en-octyne-1 (Example 139), diisobutylaluminum hydride and methyl lithium, followed by hydrolysis of the intermediate 15-triphenylmethoxy derivatives by treatment with acetic acid-tetrahydrofuran-water (4:2:1) in the manner of Example 121, and then by saponification of the intermediate methyl esters of the process described in Example 122 is productive of the product prostatrienoic acids of the table.

TABLE 30

| Example | Starting 2-(ω-carbomethoxy-2-cis-alkenyl)-cyclopent-2-en-1-one of Example | Product 9-oxo-15-hydroxy-5-cis,13-trans,17-cis-prostatrienoic acids |
| --- | --- | --- |
| 1147 | 1144 | 9-oxo-4-nor-15-hydroxy-5-cis-13-trans-17-cis-prostatrienoic acid |
| 1148 | 1145 | 9-oxo-4a-homo-15-hydroxy-5-cis-13-trans-17-cis-prostatrienoic acid |
| 1149 | 1146 | 9-oxo-4a-bishomo-15-hydroxy-5-cis-13-trans-17-cis-prostatrienoic acid |

EXAMPLES 1150-1159

Treatment of the ether-ester blocked 4-oxycyclopent-2-en-1-ones listed in Table 31 below the lithium trimethyl[3-(p-anisylidphenylmethoxy)-trans-1-octenyl]according to the procedure described in Example 960 is productive of the 9-oxo-11α,15-dihydroxy-5-cis,13-trans-prostadienoic acids of the table as well as of the corresponding 15-epi derivatives, separable from the listed 15-normal derivatives by chromatography.

TABLE 31

| Example | Starting blocked 4-oxycyclopent-2-en-1-one of Example | 9-oxo-11α,15-dihydroxy-5-cis, 13-trans-prostadienoic acids |
| --- | --- | --- |
| 1150 | 1121 | 9-oxo-11α,15-dihydroxy-5-cis,13-trans-prostadienoic acid (prostaglandin E₂) |
| 1151 | 1125 | 9-oxo-11α,15-dihydroxy-5-cis,13-trans-prostadienoic acid (prostaglandin E₂) |
| 1152 | 1130 | 9-oxo-11α,15-dihydroxy-5-cis,13-trans-prostadienoic acid (prostaglandin E₂) |
| 1153 | 1122 | 9-oxo-11α,15-dihydroxy-4-nor-5-cis,13-trans-prostadienoic acid |
| 1154 | 1126 | 9-oxo-11α,15-dihydroxy-4-nor-5-cis,13-trans- |

TABLE 31-continued

| Example | Starting blocked 4-oxycyclopent-2-en-1-one of Example | 9-oxo-11α,15-dihydroxy-5-cis, 13-trans-prostadienoic acids |
|---|---|---|
| | | prostadienoic acid |
| 1155 | 1123 | 9-oxo-11α,15-dihydroxy-4a-homo-5-cis,13-trans-prostadienoic acid |
| 1156 | 1127 | 9-oxo-11a,15-dihydroxy-4a-homo-5-cis,13-trans-prostadienoic acid |
| 1158 | 1124 | 9-oxo-11α,15-dihydroxy-4a,4b-homo-5-cis,13-trans-prostadienoic acid |
| 1159 | 1128 | 9-oxo-11α,15-dihydroxy-4a,4b-homo-5-cis,13-trans-prostadienoic acid |

EXAMPLES 1160-1169

Treatment by the procedure described in Example 123 of the ether-ester blocked 4-oxycyclopent-2-en-1-ones listed in Table 32 below with lithium diisobutyl-methyl(3-triphenylmethoxy-1-trans-5-cis-octadienyl-)alanate, prepared from 3-triphenylmethoxy-cis-5-en-octyne-1- (Example 139) by the procedure of Example 120, followed by the cleavage of blocking groups and isolation of products by the method described in Example 124 is productive of the 9-oxo-11α,15-dihydroxy-5-cis,13-trans,17-cis-prostatrienoic acids of the table; also formed are the corresponding 15-epi derivatives which are separable by chromatography from the listed 15-normal derivatives.

TABLE 32

| Example | Starting blocked 4-oxycyclopent-2-en-1-one of Example | Product 9-oxo-11α,15-dihydroxy-5-cis,13-trans,17-cis-prostatrienoic acids |
|---|---|---|
| 1160 | 1121 | 9-oxo-11α,15-dihydroxy-5-cis,13-trans,17-cis-prostatrienoic acid (prostaglandin E₃) |
| 1161 | 1125 | 9-oxo-11α,15-dihydroxy-5-cis,13-trans,17-cis-prostatrienoic acid (prostaglandin E₃) |
| 1162 | 1130 | 9-oxo-11α,15-dihydroxy-5-cis,13-trans,17-cis-prostatrienoic acid (prostaglandin E₃) |
| 1163 | 1122 | 9-oxo-11α,15-dihydroxy-4-nor-5-cis,13-trans,17-cis-prostatrienoic acid |
| 1164 | 1126 | 9-oxo-11α,15-dihydroxy-4-nor-5-cis,13-trans,17-cis-prostatrienoic acid |
| 1165 | 1123 | 9-oxo-11α,15-dihydroxy-4a-homo-5-cis,13-trans,17-cis-prostatrienoic acid |
| 1166 | 1127 | 9-oxo-11α,15-dihydroxy-4a-homo-5-cis,13-trans,17-cis-prostatrienoic acid |
| 1168 | 1124 | 9-oxo-11α,15-dihydroxy-4a,4b-bishomo-5-cis,13-trans,17-cis-prostatrienoic acid |
| 1169 | 1128 | 9-oxo-11α,15-dihydroxy-4a,4b-bishomo-5-cis-13-trans,17-cis-prostatrienoic acid |

EXAMPLE 1170

Preparation of 9-oxo-11α,15-dihydroxy-5-cis,13-cis-prostadienoic acid

Treatment in the manner described in Example 733 of 4-tetrahydropyranyloxy-2-(6-carbotetrahy-dropyranyloxy-2-cis-hexenyl)cycylopent-2-en-1-one (Example 1121) with the Grignard reagent prepared from magnesium and 1-bromo-3-triphenylmethoxy-trans-1-octene (Example 728) also as described in Example 733 in the presence of cuprous iodide tri-n-butyl-phosphine complex is productive after chromatography of prostaglandin E₂ and 9-oxo-11α, 15-dihydroxy-5-cis,13-cis-prostadienoic acid.

EXAMPLES 1171 and 1172

Treatment of the two 9-oxo derivative listed in Table 33 below with lithium perhydro-9b-boraphenalylhy-dride in the manner described in Example 737 furnishes the indicated 9α,15-dihydroxy-b 13-cis-prostenoic acids.

TABLE 33

| Example | Starting 9-oxo-derivative of Example | Product 9α,15-dihydroxy-13-cis-prostenoic acids |
|---|---|---|
| 1171 | 736 | 9α,15-dihydroxy-5-cis-prostenoic acidi |
| 1172 | 1170 | 9α,15-dihydroxy-5-cis-prostadienoic acid |

EXAMPLE 1173

Preparation of 1-bromo-4,4-dimethyl-3-tetrahydropyranyloxy-trans-1-octene

To an ice cooled solution of 3.5 g. (50 moles) of 2-methyl-2-butene in 25 ml. of tetrahydrofuran under an inert atmosphere is added 25 ml. of 1 M diborane in tetrahydrofuran dropwise over 10 minutes. The mixture is stirred at 0°–5° C. for 2 hours and then the solvent is removed under vacuum. The residue is dissolved in 20 ml. of carbon tetrachloride and to the resulting solution cooled to 0° C. is added a solution of 5.25 g. (22 mole) of 4,4-dimethyl-3-tetrahydropyranyloxy-1-octyne (Example 995) in 10 ml. of carbon tetrachloride over 10 minutes. The cooling bath is removed and the mixture is allowed to stir at ambient temperature for 1.5 hours. The mixture is cooled to 0° C. and a solution of 3.52 g. (22 moles) of bromine in 15 ml. of carbon tetrachloride is added over 10 minutes. The cooling bath is removed and the mixture is refluxed for 6 hours under an inert atmosphere. The mixture is cooled and poured into dilute sodium hydroxide solution. The organic phase is washed with water and saturated brine, dried ($Na_2SO_4$), and evaporated. The residue is chromatographed upon silica gel and the title compound is isolated with 5% ethyl acetate in benzene.

EXAMPLE 1174

Preparation of 1-bromo-4,4-dimethyl-trans-1-octen-3-ol

A mixture of 3.19 g. (10 moles) of 1-bromo-4,4-dimethyl-3-tetrahydropyranyloxy-trans-1-octene (Example 1173) and 90 ml. of 3:1:1 tetrahydrofuran-acetic acid-water is stirred at ambient temperatures for 20 hours. The solvent is evaporated in vacuo and the residue is chromatographed on silica gel. The title compound is isolated using 10-20% ethyl acetate is benzene.

EXAMPLE 1175

Preparation of
1-bromo-4,4-dimethyl-3-triphenylmethoxy-trans-1-octene

Treatment of 1.88 g. (8 moles) of 1-bromo-4,4-dimethyl-trans-1-octen-3-ol (Example 1174) with 2.58 g. (8 moles) of triphenylmethyl bromide in 20 ml. of pyridine and purification of Florisil ®, all as described in Example 728 gives the title compound.

EXAMPLE 1176

Preparation of
1-bromo-5,5-dimethyl-3-tetrahydropyranyloxy-trans-1-octene

Treatment of 7.15 g. (30 moles) of 5,5-dimethyl-3-tetrahydropyranyloxy-1-octyne (Example 999) with 33 moles of disiamylborane in carbon tetrachloride followed by 30 moles of bromide in carbon tetrachloride, refluxing the resulting mixture, and isolation by chromatography on silica gel, all as described in Example 1173 gives the title compound.

EXAMPLE 1177

Preparation of 1-bromo-5,5-dimethyl-trans-1-octen-3-ol

Treatment of 7.35 g. (23 moles) of 1-bromo-5,5-dimethyl-3-tetrahydropyranyloxy-trans-1-octene (Example 1176) with 200 ml. of 3:1:1 tetrahydrofuran-acetic acid-water and purification on silica gel all as described in Example 1174 gives the title compound.

EXAMPLE 1178

Preparation of
1-bromo-5,5-dimethyl-3-triphenylmethoxy-trans-1-octene

Treatment of 3.53 g. (15 moles) of 1-bromo-5,5-dimethyl-trans-1-octen-3-ol (Example 1177) with 4.85 g. (15 moles) of triphenylmethyl bromide in 35 ml. of pyridine and purification on Florisil ®, all as described in Example 728 gives the title compound.

EXAMPLE 1179

Preparation of
1-iodo-3-triphenylmethoxy-trans-1-octene

To a mixture of 0.650 g. (16.91 mole) of sodium borohydride and 3.17 g. (45.2 moles) of 2-methyl-2-butene in 40 ml. of diglyme cooled to −5° C. under an inert atmospere is added over 15 minutes 3.24 g. (22.6 moles) of boron trifluoride ethereate and the resulting mixture is stirred at 0° C. for 2 hours. To this mixture is then added over 5 minutes 8.32 g. (22.6 moles) of 3-triphenylmethoxy-1-octyne (Example 119) in 10 ml. of diglyme, the cooling bath is removed, and the mixture is stirred at ambient temperatures for 1.5 hours. The mixture is cooled to 0° C. and 6.0 g. of finely divided anhydrous trimethylamine oxide is added over 10 minutes. The cooling bath is removed and the mixture is stirred at ambient temperatures for 0.5 hour. The mixture is then poured into 200 ml. of 15% sodium hydrooxide solution, a solution of 16 g. (63 moles) of iodine in 20 ml. of tetrahydrofuran is added immediately, and the resulting mixture is stirred for 0.5 hour. The organic phase is separated and the aqueous phase is washed with ether. The combined organic phase and washings are decolorized with 5% sodium thiosulfate solution, washed with saturated brine, dried ($Na_2SO_4$), and evaporated. The residue is dry-columned chromatographed upon alumina using hexane as eluent and the title compound is isolated as an oil.

EXAMPLE 1180

Preparation of 3-triphenylmethoxy-cis-oct-5-en-1-yne

Treatment of 22 g. of cis-oct-5-en-1-yne-3-ol, prepared according to the procedure of J. Fried, C.H. Lin, J.C. Sih, P. Dalven, G.F. Cooper, J. Amer. Chem. Soc., 94, 4342 (1972), with 58 g. of triphenylmethyl bromide in 100 ml. of pyridine and purification on Florisil ®, all as described in Example 728 gives the title compound.

EXAMPLE 1181

Preparation of
1-iodo-3-triphenylmethoxy-trans-1,cis-5-octadiene

Treatment of 20 g. of 3-triphenylmethoxy-cis-oct-5-en-1-yne with 55 moles of disiamylborane in diglyme, followed by trimethylamine oxide, aqueous sodium hydroxide, and iodine, and purification of alumina, all as described in Example 1179, gives the title compound.

EXAMPLE 1182

Preparation of
1-bromo-3-triphenylmethoxy-trans-1,cis-5-octadiene

Treatment of 15 g. of 3-triphenylmethoxy-cis-oct-5-en-1-yne (Example 1180) with 41 moles of disiamylborane in tetrahydrofuran, replacing the solvent with carbontetrachloride, addition of 41 moles of bromine, and refluxing the mixture, all as described in Example 1173, and purification of the material upon Florisil ®as described in Example 728 gives the title compound.

EXAMPLE 1183

Preparation of
1-iodo-3-triphenylmethoxy-trans-1-decene

Treatment of 3-triphenylmethoxy-1-decyne (Example 129) with disamylborane, trimethylamine oxide and iodine by the procedure described in Example 1179 is productive of the subject compound.

EXAMPLE 1184

Preparation of
1-iodo-3-triphenylmethoxy-trans-1-nonene

Treatment of 3-triphenylmethoxy-1-nonyne (Example 128) with disiamylborane, trimethylamine oxide and iodine by the process described in Example 1179 is productive of the subject compound.

EXAMPLE 1185

Preparation of
1-bromo-3-triphenylmethoxy-trans-1-decene

Treatment of 3-triphenylmethoxy-1-decyne (Example 129) with disiamylborane and the bromide by the procedure described in Example 1173 is productive of the title compound.

EXAMPLE 1186

Preparation of
1-bromo-3-triphenylmethoxy-trans-1-nonene

Treatment of 3-triphenylmethoxy-1-nonyne (Example 128) with disiamylborane and the bromine by the procedure described in Example 1173 is productive of the title compound.

EXAMPLE 1187

Preparation of the Grignard reagent of 1-bromo-3-triphenylmethoxy-trans-1-octene at 33° C.

To a slurry of 0.585 g. (0.0241 g. atom) of magnesium and 5 ml. of tetrahydrofuran under an argon atmosphere is added 2 ml. of a solution of 7.536 (0.0168 mole) of 1-bromo-3-triphenylmethoxy-trans-1-octene (Example 728) in 10 ml. of tetrahydrofuran. The mixture is warmed to 35° C. and reaction is initiated with 1 drop of methyl iodide. The reaction is allowed to exotherm to 37° C. and then to cool to 33° C. whereupon the remainder of the halide is added at a rate to maintain 33° C. After complete addition of the halide, the mixture is stirred at 33° C. for 1 hour and is separated from the excess magnesium to yield a tetrahydrofuran solution of the title Grignard reagent.

EXAMPLE 1188

Preparation of 11-deoxy-8β-methyl-prostaglandin $E_1$ methyl ester, 11-deoxy-8α-methyl-8-iso-prostaglandin $E_1$ methyl ester, methyl 15-hydroxy-8β-methyl-9-oxo-13-cis-prostenoate, and methyl 15-hydroxy-8α-methyl-9-oxo-8-iso-13-cis-prostenoate The Grignard reagent, prepared as described in Example 1187 from 0.585 g. of magnesium, 7.536 g. of 1-bromo-3-triphenylmethoxy-trans-1-octene (Example 728), and 10 ml. of tetrahydrofuran, is added to an ice cooled solution of 3.76 g. of 2-(6-carbomethoxyhexyl)-2-cyclopentenone (Example 83) and 0.305 g. of copper (I) iodide-tri-n-butylphosphine complex in 10 ml. of tetrahydrofuran over 10 minutes under an inert atmosphere. The mixture is stirred with cooling for 0.5 hour and to it is then added 46 g. of methyl iodide. The cooling bath is removed and the mixture is stirred at ambient temperatures for 48 hours. The mixture is poured into saturated ammonium chloride solution and is extracted into ether. The organic phase is washed with saturated brine and is evaporated. The residue is heated to 80° C. with 100 ml. of 80% aqueous acetic acid for 0.5 hour and the mixture is then evaporated to dryness. The residue is dry-column chromatography upon silica gel using 4:1 benzene-ethyl acetate as eluent to afford a mixture of 11-deoxy-8β-methyl-prostaglandin $E_1$ methyl ester and 11-deoxy-8α-methyl-8-iso-prostaglandin $E_1$ methyl ester and a mixture of methyl 15-hydroxy-8α-methyl-9-oxo-13-cis-prostenoate and methyl 15-hydroxy-8α-methyl-9-oxo-8-iso-13-cis-prostenoate.

Further separation of the 8β and 8α isomers is accomplished by a combination of partition chromatography and thin layer chromatography.

EXAMPLES 1190–1205

Treatment by the procedure of Example 1188 of the cyclopentenones listed in Table 34 below with the Grignard reagent, prepared as described in Example 1187 from the listed 1-bromo-3- triphenylmethoxy-1-trans-alkenes, and then with methyl iodide furnishes the product 8α and 8β methyl prostenoates of the table. The products are all obtained via the corresponding 15-O-triphenylmethyl derivatives, which are hydrolytically cleaved as described in Example 1188.

TABLE 34

| Example | Starting cycloalkene of Example | Starting 1-bromo-3--triphenylmethoxy-1-trans-alkene of Example | Product 8-alkyl prostenoates |
|---|---|---|---|
| 1190 | 13 | 1175 | ethyl 8-β-methyl-9-oxo-15-hydroxy-16,16-dimethyl-13-trans-prostenoate<br>ethyl 8α-methyl-9-oxo-15-hydroxy-16,16-dimethyl-8-iso-13-trans-prostenoate<br>ethyl 8β-methyl-9-oxo-15-hydroxy-16,16-dimethyl-13-cis-prostenoate<br>ethyl 8α-methyl-9-oxo-15-hydroxy-16,16-dimethyl-8-iso-13-cis-prostenoate |
| 1191 | 13 | 1178 | ethyl 8β-methyl-9-oxo-15-hydroxy-17,17-dimethyl-13-trans-prostenoate<br>ethyl 8α-methyl-9-oxo-15-hydroxy-17,17-dimethyl-8-iso-13-trans-prostenoate<br>ethyl 8β-methyl-9-oxo-15-hydroxy-17,17-dimethyl-13-cis-prostenoate<br>ethyl 8α-methyl-9-oxo-15-hydroxy-17,17-dimethyl-8-iso-13-cis-prostenoate |
| 1192 | 13 | 1182 | ethyl 8β-methyl-9-oxo-15-hydroxy-13-trans,17-cis-prostadienoate<br>ethyl 8α-methyl-9-oxo-15-hydroxy-8-iso-13-trans,17-cis-prostadienoate<br>ethyl 8β-methyl-9-oxo-15-hydroxy-13-cis,17-cis-prostadienoate<br>ethyl 8α-methyl-9-oxo-15-hydroxy-8-iso-13-cis, 17-cis-prostadienoate |
| 1193 | 13 | 1185 | ethyl 8β-methyl-9-oxo-15-hydroxy-20-ethyl-13-trans-prostenoate<br>ethyl 8α-methyl-9-oxo-15-hydroxy-20-ethyl-8-iso-13-trans-prostenoate<br>ethyl 8β-methyl-9-oxo-15-hydroxy-20-ethyl-13-cis-prostenoate<br>ethyl 8α-methyl-9-oxo-15-hydroxy-8-iso-20-ethyl-13-cis-prostenoate |
| 1194 | 84 | 1186 | decyl 8β-methyl-9-oxo-15-hydroxy-20-methyl-13-trans-prostenoate<br>decyl 8α-methyl-9-oxo-15-hydroxy-20-methyl-8-iso-13-trans-prostenoate<br>decyl 8β-methyl-9-oxo-15-hydroxy-20-methyl-13-cis-prostenoate<br>decyl 8α-methyl-9-oxo-15-hydroxy-20-methyl-8-iso-13-cis-prostenoate |
| 1195 | 23 | 728 | ethyl 8β-methyl-9-oxo-15-hydroxy-8a,7b-bishomo-13-trans-prostenoate<br>ethyl 8α-methyl-9-oxo-15-hydroxy-7a,7b-bishomo-8-iso-13-trans-prostenoate |

TABLE 34-continued

| Example | Starting cycloalkene of Example | Starting 1-bromo-3-triphenylmethoxy-1-trans-alkene of Example | Product 8-alkyl prostenoates |
|---|---|---|---|
| 1196 | 31 | 1185 | ethyl 8β-methyl-9-oxo-15-hydroxy-7a,7b-bishomo-13-cis-prostenoate<br>ethyl 8α-methyl-9-oxo-15-hydroxy-7a,7b-bishomo-8-iso-13-cis-prostenoate<br>ethyl 8β-methyl-9-oxo-15-hydroxy-2,20-bisethyl-13-trans-prostenoate<br>bisethyl-8-iso-13-trans-prostenoate<br>ethyl 8β-methyl-9-oxo-15-hydroxy-2,20-bisethyl-13-cis-prostenoate<br>ethyl 8α-methyl-9-oxo-15-hydroxy-2,20-bisethyl-8-iso-3-cis-prostenoate |
| 1197 | 46 | 1175 | ethyl 8β-methyl-9-oxo-15-hydroxy-3-oxa-16,16-dimethyl-13-trans-prostenoate<br>ethyl 8α-methyl-9-oxo-15-hydroxy-3-oxa-16,16-dimethyl-8-iso-13-trans-prostenoate<br>ethyl 8β-methyl-9-oxo-15-hydroxy-3-oxa-16,16-dimethyl-13-cis-prostenoate<br>ethyl 8α-methyl-9-oxo-15-hydroxy-3-oxa-16,16-dimethyl-8-iso-13-cis-prostenoate |
| 1198 | 46 | 1182 | ethyl 8β-methyl-9-oxo-15-hydroxy-3-oxa-13-trans,17-cis-prostadienoate<br>ethyl 8α-methyl-9-oxo-15-hydroxy-3-oxa-8-iso-13-trans,17-cis-prostadienoate<br>ethyl 8β-methyl-9-oxo-15-hydroxy-3-oxa-13-cis,17-cis-prostadienoate<br>ethyl 8α-methyl-9-oxo-15-hydroxy-3-oxa-8-iso-13-cis,17-cis-prostadienoate |
| 1199 | 53 | 1186 | ethyl 8β-methyl-9-oxo-15-hydroxy-7-nor-20-methyl-13-trans-prostenoate<br>ethyl 8α-methyl-9-oxo-15-hydroxy-7-nor-20-methyl-8-iso-13-trans-prostenoate<br>ethyl 8β-methyl-9-oxo-15-hydroxy-7-nor-20-methyl-13-cis-prostenoate<br>ethyl 8α-methyl-9-oxo-15-hydroxy-7-nor-20-methyl-8-iso-13-cis-prostenoate |
| 1200 | 90 | 1178 | ethyl 8β-methyl-9-oxo-15-hydroxy-2-fluoro-17,17-dimethyl-13-trans-prostenoate<br>ethyl 8α-methyl-9-oxo-15-hydroxy-2-fluoro-17,17-dimethyl-8-iso-13-trans-prostenoate<br>ethyl 8β-methyl-9-oxo-15-hydroxy-2-fluoro-17,17-dimethyl-13-cis-prostenoate<br>ethyl 8α-methyl-9-oxo-15-hydroxy-2-fluoro-17,17-dimethyl-8-iso-13-cis-prostenoate |
| 1201 | 111 | 728 | ethyl 8β-methyl-9-oxo-15-hydroxy-10a-homo-13-trans-prostenoate<br>ethyl 8α-methyl-9-oxo-15-hydroxy-10a-homo-8-iso-13-trans-prostenoate<br>ethyl 8β-methyl-9-oxo-15-hydroxy-10a-homo-13-cis-prostenoate<br>ethyl 8α-methyl-9-oxo-15-hydroxy-10a-homo-8-iso-13-cis-prostenoate |
| 1202 | 79 | 1186 | ethyl 8β-methyl-9-oxo-15-hydroxy-2-phenyl-20-methyl-13-trans-prostenoate<br>ethyl 8α-methyl-9-oxo-15-hydroxy-2-phenyl-20-methyl-8-iso-13-trans-prostenoate<br>ethyl 8β-methyl-9-oxo-15-hydroxy-2-phenyl-20-methyl-13-cis-prostenoate<br>ethyl 8α-methyl-9-oxo-15-hydroxy-2-phenyl-20-methyl-8-iso-13-cis-prostenoate |
| 1203 | 900 | 1182 | methyl 8β-methyl-9-oxo-15-hydroxy-5-cis,13-trans,17-cis-prostatrienoate<br>methyl 8α-methyl-9-oxo-15-hydroxy-8-iso-5-cis,13-trans,17-cis-prostatrienoate<br>methyl 8β-methyl-9-oxo-15-hydroxy-5-cis,13-cis,17-cis-prostatrienoate<br>methyl 8α-methyl-9-oxo-15-hydroxy-8-iso-5-cis,13-cis,17-cis-prostatrienoate |
| 1204 | 900 | 728 | ethyl 8β-methyl-9-oxo-15-hydroxy-5-cis,13-trans-prostadienoate<br>ethyl 8α-methyl-9-oxo-15-hydroxy-8-iso-5-cis,13-trans-prostadienoate<br>ethyl 8β-methyl-9-oxo-15-hydroxy-5-cis,13-cis-prostadienoate<br>ethyl 8α-methyl-9-oxo-15-hydroxy-8-iso-5-cis,13-cis-prostadienoate |
| 1205 | 900 | 1185 | ethyl 8β-methyl-9-oxo-15-hydroxy-20-ethyl-5-cis,13-trans-prostadienoate<br>ethyl 8α-methyl-9-oxo-15-hydroxy-20-ethyl-8-iso-cis,13-trans-prostadienoate<br>ethyl 8β-methyl-9-oxo-15-hydroxy-20-ethyl-5-cis,13-cis-prostadienoate<br>ethyl 8α-methyl-9-oxo-15-hydroxy-20-ethyl-8-iso-5-cis,13-cis-prostadienoate |

Examples 1206-1273

Treatment of the designated 9-oxo-prostenoic acid and ester derivatives listed in Table 35 below with sodium borohydride in ethanol as described in Example 257 gives the product 9α and 9β hydroxy derivatives of the table, which are separable by standard chromatographic techniques.

TABLE 35

| Example | Starting 9-oxo-derivative | Product-methyl derivatives |
|---|---|---|
| 1206 | 11-deoxy-8β-methyl-prostaglandin E₁ methyl ester (Example 1188) | 11-deoxy-8β-methyl-prostaglandin F₁α and F₁β methyl esters |
| 1207 | 11-deoxy-8α-methyl-8-iso-prostaglandin E₁ methyl ester (Example 1188) | 11-deoxy-8α-methyl-8-iso-prostaglandin F₁α and F₁β methyl esters |
| 1208 | methyl 15-hydroxy-8β-methyl-9-oxo-13-cis-prostenoate (Example 1188) | methyl 9α/β, 15-dihydroxy-8β-methyl-13-cis-prostenoates |
| 1209 | methyl 15-hydroxy-8α-methyl-9-oxo-13-cis-prostenoate (Example 1188) | methyl 9α/β, 15-dihydroxy 8α-methyl-8-iso-13-cis-prostenoates |
| 1210 | ethyl 8β-methyl-9-oxo-15-hydroxy-16,16-dimethyl-13-trans-prostenoate (Example 1190) | ethyl 8β-methyl-9α/β,15-dihydrox-16,16-dimethyl-13-trans-prostenoates |
| 1211 | ethyl 8α-methyl-9-oxo-15-hydroxy-16,16-dimethyl-8-iso-13-trans-prostenoate (Example 1190) | ethyl 8α-methyl-9α/β15-dihydroxy-16,16-dimethyl-8-iso-13-trans-prostenoates |
| 1212 | ethyl 8β-methyl-9-oxo-15-hydroxy-16,16-dimethyl-13-cis-prostenoate (Example 1190) | ethyl 8β-methyl-9α/β,15-dihydroxy-16,16-dimethyl-13-cis-prostenoates |
| 1213 | ethyl 8α-methyl-9-oxo-15-hydroxy-16,16-dimethyl-8-iso--13-cis-prostenoate (Example 1190) | ethyl 8α-methyl-9α/β,15-dihydroxy-16,16-dimethyl-8-iso-13-cis-prostenoates |
| 1214 | ethyl-8β-methyl-9-oxo-15-hydroxy-17,17-dimethyl-13-trans-prostenoate (Example 1191) | ethyl 8β-methyl-9α/β,15-dihydroxy-17,17-dimethyl-13-trans-prostenoates |
| 1215 | ethyl 8α-methyl-9-oxo-15-hydroxy-17,17-dimethyl-8-iso-13-trans-prostenoate (Example 1191) | ethyl 8α-methyl-9α/β,15-dihydroxy-17,17-dimethyl-8-iso-13-trans-prostenoates |
| 1216 | ethyl 8β-methyl-9-oxo-15-hydroxy-17,17-dimethyl-13-cis-prostenoate (Example 1191) | ethyl 8β-methyl-9α/β,15-dihydroxy-17,17-dimethyl-13-cis-prostenoates |
| 1217 | ethyl 8α-methyl-9-oxo-15-hydroxy-17,17-dimethyl-8-iso-13-cis-prostenoate (Example 1191) | ethyl 8α-methyl-9α/β,15-dihydroxy-17,17-dimethyl-8-iso-13-cis-prostenoates |
| 1218 | ethyl 8β-methyl-9-oxo-15-hydroxy-13-trans-17-cis-prostadienoate (Example 1192) | ethyl 8β-methyl-9α/β,15-dihydroxy-13-trans,17-cis-prostadienoates |
| 1219 | ethyl 8α-methyl-9-oxo-15-hydroxy-8-iso-13-trans,17-cis-prostadienoate (Example 1192) | ethyl 8α-methyl-9α/β,15-dihydroxy-8-iso-13-trans 17-cis-prostadienoates |
| 1220 | ethyl 8β-methyl-9-oxo-15-hydroxy-13-cis,-17-cis-prostadienoate (Example 1192) | ethyl 8β-methyl-9α/β,15-dihydroxy-13-cis,17-cis-prostadienoates |
| 1221 | ethyl 8α-methyl-9-oxo-15-hyroxy-8-iso-13-cis,17-cis-prostadienoate (Example 1192) | ethyl 8α-methyl-9α/β, 15-dihydroxy-8-iso-13-cis-17-cis-prostadienoates |
| 1222 | ethyl 8β-methyl-9-oxo-15-hydroxy-20-ethyl-13-trans-prostenoate (Example 1193) | ethyl 8β-methyl-9α/β,15-dihydroxy-20-ethyl-13-trans-prostenoates |
| 1223 | ethyl 8α-methyl-9-oxo-15-hydroxy-20-ethyl-8-iso-13-trans-prostenoate (Example 1193) | ethyl 8α-methyl-9α/β,15-dihydroxy-20-ethyl-8-iso-13-trans-prostenoates |
| 1224 | ethyl 8β-methyl-9-oxo-15-hydroxy-20-ethyl-13-cis-prostenoate (Example 1193) | ethyl 8β-methyl-9α/β,15-dihydroxy-20-ethyl-13-cis-prostenoates |
| 1225 | ethyl 8α-methyl-9-oxo-15-hydroxy-20-ethyl-8-iso-13-cis-prostenoate (Example 1193) | ethyl 8α-methyl-9α/β,15-dihydroxy-20-ethyl-8-iso-13-cis-prostenoates |
| 1226 | decyl 8β-methyl-9-oxo-15-hydroxy-20-methyl-13-trans-prostenoate (Example 1194) | decyl 8β-methyl-9α/β,15-dihydroxy-20-methyl-13-trans-prostenoates |
| 1227 | decyl 8α-methyl-9-oxo-15-hydroxy-20-methyl-8-iso-13-trans-prostenoate (Example 1194) | decyl 8α-methyl-9α/β,15-dihydroxy-20-methyl-8-iso-13-trans-prostenoates |
| 1228 | decyl 8β-methyl-9-oxo-15-hydroxy-20-methyl-13-cis-prostenoate (Example 1194) | decyl 8β-methyl-9α/β,15-dihydroxy-20-methyl-13-cis-prostenoates |
| 1229 | ethyl 8α-methyl-9-oxo-15-hydroxy-20-methyl-8-iso-13-cis-prostenoate (Example 1194) | ethyl 8α-methyl-9α/β,15-dihydroxy-20-methyl-8-iso-13-cis-prostenoates |
| 1230 | ethyl 8β-methyl-9-oxo-15-hydroxy-7a,7b-bishomo-13-trans-prostenoate (Example 1195) | ethyl 8β-methyl-9α/β,15-dihydroxy-7a,7b-bis homo-13-trans-prostenoates |
| 1231 | ethyl 8α-methyl-9-oxo-15-hydroxy-7a,7b-bishomo-8-iso-13-trans-prostenoate (Example 1195) | ethyl 8α-methyl-9α/β,15-dihydroxy-7a,7b-bis homo-8-iso-13-trans-prostenoates |
| 1232 | ethyl 8β-methyl-9-oxo-15-hydroxy-7a,7b-bishomo-13-cis-prostenoate (Example 1195) | ethyl 8β-methyl-9α/β,15-dihydroxy-7a,7b-bis homo-13-cis-prostenoates |
| 1233 | ethyl 8α-methyl-9-oxo-15-hydroxy-7a,7b-bishomo-8-iso-13-cis-prostenoate (Example 1195) | ethyl 8α-methyl-9α/β,15-dihydroxy-7a,7b-bis homo-8-iso-13-cis-prostenoates |
| 1234 | ethyl 8β-methyl-9-oxo-15-hydroxy-2,20-bisethyl-13-trans-prostenoate (Example 1196) | ethyl 8β-methyl-9α/β,15-dihydroxy-2,20-bis-ethyl-13-trans-prostenoates |

TABLE 35-continued

| Example | Starting 9-oxo-derivative | Product -meth-derivatives |
|---|---|---|
| 1235 | ethyl 8α-methyl-9-oxo-15-y-droxy-2,20-bis-ethyl-8-iso-13-trans-prostenoate (Example 1196) | ethyl 8α-methyl-9α/β,15-dihydroxy-2,20-bis-ethyl-13-cis-prostenoates |
| 1236 | ethyl 8β-methyl-9-oxo-15-hydroxy-2,20-bis-ethyl-13-cis prostenoate (Example 1196) | ethyl 8β-methyl-9α/β,15-dihydroxy-2,20-bis-ethyl-13-cis-prostenoates |
| 1237 | ethyl 8α-methyl-9-oxo-15-hydroxy-2,20-bis-ethyl-8-iso-13-cis-prostenoate (Example 1196) | ethyl 8α-methyl-9α/β,15-dihydroxy-2,20-bis-ethyl-8-iso-13-cis-prostenoates |
| 1238 | ethyl 8β-methyl-9-oxo-15-hydroxy-3-oxa-16,16-dimethyl-13-trans-prostenoate (Example 1197) | ethyl 8β-methyl-9α/β,15-dihydroxy-3-oxa-16,16-dimethyl-13-trans-prostenoates |
| 1239 | ethyl 8α-methyl-9-oxo-15-hydroxy-3-oxa-16,16-dimethyl-8-iso-13-trans-prostenoate (Example 1197) | ethyl 8α-methyl-9α/β,15-dihydrpxy-3-oxa-16,16-dimethyl-8-iso-13-trans-prostenoates |
| 1240 | ethyl 8β-methyl-9-oxo-15-hydroxy-3-oxa-16,16-dimethyl-13-cis-prostenoate (Example 1197) | ethyl 8β-methyl-9α/β,15-dihydroxy-3-oxa-16,16-dimethyl-13-cis-prostenoates |
| 1241 | ethyl 8α-methyl-9-oxo-15-hydroxy-3-oxa-16,16-dimethyl-8-iso-13-cis-prostenoate (Example 1197) | ethyl 8α-methyl-9α/β,15-dihydroxy-3-oxa-16,16-dimethyl-8-iso-13-cis-prostenoates |
| 1242 | ethyl 8β-methyl-9-oxo-15-hydroxy-3-oxa-13-trans,17-cis-prostadienoate (Example 1198) | ethyl 8β-methyl-9α/β,15-dihydroxy-3-oxa-13-trans,17-cis-prostadienoates |
| 1243 | ethyl 8α-methyl-9-oxo-15-hydroxy-3-oxa-8-iso-13-trans,-17-cis-prostadienoate (Example 1198) | ethyl 8α-methyl-9α/β,15-dihydroxy-3-oxa-8-iso-13-trans,17-cis-prostadienoates |
| 1244 | ethyl 8β-methyl-9-oxo-15-hydroxy-3-oxa-13-cis,17-cis-prostadienoate (Example 1198) | ethyl 8β-methyl-9α/β,15-dihydroxy-3-oxa-13-cis-17-cis-prostadienoates |
| 1245 | ethyl 8α-methyl-9-oxo-15-hydroxy-3-oxa-8-iso-13-cis,17-cis-prostadienoate (Example 1198) | ethyl 8α-methyl-9α/β,15-dihydroxy-3-oxa-8-iso-13-cis,17-cis-prostadienoates |
| 1246 | ethyl 8β-methyl-9-oxo-15-hydroxy-7-nor-20-methyl-13-trans-prostenoate (Example 1199) | ethyl 8β-methyl-9α/β,15-dihydroxy-7-nor-20-methyl-13-trans-prostenoates |
| 1247 | ethyl 8α-methyl-9-oxo-15-hydroxy-7-nor-20-methyl-8-iso-13-trans-prostenoate (Example 1199) | ethyl 8α-methyl-9α/β,15-dihydroxy-7-nor-20-methyl-8-iso-13-trans-prostenoates |
| 1248 | ethyl 8β-methyl-9-oxo-15-hydroxy-7-nor-20-methyl-13-cis-prostenoate (Example 1199) | ethyl 8β-methyl-9α/β,15-dihydroxy-7-nor-20-methyl-13-cis-prostenoates |
| 1249 | ethyl 8α-methyl-9-oxo-15-hydroxy-7-nor-20-methyl-8-iso-13-cis-prostenoate (Example 1199) | ethyl 8α-methyl-9α-9α/β,15-dihydroxy-7-nor-20-methyl-8-iso-13-cis-prostenoates |
| 1250 | ethyl 8β-methyl-9-oxo-15-hydroxy-2-fluoro-17,17-dimethyl-13-trans-prostenoate (Example 1200) | ethyl 8β-methyl-9α/β,15-dihydroxy-2-fluoro-17,-17-dimethyl-13-trans-prostenoates |
| 1251 | ethyl 8α-methyl-9-oxo-15-hydroxy-2-fluoro-17,17-dimethyl-8-iso-13-trans-prostenoate (Example 1200) | ethyl 8α-methyl-9α/β,15-dihydroxy-2-fluoro-17,-17-dimethyl-8-iso-13-trans-prostenoates |
| 1252 | ethyl 8β-methyl-9-oxo-15-hydroxy-2-fluoro-17 17-dimethyl-13-cis-prostenoate (Example 1200) | ethyl 8β-methyl-9α/β,15-dihydroxy-2-fluoro-17,-17-dimethyl-13-cis-prostenoates |
| 1253 | ethyl 8α-methyl-9-oxo-15-hydroxy-2-fluoro-17,17-dimethyl-8-iso-13-cis-prostenoate (Example 1200) | ethyl 8α-methyl-9α/β,15-dihydroxy-2-fluoro-17,-17-dimethyl-8-iso-13-cis-prostenoates |
| 1254 | ethyl 8β-methyl-9-oxo-15-hydroxy-10a-homo-13-trans-prostenoate (Example 1201) | ethyl 8β-methyl-9α/β,15-dihydroxy-10a-homo-13-trans-prostenoates |
| 1255 | ethyl 8α-methyl-9-oxo-15-hydroxy-10a-homo-8-iso-13-trans-prostenoate (Example 1201) | ethyl 8α-methyl-9α/β,15-dihydroxy-10a-homo-8-iso-13-trans-prostenoates |
| 1256 | ethyl 8β-methyl-9-oxo-15-hydroxy-10a-homo-13-cis-prostenoate (Example 1201) | ethyl 8β-methyl-9α/β,15-dihydroxy-10a-homo-13-cis-prostenoates |
| 1257 | ethyl 8α-methyl-9-oxo-15-hydroxy-10a-homo-8-iso-13-cis-prostenoate (Example 1201) | ethyl 8α-methyl-9α/β,15-dihydroxy-10a-homo-8-iso-13-cis-prostenoates |
| 1258 | ethyl 8β-methyl-9-oxo-15-hydroxy-2-phenyl-20-methyl-13-trans-prostenoate (Example 1202) | ethyl 8β-methyl-9α/β,15-dihydroxy-2-phenyl-20-methyl-13-trans-prostenoates |
| 1259 | ethyl 8α-methyl-9-oxo-15-hydroxy-2-phenyl-20-methyl-8-iso-13-trans-prostenoate (Example 1202) | ethyl 8α-methyl-9α/β,15-dihydroxy-2-phenyl-20-methyl-8-iso-13-trans-prostenoates |
| 1260 | ethyl 8β-methyl-9-oxo-15-hydroxy-2-phenyl-20-20-methyl-13-cis-prostenoate (Example 1202) | ethyl 8β-methyl-9α/β,15-dihydroxy-2-phenyl-20-methyl-13-cis-prostenoates |
| 1261 | ethyl 8α-methyl-9-oxo-15-hydroxy-2-phenyl-20-methyl-8-iso-13-cis-prostenoates (Example 1202) | ethyl 8α-methyl-9α/β,15-dihydroxy-2-phenyl-20-methyl-8-iso-13-cis-prostenoates |
| 1262 | methyl 8β-methyl-9-oxo-15-hydroxy-5-cis,13-trans,17-cis-pros- | methyl 8β-methyl-9α/β,15-dihydroxy-5-cis,13-trans,17-cis-prostatrienoates |

TABLE 35-continued

| Example | Starting 9-oxo-derivative | Product -methyl-derivatives |
|---|---|---|
| 1263 | methyl 8α-methyl-9-oxo-15-hydroxy-8-iso-5-cis,13-trans,17-cis-prostatrienoate (Example 1203) | methyl 8α-methyl-9α/β,15-dihydroxy-8-iso-5-cis,-13-trans,17-cis-prostatrienoates |
| 1264 | methyl 8β-methyl-9-oxo-15-hydroxy-5-cis,13-cis,17-cis-prostatrienoate (Example 1203) | methyl 8β-methyl-9α/β,-15-dihydroxy-5-cis,13-cis,17-cis-prostatrienoates |
| 1265 | methyl 8α-methyl-9-oxo-15-hydroxy-8-iso-5-cis,13-cis,17-cis-prostatrienoate (Example 1203) | methyl 8α-methyl-α/β,15-dihydroxy-8-iso-5-cis,-13-cis,17-cis-prostatrienoates |
| 1266 | ethyl 8β-methyl-9-oxo-15-hydroxy-5-cis,13-trans-prostadienoate (Example 1204) | ethyl 8β-methyl-9α/β,-15-dihydroxy-5-cis,13-trans-prostadienoates |
| 1267 | ethyl 8α-methyl-9-oxo-15-hydroxy-8-iso-5-cis,13-trans-prostadienoate (Example 1204) | ethyl 8α-methyl-9α/β,-15-dihydroxy-8-iso-5-cis,13-trans-prostadienoates |
| 1268 | ethyl 8β-methyl-9-oxo-15-hydroxy-5-cis,13-cis-prostadienoate (Example 1204) | ethyl 8β-methyl-9α/β,-15-dihydroxy-5-cis,13-cis-prostadienoates |
| 1269 | ethyl 8α-methyl-9-oxo-15-hydroxy-8-iso-5-cis,13-cis-prostadienoate (Example 1204) | ethyl 8α-methyl-9α/β,-15-dihydroxy-8-iso-5-cis,13-cis-prostadienoates |
| 1270 | ethyl 8α-methyl-9-oxo-15-hydroxy-20-ethyl-5-cis,13-trans-prostadienoate (Example 1205) | ethyl 8α-methyl-9α/β,-15-dihydroxy-20-ethyl-5-cis,13-trans-prostadienoates |
| 1271 | ethyl 8α-methyl-9-oxo-15-hydroxy-20-ethyl-8-iso-5-cis,13-trans-prostadienoate (Example 1205) | ethyl 8α-methyl-9α/β,-15-dihydroxy-20-ethyl-8-iso-5-cis,13-trans-prostadienoates |
| 1272 | ethyl 8β-methyl-9-oxo-15-hydroxy-20-ethyl-5-cis,13-cis-prostadienoate (Example 1205) | ethyl 8β-methyl-9α/β,-15-dihydroxy-20-ethyl-5-cis,13-cis-prostadienoates |
| 1273 | ethyl 8α-methyl-9-oxo-15-hydroxy-20-ethyl-8-iso-5-cis,13-cis-prostadienoate (Example 1205) | ethyl 8α-methyl-9α/β,-15-dihydroxy-20-ethyl-8-iso-5-cis,13-cis-prostadienoates |

Examples 1274–1299

In the manner of Example 93, the various cyclopentenones of Table 36, which follows, are converted to the corresponding 4-bromo derivatives.

TABLE 36

| Example | Starting Cyclopentenone of Example | Product 4-Bromocyclopentenones |
|---|---|---|
| 1274 | 13 | 4-bromo-2-(6-carbethoxyhexyl)-cyclopent-2-en-1-one |
| 1275 | 83 | 4-bromo-2-(6-carbo-methoxyhexyl)cyclopent-2-en-1-one |
| 1276 | 15 | 4-bromo-2-(4-carbethoxybutyl)cyclopent-2-en-1-one |
| 1277 | 14 | 4-bromo-2-(3-carbethoxypropyl)cyclopent-2-en-1-one |
| 1278 | 2 | 4-bromo-2-(4-carboxybutyl)cyclopent-2-en-1-one |
| 1279 | 5 | 4-bromo-2-(3-carboxypropyl)cyclopent-2-en-1-one |
| 1280 | 22 | 4-bromo-2-(-carboxyoctyl)cyclopent-2-en-1-one |
| 1281 | 23 | 4-bromo-2-(-carbethoxyoctyl)cyclopent-2-en-1-one |
| 1282 | 30 | 4-bromo-2-(6-carboxyoctyl)cyclopent-2-en-1-one |
| 1283 | 31 | 4-bromo-2-(6-carbethoxyoctyl)cyclopent-2-en-1-one |
| 1284 | 92 | 4-bromo-2-(6-carboxy-5,5-dimethylhexyl)cyclopent-2-en-1-one |
| 1285 | 41 | 4-bromo-2-(6-carbethoxy-5,5-dimethylhexyl)cyclopent-2-en-1-one |
| 1286 | 45 | 4-bromo-2-(6-carboxy-5-oxahexyl)cyclopent-2-en-1-one |
| 1287 | 46 | 4-bromo-2-(6-carbethoxy-5-oxahexyl)cyclopent-2-en-1-one |
| 1288 | 69 | 4-bromo-2-(6-carboxy-6-fluorohexyl)cyclopent-2-en-1-one |
| 1289 | 70 | 4-bromo-2-(6-carbethoxy-6-fluorohexyl)cyclopent-2-en-1-one |
| 1290 | 52 | 4-bromo-2-(5-carboxypentyl)cyclopent-2-en-1-one |
| 1291 | 53 | 4-bromo-2-(5-carbethoxypentyl)cyclopent-2-en-1-one |
| 1292 | 73 | 4-bromo-2-(7-carboxyheptyl)cyclopent-2-en-1-one |
| 1293 | 74 | 4-bromo-2-(7-carbethoxyheptyl)cyclopent-2-en-1-one |
| 1294 | 78 | 4-bromo-2-(6-carboxy-6-phenylhexyl)cyclopent-2-en-1-one |
| 1295 | 79 | 4-bromo-2-(6-carbethoxy-6-phenylhexyl)cyclopent-2-en-1-one |
| 1296 | 81 | 4-bromo-2-(6-carbo-n-butoxyhexyl)cyclopent-2-en-1-one |
| 1297 | 82 | 4-bromo-2-(6-carbo-isopropoxyhexyl)-cyclopent-2-en-1-one |
| 1298 | 84 | 4-bromo-2-(6-carbo-n-decyloxyhexyl)cyclopent-2-en-1-one |
| 1299 | 98 | 4-bromo-2-(6-carboxyheptyl)-cyclopent-2-en-1-one |

EXAMPLE 1300

Preparation of 4-hydroxy-2-(8-carboxyoctyl)cyclopent-2-en-1-one

To a stirred solution of 57.2 g. of crude 4-bromo-2-(8-carboxyoctyl)cyclopent-2-en-1-one (Example 1280) in 500 ml. of acetone and 325 ml. of water at 3° C. is added 44.1 g. (0.226 moles) of silver fluoborate during a 15 minute period. The mixture is stirred at 0°–3° C. for 2 hours and filtered. The filtrate is diluted with water, saturated with solid sodium chloride, and extracted with ether. The extract is washed with saturated sodium chloride solution, dried over magnesium sulfate, and concentrated. Partition chromatography of the residue on Celite gives white crystals, m.p. 58°–66° C., $\lambda_{max.}^{MeOH} = 223$ mμ (7800); ν max (KBr) = 3340 (hydroxyl groups), 1705 (carbonyl groups), and 1625 cm$^{-1}$ (olefin group).

EXAMPLE 1301

Preparation of 4-acetoxy-2-(6-carbethoxyhexyl)cyclopent-2-en-1-one

A mixture of 51.6 g. (0.137 moles) of crude 4-bromo-2-(6-carbethoxyhexyl)cyclopent-2-en-1-one (Example 1274), 27 g. (0.162 moles) of silver acetate, and 200 ml. of glacial acetic acid is stirred at reflux for 4.5 hours. The mixture is cooled, and solids are removed by filtration. The filtrate is concentrated and extracted with hot hexane. The extract is washed with saturated sodium bicarbonate solution and saturated sodium chloride solution, dried over magnesium sulfate, and concentrated to give an oil. The crude product is distilled at reduced pressure to give a liquid, b.p. 152°–163° C. (0.01 mm); $\lambda_{max.}^{MeOH} = 223$ mμ (10700); ν max. = 1745 (ester carbonyl groups), 1725 (ketone carbonyl groups), and 1235 cm$^{-1}$ (acetoxy group).

EXAMPLES 1302–1326

By the procedure of Example 94 the various 4-bromocyclopentenones of the following Table 37 are solvolyzed in acetone-water in the presence of silver fluoborate to provide the product 4-hydroxycyclopentenones of the Table.

TABLE 37

| Example | Starting 4-bromo cyclopentenones of Example | Product 4-Hydroxycyclopent-2-en-1-ones |
|---|---|---|
| 1302 | 1274 | 4-hydroxy-2-(6-carbethoxyhexyl)cyclopent-2-en-1-one |
| 1303 | 1275 | 4-hydroxy-2-(6-carbomethoxyhexyl)cyclopent-2-en-1-one |
| 1304 | 1276 | 4-hydroxy-2-(4-carbethoxybutyl)cyclopent-2-en-1-one |
| 1305 | 1277 | 4-hydroxy-2-(3-carbethoxypropyl)cyclopent-2-en-1-one |
| 1306 | 1278 | 4-hydroxy-2-(4-carboxybutyl)cyclopent-2-en-1-one |
| 1307 | 1279 | 4-hydroxy-2-(3-carboxypropyl)cyclopent-2-en-1-one |
| 1308 | 1281 | 4-hydroxy-2-(8-carbethoxyoctyl)cyclopent-2-en-1-one |
| 1309 | 1282 | 4-hydroxy-2-(6-carboxyoctyl)cyclopent-2-en-1-one |
| 1310 | 1283 | 4-hydroxy-2-(6-carbethoxyoctyl)cyclopent-2-en-1-one |
| 1311 | 1284 | 4-hydroxy-2-(6-carboxy-5,5-dimethylhexyl)-cyclopent-2-en-1-one |
| 1312 | 1285 | 4-hydroxy-2-(6-carbethoxy-5,5-dimethylhexyl)cyclopent-2-en-1-one |
| 1313 | 1286 | 4-hydroxy-2-(6-carboxy-5-oxahexyl)cyclopent-2-en-1-one |
| 1314 | 1287 | 4-hydroxy-2-(6-carbethoxy-5-oxahexyl)-cyclopent-2-en-1-one |
| 1315 | 1288 | 4-hydroxy-2-(6-carboxy-6-fluorohexyl)cyclopent-2-en-1-one |

TABLE 37—continued

| Example | Starting 4-bromo cyclopentenones of Example | Product 4-Hydroxycyclopent-2-en-1-ones |
|---|---|---|
| 1316 | 1289 | 4-hydroxy-2-(6-carbethoxy-6-fluorohexyl)-cyclopent-2-en-1-one |
| 1317 | 1290 | 4-hydroxy-2-(5-carboxypentyl)cyclopent-2-en-1-one |
| 1318 | 1291 | 4-hydroxy-2-(5-carbethoxypentyl)cyclopent-2-en-1-one |
| 1319 | 1292 | 4-hydroxy-2-(7-carboxyheptyl)cyclopent-2-en-1-one |
| 1320 | 1293 | 4-hydroxy-2-(7-carbethoxyheptyl)cyclopent-2-en-1-one |
| 1321 | 294 | 4-hydroxy-2-(6-carboxy-6-phenylhexyl)cyclopent-2-en-1-one |
| 1322 | 1295 | 4-hydroxy-2-(6-carbethoxy-6-phenylhexyl)-cyclopent-2-en-1-one |
| 1323 | 1296 | 4-hydroxy-2-(6-carbo-n-butoxyhexyl)cyclopent-2-en-1-one |
| 1324 | 1297 | 4-hydroxy-2-(6-carbo-isopropoxyhexyl)cyclopent-2-en-1-one |
| 1325 | 1298 | 4-hydroxy-2-(6-carbo-n-decyloxyhexyl)cyclopent-2-en-1-one |
| 1326 | 1299 | 4-hydroxy-2-(6-carboxyheptyl)cyclopent-2-en-1-one |

EXAMPLES 1327–1337

By the procedure of Example 95, the various 4-hydroxycyclopentenones of Table 38, which follows, are converted to the tetrahydropyranyl 4-tetrahydropyranyloxycyclopentenone esters of the table.

TABLE 38

| Example | Starting 4-hydroxycyclopentenone of Example | Product Tetrahydropyran-2'-yl 4-tetrhaydropyran-2'-yl-oxycyclopent-2-en-1-ones |
|---|---|---|
| 1327 | 1306 | 4-tetrahydropyran-2'-yloxy-2-(4-carbotetrahydropyran-2'-yloxy-butyl)cyclopent-2-en-1-one |
| 1328 | 1307 | 4-tetrahydropyran-2'-yloxy-2-(3-carbotetrahydropyran-2'-yloxy-propyl)cyclopent-2-en-1-one |
| 1329 | 1300 | 4-tetrahydropyran-2'-yloxy-2-(8-carbotetrahydropyran-2'-yloxy-octyl)cyclopent-2-en-1-one |
| 1330 | 1309 | 4-tetrahydropyran-2'-yloxy-2-(6-carbotetrahydropyran-2'-yloxy-octyl)cyclopent-2-en-1-one |
| 1331 | 1311 | 4-tetrahydropyran-2'-yloxy-2-(6-carbotetrahydropyran-2'-yloxy-5,5-dimethylhexyl)-cyclopent-2-en-1-one |
| 1332 | 1313 | 4-tetrahydropyran-2'-yloxy-2-(6-carbotetrahydropyran-2'-yloxy-5-oxahexyl)cyclopent-2-en-1-one |
| 1333 | 1315 | 4-tetrahydropyran-2'-yloxy-2-(6-carbotetrahydropyran-2'-yloxy-6-fluorohexyl)cyclopent-2-en-1-one |
| 1334 | 1317 | 4-tetrahydropyran-2'-yloxy-2-(5-carbotetrahydropyran-2'-yloxy-pentyl)cyclopent-2-en-1-one |

TABLE 38—continued

| Example | Starting 4-hydroxycyclopentenone of Example | Product Tetrahydropyran-2'-yl 4-tetrhaydropyran-2'-yl-oxycyclopent-2-en-1-ones |
|---|---|---|
| 1335 | 1319 | 4-tetrahydropyran-2'-yloxy-2-(7-carbotetra-hydropyran-2'-yloxyheptyl)cyclopent-2-en-1-one |
| 1336 | 1321 | 4-tetrahydropyran-2'-yloxy-2-(6-carbotetra-hydropyran-2'-yloxy-6-phenylhexyl)cyclopent-2-en-1-one |
| 1337 | 1326 | 4-tetrahydropyran-2'-yloxy-2-(6-carbotetra-hydropyran-2'-yloxy-heptyl)cyclopent-2-en-1-one |

EXAMPLE 1338

Preparation of 4-tetrahydropyranyloxy-2-(6-carbethoxyhexyl)cyclopent-2-en-1-one To a stirred solution of 674 mg. (2.64 mmoles) of 4-hydroxy-2-(6-carbethoxyhexyl)cyclopent-2-en-1-one (Example 1302) and 2.22 g. (26.4 mmoles) of dihydropyran in 2.6 ml. of methylene chloride is added 5.0 mg. (0.026 mmoles) of p-toluenesulfonic acid monohydrate. After stirring for 20 minutes at room temperature the solution is diluted with ether and poured into saturated sodium chloride solution containing a little sodium bicarbonate. The organic phase is separated and washed with saturated sodium chloride solution. The extract is dried over magnesium sulfate, and volatile matter is evaporated at reduced pressure to give an oil, $\lambda_{max}^{MeOH}$ = 224 m$\mu$ (7950); max. = 1735 (ester carbonyl group), 1710 (ketone carbonyl group), and 1030 cm$^{-1}$ (tetrahydropyranyloxy group).

EXAMPLE 1339–1352

In the manner of Example 1338 the alkyl 4-hydroxycyclopentenone esters of Table 39, which follows, are converted to the corresponding 4-tetrahydropyranyloxy alkyl esters of the table.

TABLE 39

| Example | Starting 4-hydroxycyclopentenone Esters of Example | 4-tetrahydropyran-2'yloxycyclopent-2-en-1-one esters |
|---|---|---|
| 1339 | 1303 | 4-tetrahydropyran-2'-yloxy-2-(6-carbomethoxyhexyl)cyclopent-2-en-1-one |
| 1340 | 1304 | 4-tetrahydropyran-2'-yloxy-2-(4-carbethoxybutyl)cyclopent-2-en-1-one |
| 1341 | 1305 | 4-tetrahydropyran-2'-yloxy-2-(3-carbethoxypropyl)cyclopent-2-en-1-one |
| 1342 | 1308 | 4-tetrahydropyran-2'-yloxy-2-(8-carbethoxyoctyl)cyclopent-2-en-1-one |
| 1343 | 1310 | 4-tetrahydropyran-2'-yloxy-2-(6-carbethoxyoctyl)cyclopent-2-en-1-one |
| 1344 | 1312 | 4-tetrahydropyran-2'-yloxy-2-(6-carbethoxy-5,5-dimethylhexyl)cyclopent-2-en-1-one |
| 1345 | 1314 | 4-tetrahydropyran-2'-yloxy-2-(6-cabethoxy-5-oxahexyl)cyclopent-2-en-1-one |
| 1346 | 1316 | 4-tetrahydropyran-2'-yloxy-2-(6-carbethoxy-6-fluorohexyl)cyclopent-2-en-1-one |
| 1347 | 1318 | 4-tetrahydropyran-2'-yloxy-2-(5-carbethoxypentyl)cyclopent-2-en-1-one |
| 1348 | 1320 | 4-tetrahydropyran-2'-yloxy-2-(7-carbethoxyheptyl)cyclopent-2-en-1-one |
| 1349 | 1322 | 4-tetrahydropyran-2'-yloxy-2-(6-carbethoxy-6-phenylhexyl)cyclopent-2-en-1-one |
| 1350 | 1323 | 4-tetrahydropyran-2'-yloxy-2-(6-carbo-n-butoxyhexyl)cyclopent-2-en-1-one |
| 1351 | 1324 | 4-tetrahydropyran-2'-yloxy-2-(6-carbo-iso-propoxyhexyl)cyclopent-2-en-1-one |
| 1352 | 1325 | 4-tetrahydropyran-2'-yloxy-2-(6-carbo-n-decyloxyhexyl)cyclopent-2-en-1-one |

EXAMPLE 1353

Preparation of 8$\beta$-methyl-prostaglandin E$_1$, 8$\alpha$-methyl-8-iso-prostaglandin E$_1$, 8$\beta$-methyl-9-oxo-11$\alpha$,15-dihydroxy-13-cis-prostenoic acid, and 8$\alpha$-methyl-9-oxo-11$\alpha$,15-dihydroxy-8-iso-13-cis-prostenoic acid The Grignard reagent, prepared as described in Example 1187 from 1.54 g. of magnesium, 22.5 g. of 1-bromo-3-triphenylmethoxy-trans-1-octene (Example 728), and 30 ml. of tetrahydrofuran, is added to an ice cooled solution of 17.75 g. of 11-tetrahydropyranyloxy-2-(6-carbotetrahydropyranyloxyhexyl)-2-cyclopentenone (Example 95) and 1.25 g. of copper (I) iodine-tri-n-butylphosphine complex in 30 ml. of tetrahydrofuran over 15 minutes under an inert atmosphere. The mixture is stirred with cooling for 0.5 hours. To the mixture is then added 100 g. of methyl iodide, the cooling bath is then removed and the mixture is stirred at ambient temperatures for 48 hours. The mixture is then poured into ice cold saturated ammonium chloride solution and the layers are separated. The aqeous phase is washed with ether and combined organic phase and washings are washed with saturated brine, and evaporated in vacuo. The residue is heated to 45° C. for 5 hours with 840 ml. of 4:2:1 tetrahydrofuran-acetic acid-water under an inert atmosphere and is then evaporated to dryness in vacuo. The residue is chromatographed upon Silic AR CC-4 ® using a benzene-ethyl acetate gradient as eluent to yield the title compounds as a mixture of 8$\beta$-methyl-prostaglandin E$_1$ and 8$\alpha$-methyl-8-iso-prostaglandin E$_1$ and a mixture of 8$\beta$-methyl-9-oxo-11$\alpha$,15-dihydroxy-13-cis-prostenoic acid and 8$\alpha$-methyl-9-oxo-11$\alpha$,15-dihydroxy 8-iso-cis-8$\alpha$ isomers; resolution of the mixtures is then accomplished by a combination of partition chromatography and thin-layer chromatography.

EXAMPLES 1354–1386

Treatment of the blocked 4-oxycyclopent-2-en-1-ones listed in Table 40 below by the procedure described in Example 1353 with the Grignard reagents, prepared by the procedure described in Example 1187 from the listed 1-bromo-3-triphenylmethoxy-1-trans-alkenes, and then with methyl iodide furnishes the product 8α- and 8β-methyl prostenoates of the table. The products of Examples 1354–1378 inclusive are initially obtained as the corresponding 15-O-triphenylmethyl-11-O-tetrahydropyranyl tetrahydropyranyl esters. These blocking groups are then cleaved by the procedure described in Example 1353 by treatment at 45° C. for five hours with 4:2:1 tetrahydrofuran:acetic acid:-water. The alkyl esters products of Examples 1379–1385 inclusive are obtained initially as the corresponding 15-O-triphenylmethyl-11-O-tetrahydropyranyl derivatives. These 11- and 15-hydroxy blocking groups are then cleaved by the deblocking procedure described in Example 1353. The products of Example 1386 are initially obtained as the corresponding 15-O-triphenylmethyl derivatives, which are cleaved hydrolytically to the listed free 15-ols by the process described in Example 1353.

TABLE 40

| Example | Starting blocked 4-xoycyclopent-2-en-1-one of Example | Starting 1-bromo-3-triphenylmethoxy-1-trans-alkene of Example | Product 8-methylprostenoic acid |
|---|---|---|---|
| 1354 | 95 | 1175 | 8β-methyl-9-oxo-11α,15-dihydroxy-16,16-dimethyl-13-trans-prostenoic acid<br>8α-methyl-9-oxo-11α,15-dihydroxy-16,16-dimethyl-89-iso-13-trans-prostenoic acid<br>8β-methyl-9-oxo-11α,15-dihydrpxy-16,16-dimethyl-13-cis-prostenoic acid<br>8α-methyl-9-oxo-11α,15-dihydroxy-16,16-dimethyl-8-iso-13-cis-prostenoic acid |
| 1355 | 95 | 1178 | 8β-methyl-9-oxo-11α,15-dihydroxy,17,17-dimethyl-13-trans-prostenoic acid<br>8α-methyl-9-oxo-11α,15-dihydroxy-17,17-dimethyl-8-iso-13-trans-prostenoic acid<br>8β-methyl-9-oxo-11α,15-dihydroxy-17,17-dimethyl-13-cis-prostenoic acid<br>8α-methyl-9-oxo-11α,15-dihydroxy-17,17-dimethyl-8-iso-13-cis-prostenoic acid |
| 1356 | 95 | 1182 | 8β-methyl-9-oxo-11α,15-dihydroxy-13-trans,17-cis-prostadienoic acid<br>8α-methyl-9-oxo-11α,15-dihydroxy-8-iso-13-trans,17-cis-prostadienoic acid<br>8β-methyl-9-oxo-11α,15-dihydroxy-13-cis,17-cis-prostadienoic acid<br>8α-methyl-9-oxo-11α,15-dihydroxy-8-iso-13-cis,17-cis-prostadienoic acid |
| 1357 | 95 | 1185 | 8β-methyl-9-oxo-11α,15-dihydroxy-20-ethyl-13-trans-prostenoic acid<br>8α-methyl-9-oxo-11α,15-dihydroxy-20-ethyl-8-iso-13-trans-prostenoic acid<br>8β-methyl-9-oxo-11α,15-dihydroxy-20-ethyl-13-cis-prostenoic acid<br>8α-methyl-9-oxo-11α,15-dihydroxy-20-ethyl-8-iso-13-cis-prostenoic acid |
| 1358 | 1327 | 728 | 8β-methyl-9-oxo-11α,15-dihydroxy-6,7-dinor-13-trans-prostenoic acid<br>8α-methyl-9-oxo-11α,15-dihydroxy-6,7-dinor-8-iso-13-trans-prostenoic acid<br>8β-methyl-9-oxo-11α,15-dihydroxy-6,7-dinor-13-cis-prostenoic acid<br>8α-methyl-9-oxo-11α,15-dihydroxy-6,7-dinor-8-iso-13-cis-prostenoic acid |
| 1359 | 1328 | 1186 | 8β-methyl-9-oxo-11α,15-dihydroxy-5,6,7-trinor-20-methyl-13-trans-prostenoic acid<br>8α-methyl-9-oxo-11α,15-dihydroxy-5,6,7-trinor-20-methyl-8-iso-13-trans-prostenoic acid<br>8β-methyl-9-oxo-11α,15-dihydroxy-5,6,7-trinor-20-methyl-13-cis-prostenoic acid<br>8α-methyl-9-oxo-11α,15-dihydroxy-5,6,7-trinor-20-methyl-8-iso-13-cis-prostenoic acid |
| 1360 | 1329 | 728 | 8β-methyl-9-oxo-11α,15-dihydroxy-7a,7b-bishomo-13-trans-prostenoic acid<br>8α-methyl-9-oxo-11α,15-dihydroxy-7a,7b-bishomo-8-iso-13-trans-prostenoic acid<br>8β-methyl-9-oxo-11α,15-dihydroxy-7a,7b-bishomo-13-cis-prostenoic acid<br>8α-methyl-9-oxo-11α,15-dihydroxy-7a,7b-bishomo-8-iso-13-cis-prostenoic acid |
| 1361 | 1330 | 728 | 8β-methyl-9-oxo-11α,15-dihydroxy-2-ethyl-13-trans-prostenoic acid<br>8α-methyl-9-oxo-11α,15-dihydroxy-2-ethyl-8-iso-13-trans-prostenoic acid<br>8β-methyl-9-oxo-11α,15-dihydroxy-2-ethyl-13-cis-prostenoic acid<br>8α-methyl-9-oxo-11α,15-dihydroxy-2-ethyl-8-iso-13-cis-prostenoic acid |
| 1362 | 1331 | 1186 | 8β-methyl-9-oxo-11α,15-dihydroxy-3,3,20-trimethyl-13-trans-prostenoic acid<br>8α-methyl-9-oxo-11α,15-dihydroxy-3,3,20-trimethyl-8-iso-13-trans-prostenoic acid<br>8β-methyl-9-oxo-11α,15-dihydroxy-3,3,20-trimethyl-13-cis-prostenoic acid<br>8α-methyl-9-oxo-11α,15-dihydroxy-3,3,20-trimethyl-8-iso-13-cis-prostenoic acid |

TABLE 40-continued

| Example | Starting blocked 4-xoycyclopent-2-en-1-one of Example | Starting 1-bromo-3-triphenylmethoxy-1-trans-alkene of Example | Product 8-methylprostenoic acid |
|---|---|---|---|
| 1363 | 1332 | 728 | 8β-methyl-9-oxo-11α,15-dihydroxy-3-oxa-13-trans-prostenoic acid<br>8α-methyl-9-oxo-11α,15-dihydroxy-3-oxa-8-iso-13-trans-prostenoic acid<br>8β-methyl-9-oxo-11α,15-dihydroxy-3-oxa-13-cis-prostenoic acid<br>8α-methyl-9-oxo-11α,15-dihydroxy-3-oxa-8-iso-13-cis-prostenoic acid |
| 1364 | 1332 | 1175 | 8β-methyl-9-oxo-11α,15-dihydroxy-3-oxa-16,16-dimethyl-13-trans-prostenoic acid<br>8α-methyl-9-oxo-11α,15-dihydroxy-3-oxa-16,16-dimethyl-8-iso-13-trans-prostenoic acid<br>8β-methyl-9-oxo-11α,15-dihydroxy-3-oxa-16,16-dimethyl-13-cis-prostenoic acid<br>8αmethyl-9-oxo-11α,15-dihydroxy-3-oxa-16,16-dimethyl-8-iso-13-cis-prostenoic acid |
| 1365 | 1332 | 1182 | 8β-methyl-9-oxo-11α,15-dihydroxy-3-oxa-13-trans,17-cis-prostadienoic acid<br>8α-methyl-9-oxo-11α,15-dihydroxy-3-oxa-8-iso-13-trans,17-cis-prostadienoic acid<br>8β-methyl-9-oxo-11α,15-dihydroxy-3-oxa-13-cis,17-cis-prostadienoic acid<br>8α-methyl-9-oxo-11α,15-dihydroxy-3-oxa-8-iso-13-cis,17-cis-prostadienoic acid |
| 1366 | 1332 | 1185 | 8β-methyl-9-oxo-11α,15-dihydroxy-3-oxa-20-ethyl-13-trans-prostenoic acid<br>8α-methyl-9-oxo-11α,15-dihydroxy-3-oxa-20-ethyl-8-iso-13-trans-prostenoic acid<br>8β-methyl-9-oxo-11α,15-dihydroxy-3-oxa-20-ethyl-13-cis-prostenoic acid<br>8α-methyl-9-oxo-11α,15-dihydroxy-3-oxa-20-ethyl-8-iso-13-cis-prostenoic acid |
| 1367 | 1333 | 1178 | 8β-methyl-9-oxo-11α,15-dihydroxy-2-fluoro-17,17-dimethyl-13-trans-prostenoic acid<br>8α-methyl-9-oxo-11α,15-dihydroxy-2-fluoro-17,17-dimethyl-8-iso-13-trans-prostenoic acid<br>8β-methyl-9-oxo-11α,15-dihydroxy-2-fluoro-17,17-dimethyl-13-cis-prostenoic acid<br>8α-methyl-9-oxo-11α,15-dihydroxy-2-fluoro-17,17-dimethyl-8-iso-13-cis-prostenoic acid |
| 1368 | 1334 | 728 | 8β-methyl-9-oxo-11α,15-dihydroxy-7-nor-13-trans-prostenoic acid<br>8α-methyl-9-oxo-11α,15-dihydroxy-7-nor-8-iso-13-trans-prostenoic acid<br>8β-methyl-9-oxo-11α,15-dihydroxy-7-nor-13-cis-prostenoic acid<br>8α-methyl-9-oxo-11α,15-dihydroxy-7-nor-8-iso-13-cis-prostenoic acid |
| 1369 | 1335 | 1175 | 8β-methyl-9-oxo-11α,15-dihydroxy-7a-homo-16,16-dimethyl-13-trans-prostenoic acid<br>8α-methyl-9-oxo-11α,15-dihydroxy-7a-homo-16,16-dimethyl-8-iso-13-trans-prostenoic acid<br>8β-methyl-9-oxo-11α,15-dihydroxy-7a-homo-16,16-dimethyl-13-cis-prostenoic acid<br>8α-methyl-9-oxo-11α,15-dihydroxy-7a-homo-16,16-dimethyl-8-iso-13-cis-prostenoic acid |
| 1370 | 1336 | 728 | 8β-methyl-9-oxo-11α,15-dihydroxy-2-phenyl-13-trans-prostenoic acid<br>8α-methyl-9-oxo-11α,15-dihydroxy-2-phenyl-8-iso-13-trans-prostenoic acid<br>8β-methyl-9-oxo-11α,15-dihydroxy-2-phenyl-13-cis-prostenoic acid<br>8α-methyl-9-oxo-11α,15-dihydroxy-2-phenyl-8-iso-13-cis-prostenoic acid |
| 1371 | 1337 | 1182 | 8β-methyl-9-oxo-11α,15-dihydroxy-2-methyl-13-trans,17-cis-prostadienoic acid<br>8α-methyl-9-oxo-11α,15-dihydroxy-2-methyl-8-iso-13-trans,17-cis-prostadienoic acid<br>8β-methyl-9-oxo-11α,15-dihydroxy-2-methyl-13-cis,17-cis-prostadienoic acid<br>8α-methyl-9-oxo-11α,15-dihydroxy-2-methyl-8-iso-13-cis,17-cis-prostadienoic acid |
| 1372 | 1121 | 728 | 8β-methyl-9-oxo-11α,15-dihydroxy-5-cis,13-trans-prostadienoic acid<br>8α-methyl-9-oxo-11α,15-dihydroxy-8-iso-5-cis,13-trans-prostadienoic acid<br>8β-methyl-9-oxo-11α,15-dihydroxy-5-cis,13-cis-prostadienoic acid<br>8α-methyl-9-oxo-11α,15-dihydroxy-8-iso-5-cis,13-cis-prostadienoic acid |
| 1373 | 1121 | 1182 | 8β-methyl-9-oxo-11α,15-dihydroxy-5-cis,13-trans,17-cis-prostatrienoic acid<br>8α-methyl-9-oxo-11α,15-dihydroxy-8-iso-5-cis,13-trans,17-cis-prostatrienoic acid<br>8β-methyl-9-oxo-11α,15-dihydroxy-5-cis,13-cis,17-cis-prostatrienoic acid<br>8α-methyl-9-oxo-11α,15-dihydroxy-8-iso-5-cis,13-cis,17-cis-prostatrienoic acid |
| 1374 | 1121 | 1175 | 8β-methyl-9-oxo-11α,15-dihydroxy-16,16-dimethyl-5-cis,13-trans-prostadienoic acid |

TABLE 40-continued

| Example | Starting blocked 4-xoycyclopent-2-en-1-one of Example | Starting 1-bromo-3-triphenylmethoxy-1-trans-alkene of Example | Product 8-methylprostenoic acid |
|---|---|---|---|
| | | | 8α-methyl-9-oxo-11α,15-dihydroxy-16,16-dimethyl-8-iso-5-cis,13-trans-prostadienoic acid |
| | | | 8β-methyl-9-oxo-11α,15-dihydroxy-16,16-dimethyl-5-cis,13-cis-prostadienoic acid |
| | | | 8α-methyl-9-oxo-11α,15-dihydroxy-16,16-dimethyl-8-iso-5-cis,13-cis-prostadienoic acid |
| 1375 | 1122 | 1186 | 8β-methyl-9-oxo-11α,15-dihydroxy-4-nor-20-methyl-5-cis,13-trans-prostadienoic acid |
| | | | 8α-methyl-9-oxo-11α,15-dihydroxy-4-nor-20-methyl-8-iso-5-cis,13-trans-prostadienoic acid |
| | | | 8β-methyl-9-oxo-11α,15-dihydroxy-4-nor-20-methyl-5-cis,13-cis-prostadienoic acid |
| | | | 8β-methyl-9-oxo-11α,15-dihydroxy-4-nor-20-methyl-8-iso-5-cis,13-cis-prostadienoic acid |
| 1376 | 1123 | 1178 | 8β-methyl-9-oxo-11α,15-dihydroxy-4a-homo-17,17-dimethyl-5-cis,13-trans-prostadienoic acid |
| | | | 8α-methyl-9-oxo-11α,15-dihydroxy-4a-homo-17,17-dimethyl-8-iso-5-cis,13-cis-prostadienoic acid |
| | | | 8β-methyl-9-oxo-11α,15-dihydroxy-4a-homo-17,17-dimethyl-5-cis,13-cis-prostadienoic acid |
| | | | 8α-methyl-9-oxo-11α,15-dihydroxy-4a-homo-17,17-dimethyl-8-iso-5-cis,13-cis-prostadienoic acid |
| 1377 | 1124 | 1185 | 8β-methyl-9-oxo-11α,15-dihydroxy-4a,4b-bis-homo-20-ethyl-5-cis,13-trans-prostadienoic acid |
| | | | 8α-methyl-9-oxo-11α,15-dihydroxy-4a,4b-bis-homo-20-ethyl-8-iso-5-cis,13-trans-prostadienoic acid |
| | | | 8β-methyl-9-oxo-11α,15-dihydroxy-4a,4b-bis-homo-20-ethyl-5-cis,13-cis-prostadienoic acid |
| | | | 8α-methyl-9-oxo-11α,15-dihydroxy-4a,4b-bis-homo-20-ethyl-8-iso-5-cis,13-cis-prostadienoic acid |
| 1378 | 1124 | 1182 | 8β-methyl-9-oxo-11α,15-dihydroxy-4a,4b-bis-homo-5-cis,13-trans,17-cis-prostatrienoic acid |
| | | | 8α-methyl-9-oxo-11α,15-dihydroxy-4a,4b-bis-homo-8-iso-5-cis,13-trans,17-cis-prostatrienoic acid |
| | | | 8β-methyl-9-oxo-11α,15-dihydroxy-4a,4b-bis-homo-5-cis,13-cis,17-cis-prostatrienoic acid |
| | | | 8α-methyl-9-oxo-11α,15-dihydroxy-4a,4b-bis-homo-8-iso-5-cis,13-cis-17-cis-prostatrienoic acid |
| 1379 | 1339 | 1186 | Methyl 8β-methyl-9-oxo-11α,15-dihydroxy-20-methyl-13-trans-prostenoate |
| | | | Methyl 8α-methyl-9-oxo-11α,15-dihydroxy-20-methyl-8-iso-13-trans-prostenoate |
| | | | Methyl 8β-methyl-9-oxo-11α,15-dihydroxy-20-methyl-13-cis-prostenoate |
| | | | Methyl 8α-methyl-9-oxo-11α,15-dihydroxy-20-methyl-8-iso-13-cis-prostenoate |
| 1380 | 1342 | 1182 | Ethyl 8β-methyl-9-oxo-11α,15-dihydroxy-7a,7b-bishomo-13-trans,17-cis-prostadienoate |
| | | | Ethyl 8α-methyl-9-oxo-11α,15-dihydroxy-7a,7b-bishomo-8-iso-13-trans,17-cis-prostadienoate |
| | | | Ethyl 8β-methyl-9-oxo-11α,15-dihydroxy-7a,7b-bishomo-13-cis,17-cis-prostadienoate |
| | | | bishomo-8-iso-13-cis,17-cis-prostadienoate |
| 1381 | 1343 | 1175 | Ethyl 8β-methyl-9-oxo-11α,15-dihydroxy-2-ethyl-16,16-dimethyl-13-trans-prostenoate |
| | | | Ethyl 8α-methyl-9-oxo-11α,15-dihydroxy-2-ethyl-16-16-dimethyl-8-iso-13-trans-prostenoate |
| | | | Ethyl 8β-methyl-9-oxo-11α,15-dihydroxy-2-ethyl-16,16-dimethyl-13-cis-prostenoate |
| | | | Ethyl 8a-methyl-9-oxo-11α,15-dihydroxy-2-ethyl-16,16-dimethyl-8-iso-13-cis-prostenoate |
| 1382 | 1344 | 1178 | Ethyl 8β-methyl-9-oxo-11α,15-dihydroxy-3,3-17,17-tetramethyl-13-trans-prostenoate |
| | | | Ethyl 8α-methyl-9-oxo-11α,15-dihydroxy-3,3-17,17-tetramethyl-8-iso-13-trans-prostenoate |
| | | | Ethyl 8β-methyl-9-oxo-11α,15-dihydroxy-3,3-17,17-tetramethyl-13-cis-prostenoate |
| | | | Ethyl 8α-methyl-9-oxo-11α,15-dihydroxy-3,3-17,17-tetramethyl-8-iso-13-cis-prostenoate |
| 1383 | 1345 | 1178 | Ethyl 8β-methyl-9-oxo-11α,15-dihydroxy-3-oxa-17,17-dimethyl-13-trans-prostenoate |
| | | | Ethyl 8α-methyl-9-oxo-11α,15-dihydroxy-3-oxa-17,17-dimethyl-8-iso-13-trans-prostenoate |
| | | | Ethyl 8β-methyl-9-oxo-11α,15-dihydroxy-3-oxa-17,17-dimethyl-13-cis-prostenoate |

TABLE 40-continued

| Example | Starting blocked 4-xoycyclopent-2-en-1-one of Example | Starting 1-bromo-3-triphenylmethoxy-1-trans-alkene of Example | Product 8-methylprostenoic acid |
|---|---|---|---|
| 1384 | 1350 | 728 | Ethyl 8α-methyl-9-oxo-11α,15-dihydroxy-3-oxa-17,17-dimethyl-8-iso-13-cis-prostenoate<br>Butyl 8β-methyl-9-oxo-11α,15-dihydroxy-13-trans-prostenoate<br>Butyl 8α-methyl-9-oxo-11α,15-dihydroxy-8-iso-13-trans-prostenoate<br>Butyl 8β-methyl-9-oxo-11α,15-dihydroxy-13-cis-prostenoate<br>Butyl 8α-methyl-9-oxo-11α,15-dihydroxy-8-iso-13-cis-prostenoate |
| 1385 | 1352 | 1182 | Decyl 8β-methyl-9-oxo-11α,15-dihydroxy-13-trans,17-cis-prostadienoate<br>Decyl 8α-methyl-9-oxo-11α,15-dihydroxy-8-iso-13-trans,17-cis-prostadienoate<br>Decyl 8β-methyl-9-oxo-11α,15-dihydroxy-13-cis-17-cis-prostadienoate<br>Decyl 8α-methyl-9-oxo-11α,15-dihydroxy-8-iso-13-cis,17-cis-prostadienoate |
| 1386 | 1301 | 728 | Ethyl 8β-methyl-9-oxo-11α-acetoxy-15-hydroxy-13-trans-prostenoate<br>Ethyl 8α-methyl-9-oxo-11α-acetoxy-15-hydroxy-8-iso-13-trans-prostenoate<br>Ethyl 8β-methyl-9-oxo-11α-acetoxy-15-hydroxy-13-cis-prostenoate<br>Ethyl 8α-methyl-9-oxo-11α-acetoxy-15-hydroxy-8-iso-13-cis-prostenoate |

EXAMPLE 1387

Preparation of 8β-methyl-prostaglandin A₁

A mixture of 0.30 g. of 8β-methyl-prostaglandin E₁ (Example 1353) and 10 ml. of 1:9 aqueous acetic acid is heated to 65° C. for 18 hours under an inert atmosphere. The solvent is removed in vacuo and the residue is purified upon Silic AR-CC-4 ® using a benzene-ethylacetate gradient to yield the title compound.

EXAMPLES 1388–1522

Treatment of the designated 8-methyl-9-oxo-11-hydroxy-prostenoic acid derivatives of Table 41 below with 1:9 aqueous acid and purification all as described in Example 1387 gives the corresponding 8-methyl-9-oxo-10,13-prostadienoic acids and esters of the table.

TABLE 41

| Example | Starting 9-oxo-11-hydroxy derivative | Product 8-methyl-9-oxo-10,13-prostadienoic acids or esters |
|---|---|---|
| 1388 | 8α-methyl-8-iso-prostaglandin E₁ (Example 1353) | 8α-methyl-8-iso-prostaglandin A₁ |
| 1389 | 8β-methyl-9-oxo-11α,15-dihydroxy-13-cis-prostenoic acid (Example 1353) | 8β-methyl-11α,15-dihydroxy-10,13-cis-prostadienoic acid |
| 1390 | 8α-methyl-9-oxo-11,15-dihydroxy-8-iso-13-cis-prostenoic acid (Example 1353) | 8α-methyl-11α,15-dihydroxy-8-iso-10,13-cis-prostadienoic acid |
| 1391 | 8β-methyl-9-oxo-11α,15-dihydroxy-16,16-dimethyl-13-trans-prostenoic acid (Example 1354) | 8β-methyl-9-oxo-15-hydroxy-16,16-dimethyl 10,13-trans-prostadienoic acid |
| 1392 | 8α-methyl-9-oxo-11α,15-dihydroxy-16,16-dimethyl-8-iso-13-trans-prostenoic acid (Example 1354) | 8α-methyl-9-oxo-15-hydroxy-16,16-dimethyl-8-iso-10,13-trans-prostadienoic acid |
| 1393 | 8β-methyl-9-oxo-11α,15-dihydroxy-16,16-dimethyl-13-cis-prostenoic acid (Example 1354) | 8β-methyl-9-oxo-15-hydroxy-16,16-dimethyl 10,13-cis-prostadienoic acid |
| 1394 | 8α-methyl-9-oxo-11α,15-dihydroxy-16,16-dimethyl-8-iso-13-cis-prostenoic acid (Example 1354) | 8α-methyl-9-oxo-15-hydroxy-16,16-dimethyl-8-iso-10,13-cis-prostadienoic acid |
| 1395 | 8β-methyl-9-oxo-11α,15-dihydroxy-17,17-dimethyl 13-trans-prostenoic acid (Example 1355) | 8β-methyl-9-oxo-15-hydroxy-17,17-dimethyl 10,13-trans-prostadienoic acid |
| 1396 | 8α-methyl-9-oxo-11α,15-dihydroxy-17,17-dimethyl-8-iso-13-trans-prostenoic acid (Example 1355) | 8α-methyl-9-oxo-15-hydroxy-17,17-dimethyl-8-iso-10,13-trans-prostadienoic acid |
| 1397 | 8β-methyl-9-oxo-11α,15-dihydroxy-17,17-dimethyl 13-cis-prostenoic acid (Example 1355) | 8β-methyl-9-oxo-15-hydroxy-17,17-dimethyl 10,13-cis-prostadienoic acid |
| 1398 | 8α-methyl-9-oxo-11α,15-dihydroxy-17,17-dimethyl-8-iso-13-cis-prostenoic acid (Example 1355) | 8α-methyl-9-oxo-15-hydroxy-17,17-dimethyl-8-iso-10,13-cis-prostadienoic acid |
| 1399 | 8β-methyl-9-oxo-11α,15-dihydroxy-13-trans,17-cis-prostadienoic acid (Example 1356) | 8β-methyl-9-oxo-15-hydroxy-10,13-trans,17-cis-prostatrienoic acid |
| 1400 | 8α-methyl-9-oxo-11α,15-dihydroxy-8-iso-13-trans,17-cis-prostadienoic acid (Example 1356) | 8α-methyl-9-oxo-15-hydroxy-8-iso-10,13-trans-17-cis-prostatrienoic acid |
| 1401 | 8β-methyl-9-oxo-11α,15-dihydroxy-13-cis,17-cis-prostadienoic acid (Example 1356) | 8β-methyl-9-oxo-15-hydroxy-10,13-cis,17-cis-prostatrienoic acid |
| 1402 | 8α-methyl-9-oxo-11α,15-dihydro- | 8α-methyl-9-oxo-15-hydroxy-8-iso-10,13-cis,- |

TABLE 41-continued

| Example | Starting 9-oxo-11-hydroxy derivative | Product 8-methyl-9-oxo-10,13-prostadienoic acids or esters |
|---|---|---|
| | xy-8-iso-13-cis,-17-cis-prostadienoic acid (Example 1356) | 17-cis-prostatrienoic acid |
| 1403 | 8β-methyl-9-oxo-11α,15-dihydroxy-20-ethyl-13-trans-prostenoic acid (Example 1357) | 8β-methyl-9-oxo-15-hydroxy-20-ethyl-10,13-trans-prostadienoic acid |
| 1404 | 8α-methyl-9-oxo-11α,15-dihydroxy-20-ethyl-8-iso-13-trans-prostenoic acid (Example 1357) | 8α-methyl-9-oxo-15-hydroxy-20-ethyl-8-iso-10,13-trans-prostadienoic acid |
| 1405 | 8β-methyl-9-oxo-11α,15-dihydroxy-20-ethyl-13-cis-prostenoic acid (Example 1357) | 8β-methyl-9-oxo-15-hydroxy-20-ethyl-10,13-cis-prostadienoic acid |
| 1406 | 8α-methyl-9-oxo-11α,15-dihydroxy-20-ethyl-8-iso-13-cis-prostenoic acid (Example 1357) | 8α-methyl-9-oxo-15-hydroxy-20-ethyl-8-iso-10,13-cis-prostadienoic acid |
| 1407 | 8β-methyl-9-oxo-11α,15-dihydroxy-6,7-dinor-13-trans-prostenoic acid (Example 1358) | 8β-methyl-9-oxo-15-hydroxy-6,7-dinor-10,13-trans-prostadienoic acid |
| 1408 | 8α-methyl-9-oxo-11α,15-dihydroxy-6,7-dinor-8-iso-13-trans-prostenoic acid (Example 1358) | 8α-methyl-9-oxo-15-hydroxy-6,7-dinor-8-iso-10,13-trans-prostadienoic acid |
| 1409 | 8β-methyl-9-oxo-11α,15-dihydroxy-6,7-dinor-13-cis-prostenoic acid (Example 1358) | 8β-methyl-9-oxo-15-hydroxy-6,7-dinor-10,13-cis-prostadienoic acid |
| 1410 | 8α-methyl-9-oxo-11α,15-dihydroxy-6,7-dinor-8-iso-13-cis-prostenoic acid (Example 1358) | 8α-methyl-9-oxo-15-hydroxy-6,7-dinor-8-iso-10,13-cis-prostadienoic acid |
| 1411 | 8β-methyl-9-oxo-11α,15-dihydroxy-5,6,7-trinor-20-methyl 13-trans-prostenoic acid (Example 1359) | 8β-methyl-9-oxo-15-hydroxy-5,6,7-trinor-20-methyl 10,13-trans-prostadienoic acid |
| 1412 | 8α-methyl-9-oxo-11α,15-dihydroxy-5,6,7-trinor-20-methyl-8-iso-13-trans-prostenoic acid (Example 1359) | 8α-methyl-9-oxo-15-hydroxy-5,6,7-trinor-20-methyl-8-iso-10,13-trans-prostadienoic acid |
| 1413 | 8β-methyl-9-oxo-11α,15-dihydroxy-5,6,7-trinor-20-methyl 13-cis-prostenoic acid (Example 1359) | 8β-methyl-9-oxo-15-hydroxy-5,6,7-trinor-20-methyl 10,13-cis-prostadienoic acid |
| 1414 | 8α-methyl-9-oxo-11α,15-dihydroxy-5,6,7-trinor-20-methyl-8-iso-13-cis-prostenoic acid (Example 1359) | 8α-methyl-9-oxo-15-hydroxy-5,6,7-trinor-20-methyl-8-iso-10,13-cis-prostadienoic acid |
| 1415 | 8β-methyl-9-oxo-11α,15-dihydroxy-7a,7b-bishomo-13-trans-prostenoic acid (Example 1360) | 8β-methyl-9-oxo-15-hydroxy-7a,7b-bishomo-10,13-trans-prostadienoic acid |
| 1416 | 8α-methyl-9-oxo-11α,15-dihydroxy-7a,7b-bishomo-8-iso-13-trans-prostenoic acid (Example 1360) | 8α-methyl-9-oxo-15-hydroxy-7a,7b-bishomo-8-iso-10,13-trans-prostadienoic acid |
| 1417 | 8β-methyl-9-oxo-11α,15-dihydroxy-7a,7b-bishomo-13-cis-prostenoic acid (Example 1360) | 8β-methyl-9-oxo-15-hydroxy-7a,7b-bishomo-10,13-cis-prostadienoic acid |
| 1418 | 8α-methyl-9-oxo-11α,15-dihydroxy-7a,7b-bishomo-8-iso-13-cis-prostenoic acid (Example 1360) | 8α-methyl-9-oxo-15-hydroxy-7a,7b-bishomo-8-iso-10,13-cis-prostadienoic acid |
| 1419 | 8β-methyl-9-oxo-11α,15-dihydroxy-2-ethyl-13-trans-prostenoic acid (Example 1361) | 8β-methyl-9-oxo-15-hydroxy-2-ethyl-10,13-trans-prostadienoic acid |
| 1420 | 8α-methyl-9-oxo-11α,15-dihydroxy-2-ethyl-8-iso-13-trans-prostenoic acid (Example 1361) | 8α-methyl-9-oxo-15-hydroxy-2-ethyl-8-iso-10,13-trans-prostadienoic acid |
| 1421 | 8β-methyl-9-oxo-11α,15-dihydroxy-2-ethyl-13-cis-prostenoic acid (Example 1361) | 8β-methyl-9-oxo-15-hydroxy-2-ethyl-10,13-cis-prostadienoic acid |
| 1422 | 8α-methyl-9-oxo-11α,15-dihydroxy-2-ethyl-8-iso-13-cis-prostenoic acid (Example 1361) | 8α-methyl-9-oxo-15-hydroxy-2-ethyl-8-iso-10,13-cis-prostadienoic acid |
| 1423 | 8β-methyl-9-oxo-11α,15-dihydroxy-3,3,20-trimethyl-13-trans-prostenoic acid (Example 1362) | 8β-methyl-9-oxo-15-hydroxy-3,3,20-trimethyl-10,13-trans-prostadienoic acid |
| 1424 | 8α-methyl-9-oxo-11α,15-dihydroxy-3,3,20-trimethyl-8-iso-13-trans-prostenoic acid (Example 1362) | 8α-methyl-9-oxo-15-hydroxy-3,3,20-trimethyl-8-iso-10,13-trans-prostadienoic acid |
| 1425 | 8β-methyl-9-oxo-11α,15-dihydroxy-3,3,20-trimethyl-13-cis-prostenoic acid (Example 1362) | 8β-methyl-9-oxo-15-hydroxy-3,3,20-trimethyl-10,13-cis-prostadienoic acid |
| 1426 | 8α-methyl-9-oxo-11α,15-dihydroxy-3,3,20-trimethyl-8-iso-13-cis-prostenoic acid (Example 1362) | 8α-methyl-9-oxo-15-hydroxy-3,3,20-trimethyl-8-iso-10,13-cis-prostadienoic acid |
| 1427 | 8β-methyl-9-oxo-11α,15-dihydroxy-3-oxa-13-trans-prostenoic acid (Example 1363) | 8β-methyl-9-oxo-15-hydroxy-3,-oxa-10,13-trans-prostadienoic acid |
| 1428 | 8α-methyl-9-oxo-11α,15-dihydroxy-3-oxa-8-iso-13-trans-prostenoic acid (Example 1363) | 8α-methyl-9-oxo-15-hydroxy-3-oxa-8-iso-10,13,trans-prostadienoic acid |
| 1429 | 8β-methyl-9-oxo-11α,15-dihydroxy-3-oxa-13-cis-prostenoic acid (Example 1363) | 8β-methyl-9-oxo-15-hydroxy-3-oxa-10,13-cis-prostadienoic acid |
| 1430 | 8α-methyl-9-oxo-11α,15-dihydroxy-3-oxa-8-iso-13-cis-prostenoic acid (Example 1363) | 8α-methyl-9-oxo-15-hydroxy-3-oxa-8-iso-10,13-cis-prostadienoic acid |
| 1431 | 8β-methyl-9-oxo-11α,15-dihydroxy-3-oxa-16,16- | 8β-methyl-9-oxo-15-hydroxy-3-oxa-16,16-dimethyl-10,13-trans-pro- |

TABLE 41-continued

| Example | Starting 9-oxo-11-hydroxy derivative | Product 8-methyl-9-oxo-10,13-prostadienoic acids or esters |
|---|---|---|
| | dimethyl-13-trans-prostenoic acid (Example 1364) | stadienoic-acid |
| 1432 | 8α-methyl-9-oxo-11α,15-dihydroxy-3-oxa-16,16-dimethyl-8-iso-13-trans-prostenoic acid (Example 1364) | 8α-methyl-9-oxo-15-hydroxy-3-oxa-16,16-dimethyl-8-iso-10,13-trans-prostadienoic acid |
| 1433 | 8β-methyl-9-oxo-11α,15-dihydroxy-3-oxa-16,16-dimethyl-13-cis-prostenoic acid (Example 1364) | 8β-methyl-9-oxo-15-hydroxy-3-oxa-16,16-dimethyl-10,13-cis-prostadienoic acid |
| 1434 | 8α-methyl-9-oxo-11α,15-dihydroxy-3-oxa-16,16-dimethyl-8-iso-13-cis-prostenoic acid (Example 1364) | 8α-methyl-9-oxo-15-hydroxy-3-oxa-16,16-dimethyl-8-iso-10,13-cis-prostadienoic acid |
| 1435 | 8β-methyl-9-oxo-11α,15-dihydroxy-3-oxa-13-trans,17-cis-prostadienoic acid (Example 1365) | 8β-methyl-9-oxo-15-hydroxy-3-oxa-10,13-trans,17-cis-prostatrienoic acid |
| 1436 | 8α-methyl-9-oxo-11α,15-dihydroxy-3-oxa-8-iso-13-trans,17-cis-prostadienoic acid (Example 1365) | 8α-methyl-9-oxo-15-hydroxy-3-oxa-8-iso-10,13-trans,17-cis-prostatrienoic acid |
| 1437 | 8β-methyl-9-oxo-11α,15-dihydroxy-3-oxa-13-cis,17-cis-prostadienoic acid (Example 1365) | 8β-methyl-9-oxo-15-hydroxy-3-oxa-10,13-cis,17-cis-prostatrienoic acid |
| 1438 | 8α-methyl-9-oxo-11α,15-dihydroxy-3-oxa-8-iso-13-cis,17-cis-prostadienoic acid (Example 1365) | 8α-methyl-9-oxo-15-hydroxy-3-oxa-8-iso-10,13-cis,17-cis-prostatrienoic acid |
| 1439 | 8β-methyl-9-oxo-11α,15-dihydroxy-3-oxa-20-ethyl-13-trans-prostenoic acid (Example 1366) | 8β-methyl-9-oxo-15-hydroxy-3-oxa-20-ethyl-10,13-trans-prostadienoic acid |
| 1440 | 8α-methyl-9-oxo-11α,15-dihydroxy-3-oxa-20-ethyl-8-iso-13-trans-prostenoic acid (Example 1366) | 8α-methyl-9-oxo-15-hydroxy-3-oxa-20-ethyl-8-iso-10,13-trans-prostadienoic acid |
| 1441 | 8β-methyl-9-oxo-11α,15-dihydroxy-3-oxa-20-ethyl-13-cis-prostenoic acid (Example 1366) | 8β-methyl-9-oxo-15-hydroxy-3-oxa-20-ethyl-10,13-cis-prostadienoic acid |
| 1442 | 8α-methyl-9-oxo-11α,15-dihydroxy-3-oxa-20-ethyl-8-iso-13-cis-prostenoic acid (Example 1366) | 8β-methyl-9-oxo-15-hydroxy-3-oxa-20-ethyl-8-iso-10,13-cis-prostadienoic acid |
| 1443 | 8β-methyl-9-oxo-11α,15-dihydroxy-2-fluoro-17,17-dimethyl-13-trans-prostenoic acid (Example 1367) | 8β-methyl-9-oxo-15-hydroxy-2-fluoro-17,17-dimethyl-10,13-trans-prostadienoic acid |
| 1444 | 8α-methyl-9-oxo-11α,15-dihydroxy-2-fluoro-17,17-dimethyl-8-iso-13-trans-prostenoic acid (Example 1367) | 8α-methyl-9-oxo-15-hydroxy-2-fluoro-17,17-dimethyl-8-iso-10,13-trans-prostadienoic acid |
| 1445 | 8β-methyl-9-oxo-11α,15-dihydroxy-2-fluoro-17,17-dimethyl-13-cis-prostenoic acid (Example 1367) | 8β-methyl-9-oxo-15-hydroxy-2-fluoro-17,17-dimethyl-10,13-cis-prostadienoic acid |
| 1446 | 8α-methyl-9-oxo-11α,15-dihydroxy-2-fluoro-17,17-dimethyl-8-iso-13-cis-prostenoic acid (Example 1367) | 8α-methyl-9-oxo-15-hydroxy-2-fluoro-17,17-dimethyl-8-iso-10,13-cis-prostadienoic acid |
| 1447 | 8β-methyl-9-oxo-11α,15-dihydroxy-7-nor-13-trans-prostenoic acid (Example 1368) | 8β-methyl-9-oxo-15-hydroxy-7-nor-10,13-trans-prostadienoic acid |
| 1448 | 8α-methyl-9-oxo-11α,15-dihydroxy-7-nor-8-iso-13-trans-prostenoic acid (Example 1368) | 8α-methyl-9-oxo-15-hydroxy-7-nor-8-iso-10,13-trans-prostadienoic acid |
| 1449 | 8β-methyl-9-oxo-11α,15-dihydroxy-7-nor-13-cis-prostenoic acid (Example 1368) | 8β-methyl-9-oxo-15-hydroxy-7-nor-10,13-cis-prostadienoic acid |
| 1450 | 8α-methyl-9-oxo-11α,15-dihydroxy-7-nor-8-iso-13-cis-prostenoic acid (Example 1368) | 8α-methyl-9-oxo-15-hydroxy-7-nor-8-iso-10,13-cis-prostadienoic acid |
| 1451 | 8β-methyl-9-oxo-11α,15-dihydroxy-7a-homo-16,16-dimethyl-13-trans-prostenoic acid (Example 1369) | 8β-methyl-9-oxo-15-hydroxy-7a-homo-16,16-dimethyl-10,13-trans-prostadienoic acid |
| 1452 | 8α-methyl-9-oxo-11α,15-dihydroxy-7a-homo-16,16-dimethyl-8-iso-13-trans-prostenoic acid (Example 1369) | 8α-methyl-9-oxo-15-hydroxy-7a-homo-16,16-dimethyl-8-iso-10,13-trans-prostadienoic acid |
| 1453 | 8β-methyl-9-oxo-11α,15-dihydroxy-7a-homo-16,16-dimethyl-13-cis-prostenoic acid (Example 1369) | 8β-methyl-9-oxo-15-hydroxy-7a-homo-16,16-dimethyl-10,13-cis-prostadienoic acid |
| 1454 | 8α-methyl-9-oxo-11α,15-dihydroxy-7a-homo-16,16-dimethyl-8-iso-13-cis-prostenoic acid (Example 1369) | 8α-methyl-9-oxo-15-hydroxy-7a-homo-16,16-dimethyl-8-iso-10,13-cis-prostadienoic acid |
| 1455 | 8β-methyl-9-oxo-11α,15-dihydroxy-2-phenyl-13-trans-prostenoic acid (Example 1370) | 8β-methyl-9-oxo-15-hydroxy-2-phenyl-10,13-trans-prostadienoic acid |
| 1456 | 8α-methyl-9-oxo-11α,15-dihydroxy-2-phenyl-8-iso-13-trans-prostenoic acid (Example 1370) | 8α-methyl-9-oxo-15-hydroxy-2-phenyl-8-iso-10,13-trans-prostadienoic acid |
| 1457 | 8β-methyl-9-oxo-11α,15-dihydroxy-2-phenyl-13-cis-prostenoic acid (Example 1370) | 8β-methyl-9-oxo-15-hydroxy-2-phenyl-10,13-cis-prostadienoic acid |
| 1458 | 8α-methyl-9-oxo-11α,15-dihydroxy-2-phenyl-8-iso-13-cis-prostenoic acid (Example 1370) | 8α-methyl-9-oxo-15-hydroxy-2-phenyl-8-iso-10,13-cis-prostadienoic acid |

TABLE 41-continued

| Example | Starting 9-oxo-11-hydroxy derivative | Product 8-methyl-9-oxo-10,13-prostadienoic acids or esters |
|---|---|---|
| 1459 | 8β-methyl-9-oxo-11α,15-dihydroxy-2-methyl-13-trans,17-cis-prostadienoic acid (Example 1371) | 8β-methyl-9-oxo-15-hydroxy-2-methyl-10,13-trans,17-cis-prostatrienoic acid |
| 1460 | 8α-methyl-9-oxo-11α,15-dihydroxy-2-methyl-8-iso-13-trans,17-cis-prostadienoic acid (Example 1371) | 8α-methyl-9-oxo-15-hydroxy-2-methyl-8-iso-10,13-trans,17-cis-prostatrienoic acid |
| 1461 | 8β-methyl-9-oxo-11α,15-dihydroxy-2-methyl-13-cis,17-cis-prostadienoic acid (Example 1371) | 8β-methyl-9-oxo-15-hydroxy-2-methyl-10,13-cis,17-cis-prostatrienoic acid |
| 1462 | 8α-methyl-9-oxo-11α,15-dihydroxy-2-methyl-8-iso-13-cis,17-cis-prostadienoic acid (Example 1371) | 8α-methyl-9-oxo-15-hydroxy-2-methyl-8-iso-10,13-cis,17-cis-prostatrienoic acid |
| 1463 | 8β-methyl-9-oxo-11α,15-dihydroxy-5,cis,13-trans-prostadienoic acid (Example 1372) | 8β-methyl-9-oxo-15-hydroxy-5,cis,10,13-trans-prostatrienoic acid |
| 1464 | 8α-methyl-9-oxo-11α,15-dihydroxy-8-iso-5,cis,13-trans-prostadienoic acid (Example 1372) | 8α-methyl-9-oxo-15-hydroxy-8-iso-5,cis,10,13-trans-prostatrienoic acid |
| 1465 | 8β-methyl-9-oxo-11α,15-dihydroxy-5,cis,13-cis-prostadienoic acid (Example 1372) | 8β-methyl-9-oxo-15-hydroxy-5,cis,10,13-cis-prostatrienoic acid |
| 1466 | 8α-methyl-9-oxo-11α,15-dihydroxy-8-iso-5,cis,13-cis-prostadienoic acid (Example 1372) | 8α-methyl-9-oxo-15-hydroxy-8-iso-5,cis,10,13-cis-prostatrienoic acid |
| 1467 | 8β-methyl-9-oxo-11α,15-dihydroxy-5-cis,13-trans,17-cis-prostatrienoic acid (Example 1373) | 8β-methyl-9-oxo-15-hydroxy-5-cis,10,13-trans,17-cis-prostatetraenoic acid |
| 1468 | 8α-methyl-9-oxo-11α,15-dihydroxy-8-iso-5-cis,13-trans,17-cis-prostatrienoic acid (Example 1373) | 8α-methyl-9-oxo-15-hydroxy-8-iso-5-cis,10,13-trans,17-cis-prostatetraenoic acid |
| 1469 | 8β-methyl-9-oxo-11α,15-dihydroxy-5-cis,13-cis,17-cis-prostatrienoic acid (Example 1373) | 8β-methyl-9-oxo-15-hydroxy-5-cis,10,13-cis,17-cis-prostatetraenoic acid |
| 1470 | 8α-methyl-9-oxo-11α,15-dihydroxy-8-iso-5-cis,13-cis,17-cis-prostatrienoic acid (Example 1373) | 8α-methyl-9-oxo-15-hydroxy-8-iso-5-cis,10,13-cis,17-cis-prostatetraenoic acid |
| 1471 | 8β-methyl-9-oxo-11α,15-dihydroxy-16,16-dimethyl-13-trans-prostadienoic acid (Example 1374) | 8β-methyl-9-oxo-15-hydroxy-16,16-dimethyl-5-cis,10,13-trans-prostatrienoic acid |
| 1472 | 8α-methyl-9-oxo-11α,15-dihydroxy-16,16-dimethyl-8-iso-5-cis,13-trans-prostadienoic acid (Example 1374) | 8α-methyl-9-oxo-15-hydroxy-16,16-dimethyl-8-iso-5-cis,10,13-trans-prostatrienoic acid |
| 1473 | 8β-methyl-9-oxo-11α,15-dihydroxy-16,16-dimethyl-5-cis,13-cis-prostadienoic acid (Example 1374) | 8β-methyl-9-oxo-15-hydroxy-16,16-dimethyl-5-cis,10,13-cis-prostatrienoic acid |
| 1474 | 8α-methyl-9-oxo-11α,15-dihydroxy-16,16-dimethyl-8-iso-5-cis,13-cis-prostadienoic acid (Example 1374) | 8α-methyl-9-oxo-15-hydroxy-16,16-dimethyl-8-iso-5-cis,10,13-cis-prostatrienoic acid |
| 1475 | 8β-methyl-9-oxo-11α,15-dihydroxy-4-nor-20-methyl-5-cis,13-trans-prostadienoic acid (Example 1375) | 8β-methyl-9-oxo-15-hydroxy-4-nor-20-methyl-5-cis,10,13-trans-prostatrienoic acid |
| 1476 | 8α-methyl-9-oxo-11α,15-dihydroxy-4-nor-20-methyl-8-iso-5-cis,13-trans-prostadienoic acid (Example 1375) | 8α-methyl-9-oxo-15-hydroxy-4-nor-20-methyl-8-iso-5-cis,10,13-trans-prostatrienoic acid |
| 1477 | 8β-methyl-9-oxo-11α,15-dihydroxy-4-nor-20-methyl-5-cis,13-cis-prostadienoic acid (Example 1375) | 8β-methyl-9-oxo-15-hydroxy-4-nor-20-methyl-5-cis,10,13-cis-prostatrienoic acid |
| 1478 | 8α-methyl-9-oxo-11α,15-dihydroxy-4-nor-20-methyl-8-iso-5-cis,13-cis-prostadienoic acid (Example 1375) | 8α-methyl-9-oxo-15-hydroxy-4-nor-20-methyl-8-iso-5-cis,10,13-cis-prostatrienoic acid |
| 1479 | 8β-methyl-9-oxo-11α,15-dihydroxy-4a-homo-17,17-dimethyl-5-cis,13-trans-prostadienoic acid (Example 1376) | 8β-methyl-9-oxo-15-hydroxy-4a-homo-17,17-dimethyl-5-cis,10,13-trans-prostatrienoic acid |
| 1480 | 8α-methyl-9-oxo-11α,15-dihydroxy-4a-homo-17,17-dimethyl-8-iso-5-cis,13-trans-prostadienoic acid (Example 1376) | 8α-methyl-9-oxo-5-hydroxy-4a-homo-17,17-dimethyl-8-iso-5-cis,10,13-trans-prostatrienoic acid |
| 1481 | 8β-methyl-9-oxo-11α,15-dihydroxy-4a-homo-17,17-dimethyl-5-cis,13-cis-prostadienoic acid (Example 1376) | 8β-methyl-9-oxo-15-hydroxy-4a-homo-17,17-dimethyl-5-cis,10,13-cis-prostatrienoic acid |
| 1482 | 8α-methyl-9-oxo-11α,15-dihydroxy-4a-homo-17,17-dimethyl-8-iso-5-cis,13-cis-prostadienoic acid (Example 1376) | 8α-methyl-9-oxo-15-hydroxy-4a-homo-17,17-dimethyl-8-iso-5-cis,10,13-cis-prostatrienoic acid |
| 1483 | 8β-methyl-9-oxo-11α,15-dihydroxy-4a,4b-bishomo-20-ethyl-5-cis,13-trans-prostadienoic acid (Example 1377) | 8β-methyl-9-oxo-15-hydroxy-4a,4b-bishomo-20-ethyl-5-cis,10,13-trans-prostatrienoic acid |
| 1484 | 8α-methyl-9-oxo-11α,15-dihydroxy-4a,4b-bishomo-20-ethyl-8- | 8α-methyl-9-oxo-15-hydroxy-4a,4b-bishomo-20-ethyl-8-iso-5-cis,10,13-trans-prostatrie- |

TABLE 41-continued

| Example | Starting 9-oxo-11-hydroxy derivative | Product 8-methyl-9-oxo-10,13-prostadienoic acids or esters |
|---|---|---|
| | iso-5-cis,13-trans-prostadienoic acid (Example 1377) | noic acid |
| 1485 | 8β-methyl-9-oxo-11α,15-dihydroxy-4a,4b-bishomo-20-ethyl-5-cis,13-cis-prostadienoic acid (Example 1377) | 8β-methyl-9-oxo-15-hydroxy-4a,4b-bishomo-20-ethyl-5-cis,10,13-cis-prostatrienoic acid |
| 1486 | 8α-methyl-9-oxo-11α,15-dihydroxy-4a,4b-bishomo-20-ethyl-8-iso-5-cis,13-cis-prostadienoic acid (Example 1377) | 8α-methyl-9-oxo-15-hydroxy-4a,4b-bishomo-20-ethyl-8-iso-5-cis,10,13-cis-prostatrienoic acid |
| 1487 | 8β-methyl-9-oxo-11α,15-dihydroxy-4a,4b-bishomo-5-cis,13-trans,17-cis-prostatrienoic acid (Example 1378) | 8β-methyl-9-oxo-15-hydroxy-4a,4b-bishomo-5-cis,10,13-trans,17-cis-prostatetraenoic acid |
| 1488 | 8α-methyl-9-oxo-11α,15-dihydroxy-4a,4b-bishomo-8-iso-5-cis,13-trans,17-cis-prostatrienoic acid (Example 1378) | 8α-methyl-9-oxo-15-hydroxy-4a,4b-bishomo-8-iso-5-cis,10,13-trans,17-cis-prostatetraenoic acid |
| 1489 | 8β-methyl-9-oxo-11α,15-dihydroxy-4a,4b-bishomo-5-cis,13-cis-17-cis-prostatrienoic acid (Example 1378) | 8β-methyl-9-oxo-15-hydroxy-4a,4b-bishomo-5-cis,10,13-cis-17-cis-prostatetraenoic acid |
| 1490 | 8α-methyl-9-oxo-11α,15-dihydroxy-4a,4b-bishomo-8-iso-5-cis,13-cis-17-cis-prostatrienoic acid (Example 1378) | 8β-methyl-9-oxo-15-hydroxy-4a,4b-bishomo-8-iso-5-cis,10,13-cis-17-cis-prostatetraenoic acid |
| 1491 | methyl 8β-methyl-9-oxo-11α,15-dihydroxy-20-methyl-13-trans-prostenoate (Example 1379) | methyl 8β-methyl-9-oxo-15-hydroxy-20-methyl-10,13-trans-prostadienoate |
| 1492 | methyl 8α-methyl-9-oxo-11α,15-dihydroxy-20-methyl-8-iso-13-trans-prostenoate (Example 1379) | methyl 8α-methyl-9-oxo-15-hydroxy-20-methyl-8-iso-10,13-trans-prostadienoate |
| 1493 | methyl 8β-methyl-9-oxo-11α,15-dihydroxy-20-methyl-13-cis-prostenoate (Example 1379) | methyl 8β-methyl-9-oxo-15-hydroxy-20-methyl-10,13-cis-prostadienoate |
| 1494 | methyl 8α-methyl-9-oxo-11α,15-dihydroxy-20-methyl-8-iso-13-cis-prostenoate (Example 1379) | methyl 8α-methyl-9-oxo-15-hydroxy-20-methyl-8-iso-10,13-cis-prostadienoate |
| 1495 | ethyl 8β-methyl-9-oxo-11α,15-dihydroxy-7a,7b-bishomo-13-trans,17-cis-prostadienoate (Example 1380) | ethyl 8β-methyl-9-oxo-15-hydroxy-7a,7b-bishomo-10,13-trans,17-cis-prostatrienoate |
| 1496 | ethyl 8α-methyl-9-oxo-11α,15-dihydroxy-7a,7b-bishomo-8-iso-13-trans,17-cis-prostadienoate (Example 1380) | ethyl 8α-methyl-9-oxo-15-hydroxy-7a,7b-bishomo-8-iso-10,13-trans,17-cis-prostatrienoate |
| 1497 | ethyl 8β-methyl-9-oxo-11α,15-dihydroxy-7a,7b-bishomo-13-cis,17-cis-prostadienoate (Example 1380) | ethyl 8β-methyl-9-oxo-15-hydroxy-7a,7b-bishomo-10,13-cis,17-cis-prostatrienoate |
| 1498 | ethyl 8α-methyl-9-oxo-11α,15-dihydroxy-7a,7b-bishomo-8-iso-13-cis,17-cis-prostadienoate (Example 1380) | ethyl 8α-methyl-9-oxo-15-hydroxy-7a,7b-bishomo-8-iso-10,13-cis,17-cis-prostatrienoate |
| 1499 | ethyl 8β-methyl-9-oxo-11α,15-dihydroxy-2-ethyl-16,16-dimethyl-13-trans-prostenoate (Example 1381) | ethyl 8β-methyl-9-oxo-15-hydroxy-2-ethyl-16,16-dimethyl-10,13-trans-prostadienoate |
| 1500 | ethyl 8α-methyl-9-oxo-11α,15-dihydroxy-2-ethyl-16,16-dimethyl-8-iso-13-trans-prostenoate (Example 1381) | ethyl 8α-methyl-9-oxo-15-hydroxy-2-ethyl-16,16-dimethyl-8-iso-10,13-trans-prostadienoate |
| 1501 | ethyl 8β-methyl-9-oxo-11α,15-dihydroxy-2-ethyl-16,16-dimethyl-13-cis-prostenoate (Example 1381) | ethyl 8β-methyl-9-oxo-15-hydroxy-2-ethyl-16,16-dimethyl-10,13-cis-prostadienoate |
| 1502 | ethyl 8α-methyl-9-oxo-11α,15-dihydroxy-2-ethyl-16,16-dimethyl-8-iso-13-cis-prostenoate (Example 1381) | ethyl 8α-methyl-9-oxo-15-hydroxy-2-ethyl-16,16-dimethyl-8-iso-10,13-cis-prostadienoate |
| 1503 | ethyl 8β-methyl-9-oxo-11α,15-dihydroxy-3,3,17,17-tetramethyl-13-trans-prostenoate (Example 1382) | ethyl 8β-methyl-9-oxo-15-hydroxy-3,3,17,17-tetramethyl-10,13-trans-prostadienoate |
| 1504 | ethyl 8α-methyl-9-oxo-11α,15-dihydroxy-3,3,17,17-tetramethyl-8-iso-13-trans-prostenoate (Example 1382) | ethyl 8α-methyl-9-oxo-15-hydroxy-3,3,17,17-tetramethyl-8-iso-10,13-trans-prostadienoate |
| 1505 | ethyl 8β-methyl-9-oxo-11α,15-dihydroxy-3,3,17,17-tetramethyl-13-cis-prostenoate (Example 1382) | ethyl 8β-methyl-9-oxo-15-hydroxy-3,3,17,17-tetramethyl-10,13-cis-prostadienoate |
| 1506 | ethyl 8α-methyl-9-oxo-11α,15-dihydroxy-3,3,17,17-tetramethyl-8-iso-13-cis-prostenoate (Example 1382) | ethyl 8α-methyl-9-oxo-15-hydroxy-3,3,17,17-tetramethyl-8-iso-10,13-cis-prostadienoate |
| 1507 | ethyl 8β-methyl-9-oxo-11α,15-dihydroxy-3-oxa-17,17-dimethyl-13-trans-prostenoate (Example 1383) | ethyl 8β-methyl-9-oxo-15-hydroxy-3-oxa-17,17-dimethyl-10,13-trans-prostadienoate |
| 1508 | ethyl 8α-methyl-9-oxo-11α,15-dihydroxy-3-oxa-17,17-dimethyl-8-iso-13-trans-prostenoate (Example 1383) | ethyl 8α-methyl-9-oxo-15-hydroxy-3-oxa-17,17-dimethyl-8-iso-10,13-trans-prostadienoate |
| 1509 | ethyl 8α-methyl-9-oxo-11α,15-dihydroxy-3-oxa-17,17-dimethyl-13-cis-prostenoate (Example 1383) | ethyl 8β-methyl-9-oxo-15-hydroxy-3-oxa-17,17-dimethyl-10,13-cis-prostadienoate |

TABLE 41-continued

| Example | Starting 9-oxo-11-hydroxy derivative | Product 8-methyl-9-oxo-10,13-prostadienoic acids or esters |
|---|---|---|
| 1510 | ethyl 8α-methyl-9-oxo-11α,15-dihydroxy-3-oxa-17,17-dimethyl-8-iso-13-cis-prostenoate (Example 1383) | ethyl 8α-methyl-9-oxo-15-hydroxy-3-oxa-17,17-dimethyl-8-iso-10,13-cis-prostadienoate |
| 1511 | butyl 8β-methyl-9-oxo-11α,15-dihydroxy-13-trans-prostenoate (Example 1384) | butyl 8β-methyl-9-oxo-15-hydroxy-10,13-trans-prostadienoate |
| 1512 | buty 8α-methyl-9-oxo-11α,15-dihydroxy-8-iso-13-trans-prostenoate (Example 1384) | butyl 8α-methyl-9-oxo-15-hydroxy-8-iso-10,13-trans-prostadienoate |
| 1513 | butyl 8β-methyl-9-oxo-11α,15-dihydroxy-13-cis-prostenoate (Example 1384) | butyl 8β-methyl-9-oxo-15-hydroxy-13-cis-prostadienoate |
| 1514 | butyl 8α-methyl-9-oxo-11α,15-dihydroxy-8-iso-13-cis-prostenoate (Example 1384) | butyl 8α-methyl-9-oxo-15-hydroxy-8-iso-10,13-cis-prostadienoate |
| 1515 | decyl 8β-methyl-9-oxo-11α,15-dihydroxy-13-trans-17-cis-prostadienoate (Example 1385) | decyl 8β-methyl-9-oxo-15-hydroxy-10,13-trans-17-cis-prostatrienoate |
| 1516 | decyl 8α-methyl-9-oxo-11α,15-dihydroxy-8-iso-13-trans,17-cis-prostadienoate (Example 1385) | decyl 8α-methyl-9-oxo-15-hydroxy-8-iso-10,13-trans,17-cis-prostatrienoate |
| 1517 | decyl 8β-methyl-9-oxo-11α,15-dihydroxy-13-cis-17-cis-prostadienoate (Example 1385) | decyl 8β-methyl-9-oxo-15-hydroxy-10,13-cis-17-cis-prostatrienoate |
| 1518 | decyl 8α-methyl-9-oxo-11α,15-dihydroxy-8-iso-13-cis-17-cis-prostadienoate (Example 1385) | decyl 8α-methyl-9-oxo-15-hydroxy-8-iso-10,13-cis-17-cis-prostatrienoate |
| 1519 | ethyl 8β-methyl-9-oxo-11α-acetoxy-15-hydroxy-13-trans-prostanoate (Example 1386) | ethyl 8β-methyl-9-oxo-15-hydroxy-10,13-trans-prostadienoate |
| 1520 | ethyl 8α-methyl-9-oxo-11α-acetoxy-15-hydroxy-8-iso-13-trans-prostenoate (Example 1386) | ethyl 8α-methyl-9-oxo-15-hydroxy-8-iso-10,13-trans-prostadienoate |
| 1521 | ethyl 8β-methyl-9-oxo-11α-acetoxy-15-hydroxy-13-cis-prostenoate (Example 1386) | ethyl 8β-methyl-9-oxo-15-hydroxy-10,13-cis-prostadienoate |
| 1522 | ethyl 8α-methyl-9-oxo-11α-acetoxy-15-hydroxy-8-iso-13-cis-prostenoate (Example 1386) | ethyl 8α-methyl-9-oxo-15-hydroxy-8-iso-10,13-cis-prostadienoate |

EXAMPLES 1523-1654

Treatment of the designated 9-oxo-prostenoic acid and ester derivatives listed in Table 42 below with sodium borohydride in ethanol as described in Example 257 gives the product 9α and 9β hydroxy derivatives of the table, which are separable by standard chromatographic techniques.

TABLE 42

| Example | Starting 8-methyl-9-oxo-11α,15-dihydroxy-13-prostenoic acid or ester | Product 8-methyl-9α/β,-11α,15-trihydroxy-13-prostenoic acid or ester |
|---|---|---|
| 1523 | 8β-methyl-prostaglandin $E_1$ (Example 1353) | 8β-methyl-prostaglandin $F_1\alpha/F_1\beta$ |
| 1524 | 8α-methyl-8-iso-prostaglandin $E_1$ (Examle 1353) | 8α-methyl-8-iso-prostaglandin $F_1\alpha/F_1\beta$ |
| 1525 | 8β-methyl-9-oxo-11α-15-dihydroxy-13-cis-prostenoic acid (Example 1353) | 8β-methyl-9α/β,11α,-15-trihydroxy-13-cis-prostenoic acid |
| 1526 | 8α-methyl-9-oxo-11α,15-dihydroxy-8-iso-13-cis-prostenoic acid (Example 1353) | 8α-methyl-9α/β, 11α, 15-trihydroxy-8-iso-13-cis-prostenoic acid |
| 1527 | 8β-methyl-9-oxo-11α,15-dihydroxy-16,16-dimethyl-13-trans-prostenoic acid (Example 1354) | 8β-methyl-9α/β,11α,-15-trihydroxy-16,16-dimethyl-13-trans-prostenoic acid |
| 1528 | 8α-methyl-9-oxo-11α,15-dihydroxy-16,16-dimethyl-8-iso-13-trans-prostenoic acid (Example 1354) | 8α-methyl-9α/β,11α,-15-trihydroxy-16,16-dimethyl-8-13-trans-prostenoic acid |
| 1529 | 8β-methyl-9-oxo-11α,15-dihydroxy-16,16-dimethyl-13-,cis-prostenoic acid (Example 1354) | 8β-methyl-9α/β,11α-15-trihydroxy-16,16-dimethyl-13-cis-prostenoic acid |
| 1530 | 8α,methyl-9-oxo-11α,15-dihydroxy-16,16-dimethyl-8-iso-13-cis-prostenoic acid (Example 1354) | 8α-methyl-9α/β,11α, 15-trihydroxy-16,16-dimethyl-8-iso-13-cis-prostenoic acid |
| 1531 | 8β-methyl-9-oxo-11α-15-dihydroxy-17,17-dimethyl-13-trans-prostenoic acid (Example 1355) | 8β-methyl-9α/β,11α,-15-trihydroxy-17,17-dimetyl-13-trans-prostenoic acid |
| 1532 | 8α-methyl-9-oxo-11α,15-dihydroxy-8-iso-17,17-dimethyl-13-trans-prostenoic acid (Example 1355) | 8α-methyl-9α/β,11α,-15-trihydroxy-17,17-dimethyl-8-iso-13-trans-prostenoic acid |
| 1533 | 8β-methyl-9-oxo-11α,15-dihydroxy-17,17-dimethyl-13-cis-prostenoic acid (Example 1355) | 8β-methyl-9α/β,11α,-15-trihydroxy-17,17-dimethyl-13-cis-prostenoic acid |
| 1534 | 8α-methyl-9-oxo-11α,15-dihydroxy-17,17-dimethyl-8-iso-13-cis-prostenoic acid (Example 1355) | 8α-methyl-9α/β,11α,-15-trihydroxy-8-iso-17,17-dimethyl-13-cis-prostenoic acid |
| 1535 | 8β-methyl-9-oxo-11α-15-dihydroxy-13-trans-17-cis-prostadienoic acid (Example 1356) | 8β-methyl-9α/β,11α-15-trihydroxy-13-trans,17-cis-prostadienoic acid |
| 1536 | 8α-methyl-9-oxo-11α-15-dihydroxy-8-iso-13-trans,17-cis-prostadienoic acid (Example 1356) | 8α-methyl-9α/β,11α,-15-trihydroxy-8-iso-13-trans-17-cis-prostadienoic acid |
| 1537 | 8β-methyl-9-oxo-11α-15-dihydroxy-13-cis,17-cis-prostadienoic acid (Example 1356) | 8β-methyl-9α/β,11α,-15-trihydroxy-13-cis,17-cis-prostadienoic acid |
| 1538 | 8α-methyl-9-oxo-11α-15-dihydroxy-8-iso-13-trans-17-cis-prostadienoic acid (Example 1356) | 8α-methyl-9α/β,11α,-15-trihydroxy-8-iso-13-cis,17-cis-prostadienoic acid |
| 1539 | 8β-methyl-9-oxo-11α-15-dihydroxy-20-ethyl-13-trans-prostenoic acid (Example 1357) | 8β-methyl-9α/β,11α,-15-trihydroxy-20-ethyl-13-trans-prostenoic acid |
| 1540 | 8α-methyl-9-oxo-11α-15-dihydroxy-20-ethyl-8-iso-13-trans- | 8α-methyl-9α/β,11α,-15-trihydroxy-20-ethyl-8-iso-13- |

TABLE 42-continued

| Example | Starting 8-methyl-9-oxo-11α,15-dihydroxy-13-prostenoic acid or ester | Product 8-methyl-9α/β,-11α,15-trihydroxy-13-prostenoic acid or ester |
|---|---|---|
| | prostenoic acid (Example 1357) | trans-prostenoic acid |
| 1541 | 8β-methyl-9-oxo-11α-15-dihydroxy-20-ethyl-13-cis-prostenoic acid (Example 1357) | 8β-methyl-9α/β,11α,-15-trihydroxy-20-ethyl-13-cis-prostenoic acid |
| 1542 | 8α-methyl-9-oxo-11α-15-dihydroxy-20-ethyl-8-iso-13-cis-prostenoic acid (Example 1357) | 8α-methyl-9α/β,11α,-15-trihydroxy-20-ethyl-8-iso-13-cis-prostenoic acid |
| 1543 | 8β-methyl-9-oxo-11α,-15-dihydroxy-6,7-dinor-13-trans-prostenoic acid (Example 1358) | 8β-methyl-9α/β,11α,-15-trihydroxy-6,7-dinor-13-trans-prostenoic acid |
| 1544 | 8α-methyl-9-oxo-11α,-15-dihydroxy-6,7-dinor-8-iso-13-trans-prostenoic acid (Example 1358) | 8α-methyl-9α/β,11α,-15-trihydroxy-6,7-dinor-8-iso-13-trans-prostenoic acid |
| 1545 | 8β-methyl-9-oxo-11α,-15-dihydroxy-6,7-dinor-13-cis-prostenoic acid (Example 1358) | 8β-methyl-9α/β,11α,-15-trihydroxy-6,7-dinor-13-cis-prostenoic acid |
| 1546 | 8α-methyl-9-oxo-11α,-15-dihydroxy-6,7-dinor-8-iso-13-cis-prostenoic acid (Example 1358) | 8α-methyl-9α/β,11α,-15-trihydroxy-6,7-dinor-8-iso-13-cis-prostenoic acid |
| 1547 | 8β-methyl-9-oxo-11α,-15-dihydroxy-5,6,7-trinor-20-methyl-13-trans-prostenoic acid (Example 1359) | 8β-methyl-9α/β,11α,-15-trihydroxy-5,6,7-trinor-20-methyl-13-trans-prostenoic acid |
| 1548 | 8α-methyl-9-oxo-11α,-15-dihydroxy-5,6,7-trinor-20-methyl-8-iso-13-trans-prostenoic acid (Example 1359) | 8α-methyl-9α/β,11α,-15-trihydroxy-5,6,7-trinor-20-methyl-8-iso-13-trans-prostenoic acid |
| 1549 | 8β-methyl-9-oxo-11α-15-dihydroxy-5,6,7,-trinor-20-methyl-13-cis-prostenoic acid (Example 1359) | 8β-methyl-9α/β,11α,-15-trihydroxy-5,6,7-trinor-20-methyl-13-cis-prostenoic acid |
| 1550 | 8α-methyl-9-oxo-11α,-15-dihydroxy-5,6,7-trinor-20-methyl-8-iso-13-cis-prostenoic acid (Example 1359) | 8α-methyl-9α/β,11α,-15-trihydroxy-5,6,7-trinor-20-methyl-8-iso-13-cis-prostenoic acid |
| 1551 | 8β-methyl-9-oxo-11α,-15-dihydroxy-7a,7b-bishomo-13-trans-prostenoic acid (Example 1360) | 8β-methyl-9α/β,11α,-15-trihydroxy-7a,7b-bishomo-13-trans-prostenoic acid |
| 1552 | 8α-methyl-9-oxo-11α,-15-dihydroxy-7a,7b-bishomo-8-iso-13-trans-prostenoic acid (Example 1360) | 8α-methyl-9α/β,11α,-15-trihydroxy-7a,7b-bishomo-8-iso-13-trans prostenoic acid |
| 1553 | 8β-methyl-9-oxo-11α,-15-dihydroxy-7a,7b-bishomo-13-cis-prostenoic acid (Example 1360) | 8β-methyl-9α/β,11α,15-trihydroxy-7a,-7b-bishomo-13-cis-prostenoic acid |
| 1554 | 8α-methyl-9-oxo-11α,-15-dihydroxy-7a,7b-bishomo-8-iso-13-cis-prostenoic acid (Example 1360) | 8α-methyl-9α/β,11α,-15-trihydroxy-7a,7b-bishomo-8-iso-13-cis-prostenoic acid |
| 1555 | 8β-methyl-9-oxo-11α,-15-dihydroxy-2-ethyl-13-trans-prostenoic acid (Example 1361) | 8β-methyl-9α/β,11α,-15-trihydroxy-2-ethyl-13-trans-prostenoic acid |
| 1556 | 8α-methyl-9-oxo-11α,-15-dihydroxy-2-ethyl-8-iso-13-trans-prostenoic acid (Example 1361) | 8α-methyl-9α/β,11α,-15-trihydroxy-2-ethyl-8-iso-13-trans-prostenoic acid |
| 1557 | 8β-methyl-9-oxo-11α,-15-dihydroxy-2-ethyl-13-cis-prostenoic acid (Example 1361) | 8β-methyl-9α/β,11α,-15-trihydroxy-2-ethyl-13-cis-prostenoic acid |
| 1558 | 8α-methyl-9-oxo-11α,-15-dihydroxy-2-ethyl-8-iso-13-cis-prostenoic acid (Example 1361) | 8α-methyl-9α/β,11α-15,trihydroxy-2-ethyl-8-iso-13-cis-prostenoic acid |
| 1559 | 8β-methyl-9-oxo-11α,-15-dihydroxy-3,3,20-trimethyl-8-iso-13-trans-prostenoic acid (Example 1362) | 8β-methyl-9α/β,11α,-15-trihydroxy-3,3,20-trimethyl-13-trans-prostenoic acid |
| 1560 | 8α-methyl-9-oxo-11α,-15-dihydroxy-3,3,20-trimethyl-8-iso-13-trans-prostenoic acid (Example 1362) | 8β-methyl-9α/β,11α,-15-trihydroxy-3,3,20-trimethyl-8-iso-13-trans-prostenoic acid |
| 1561 | 8β-methyl-9-oxo-11α,-15-dihydroxy-3,3,20-trimethyl-13-cis-prostenoic acid (Example 1362) | 8β-methyl-9α/β,11α,-15-trihydroxy-3,3,20-trimethyl-13-cis-prostenoic acid |
| 1562 | 8α-methyl-9-oxo-11α,-15-dihydroxy-3,3,20-trimethyl-8-iso-13-cis-prostenoic acid (Example 1362) | 8α-methyl-9α/β,11α,-15-trihydroxy-3,3,20-trimethyl-8-iso-13-cis-prostenoic acid |
| 1563 | 8β-methyl-9-oxo-11α,-15-dihydroxy-3-oxa-13-trans-prostenoic acid (Example 1363) | 8β-methyl-9α/β,11α,-15-trihydroxy-3-oxa-13-trans-prostenoic acid |
| 1564 | 8α-methyl-9-oxo-11α,-15-dihydroxy-3-oxa-8-iso-13-trans-prostenoic acid (Example 1363) | 8α-methyl-9α/β,11α,-15-trihydroxy-3-oxa-8-iso-13-trans-prostenoic acid |
| 1565 | 8β-methyl-9-oxo-11α,-15-dihydroxy-3-oxa-8 8-iso-13-cis-prostenoic acid (Example 1363) | 8β-methyl-9α/β,11α,-15-trihydroxy-3-oxa-8-iso-13-cis-prostenoic acid |
| 1566 | 8α-methyl-9-oxo-11α,-15-dihydroxy-3-oxa-8-iso-13-cis-prostenoic acid (Example 1363) | 8α-methyl-9α/β,11α,-15-trihydroxy-3-oxa-8-iso-13-cis-prostenoic acid |
| 1567 | 8β-methyl-9-oxo-11α,-15-dihydroxy-3-oxa-16,16-dimethyl-13-trans-prostenoic acid (Example 1364) | 8β-methyl-9α/β-11α,-15-trihydroxy-3-oxa-16,16-dimethyl-13-trans-prostenoic acid |
| 1568 | 8α-methyl-9-oxo-11α,-15-dihydroxy-3-oxa-16,16-dimethyl-8-iso-13-trans-prostenoic acid (Example 1364) | 8α-methyl-9α/β-11α,-5-trihydroxy-3-oxa-16,16-dimethyl-8-iso-13-trans-prostenoic acid |
| 1569 | 8α-methyl-9-oxo-11α,-15-dihydroxy-3-oxa-16,16-dimethyl-13-cis-prostenoic acid (Example 1364) | 8β-methyl-9α/β-11α,-15-trihydroxy-3-oxa-16,16-dimethyl-13-cis-prostenoic acid |
| 1570 | 8α-methyl-9-oxo-11α,-15-dihydroxy-3-oxa-16,16-dimethyl-8-iso-13-cis-prostenoic acid (Example 1364) | 8α-methyl-9α/β-11α,-15-trihydroxy-3-oxa-16,16-dimethyl-8-iso-13-cis-prostenoic acid |
| 1571 | 8β-methyl-9-oxo-11α,-15-dihydroxy-3-oxa-13-trans,17-cis-prostadienoic acid (Example 1365) | 8β-methyl-9α/β,11α,-15-trihydroxy-3-oxa-13-trans,17-cis-prostadienoic acid |
| 1572 | 8α-methyl-9-oxo-11α,-15-dihydroxy-3-oxa-8-iso-13-trans,17-cis-prostadienoic acid (Example 1365) | 8α-methyl-9α/β,11α,-15-trihydroxy-3-oxa-8-iso-13-trans,17-cis-prostadienoic acid |
| 1573 | 8β-methyl-9-oxo-11α,-15-dihydroxy-3-oxa-13-cis,17-cis-prostadienoic acid (Example 1365) | 8β-methyl-9α/β,11α,-15-trihydroxy-3-oxa-13-cis,17-cis-prostadienoic acid |
| 1574 | 8α-methyl-9-oxo-11α,- | 8α-methyl-9α/β,11α,- |

TABLE 42-continued

| Example | Starting 8-methyl-9-oxo-11α,15-dihydroxy-13-prostenoic acid or ester | Product 8-methyl-9α/β,-11α,15-trihydroxy-13-prostenoic acid or ester |
|---|---|---|
| | 15-dihydroxy-3-oxa-8-iso-13-cis,17-cis-prostadienoic acid (Example 1365) | 15-trihydroxy-3-oxa-8-iso-13-cis,17-cis-prostadienoic acid |
| 1575 | 8β-methyl-9-oxo-11α,15-dihydroxy-3-oxa-20-ethyl-13-trans-prostenoic acid (Example 1366) | 8β-methyl-9α/β,11α,-15-trihydroxy-3-oxa-20-ethyl-13-trans-prostenoic acid |
| 1576 | 8α-methyl-9-oxo-11α,15-dihydroxy-3-oxa-20-ethyl-8-iso-13-trans-prostenoic acid (Example 1366) | 8α-methyl-9α/β,11α,-15-trihydroxy-3-oxa-20-ethyl-8-iso-13-trans-prostenoic acid |
| 1577 | 8β-methyl-9-oxo-11α,15-dihydroxy-3-oxa-20-ethyl-13-cis-prostenoic acid (Example 1366) | 8β-methyl-9α/β,11α,-15-trihydroxy-3-oxa-20-ethyl-13-cis-prostenoic acid |
| 1578 | 8α-methyl-9-oxo-11α,-15-dihydroxy-3-oxa-20-ethyl-8-iso-13-cis-prostenoic acid (Example 1366) | 8α-methyl-9α/β,11α,-15-trihydroxy-3-oxa-20-ethyl-8-iso-13-cis-prostenoic acid |
| 1579 | 8β-methyl-9-oxo-11α,-15-dihydroxy-2-fluoro-17,17-dimethyl-13-trans-prostenoic acid (Example 1367) | 8β-methyl-9α/β,11α,-15-trihydroxy-2-fluoro-17,17-dimethyl-13-trans-prostenoic acid |
| 1580 | 8α-methyl-9-oxo-11α,-15-dihydroxy-2-fluoro-17,17-dimethyl-8-iso-13-trans-prostenoic acid (Example 1367) | 8α-methyl-9α/β,11α,-15-trihydroxy-2-fluoro-17,17-dimethyl-8-iso-13-trans-prostenoic acid |
| 1581 | 8β-methyl-9-oxo-11α,-15-dihydroxy-2-fluoro-17,17-dimethyl-13-cis-prostenoic acid (Example 1367) | 8β-methyl 9α/β,11α,-15-trihydroxy-2-fluoro-17,17-dimethyl-13-cis-prostenoic acid |
| 1582 | 8α-methyl-9-oxo-11α,-15-dihydroxy-2-fluoro-17,17-dimethyl-8-iso-13-cis-prostenoic acid (Example 1367) | 8α-methyl-9α/β,11α,-15-trihydroxy-2-fluoro-17,17-dimethyl-8-iso-13-cis-prostenoic acid |
| 1583 | 8β-methyl-9-oxo-11α,-15-dihydroxy-7-nor-13-trans-prostenoic acid (Example 1368) | 8β-methyl-9α/β,11α,-15-trihydroxy-7-nor-13-trans-prostenoic acid |
| 1584 | 8α-methyl-9-oxo-11α,-15-dihydroxy-7-nor-8-iso-13-trans-prostenoic acid (Example 1368) | 8α-methyl-9α/β,11α,-15-trihydroxy-7-nor-8-iso-13-trans-prostenoic acid |
| 1585 | 8β-methyl-9-oxo-11α,-15-dihydroxy-7-nor-13-cis-prostenoic acid (Example 1368) | 8β-methyl-9α/β,11α,-15-trihydroxy-7-nor-13-cis-prostenoic acid |
| 1586 | 8α-methyl-9-oxo-11α,-15-dihydroxy-7-nor-8-iso-13-cis-prostenoic acid (Example 1368) | 8α-methyl-9α/β,11α,-15-trihydroxy-7-nor-8-iso-13-cis-prostenoic acid |
| 1587 | 8β-methyl-9-oxo-11α,-15-dihydroxy-7a-homo-16,16-dimethyl-13-trans-prostenoic acid (Example 1369) | 8β-methyl-9α/β,11α,-15-trihydroxy-7a-homo-16,16-dimethyl-13-trans-prostenoic acid |
| 1588 | 8α-methyl-9-oxo-11α,-15-dihydroxy-7a-homo-16,16-dimethyl-8-iso-13-trans-prostenoic acid (Example 1369) | 8α-methyl-9α/β,11α,-15-trihydroxy-7a-homo-16,16-dimethyl-8-iso-13-trans-prostenoic acid |
| 1589 | 8β-methyl-9-oxo-11α,-15-dihydroxy-7a-homo-16,16-dimethyl-13-cis-prostenoic acid (Example 1369) | 8β-methyl-9α/β,11α,-15-trihydroxy-7a-homo-16,16-dimethyl-13-cis-prostenoic acid |
| 1590 | 8α-methyl-9-oxo-11α,- | 8α-methyl-9α/β,11α,- |
| | 15-dihydroxy-7a-homo-16,16-dimethyl-8-iso-13-cis-prostenoic acid (Example 1369) | 15-trihydroxy-7a-homo-16,16-dimethyl-8-iso-13-cis-prostenoic acid |
| 1591 | 8β-methyl-9-oxo-11α,-15-dihydroxy-2-phenyl-13-trans-prostenoic acid (Example 1370) | 8β-methyl-9α/β,11α,-15-trihydroxy-2-phenyl-13-trans-prostenoic acid |
| 1592 | 8α-methyl-9-oxo-11α,-15-dihydroxy-2-phenyl-8-iso-13-trans-prostenoic acid (Example 1370) | 8α-methyl-9α/β,11α,-15-trihydroxy-2-phenyl-8-iso-13-trans-prostenoic acid |
| 1593 | 8β-methyl-9-oxo-11α,-15-dihydroxy-2-phenyl-13-cis-prostenoic acid (Example 1370) | 8β-methyl-9α/β,11α,-15-trihydroxy-2-phenyl-13-cis-prostenoic acid |
| 1594 | 8α-methyl-9-oxo-11α,-15-dihydroxy-2-phenyl-8-iso-13-cis-prostenoic acid (Example 1370) | 8α-methyl-9α/β,11α,-15-trihydroxy-2-phenyl-8-iso-13-cis-prostenoic acid |
| 1595 | 8β-methyl-9-oxo-11α,-15-dihydroxy-2-methyl-13-trans-17-cis-prostadienoic acid (Example 1371) | 8β-methyl-9α/β,11α,-15-trihydroxy-2-methyl-13-trans,17-cis-prostadienoic acid |
| 1596 | 8α-methyl-9-oxo-11α,-15-dihydroxy-2-methyl-8-iso-13-trans,17-cis-prostadienoic acid (Example 1371) | 8α-methyl-9α/β,11α-15-trihydroxy-2-methyl-8-iso-13-cis-acid |
| 1597 | 8β-methyl-9-oxo-11α,-15-dihydroxy-2-methyl-13-cis,17-cis-prostadienoic acid (Example 1371) | 8β-methyl-9α/β,11α,-15-trihydroxy-2-methyl-13-cis,17-cis-prostadienoic acid |
| 1598 | 8α-methyl-9-oxo-11α,-15-dihydroxy-2-methyl-8-iso-13-cis,17-cis-prostadienoic acid (Example 1371) | 8α-methyl-9α/β,11α,-15-trihydroxy-2-methyl-8-iso-13-cis,17-cis-prostadienoic acid |
| 1599 | 8β-methyl-9-oxo-11α,-15-dihydroxy-5,cis,-13-trans-prostadienoic acid (Example 1372) | 8β-methyl-9α/β,11α,-15-trihydroxy-5 cis-13-trans-prostadienoic acid |
| 1600 | 8α-methyl-9-oxo-11α,-15-dihydroxy-8-iso-5-cis-13-trans-prostadienoic acid (Example 1372) | 8α-methyl-9α/β,11α,-15-trihydroxy-8-iso-5 cis,13-trans-prostadienoic acid |
| 1601 | 8β-methyl-9-oxo-11α,-15-dihydroxy-5,cis,13-cis-prostadienoic acid (Example 1372) | 8β-methyl-9α/β,11α,-15-trihydroxy-5 cis-13-cis-prostadienoic acid |
| 1602 | 8α-methyl-9-oxo-11α,-15-dihydroxy-8-iso-5-cis-13-cis-prostadienoic acid (Example 1372) | 8α-methyl-9α/β,11α,-15-trihydroxy-8-iso-5 cis 13-cis-prostadienoic acid |
| 1603 | 8β-methyl-9-oxo-11α,-15-dihydroxy-5-cis,-13-trans,17-cis-prostatrienoic acid (Example 1373) | 8β-methyl-9α/β,11α,-15-trihydroxy-5-cis,-13-trans,17-cis- |
| 1604 | 8α-methyl-9-oxo-11α,-15-dihydroxy-8-iso-5-cis,13-trans,17-cis-prostatrienoic acid (Example 1373) | 8α-methyl-9α/β,11α,-15-dihydroxy-8-iso-5-cis,13-trans,17-cis-prostatrienoic acid |
| 1605 | 8β-methyl-9-oxo-11α,-15-dihydroxy-5-cis,-13-cis,17-cis-prostatrienoic acid (Example 1373) | 8β-methyl-9α/β,11α,-15-trihydroxy-5-cis,-13-cis,17-cis-prostatrienoic acid |
| 1606 | 8α-methyl-9-oxo-11α,-15-dihydroxy-8-iso-5-cis,13-cis,17-cis-prostatrienoic acid (Example 1373) | 8α-methyl-9α/β,11α,-15-trihydroxy-8-iso-5-cis,13-cis,17-cis-prostatrienoic acid |

TABLE 42-continued

| Example | Starting 8-methyl-9-oxo-11α,15-dihydroxy-13-prostenoic acid or ester | Product 8-methyl-9α/β,11α,15-trihydroxy-13-prostenoic acid or ester |
|---|---|---|
| 1607 | 8β-methyl-9-oxo-11α,15-dihydroxy-16,16-dimethyl-5-cis,13-trans-prostadienoic (Example 1374) | 8β-methyl-9α/β,11α,15-trihydroxy-16,16-dimethyl-5-cis,13-trans-prostadienoic acid |
| 1608 | 8α-methyl-9-oxo-11α,15-dihydroxy-16,16-dimethyl-8-iso-5-cis,13-trans-prostadienoic acid (Example 1374) | 8α-methyl-9α/β,11α,15-trihydroxy-16,16-dimethyl-8-iso-5-cis,13-trans-prostadienoic acid |
| 1609 | 8β-methyl-9-oxo-11α,15-dihydroxy-16,16-dimethyl-5-cis,13-cis-prostadienoic acid (Example 1374) | 8β-methyl-9α/β,11α,15-trihydroxy-16,16-dimethyl-5-cis,13-cis-prostadienoic acid |
| 1610 | 8α-methyl-9-oxo-11α,15-dihydroxy-16,16-dimethyl-8-iso-5-cis,13-cis-prostadienoic acid (Example 1374) | 8α-methyl-9α/β,11α,15-trihydroxy-16,16-dimethyl-8-iso-5-cis,13-cis-prostadienoic acid |
| 1611 | 8β-methyl-9-oxo-11α,15-dihydroxy-4-nor-20-methyl-5-cis,13-trans-prostadienoic acid (Example 1375) | 8β-methyl-9α/β,11α,15-trihydroxy-4-nor-20-methyl-5-cis,13-trans-prostadienoic acid |
| 1612 | 8α-methyl-9-oxo-11α,15-dihydroxy-4-nor-20-methyl-8-iso-5-cis,13-trans-prostadienoic acid (Example 1375) | 8α-methyl-9α/β,11α,15-trihydroxy-4-nor-20-methyl-8-iso-5-cis,13-trans-prostadienoic acid |
| 1613 | 8β-methyl-9-oxo-11α,15-dihydroxy-4-nor-20-methyl-5-cis,13-cis-prostadienoic acid (Example 1375) | 8β-methyl-9α/β,11α,15-trihydroxy-4-nor-20-methyl-5-cis,13-cis-prostadienoic acid |
| 1614 | 8α-methyl-9-oxo-11α,15-dihydroxy-4-nor-20-methyl-8-iso-5-cis,13-cis-prostadienoic acid (Example 1375) | 8α-methyl-9α/β,11α,15-trihydroxy-4-nor-20-methyl-8-iso-5-cis,13-cis-prostadienoic acid |
| 1615 | 8β-methyl-9-oxo-11α,15-dihydroxy-4a-homo-17,17-dimethyl-5-cis,13-trans-prostadienoic acid (Example 1376) | 8β-methyl-9α/β,11α,15-trihydroxy-4a-homo-17,17-dimethyl-5-cis,13-trans-prostadienoic acid |
| 1616 | 8α-methyl-9-oxo-11α,15-dihydroxy-4a-homo-17,17-dimethyl-8-iso-5-cis,13-trans-prostadienoic acid (Example 1376) | 8α-methyl-9α/β,11α,15-trihydroxy-4a-homo-17,17-dimethyl-8-iso-5-cis,13-cis-prostadienoic acid |
| 1617 | 8β-methyl-9-oxo-11α,15-dihydroxy-4a-homo-17,17-dimethyl-5-cis,13-cis-prostadienoic acid (Example 1376) | 8β-methyl-9α/β,11α,15-trihydroxy-4a-homo-17,17-dimethyl-5-cis,13-cis-prostadienoic acid |
| 1618 | 8α-methyl-9-oxo-11α,15-dihydroxy-4a-homo-17,17-dimethyl-8-iso-5-cis,13-cis-prostadienoic acid (Example 1376) | 8α-methyl-9α/β,11α,15-trihydroxy-4a-homo-17,17-dimethyl-8-iso-5-cis,13-cis-prostadienoic acid |
| 1619 | 8β-methyl-9-oxo-11α,15-dihydroxy-4a,4b-bishomo-20-ethyl-5-cis,13-trans-prostadienoic acid (Example 1377) | 8β-methyl-9α/β,11α,15-trihydroxy-4a,4b-bishomo-20-ethyl-5-cis,13-trans-prostadienoic acid |
| 1620 | 8α-methyl-9-oxo-11α,15-dihydroxy-4a,4b-bishomo-20-ethyl-8-iso-5-cis,13-trans-prostadienoic acid (Example 1377) | 8α-methyl-9α/β,11α,15-trihydroxy-4a,4b-bishomo-20-ethyl-8-iso-5-cis,13-trans-prostadienoic acid |
| 1621 | 8β-methyl-9-oxo-11α,15-dihydroxy-4a,4b-bishomo-20-ethyl-5-cis,13-cis-prostadienoic acid (Example 1377) | 8β-methyl-9α/β,11α,15-trihydroxy-4a,4b-bishomo-20-ethyl-5-cis,13-cis-prostadienoic acid |
| 1622 | 8α-methyl-9-oxo-11α,15-dihydroxy-4a,4b-bishomo-20-ethyl-8-iso-5-cis,13-cis-prostadienoic acid (Example 1377) | 8α-methyl-9α/β,11α,15-trihydroxy-4a,4b-bishomo-20-ethyl-8-iso-5-cis,13-cis-prostadienoic |
| 1623 | 8β-methyl-9-oxo-11α,15-dihydroxy-4a,4b-bis-homo-5-cis,13-trans,17-cis-prostatrienoic acid (Example 1378) | 8β-methyl-9α/β,11α,15-trihydroxy-4a,4b-bishomo-5-cis,13-trans,17-cis-prostatrienoic acid |
| 1624 | 8α-methyl-9-oxo-11α,15-dihydroxy-4a,4b-bis-homo-8-iso-5-cis,13-trans,17-cis-prostatrienoic acid (Example 1378) | 8α-methyl-9α/β,11α,15-trihydroxy-4a,4b-bis-homo-8-iso-5-cis,13-trans-17-cis-prostatrienoic acid |
| 1625 | 8β-methyl-9-oxo-11α,15-dihydroxy-4a,4b-bis-homo-5-cis,13-cis,17-cis-prostatrienoic acid (Example 1378) | 8β-methyl-9α/β,11α,15-trihydroxy-4a,4b-bishomo-5-cis,13-cis-17-cis-prostatrienoic acid |
| 1626 | 8α-methyl-9-oxo-11α,15-dihydroxy-4a,4b-bis-homo-8-iso-5-cis,13-cis,17-cis-prostatrienoic acid (Example 1378) | 8α-methyl-9α/β,11α,15-trihydroxy-4a,4b-bis-homo-8-iso-5-cis,13-cis,17-cis-prostatrienoic acid |
| 1627 | methyl 8β-methyl-9-oxo-11α,15-dihydroxy-20-methyl-13-trans-prostenoate (Example 1379) | methyl 8β-methyl-9α/β,11α,15-trihydroxy-20-methyl-13-trans-prostenoate |
| 1628 | methyl 8α-methyl-9-oxo-11α,15-dihydroxy-20-methyl-8-iso-13-trans-prostenoate (Example 1379) | methyl 8α-methyl-9α/β,11α,15-trihydroxy-20-methyl-8-iso-13-trans-prostenoate |
| 1629 | methyl 8β-methyl-9-oxo-11β,15-dihydroxy-20-methyl-13-cis-prostenoate (Example 1379) | methyl 8β-methyl-9α/β,11α,15-trihydroxy-20-methyl-13-cis-prostenoate |
| 1630 | methyl 8α-methyl-9-oxo-11α,15-dihydroxy-20-methyl-8-iso-13-cis-prostenoate (Example 1379) | methyl 8α-methyl-9α/β,11α,15-trihydroxy-20-methyl-8-iso-13-cis-prostenoate |
| 1631 | ethyl 8β-methyl-9-oxo-11α,15-dihydroxy-7a,7b-bis-homo-13-trans,17-cis-prostadienoate (Example 1380) | ethyl 8β-methyl-9α/β,11α,15-trihydroxy-7a,7b-bis-homo-13-trans,17-cis-prostadienoate |
| 1632 | ethyl 8α-methyl-9-oxo-11α,15-dihydroxy-7a,7b-bis-homo-8-iso-13-trans,17-cis-prostadienoate (Example 1380) | ethyl 8α-methyl-9α/β,11α,15-trihydroxy-7a,7b-bis-homo-8-iso-13-trans,17-cis-prostadienoate |
| 1633 | ethyl 8β-methyl-9-oxo-11α,15-dihydroxy-7a,7b-bis-homo-13-cis-17-cis-prostadienoate (Example 1380) | ethyl 8β-methyl-9α/β,11α,15-trihydroxy-7a,7b-bis-homo-13-cis,17-cis-prostadienoate |
| 1634 | ethyl 8α-methyl-9-oxo-11α,15-dihydroxy-7a,7b-bis-homo-8-iso-13-cis,17-cis-prostadienoate (Example 1380) | ethyl 8α-methyl-9α/β,11α,15-trihydroxy-7a,7b-bis-homo-8-iso-13-cis,17-cis-prostadienoate |
| 1635 | ethyl 8β-methyl-9-oxo-11α,15-dihydroxy-2-ethyl-16,16-dimethyl-13-trans-prostenoate (Example 1381) | ethyl 8β-methyl-9α/β,11α,15-trihydroxy-2-ethyl-16,16-dimethyl-13-trans-prostenoate |
| 1636 | ethyl 8α-methyl-9-oxo-11α,15-dihydroxy-2-ethyl-16,16-dimethyl-8-iso-13-trans-prostenoate (Example 1381) | ethyl 8α-methyl-9α/β,11α,15-trihydroxy-2-ethyl-16,16-dimethyl-8-iso-13-trans-prostenoate |
| 1637 | ethyl 8β-methyl-9-oxo-11α,15-dihydroxy- | ethyl 8β-methyl-9α/β,11α,15-tri- |

TABLE 42-continued

| Example | Starting 8-methyl-9-oxo-11α,15-di-hydroxy-13-prosten-oic acid or ester | Product 8-methyl-9α/β,-11α,15-trihydroxy-13-prostenoic acid or ester |
|---|---|---|
| | 2-ethyl-16,16-dimethyl-13-cis-prostenoate (Example 1381) | hydroxy-2-ethyl-16,16-dimethyl-13-cis-prostenoate |
| 1638 | ethyl 8α-methyl-9-oxo-11α,15-dihydroxy-2-ethyl-16,16-dimethyl-8-iso-13-cis-prostenoate (Example 1381) | ethyl 8α-methyl-9α/β,11α,15-trihydroxy-2-ethyl-16,16-dimethyl-8-iso-13-cis-prostenoate |
| 1639 | ethyl 8β-methyl-9-oxo-11α,15-dihydroxy-3,3,17,17-tetramethyl-13-trans-prostenoate (Example 1382) | ethyl 8β-methyl-9α/β,11α,15-trihydroxy-3,3,17,17-tetramethyl-13-trans-prostenoate |
| 1640 | ethyl 8α-methyl-9-oxo-11α,15-dihydroxy-3,3,17,17-tetramethyl-8-iso-13-trans-prostenoate (Example 1382) | ethyl 8α-methyl-9α/β,11α,15-trihydroxy-3,3,17,17-tetramethyl-8-iso-13-trans-prostenoate |
| 1641 | ethyl 8β-methyl-9-oxo-11α,15-dihydroxy-3,3,17,17-tetramethyl-13-cis-prostenoate (Example 1382) | ethyl 8β-methyl-9α/β,11α,15-trihydroxy-3,3,17,17-tetramethyl-13-cis-prostenoate |
| 1642 | ethyl 8α-methyl-9-oxo-11α,15-dihydroxy-3,3,17,17-tetramethyl-8-iso-13-cis-prostenoate (Example 1382) | ethyl 8α-methyl-9α/β,11α,15-trihydroxy-3,3,17,17-tetramethyl-8-iso-13-cis-prostenoate |
| 1643 | ethyl 8β-methyl-9-oxo-11α,15-dihydroxy-3-oxa-17,17-dimethyl-13-trans-prostenoate (Example 1383) | ethyl 8β-methyl-9α/β,11α,15-trihydroxy-3-oxa-17,17-dimethyl-13-trans-prostenoate |
| 1644 | ethyl 8α-methyl-9-oxo-11α,15-dihydroxy-3-oxa-17,17-dimethyl-8-iso-13-trans-prostenoate (Example 1383) | ethyl 8α-methyl-9α/β,11α,15-trihydroxy-3-oxa-17,17-dimethyl-8-iso-13-trans-prostenoate |
| 1645 | ethyl 8β-methyl-9-oxo-11α,15-dihydroxy-3-oxa-17,17-dimethyl-13-cis-prostenoate (Example 1383) | ethyl 8β-methyl-9α/β,11α,15-trihydroxy-3-oxa-17,17-dimethyl-13-cis-prostenoate |
| 1646 | ethyl 8α-methyl-9-oxo-11α,15-dihydroxy-3-oxa-17,17-dimethyl-8-iso-13-cis-prostenoate (Example 1383) | ethyl 8α-methyl-9α/β,11α,15-trihydroxy-3-oxa-17,17-dimethyl-8-iso-13-cis-prostenoate |
| 1647 | butyl 8β-methyl-9-oxo-11α,15-dihydroxy-13-trans-prostenoate (Example 1384) | butyl 8β-methyl-9α/β,11α,15-trihydroxy-13-trans-prostenoate |
| 1648 | butyl 8α-methyl-9-oxo-11α,15-dihydroxy-8-iso-13-trans-prostenoate (Example 1384) | butyl 8α-methyl-9α/β,11α,15-trihydroxy-8-iso-13-trans-prostenoate |
| 1649 | butyl 8β-methyl-9-oxo-11α,15-dihydroxy-13-cis-prostenoate (Example 1384) | butyl 8β-methyl-9α/β,11α,15-trihydroxy-13-cis-prostenoate |
| 1650 | butyl 8α-methyl-9-oxo-11α,15-dihydroxy-8-iso-13-cis-prostenoate (Example 1384) | butyl 8α-methyl-9α/β,11α,15-trihydroxy-8-iso-13-cis-prostenoate |
| 1651 | decyl 8β-methyl-9-oxo-11α,15-dihydroxy-13-trans,17-cis-prostadienoate (Example 1385) | decyl 8β-methyl-9α/β,11α,15-trihydroxy-13-trans,17-cis-prostadienoate |
| 1652 | decyl 8α-methyl-9-oxo-11α,15-dihydroxy-8-iso-13-trans,17-cis-prostadienoate (Example 1385) | decyl 8α-methyl-9α/β,11α,15-trihydroxy-8-iso-13-trans,17-cis-prostadienoate |
| 1653 | decyl 8β-methyl-9-oxo-11α,15-dihydroxy-13-cis,17-cis-prostadienoate (Example 1385) | decyl 8β-methyl-9α/β,11α,15-trihydroxy-13-cis,17-cis-prostadienoate |
| 1654 | decyl 8α-methyl-9-oxo-11α,15-dihydroxy-8-iso-13-cis,17-cis-prostadienoate (Example 1385) | decyl 8α-methyl-9α/β,11α,15-trihydroxy-8-iso-13-cis,17-cis-prostadienoate |

EXAMPLES 1655–1781

Saponification of the alkyl esters designated in Table 43 below by the procedure described in Example 495 is productive of the carboxylic acids of the table. The epimeric 9α and 9β hydroxy products are separable by the usual chromatographic procedures.

TABLE 43

| Example | Starting alkyl prostenoate | Product prostenoic acid |
|---|---|---|
| 1655 | 11-deoxy-8β-methyl-prostaglandin E₁ methyl ester (Example 1188) | 11-deoxy-8β-methyl-prostaglandin E₁ |
| 1656 | 11-deoxy-8α-methyl-8-iso-prostaglandin E₁ methyl ester (Example 1188) | 11-deoxy-8α-methyl-8-iso-prostaglandin E₁ |
| 1657 | methyl 15-hydroxy-8β-methyl 9-oxo-13-cis-prostenoate (Example 1188) | 15-hydroxy-8β-methyl-9-oxo-13-cis-prostenoic acid |
| 1658 | methyl-15-hydroxy-8α-methyl-8-iso-9-oxo-13-cis-prostenoate (Example 1188) | 15-hydroxy-8β-methyl-8-iso-9-oxo-13-cis-prostenoic acid |
| 1659 | 11-deoxy-8β-methyl-prostaglandin F₁α/β methyl esters (Ex. 1206) | 11-deoxy-8β-methyl-prostaglandin F₁α/β |
| 1660 | 11-deoxy-8α-methyl-8-iso-prostaglandin F₁α/β methyl esters (Example 1207) | 11-deoxy-8α-methyl-8-iso-prostaglandin F₁α/β |
| 1661 | methyl 9α,15-dihydroxy-8β-methyl-13-cis-prostenoate (Example 1208) | 9α,15-dihydroxy-8β-methyl-13-cis-prostenoic acid |
| 1662 | ethyl 8β-methyl-9-oxo-15-hydroxy-16,16-dimethyl-13-trans-prostenoate (Example 1190) | 8β-methyl-9-oxo-15-hydroxy-16,16-dimethyl-13-trans-prostenoic acid |
| 1663 | ethyl 8α-methyl-9-oxo-15-hydroxy-16,16-dimethyl-8-iso-13-trans-prostenoate (Example 1190) | 8α-methyl-9-oxo-15-hydroxy-16,16-dimethyl-8-iso-13-trans-prostenoic acid |
| 1664 | ethyl 8β-methyl-9-oxo-15-hydroxy-16,16-dimethyl-13-cis-prostenoate (Example 1190) | 8β-methyl-9-oxo-15-hydroxy-16,16-dimethyl-13-cis-prostenoic acid |
| 1665 | ethyl 8α-methyl-9-oxo-15-hydroxy-16,16-dimethyl-8-iso-13-cis-prostenoate (Example 1190) | 8α-methyl-9-oxo-15-hydroxy-16,16-dimethyl-8-iso-13-cis-prostenoic acid |
| 1666 | ethyl 8β-methyl-9-oxo-15-hydroxy-17,17-dimethyl-13-trans-prostenoate (Example 1191) | 8β-methyl-9-oxo-15-hydroxy-17,17-dimethyl-13-trans-prostenoic acid |
| 1667 | ethyl 8α-methyl-9-oxo-15-hy- | 8α-methyl-9-oxo-15-hydroxy-17,17-dimethyl- |

TABLE 43-continued

| | | |
|---|---|---|
| | droxy-17,17-dimethyl-8-iso-13-trans-prostenoate (Example 1191) | 8-iso-13-trans-prostenoic acid |
| 1668 | ethyl 8β-methyl-9-oxo-15-hydroxy-17,17-dimethyl-13-cis-prostenoate (Example 1191) | 8β-methyl-9-oxo-15-hydroxy-17,17-dimethyl-13-cis-prostenoic acid |
| 1669 | ethyl 8α-methyl-9-oxo-15-hydroxy-17,17-dimethyl-8-iso-13-cis-prostenoate (Example 1191) | 8α-methyl-9-oxo-15-hydroxy-17,17-dimethyl-8-iso-13-cis-prostenoic acid |
| 1670 | ethyl 8β-methyl-9-oxo-15-hydroxy-13-trans,17-cis-prostadienoate (Example 1192) | 8β-methyl-9-oxo-15-hydroxy-13-trans,17-cis-prostadienoic acid |
| 1671 | ethyl 8α-methyl-9-oxo-15-hydroxy-8-iso-13-trans,17-cis-prostadienoate (Example 1192) | 8α-methyl-9-oxo-15-hydroxy-8-iso-13-trans,17-cis-prostadienoic acid |
| 1672 | ethyl 8β-methyl-9-oxo-15-hydroxy-13-cis,17-cis-prostadienoate (Example 1192) | 8β-methyl-9-oxo-15-hydroxy-13-cis,17-cis-prostadienoic acid |
| 1673 | ethyl 8α-methyl-9-oxo-15-hydroxy-8-iso-13-cis,17-cis-prostadienoate (Example 1192) | 8α-methyl-9-oxo-15-hydroxy-8-iso-13-cis,17-cis-prostadienoic acid |
| 1674 | ethyl 8β-methyl-9-oxo-15-hydroxy-20-ethyl-13-trans-prostenoate (Example 1193) | 8β-methyl-9-oxo-15-hydroxy-20-ethyl-13-trans-prostenoic acid |
| 1675 | ethyl 8α-methyl-9-oxo-15-hydroxy-20-ethyl-8-iso-13-trans-prostenoate (Example 1193) | 8α-methyl-9-oxo-15-hydroxy-20-ethyl-8-iso-13-trans-prostenoic acid |
| 1676 | ethyl 8β-methyl-9-oxo-15-hydroxy-20-ethyl-13-cis-prostenoate (Example 1193) | 8β-methyl-9-oxo-15-hydroxy-20-ethyl-13-cis-prostenoic acid |
| 1677 | ethyl 8α-methyl-9-oxo-15-hydroxy-20-ethyl-8-iso-13-cis-prostenoate (Example 1193) | 8α-methyl-9-oxo-15-hydroxy-20-ethyl-8-iso-13-cis-prostenoic acid |
| 1678 | ethyl 8β-methyl-9-oxo-15-hydroxy-7a,7b-bishomo-13-trans-prostenoate (Example 1195) | 8β-methyl-9-oxo-15-hydroxy-7a,7b-bishomo-13-trans-prostenoic acid |
| 1679 | ethyl 8α-methyl-9-oxo-15-hydroxy-7a,7b-bishomo-8-iso-13-trans-prostenoate (Example 1195) | 8α-methyl-9-oxo-15-hydroxy-7a,7b-bishomo-8-iso-13-trans-prostenoic acid |
| 1680 | ethyl 8β-methyl-9-oxo-15-hydroxy-7a,7b-bishomo-13-cis-prostenoate (Example 1195) | 8β-methyl-9-oxo-15-hydroxy-7a,7b-bishomo-13-cis-prostenoic acid |
| 1681 | ethyl 8α-methyl-9-oxo-15-hydroxy-7a,7b-bishomo-8-iso-13-cis-prostenoate (Example 1195) | 8α-methyl-9-oxo-15-hydroxy-7a,7b-bishomo-8-iso-13-cis-prostenoic acid |
| 1682 | ethyl 8β-methyl-9-oxo-15-hydroxy-2,20-bisethyl-13-trans-prostenoate (Example 1196) | 8β-methyl-9-oxo-15-hydroxy-2,20-bisethyl-13-trans-prostenoic acid |
| 1683 | ethyl 8α-methyl-9-oxo-15-hydroxy-2,20-bisethyl-8-iso-13-trans-prostenoate (Example 1196) | 8α-methyl-9-oxo-15-hydroxy-2,20-bisethyl-8-iso-13-trans-prostenoic acid |
| 1684 | ethyl 8β-methyl-9-oxo-15-hydroxy-2,20-bisethyl-13-cis-prostenoate (Example 1196) | 8β-methyl-9-oxo-15-hydroxy-2,20-bisethyl-13-cis-prostenoic acid |
| 1685 | ethyl 8α-methyl-9-oxo-15-hydroxy-2,20-bisethyl-8-iso-13-cis-prostenoate (Example 1196) | 8α-methyl-9-oxo-15-hydroxy-2,20-bisethyl-8-iso-13-cis-prostenoic acid |
| 1686 | ethyl 8β-methyl-9-oxo-15-hydroxy-3-oxa-16,16-dimethyl-13-trans-prostenoate (Example 1197) | 8β-methyl-9-oxo-15-hydroxy-3-oxa-16,16-dimethyl-13-trans-prostenoic acid |
| 1687 | ethyl 8α-methyl-9-oxo-15-hydroxy-3-oxa-16,16-dimethyl-8-iso-13-trans-prostenoate (Example 1197) | 8α-methyl-9-oxo-15-hydroxy-3-oxa-16,16-dimethyl-8-iso-13-trans-prostenoic acid |
| 1688 | ethyl 8β-methyl-9-oxo-15-hydroxy-3-oxa-16,16-dimethyl-13-cis-prostenoate (Example 1197) | 8β-methyl-9-oxo-15-hydroxy-3-oxa-16,16-dimethyl-13-cis-prostenoic acid |
| 1689 | ethyl 8α-methyl-9-oxo-15-hydroxy-3-oxa-16,16-dimethyl-8-iso-13-cis-prostenoate (Example 1197) | 8α-methyl-9-oxo-15-hydroxy-3-oxa-16,16-dimethyl-8-iso-13-cis-prostenoic acid |
| 1690 | ethyl 8β-methyl-9-oxo-15-hydroxy-3-oxa-13-trans,17-cis-prostadienoate (Example 1198) | 8β-methyl-9-oxo-15-hydroxy-3-oxa-13-trans,17-cis-prostadienoic acid |
| 1691 | ethyl 8α-methyl-9-oxo-15-hydroxy-3-oxa-8-iso-13-trans,17-cis-prostadienoate (Example 1198) | 8α-methyl-9-oxo-15-hydroxy-3-oxa-8-iso-13-trans,17-cis-prostadienoic acid |
| 1692 | ethyl 8β-methyl-9-oxo-15-hydroxy-3-oxa-13-cis,17-cis-prostadienoate (Example 1198) | 8β-methyl-9-oxo-15-hydroxy-3-oxa-13-cis,17-cis-prostadienoic acid |
| 1693 | ethyl 8α-methyl-9-oxo-15-hydroxy-3-oxa-8-iso-13-cis,17-cis-prostadienoate (Example 1198) | 8α-methyl-9-oxo-15-hydroxy-3-oxa-8-iso-13-cis,17-cis-prostadienoic acid |
| 1694 | ethyl 8β-methyl-9-oxo-15-hydroxy-7-nor-20-methyl-13-trans-prostenoate (Example 1199) | 8β-methyl-9-oxo-15-hydroxy-7-nor-20-methyl-13-trans-prostenoic acid |
| 1695 | ethyl 8β-methyl-9-oxo-15-hydroxy-7-nor-20-methyl-8-iso-13-trans-prostenoate (Example 1199) | 8β-methyl-9-oxo-15-hydroxy-7-nor-20-methyl-8-iso-13-trans-prostenoic acid |
| 1696 | ethyl 8β-methyl-9-oxo-15-hydroxy-7-nor-20-methyl-13-cis-prostenoate (Example 1199) | 8β-methyl-9-oxo-15-hydroxy-7-nor-20-methyl-13-cis-prostenoic acid |
| 1697 | ethyl 8α-methyl- | 8α-methyl-9-oxo-15-hy- |

TABLE 43-continued

| | | |
|---|---|---|
| | 9-oxo-15-hydroxy-7-nor-20-methyl-8-iso-13-cis-prostenoate (Example 1199) | droxy-7-nor-20-methyl-8-iso-13-cis-prostenoic acid |
| 1698 | ethyl 8β-methyl-9-oxo-15-hydroxy-2-fluoro-17,17-dimethyl-13-trans-prostenoate (Example 1200) | 8β-methyl-9-oxo-15-hydroxy-2-fluoro-17,17-dimethyl-13-trans-prostenoic acid |
| 1699 | ethyl 8α-methyl-9-oxo-15-hydroxy-2-fluoro-17,17-dimethyl-8-iso-13-trans-prostenoate (Example 1200) | 8α-methyl-9-oxo-15-hydroxy-2-fluoro-17,17-dimethyl-8-iso-13-trans-prostenoic acid |
| 1700 | ethyl 8β-methyl-9-oxo-15-hydroxy-2-fluoro-17,17-dimethyl-13-cis-prostenoate (Example 1200) | 8β-methyl-9-oxo-15-hydroxy-2-fluoro-17,17-dimethyl-13-cis-prostenoic acid |
| 1701 | ethyl 8α-methyl-9-oxo-15-hydroxy-2-fluoro-17,17-dimethyl-8-iso-13-cis-prostenoate (Example 1200) | 8α-methyl-9-oxo-15-hydroxy-2-fluoro-17,17-dimethyl-8-iso-13-cis-prostenoic acid |
| 1702 | ethyl 8β-methyl-9-oxo-15-hydroxy-10a-homo-13-trans-prostenoate (Example 1201) | 8β-methyl-9-oxo-15-hydroxy-10a-homo-13-trans-prostenoic acid |
| 1703 | ethyl 8α-methyl-9-oxo-15-hydroxy-10a-homo-8-iso-13-trans-prostenoate (Example 1201) | 8α-methyl-9-oxo-15-hydroxy-10a-homo-8-iso-13-trans-prostenoic acid |
| 1704 | ethyl 8β-methyl-9-oxo-15-hydroxy-10a-homo-13-cis-prostenoate (Example 1201) | 8β-methyl-9-oxo-15-hydroxy-10a-homo-13-cis-prostenoic acid |
| 1705 | ethyl 8α-methyl-9-oxo-15-hydroxy-10a-homo-8-iso-13-cis-prostenoate (Example 1201) | 8α-methyl-9-oxo-15-hydroxy-10a-homo-8-iso-13-cis-prostenoic acid |
| 1706 | ethyl 8β-methyl-9-oxo-15-hydroxy-2-phenyl-20-methyl-13-trans-prostenoate (Example 1202) | 8β-methyl-9-oxo-15-hydroxy-2-phenyl-20-methyl-13-trans-prostenoic acid |
| 1707 | ethyl 8α-methyl-9-oxo-15-hydroxy-2-phenyl-20-methyl-8-iso-13-trans-prostenoate (Example 1202) | 8α-methyl-9-oxo-15-hydroxy-2-phenyl-20-methyl-8-iso-13-trans-prostenoic acid |
| 1708 | ethyl 8β-methyl-9-oxo-15-hydroxy-2-phenyl-20-methyl-13-cis-prostenoate (Example 1202) | 8β-methyl-9-oxo-15-hydroxy-2-phenyl-20-methyl-13-cis-prostenoic acid |
| 1709 | ethyl 8α-methyl-9-oxo-15-hydroxy-2-phenyl-20-methyl-8-iso-13-cis-prostenoate (Example 1202) | 8α-methyl-9-oxo-15-hydroxy-2-phenyl-20-methyl-8-iso-13-cis-prostenoic acid |
| 1710 | methyl 8β-methyl-9-oxo-15-hydroxy-5-cis,13-trans,17-cis-prostatrienoate (Example 1203) | 8β-methyl-9-oxo-15-hydroxy-5-cis,13-trans,17-cis-prostatrienoic acid |
| 1711 | methyl 8α-methyl-9-oxo-15-hydroxy-8-iso-5-cis,13-trans,17-cis-prostatrienoate (Example 1203) | 8α-methyl-9-oxo-15-hydroxy-8-iso-5-cis,13-trans,17-cis-prostatrienoic acid |
| 1712 | methyl 8β-methyl-9-oxo-15-hydroxy-5-cis,13-cis,17-cis-prostatrienoate (Example 1203) | 8β-methyl-9-oxo-15-hydroxy-5-cis,13-cis,17-cis-prostatrienoic acid |
| 1713 | methyl 8α-methyl-9-oxo-15-hydroxy-8-iso-5-cis,13-cis,17-cis-prostatrienoate (Example 1203) | 8α-methyl-9-oxo-15-hydroxy-8-iso-5-cis,13-cis,17-prostatrienoic acid |
| 1714 | ethyl 8β-methyl-9-oxo-15-hydroxy-5-cis,13-trans-prostadienoate (Example 1204) | 8β-methyl-9-oxo-15-hydroxy-5-cis,13-trans-prostadienoic acid |
| 1715 | ethyl 8α-methyl-9-oxo-15-hydroxy-8-iso-5-cis,13-trans-prostadienoate (Example 1204) | 8α-methyl-9-oxo-15-hydroxy-8-iso-5-cis,13-trans-prostadienoic acid |
| 1716 | ethyl 8β-methyl-9-oxo-15-hydroxy-5-cis,13-cis-prostadienoate (Example 1204) | 8β-methyl-9-oxo-15-hydroxy-5-cis,13-cis-prostadienoic acid |
| 1717 | ethyl 8α-methyl-9-oxo-15-hydroxy-8-iso-5-cis,13-cis-prostadienoate (Example 1204) | 8α-methyl-9-oxo-15-hydroxy-8-iso-5-cis,13-cis-prostadienoic acid |
| 1718 | ethyl 8β-methyl-9-oxo-15-hydroxy-20-ethyl-5-cis,13-trans-prostadienoate (Example 1205) | 8β-methyl-9-oxo-15-hydroxy-20-ethyl-5-cis,13-trans-prostadienoic acid |
| 1719 | ethyl 8α-methyl-9-oxo-15-hydroxy-20-ethyl-8-iso-5-cis,13-trans-prostadienoate (Example 1205) | 8α-methyl-9-oxo-15-hydroxy-20-ethyl-8-iso-5-cis,13-trans-prostadienoic acid |
| 1720 | ethyl 8β-methyl-9-oxo-15-hydroxy-20-ethyl-5-cis-13-cis-prostadienoate (Example 1205) | 8β-methyl-9-oxo-15-hydroxy-20-ethyl-5-cis,13-cis-prostadienoic acid |
| 1721 | ethyl 8α-methyl-9-oxo-15-hydroxy-20-ethyl-8-iso-5-cis,13-cis-prostadienoate (Example 1205) | 8α-methyl-9-oxo-15-hydroxy-20-ethyl-8-iso-5-cis,13-cis-prostadienoic acid |

| Example | Starting alkyl ester of Example | Product prostenoic acid |
|---|---|---|
| 1722 | 1210 | 8β-methyl-9α/β,15-dihydroxy-16,16-dimethyl-13-trans-prostenoic acid |
| 1723 | 1211 | 8α-methyl-9α/β,15-dihydroxy-16,16-dimethyl-8-iso-13-trans-prostenoic acid |
| 1724 | 1212 | 8β-methyl-9α/β,15-dihydroxy-16,16-dimethyl-13-cis-prostenoic acid |
| 1725 | 1213 | 8α-methyl-9α/β,15-dihydroxy-16,16-dimethyl-8-iso-13-cis-prostenoic acid |
| 1726 | 1214 | 8β-methyl-9α/β,15-dihydroxy-17,17-dimethyl-13-trans-prostenoic acid |
| 1727 | 1215 | 8α-methyl-9α/β,15-dihydroxy-17,17-dimethyl-8-iso-13-trans-prostenoic acid |

TABLE 43-continued

| | | |
|---|---|---|
| 1728 | 1216 | 8β-methyl-9α/β,15-dihydroxy-17,17-dimethyl-13-cis-prostenoic acid |
| 1729 | 1217 | 8α-methyl-9α/β,15-dihydroxy-17,17-dimethyl-8-iso-13-cis-prostenoic acid |
| 1730 | 1218 | 8β-methyl-9α/β,15-dihydroxy-13-trans,17-cis-prostadienoic acid |
| 1731 | 1219 | 8α-methyl-9α/β,15-dihydroxy-8-iso-13-trans,17-cis-prostadienoic acid |
| 1732 | 1220 | 8β-methyl-9α/β,15-dihydroxy-13-cis,17-cis-prostadienoic acid |
| 1733 | 1221 | 8α-methyl-9α/β,15-dihydroxy-8-iso-13-cis,17-cis-prostadienoic acid |
| 1734 | 1222 | 8β-methyl-9α/β,15-dihydroxy-20-ethyl-13-trans-prostenoic acid |
| 1735 | 1223 | 8α-methyl-9α/β,15-dihydroxy-20-ethyl-8-iso-13-trans-prostenoic acid |
| 1736 | 1224 | 8β-methyl-9α/β,15-dihydroxy-20-ethyl-13-cis-prostenoic acid |
| 1737 | 1225 | 8α-methyl-9α/β,15-dihydroxy-20-ethyl-8-iso-13-cis-prostenoic acid |
| 1738 | 1230 | 8β-methyl-9α/β,15-dihydroxy-7a,7b-bishomo-13-trans-prostenoic acid |
| 1739 | 1231 | 8α-methyl-9α/β,15-dihydroxy-7a,7b-bishomo-8-iso-13-trans-prostenoic acid |
| 1740 | 1232 | 8β-methyl-9α/β,15-dihydroxy-7a,7b-bishomo-13-cis-prostenoic acid |
| 1741 | 1231 | 8α-methyl-9α/β,15-dihydroxy-7a,7b-bishomo-8-iso-13-cis-prostenoic acid |
| 1742 | 1234 | 8β-methyl-9α/β,15-dihydroxy-2,20-bisethyl-13-trans-prostenoic acid |
| 1743 | 1235 | 8α-methyl-9α/β,15-dihydroxy-2,20-bisethyl-8-iso-13-trans-prostenoic acid |
| 1744 | 1236 | 8β-methyl-9α/β,15-dihydroxy-2,20-bisethyl-13-cis-prostenoic acid |
| 1745 | 1237 | 8α-methyl-9α/β,15-dihydroxy-2,20-bisethyl-8-iso-13-cis-prostenoic acid |
| 1746 | 1238 | 8β-methyl-9α/β,15-dihydroxy-3-oxa-16,16-dimethyl-13-trans-prostenoic acid |
| 1747 | 1239 | 8α-methyl-9α/β,15-dihydroxy-3-oxa-16,16-dimethyl-8-iso-13-trans-prostenoic acid |
| 1748 | 1240 | 8β-methyl-9α/β,15-dihydroxy-3-oxa-16,16-dimethyl-13-cis-prostenoic acid |
| 1749 | 1241 | 8α-methyl-9α/β,15-dihydroxy-3-oxa-16,16-dimethyl-8-iso-13-cis-prostenoic acid |
| 1750 | 1242 | 8β-methyl-9α/β,15-dihydroxy-3-oxa-13-trans,17-cis-prostadienoic acid |
| 1751 | 1243 | 8α-methyl-9α/β,15-dihydroxy-3-oxa-8-iso-13-trans,17-cis-prostadienoic acid |
| 1752 | 1244 | 8β-methyl-9α/β,15-dihydroxy-3-oxa-13-cis,17-cis-prostadienoic acid |
| 1753 | 1245 | 8α-methyl-9α/β,15-dihydroxy-3-oxa-8-iso-13-cis,17-cis-prostadienoic acid |
| 1754 | 1246 | 8β-methyl-9α/β,15-dihydroxy-7-nor-20-methyl-13-trans-prostenoic acid |
| 1755 | 1247 | 8α-methyl-9α/β,15-dihydroxy-7-nor-20-methyl-8-iso-13-trans-prostenoic acid |
| 1756 | 1248 | 8β-methyl-9α/β,15-dihydroxy-7-nor-20-methyl-13-cis-prostenoic acid |
| 1757 | 1249 | 8α-methyl-9α/β,15-dihydroxy-7-nor-20-methyl-8-iso-13-cis-prostenoic acid |
| 1758 | 1250 | 8β-methyl-9α/β,15-dihydroxy-2-fluoro-17,17-dimethyl-13-trans-prostenoic acid |
| 1759 | 1251 | 8α-methyl-9α/β,15-dihydroxy-2-fluoro-17,17-dimethyl-8-iso-13-trans-prostenoic acid |
| 1760 | 1252 | 8β-methyl-9α/β,15-dihydroxy-2-fluoro-17,17-dimethyl-13-cis-prostenoic acid |
| 1761 | 1253 | 8α-methyl-9α/β,15-dihydroxy-2-fluoro-17,17-dimethyl-8-iso-13-cis-prostenoic acid |
| 1762 | 1254 | 8β-methyl-9α/β,15-dihydroxy-10a-homo-13-trans-prostenoic acid |
| 1763 | 1255 | 8α-methyl-9α/β,15-dihydroxy-10a-homo-8-iso-13-trans-prostenoic acid |
| 1764 | 1256 | 8β-methyl-9α/β,15-dihydroxy-10a-homo-13-cis-prostenoic acid |
| 1765 | 1257 | 8α-methyl-9α/β,15-dihydroxy-10a-homo-8-iso-13-cis-prostenoic acid |
| 1766 | 1258 | 8β-methyl-9α/β,15-dihydroxy-2-phenyl-20-methyl-13-trans-prostenoic acid |
| 1767 | 1259 | 8α-methyl-9α/β,15-dihydroxy-2-phenyl-20-methyl-8-iso-13-trans-prostenoic acid |
| 1768 | 1260 | 8β-methyl-9α/β,15-dihydroxy-2-phenyl-20-methyl-13-cis-prostenoic acid |
| 1768 | 1261 | 8α-methyl-9α/β,15-dihydroxy-2-phenyl-20-methyl-8-iso-13-cis-prostenoic acid |
| 1770 | 1262 | 8β-methyl-9α/β,15-dihydroxy-5-cis,13-trans,17-cis-prostatrienoic acid |
| 1771 | 1263 | 8α-methyl-9α/β,15-dihydroxy-8-iso-5-cis,13-trans,17-cis-prostatrienoic acid |
| 1772 | 1264 | 8β-methyl-9α/β,15-dihydroxy-5-cis,13-cis,17-cis-prostatrienoic acid |
| 1773 | 1265 | 8α-methyl-9α/β,15-dihydroxy-8-iso-5-cis,13-cis,17-cis-prostatrienoic acid |
| 1774 | 1266 | 8β-methyl-9α/β,15-dihydroxy-5-cis,13-trans-prostadienoic acid |
| 1775 | 1267 | 8α-methyl-9α/β,15-dihydroxy-8-iso-5-cis,13-trans-prostadienoic acid |
| 1776 | 1268 | 8β-methyl-9α/β,15-dihydroxy-5-cis,13-cis-prostadienoic acid |
| 1777 | 1269 | 8α-methyl-9α/β,15-dihydroxy-8-iso-5-cis,13-cis-prostadienoic acid |
| 1778 | 1270 | 8β-methyl-9α/β,15-dihydroxy-20-ethyl-5-cis,13-trans-prostadienoic acid |
| 1779 | 1271 | 8α-methyl-9α/β,15-dihydroxy-20-ethyl-8-iso-5-cis,13-trans-prostadienoic acid |
| 1780 | 1272 | 8β-methyl-9α/β,15-dihydroxy-20-ethyl-5-cis,-13-cis-prostadienoic acid |

TABLE 43-continued

| | | |
|---|---|---|
| 1781 | 1273 | acid<br>8α-methyl-9α/β,15-dihydroxy-20-ethyl-8-iso-5-cis,13-cis-prostadienoic acid |

EXAMPLES 1782–1815

Catalytic hydrogenation of the 13-trans-prostenoic acids or esters listed below in Table 44 by the procedure described in Example 699 furnishes the product prostanoic acids of the table.

TABLE 44

| Example | Starting 13-trans-prostenoic acid or ester of Example | Products 8-methylprostanoic acids or esters |
|---|---|---|
| 1782 | 1206 | Methyl 8β-methyl-9α/β, 15-dihydroxy-prostanoate |
| 1783 | 1207 | Methyl 8α-methyl-9α/β, 15-dihydroxy-prostanoate |
| 1784 | 1210 | Ethyl 8β-methyl-9α/β, 15-dihydroxy-16,16-dimethyl-prostanoate |
| 1785 | 1226 | Decyl 8β-methyl-9α/β. 15-dihydroxy-20-methyl-prostanoate |
| 1786 | 1655 | 8β-methyl-9-oxo-15-dihydroxy-prostanoic acid |
| 1787 | 1656 | 8α-methyl-9-oxo-15-dihydroxy-8-iso-prostanoic acid |
| 1788 | 1659 | 8β-methyl-9α/β,15-dihydroxy-prostanoic acid |
| 1789 | 1660 | 8α-methyl-9α/β,15-dihydroxy-8-iso-prostanoic acid |
| 1790 | 1678 | 8β-methyl-9-oxo-15-hydroxy-7a,7b-bishomo-prostanoic acid |
| 1791 | 1683 | 8α-methyl-9-oxo-15-hydroxy-2,20-bisethyl-8-iso-prostanoic acid |
| 1792 | 1686 | 8β-methyl-9-oxo-15-hydroxy-3-oxa-16,16-dimethyl-prostanoic acid |
| 1793 | 1694 | 8β-methyl-9-oxo-15-hydroxy-7-nor-20-methyl-prostanoic acid |
| 1794 | 1702 | 8β-methyl-9-oxo-15-hydroxy-10a-homo-prostanoic acid |
| 1795 | 1523 | 8β-methyl-9α/β . 11α,15-trihydroxy-prostanoic acid |
| 1796 | 1524 | 8α-methyl-9α/β,11α,15-trihydroxy-8-iso-prostanoic acid |
| 1797 | 1527 | 8β-methyl-9α/β,11α,15-trihydroxy-16,16-dimethyl-prostanoic acid |
| 1798 | 1531 | 8β-methyl-9α/β,11α,15-trihydroxy-17,17-dimethyl-prostanoic acid |
| 1799 | 1539 | 8β-methyl-9α/β-11α,15-trihydroxy-20-ethyl-prostanoic acid |
| 1800 | 1552 | 8α-methyl-9α/β,11α,15-trihydroxy-7a,7b-bishomo-8-iso-prostanoic acid |
| 1801 | 1551 | 8β-methyl-9α/β,11α,15-trihydroxy-7a,7b-bishomo-prostanoic acid |
| 1802 | 1555 | 8β-methyl-9α/β,11α,15-trihydroxy-2-ethyl-prostanoic acid |
| 1803 | 1559 | 8β-methyl-9α/β,11α,15-trihydroxy-3,3,20-trimethyl-prostanoic acid |
| 1804 | 1563 | 8β-methyl-9α/β,11α,15-trihydroxy-3-oxa-prostanoic acid |
| 1805 | 1567 | 8β-methyl-9α/β,11α,15-trihydroxy-3-oxa-16,16-dimethyl-prostanoic acid |
| 1806 | 1587 | 8β-methyl-9α/β,11α,15-trihydroxy-7a-homo-16,16-dimethyl-prostanoic acid |
| 1807 | 1643 | Ethyl 8β-methyl-9α/β, 11α,15 trihydroxy-3-oxa-17,17-dimethyl-prostanoic acid |
| 1808 | 1816 | 8β,15-dimethyl-9α/β,15-dihydroxy-prostanoic acid |
| 1809 | 1817 | 8β,15-dimethyl-9-oxo-15-hydroxy-prostanoic acid |
| 1810 | 1819 | 8α,15-dimethyl-9-oxo-15-hydroxy-8-iso-prostanoic acid |
| 1811 | 1834 | 8β,15-dimethyl-9α/β, 11α,15-trihydroxy-prostanoic acid |
| 1812 | 1835 | 8β,15-dimethyl-9-oxo-11α,15-dihydroxy-prostanoic acid |
| 1813 | 1837 | 8α,15-dimethyl-9-oxo-11α,15-dihydroxy-8-iso-prostanoic acid |
| 1814 | 1843 | 8β,15-dimethyl-9-oxo-11α,15-dihydroxy-7a,7b-bishomo-prostanoic acid |
| 1815 | 1849 | 8β,15-dimethyl-9-oxo-11α,15-dihydroxy-3-oxa-prostanoic acid |

EXAMPLES 1816–1859

Treatment by the procedure described in Example 1082 of the 8-methyl-9α/β,15-dihydroxy-prostenoic acids listed in Table 45 below successively with 2,3-dichloro-5,6-dicyanobenzoquinone to give the corresponding 15-keto derivatives; 2.4 equivalents each of triethylamine and trimethylsilyl chloride to give the corresponding 9α/β-0-trimethylsilyl ether trimethylsilyl prostenoate ester in the instance of the 11α-hydroxy derivatives an additional 1.1 equivalent each of triethylamine and trimethylsilyl chloride is used and the 11α-0-trimethylsilyl ether derivative is obtained); methyl magnesium bromide to give the 15-methyl-15-hydroxy bis or tris trimethylsilyl blocked ether-ester; methanol-water-acetic acid for deblocking of the trimethylsilyl ether and ester blocking groups to give the listed 9α/β-hydroxy-15-methyl-15-hydroxy derivatives. In the 11-deoxy series treatment of these 9α/β-hydroxy-15-methyl-15-hydroxy products with Collins reagent in methylene chloride provides the corresponding 11-deoxy-9-oxo-15-hydroxy-15-methyl-prostenoic acids, also listed in the table. In the 11α-hydroxy series, treatment of the 9α/β,11α-15-trihydroxy-15-methyl derivatives with 1.1 molar equivalents each of triethylamine and trimethylsilyl chloride provides the corresponding 11α-0-trimethylsilyloxy-9α/β,15-dihydroxy derivative, which an oxidation in the usual way with Collins reagent in methylene chloride followed by silyl ether cleavage (treatment with methanol-water-acetic acid by the procedure described in Example 1082) provides the corresponding 9-oxo-11α,15-dihydroxy-15-methyl-prostenoic acids of the Table.

TABLE 45

| Example | Starting 9α/β,(or) 9α),15-dihydroxy- or 9α/β(or 9α), 11α,15-trihydroxy derivative of Example | Product 8,15-dimethyl-15-hydroxy-prostanoic acids |
|---|---|---|
| 1816 | 1659 | 8β,15-dimethyl-9α,β,15-dihydroxy-13-trans-prostenoic acid |
| 1817 | 1859 | 8β,15-dimethyl-9-oxo-15-hydroxy-13-trans-prostenoic acid |
| 1818 | 1660 | 8α,15-dimethyl-9α,15-dihydroxy-8-iso-13-trans-prostenoic acid |
| 1819 | 1660 | 8α,15-dimethyl-9-oxo-15-hydroxy-8-iso-13-trans-prostenoic acid |
| 1820 | 1730 | 8β,15-dimethyl-9α/β,15-dihydroxy-13-trans,17-cis-prostadienoic acid |
| 1821 | 1730 | 8β,15-dimethyl-9-oxo-15-hydroxy-13-trans-17-cis-prostadienoic acid |
| 1822 | 1731 | 8α,15-dimethyl-9α/β,15-dihydroxy-8-iso-13-trans,17-cis-prostadienoic acid |
| 1823 | 1731 | 8α,15-dimethyl-9-oxo-15-hydroxy-8-iso-13-trans,17-cis-prostadienoic acid |
| 1824 | 1738 | 8β,15-dimethyl-9α/β,15-dihydroxy-7a,7b-bishomo-13-trans-prostenoic acid |
| 1825 | 1738 | 8β,15-dimethyl-9-oxo-15-hydroxy-7a,7b-bishomo-13-trans-prostenoic acid |
| 1826 | 1746 | 8β,15-dimethyl-9α/β,15-dihydroxy-3-oxa-16,16-dimethyl-13-trans-prostenoic acid |
| 1827 | 1746 | 8β,15-dimethyl-9-oxo-15-hydroxy-3-oxa-16,16-dimethyl-13-trans-prostenoic acid |
| 1828 | 1750 | 8β,15-dimethyl-9α/β,15-dihydroxy-3-oxa-13-trans,17-cis-prostadienoic acid |
| 1829 | 1750 | 8β,15-dimethyl-9-oxo-15-hydroxy-3-oxa-13-trans,17-cis-prostadienoic acid |
| 1830 | 1770 | 8β,15-dimethyl-9α/β,15-dihydroxy-5-cis,13-trans,17-cis-prostatrienoic acid |
| 1831 | 1770 | 8β,15-dimethyl-9-oxo-15-hydroxy-5-cis,13-trans,17-cis-prostatrienoic acid |
| 1832 | 1778 | 8β,15-dimethyl-9α/β,15-dihydroxy-20-ethyl-5-cis,13-trans-prostadienoic acid |
| 1833 | 1778 | 8β,15-dimethyl-9-oxo-15-hydroxy-20-ethyl-5-cis,13-trans-prostadienoic acid |
| 1834 | 1523 | 8β,15-dimethyl-9α/β,11α,15-trihydroxy-13-trans-prostenoic acid |
| 1835 | 1523 | 8β,15-dimethyl-9-oxo-11α,15-dihydroxy-13-trans-prostenoic acidi |
| 1836 | 1524 | 8α,15-dimethyl-9α/β,11α,15-trihydroxy-8-iso-13-trans-prostenoic acid |
| 1837 | 1524 | 8α,15-dimethyl-9-oxo-11α,15-dihydroxy-8-iso-13-trans-prostenoic acid |
| 1838 | 1535 | 8β,15-dimethyl-9α/β,11α,15-trihydroxy-13-trans,17-cis-prostadienoic acid |
| 1839 | 1535 | 8β,15-dimethyl-9-oxo-11α,15-dihydroxy-13-trans,17-cis-prostadienoic acid |
| 1840 | 1539 | 8β,15-dimethyl-9α/β,11α,15-trihydroxy-20-ethyl-13-trans-prostenoic acid |
| 1841 | 1539 | 8β,15-dimethyl-9-oxo-11α,15-dihydroxy-20-ethyl-13-trans-prostenoic acid |
| 1842 | 1551 | 8β,15-dimethyl-9α/β,11α,15-trihydroxy-7a,7b-bishomo-13-trans-prostenoic acid |
| 1843 | 1551 | 8β,15-dimethyl-9-oxo-11α,15-dihydroxy-7a,7b-bishomo-13-trans-prostenoic acid |
| 1844 | 1555 | 8β,15-dimethyl-9α/β,11α,15-trihydroxy-2-ethyl-13-trans-prostenoic acid |
| 1845 | 1555 | 8β,15-dimethyl-9-oxo-11α,15-dihydroxy-2-ethyl-13-trans-prostenoic acid |
| 1846 | 1559 | 8β,15-dimethyl-9α/β,11α,15-trihydroxy-3,3,20-trimethyl-13-trans-prostenoic acid |
| 1847 | 1559 | 8β,15-dimethyl-9-oxo-11α,15-dihydroxy-3,3,20-trimethyl-13-trans-prostenoic acid |
| 1848 | 1563 | 8β,15-dimethyl-9α/β,11α,15-trihydroxy-3-oxa-13-trans-prostenoic acid |
| 1849 | 1563 | 8β,15-dimethyl-9-oxo-11α,15-dihydroxy-3-oxa-13-trans-prostenoic acid |
| 1850 | 1571 | 8β,15-dimethyl-9α/β,11α,15-trihydroxy-3-oxa-13-trans,17-cis-prostadienoic acid |
| 1851 | 1571 | 8β,15-dimethyl-9-oxo-11α,15-dihydroxy-3-oxa-13-trans,17-cis-prostadienoic acid |
| 1852 | 1599 | 8β,15-dimdethyl-9α/β,11α,15-trihydroxy-5-cis,13-trans-prostadienoic acid |
| 1853 | 1599 | 8β,15-dimethyl-9-oxo-11α,15-dihydroxy-5-cis,13-trans-prostadienoic acid |
| 1854 | 1603 | 8β,15-dimethyl-9α/β,11α,15-trihydroxy-5-cis,13-trans,17-cis-prostatrienoic acid |
| 1855 | 1603 | 8β,15-dimethyl-9-oxo-11α,15-dihydroxy-5-cis,13-trans,17-cis-prostatrienoic acid |
| 1856 | 1611 | 8β,15-dimethyl-9α/β,11α,15-trihydroxy-4-nor-20-methyl-5-cis,13-trans-prostadienoic acid |
| 1857 | 1611 | 8β,15-dimethyl-9-oxo-11α,15-dihydroxy-4-nor-20-methyl-5-cis,13-trans-prostadienoic acid |
| 1858 | 1623 | 8β,15-dimethyl-9α/β,11α,15-trihydroxy-4a,4b-bishomo-5-cis,13-trans,17-cis prostatrienoic acid |
| 1859 | 1623 | 8β,15-dimethyl-9-oxo-11α,15-dihydroxy-4a,4b-bishomo-5-cis,13-trans,17-cis-prostatrienoic acid |

EXAMPLES 1860–1876

Treatment of the 8,15-dimethyl-9-oxo-11α-hydroxy derivatives listed in Table 46 below with aqueous acetic acid by the procedure described in Example 1387 is productive of the corresponding 10-prostenoic acid products of the table.

TABLE 46

| Example | Starting 8,15-dimethyl-9-oxo-11α-hydroxy derivatives of Example | Product 8,15-dimethyl-9-oxo-10-prostenoic acid |
|---|---|---|
| 1860 | 1835 | 8β,15-dimethyl-9-oxo-15-hydroxy-10,13-trans-prostadienoic acid |
| 1861 | 1837 | 8α,15-dimethyl-9-oxo-15-hydroxy-8-iso-10,13-trans-prostadienoic acid |
| 1862 | 1839 | 8β,15-dimethyl-9-oxo-15-hydroxy-10,13-trans,17-cis-prostatrienoic acid |
| 1863 | 1841 | 8β,15-dimethyl-9-oxo-15-hydroxy-20-ethyl-10,13-trans-prostadienoic acid |
| 1864 | 1843 | 8β,15-dimethyl-9-oxo-15-hydroxy-7a,7b-bishomo-10,13-trans-prostadienoic acid |
| 1865 | 1845 | 8β,15-dimethyl-9-oxo-15-hydroxy-2-ethyl-10,13-trans-prostadienoic acid |
| 1866 | 1847 | 8β,15-dimethyl-9-oxo-15-hydroxy-3,3,20-trimethyl-10,13-trans-prostadienoic acid |
| 1867 | 1849 | 8β,15-dimethyl-9-oxo-15-hydroxy-3-oxa-10,13-trans-prostadienoic acid |
| 1868 | 1851 | 8β,15-dimethyl-9-oxo-15-hydroxy-3-oxa-10,13-trans,17-cis-prostatrienoic acid |
| 1869 | 1853 | 8β,15-dimethyl-9-oxo-15-hydroxy-5-cis,10,13-trans-prostatrienoic acid |
| 1870 | 1855 | 8β,15-dimethyl-9-oxo-15-hydroxy-5-cis,10,13-trans,17-cis-prostatetraenoic acid |
| 1871 | 1857 | 8β,15-dimethyl-9-oxo-15-hydroxy-4-nor-20-methyl-5-cis,10,13-trans-prostatrienoic acid |
| 1872 | 1859 | 8β,15-dimethyl-9-oxo-15-hydroxy-4a,4b-bishomo-5-cis,10,13-trans,17-cis-prostatetraenoic acid |
| 1873 | 1812 | 8β,15-dimethyl-9-oxo-15-hydroxy-10-prostenoic acid |
| 1874 | 1815 | 8β,15-dimethyl-9-oxo-15-hydroxy-3-oxa-10-prostenoic acid |
| 1875 | 1814 | 8β,15-dimethyl-9-oxo-15-hydroxy-7a,7b-bishomo-10-prostenoic acid |
| 1876 | 1813 | 8β,15-dimethyl-9-oxo-15-hydroxy-8-iso-10-prostenoic acid |

EXAMPLE 1877

Preparation of 3-methoxy-1-octyne

To an ice-cooled solution of 63 g. of 1-octyn-3-ol in 300 ml. of dimethoxyethane is added under an inert atmosphere 312 ml. of 1.6 M n-butyllithium in hexane dropwise over 1 hour. To the mixture is then added 145 g. of methyl iodide and the resulting mixture is stirred at ambient temperatures for 24 hours and then heated to 60° C. for 1 hour. The mixture is cooled and poured into cold dilute hydrochloric acid. The organic phase is separated, washed with water and saturated brine, dried (Na₂SO₄), and evaporated to an oil, dried (Na₂SO₄), and evaporated to an oil. Fractional distillation of the oil in vacuo yields the product as a colorless oil.

EXAMPLE 1878

Preparation of 1-Iodo-3-methoxy-trans-1-octene

Treatment of 3-methoxy-1-octyne (Example 1877) with disiamylborane, trimethylamine oxide, sodium hydroxide and iodine by the procedure described in Example 996 furnishes the title product.

EXAMPLE 1879

Preparation of 3-Methoxy-trans-1-octenyl lithium

Treatment of 1-iodo-3-methoxy-trans-1-octene (Example 1878) with butyl lithium in the manner of Example 961 pro provides a toluene-hexane solution of the subject trans-vinyl lithium derivative.

EXAMPLE 1880

Preparation of Lithium (3-methoxy-trans-1-octenyl)trimethylalanate

The subject alanate in hydrocarbon solution is prepared according to the method of Example 963 from a hydrocarbon solution of 3-methoxy-trans-1-octenyl lithium(Exa (Example 1879) and trimethylaluminum.

EXAMPLES 1881–1895

Treatment of the cycloalkenones listed in Table 47 with lithium(3-methoxy-trans-1-octenyl)trimethylalanate (Example 1880) by the procedure described in Example 957 with the omission of the 80% aqueous acetic acid treatment (80° C., 1 hour) followed by saponfication of the intermediate alkyl prostenoates by the procedure described in Example 122 furnishes the product 9-oxo-15-methoxy-13-trans-prostenoic acids of the table.

TABLE 47

| Example | Starting cycloalkenone of Example | Product 9-oxo-15-methoxy-13-trans-prostenoic acid |
|---|---|---|
| 1881 | 23 | 9-oxo-7a,7b-bishomo-15-methoxy-13-trans-prostenoic acid |
| 1882 | 31 | 9-oxo-2-ethyl-15-methoxy-13-trans-prostenoic acid |
| 1883 | 41 | 9-oxo-3,3-dimethyl-15-methoxy-13-trans-prostenoic acid |
| 1884 | 46 | 9-oxo-3-oxa-15-methoxy-13-trans-prostenoic acid |
| 1885 | 53 | 9-oxo-7-nor-15-methoxy-13-trans-prostenoic acid |
| 1886 | 70 | 9-oxo-2-fluoro-15-methoxy-13-trans-prostenoic acid |
| 1887 | 74 | 9-oxo-7a-homo-15-methoxy-13-trans-prostenoic acid |
| 1888 | 79 | 9-oxo-2-phenyl-15-methoxy-13-trans-prostenoic acid |
| 1889 | 99 | 9-oxo-2-methyl-15-methoxy-13-trans-prostenoic acid |
| 1890 | 111 | 9-oxo-10a-homo-15-methoxy-13-trans-prostenoic acid |
| 1891 | 118 | 9-oxo-3-thia-15-methoxy-13-trans-prostenoic acid |

TABLE 47-continued

| Example | Starting cyclo-alkenone of Example | Product 9-oxo-15-methoxy-13-trans-prostenoic acid |
|---|---|---|
| 1892 | 900 | 9-oxo-15-methoxy-5-cis,13-trans-prostadienoic acid |
| 1893 | 1144 | 9-oxo-4-nor-15-methoxy-13-trans-prostadienoic acid |
| 1894 | 1145 | 9-oxo-4-homo-15-methoxy-5-cis,13-trans-prostadienoic acid |
| 1895 | 1146 | 9-oxo-4a,4b-bishomo-15-methoxy-13-trans-prostadienoic acid |

EXAMPLES 1896–1910

Treatment of the 9-oxo-15-methoxy-13-trans-prostenoic acids listed in Table 48 below with lithium perhydro-9b-boraphenalylhydride by the procedure described in Example 737 furnishes the 9α-hydroxy-15-methoxy-13-trans-prostenoic acids of the Table.

TABLE 48

| Example | Starting 9-oxo-15-methoxy-13-trans-prostenoic acid of Example | Product 9α-hydroxy-15-methoxy-13-trans-prostenoic acid |
|---|---|---|
| 1896 | 1881 | 9α-hydroxy-7a,7b-bishomo-15-methoxy-13-trans-prostenoic acid |
| 1897 | 1882 | 9α-hydroxy-2-ethyl-15-methoxy-13-trans-prostenoic acid |
| 1898 | 1883 | 9α-hydroxy-3,3-dimethyl-15-methoxy-13-trans-prostenoic acid |
| 1899 | 1884 | 9α-hydroxy-3-oxa-15-methoxy-13-trans-prostenoic acid |
| 1900 | 1885 | 9α-hydroxy-7-nor-15-methoxy-13-trans-prostenoic acid |
| 1901 | 1886 | 9α-hydroxy-2-fluoro-15-methoxy-13-trans-prostenoic acid |
| 1902 | 1887 | 9α-hydroxy-7a-homo-15-methoxy-13-trans-prostenoic acid |
| 1903 | 1888 | 9α-hydroxy-2-phenyl-15-methoxy-13-trans-prostenoic acid |
| 1904 | 1889 | 9α-hydroxy-2-methyl-methoxy-13-trans-prostenoic acid |
| 1905 | 1890 | 9α-hydroxy-10a-homo-15-methoxy-13-trans-prostenoic acid |
| 1906 | 1891 | 9α-hydroxy-3-thia-15-methoxy-13-trans-prostenoic acid |
| 1907 | 1892 | 9α-hydroxy-15-methoxy-5-cis,13-trans-prostadienoic acid |
| 1908 | 1893 | 9α-hydroxy-4-nor-15-methoxy-5-cis,13-trans-prostadienoic acid |
| 1909 | 1894 | 9α-hydroxy-4-homo-15-methoxy-5-cis,13-trans-prostadienoic acid |
| 1910 | 1895β | 9α-hydroxy-4a,4b-bishomo-15-methoxy-13-trans-prostenoic acid |

EXAMPLE 1911

Preparation of 2-(6-carboxy-2-cis-hexenyl)-3,4-oxidocyclopentanol

A solution of 5.0 g. (35 mmoles) of 5-hydroxy-2,3-oxidocyclopentylacetaldehyde-γ-lactol (isomeric mixture; E. J. Corey and R. Noyori, Tetrahedron Letters, 1970, 311) in 25 ml. of DMSO is added during 0.5 minutes at 20° C. to a stirred solution of the Withig reagent [E. J. Corey et al., JACS, 91 5675 (1969); also Example 1108] and dimsyl sodium prepared from 23.5 g. (53 mmoles) of 4-carboxybutyltriphenylphosphonium bromide, 6.1 g. (140 mmoles) of 57% sodium hydride dispersion, and 230 ml. of DMSO (dimethylsulfoxide).

The solution is stirred at ambient temperatures for 2 hours and poured into a stirred mixture of methylene chloride, ice, and hydrochloric acid. The reaction mixture is worked up as described in Example 1105, and the crude product is purified by dry column chromatography on silica gel to provide the title compound (mixture of two stereoisomers) as an oil, IR (film) 3450, 1710, and 832 cm$^{-1}$.

EXAMPLE 1912

Preparation of 2-(6-carboxy-2-cis-hexenyl)-3,4-oxidocyclopentanone

A stirred solution of 2.98 g. (13.2 mmoles) of 2-(6-carboxy-2-cis-hexenyl)-3,4-oxidocyclopentanol (Example 1911) in 66 ml. of acetone is treated dropwise with 3.30 ml. of 8N chromic acid in 8N $M_2SO_4$ during 20 minutes at −10° to −5° C. The solution is stirred at −5° C. for 10 minutes and treated successively with a few drops of isopropanol and 12 ml. of water. The mixture is filtered, and the filtrate is concentrated saturated with sodium chloride, and extracted with ethyl acetate. The extract is washed with brine, dried over $MgSO_4$, and evaporated to give an oil, IR (film) 1740, 1710, and 840 cm$^{-1}$.

EXAMPLE 1913

Preparation of 2-(6-carboxy-2-cis-hexenyl)-4-hydroxycyclopent-2-en-1-one

A solution of (pH or 10.2–10.5) of 2.42 g. (10.8 mmoles) of 2-(6-carboxy-2-cis-hexenyl)-3,4-oxidocyclopentanone (Example 1912) 4.58 g. (43.2 mmoles) of sodium carbonate, and 216 ml. of water is allowed to stand at room temperatures under nitrogen for 24 hours. The solution is acidified at 15° C. with hydrochloric acid and extracted with ethyl acetate. The extract is washed with brine, dried over $MgSO_4$, and evaporated to give an oil; IR (film) 1700 (carbonyl groups) and 1630 cm$^{-1}$ (conjugated olefin); NMR 7.11 (1), 5.54 (2), and 4.95 (1)δ.

We claim:

1. Compounds of the formula:

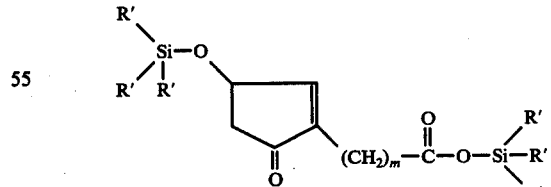

wherein m is an integer having the value of 4 to 8, inclusive, and R' are alkyl groups having from 1 to 10 carbon atoms and are not necessarily the same.

2. The compound according to claim 1 wherein m is 6 and R' in each instance is methyl; 4-trimethylsilyloxy-2-(6-carbotrimethylsilyloxyhexyl)cyclopent-2-en-1-one.

* * * * *